US012746208B2

(12) United States Patent
Song et al.

(10) Patent No.: US 12,746,208 B2
(45) Date of Patent: Sep. 29, 2026

(54) LONG-ACTING LOW-TOXICITY NOVEL CATIONIC LIPID COMPOUNDS AND COMPOSITION THEREOF

(71) Applicant: BEIJING YOUCARE KECHUANG PHARMACEUTICAL TECHNOLOGY CO., LTD., Beijing (CN)

(72) Inventors: Gengshen Song, Beijing (CN); Honglei Zhang, Beijing (CN); Xichao Chen, Beijing (CN); Huanyu Wang, Beijing (CN); Dawei Huang, Beijing (CN); Xiaowen Yu, Beijing (CN); Chuan Gao, Beijing (CN); Xiaobing Lv, Beijing (CN); Jingtang Lian, Beijing (CN); Xinlong Jiang, Beijing (CN); Boyang Li, Beijing (CN); Xinggai Peng, Beijing (CN); Yue Li, Beijing (CN); Yu Hao, Beijing (CN); Jinyu Zhang, Beijing (CN)

(73) Assignee: BEIJING YOUCARE KECHUANG PHARMACEUTICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/997,563

(22) PCT Filed: Jan. 19, 2023

(86) PCT No.: PCT/CN2023/073230

§ 371 (c)(1),
(2) Date: Jan. 22, 2025

(87) PCT Pub. No.: WO2024/145965

PCT Pub. Date: Jul. 11, 2024

(65) Prior Publication Data

US 2026/0007613 A1 Jan. 8, 2026

(30) Foreign Application Priority Data

Jan. 5, 2023 (CN) ......................... 202310010912.6

(51) Int. Cl.

| | |
|---|---|
| ***A61K 9/51*** | (2006.01) |
| ***A61K 9/00*** | (2006.01) |
| ***A61K 31/7105*** | (2006.01) |
| ***A61K 31/711*** | (2006.01) |
| ***A61K 31/713*** | (2006.01) |
| ***A61K 38/16*** | (2006.01) |
| ***A61K 39/00*** | (2006.01) |
| ***A61K 47/18*** | (2017.01) |
| ***C07C 229/16*** | (2006.01) |

(52) U.S. Cl.

CPC .......... *A61K 9/5123* (2013.01); *A61K 9/0019* (2013.01); *A61K 9/5192* (2013.01); *A61K 31/7105* (2013.01); *A61K 31/711* (2013.01); *A61K 31/713* (2013.01); *A61K 38/16* (2013.01); *A61K 39/00* (2013.01); *A61K 47/18* (2013.01); *C07C 229/16* (2013.01); *A61K 2039/53* (2013.01)

(58) Field of Classification Search

CPC ........ A61K 9/5123; A61P 25/00; A61P 31/00; A61P 35/00; A61P 37/00; A61P 37/06; C07B 2200/07

See application file for complete search history.

(56) References Cited

U.S. PATENT DOCUMENTS

| | | | |
|---|---|---|---|
| 2018/0273467 | A1 | 9/2018 | Benenato |
| 2021/0128488 | A1 | 5/2021 | Du |

FOREIGN PATENT DOCUMENTS

| | | | |
|---|---|---|---|
| CA | 2998810 | A1 | 3/2017 |
| CN | 103380113 | A | 3/2018 |
| CN | 108358812 | A | 8/2018 |
| CN | 110325511 | A | 10/2019 |
| CN | 110520409 | A | 11/2019 |
| CN | 112979483 | A | 6/2021 |
| CN | 113018449 | A | 6/2021 |
| CN | 108368028 | A | 9/2021 |
| CN | 114044741 | A | 2/2022 |

(Continued)

OTHER PUBLICATIONS

China National Intellectual Property Administration (ISA/CN); International Search Report with Translation; corresponding application PCT/CN2023/073230; Date of Mailing: Aug. 14, 2023; pp. 1-6.

(Continued)

*Primary Examiner* — Robert S Cabral
(74) *Attorney, Agent, or Firm* — Taft Stettinius & Hollister LLP; Stephen F. Rost

(57) ABSTRACT

Provided in the present invention are long-acting low-toxicity novel cationic lipid compounds, which are compounds shown as formula (I), or N-oxides, solvates, pharmaceutically acceptable salts or stereoisomers thereof. Further provided are a composition comprising the compounds and the use thereof for the delivery of therapeutic or prophylactic agents.

(I)

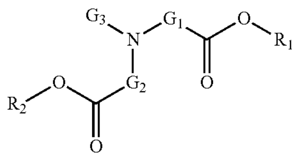

25 Claims, 10 Drawing Sheets

(56) References Cited

FOREIGN PATENT DOCUMENTS

| | | | |
|---|---|---|---|
| CN | 114728887 | A | 7/2022 |
| CN | 114957027 | A | 8/2022 |
| CN | 115745820 | A | 3/2023 |
| WO | 2017049245 | A3 | 3/2017 |

OTHER PUBLICATIONS

China National Intellectual Property Administration (ISA/CN); Written Opinion of the International Searching Authority; corresponding application PCT/CN2023/073230; Non English.

China National Intellectual Property Administration; Notification of the First Office Action; Corresponding Application No. 202310010912.6; Mail Date: Mar. 13, 2023; pp. 1-6; Translation.

Shuo Sun et al: "Combinatorial Library of Lipidoids for In Vitro DNA Delivery" Bioconjugate Chemistry, vo1. 23, No. 1,Jan. 18, 2012, pp. 135-140.

European Patent Office, Germany; Extended European search report dated Mar. 23, 2026 of corresponding EP application No. 23914121.1.

LONG-ACTING LOW-TOXICITY NOVEL CATIONIC LIPID COMPOUNDS AND COMPOSITION THEREOF

CROSS-REFERENCE TO RELATED APPLICATION

The application is a U.S. national stage application under 35 U.S.C. § 371 of PCT International Application Ser. No. PCT/CN2023/073230, filed Jan. 19, 2023, which claims priority to Chinese Patent Application Ser. No. CN202310010912.6, filed Jan. 5, 2023, the entire contents of which are incorporated herein by reference in their entirety.

TECHNICAL FIELD

The present disclosure belongs to the field of medicine. The present disclosure specifically relates to a cationic lipid compound, a composition containing the same and uses thereof.

BACKGROUND

Effective targeted delivery of biologically active substances such as small molecule drugs, peptides, proteins and nucleic acids, especially nucleic acids, is a persistent medical problem. Nucleic acid therapeutics face great challenges due to low cell permeability and high susceptibility to degradation of certain nucleic acid molecules, including RNA.

It has been demonstrated that compositions, liposomes and liposome complexes (lipoplexes) containing a cationic lipid as delivery carriers effectively deliver biologically active substances, such as small molecule drugs, polypeptides, proteins and nucleic acids, into cells and/or intracellular compartments. These compositions generally comprise one or more "cationic" and/or amino (ionizable) lipids, and comprise a neutral lipid, a structured lipid, and a polymer-conjugated lipid. Cationic and/or ionizable lipids include, for example, amine-containing lipids that can be readily protonated. Although a variety of such lipid-containing nanoparticle compositions have been demonstrated, safety, efficacy and specificity remain to be improved. Notably, the increased complexity of lipid nanoparticles (LNPs) complicates their production and may increase their toxicity, which is a major concern that could limit their clinical application. For example, LNP siRNA particles such as patisiran require preadministration of steroids and antihistamines to eliminate unwanted immune responses (T. Coelho, D. Adams, A. Silva, et al., Safety and efficacy of RNAi therapy for transthyretin amyloidosis, N Engl J Med, 369 (2013) 819-829). Accordingly, there is a need to develop improved cationic lipid compounds, and compositions comprising the same, that facilitate the delivery of therapeutic and/or prophylactic agents such as nucleic acids to cells.

SUMMARY

One aspect of the present disclosure provides a novel cationic lipid compound, which is a compound of formula (I)

I

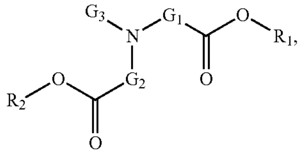

or an N-oxide, solvate, pharmaceutically acceptable salt or stereoisomer thereof, wherein:

$G_1$ is $C_{1-8}$ alkylene;

$G_2$ is $C_{2-8}$ alkylene;

$R_1$ is $C_{6-25}$ linear or branched alkyl;

$R_2$ is $C_{12-25}$ linear or branched alkyl;

$G_3$ is: $HO(CH_2)_2N(R_3)CH_2CH(OH)CH_2$—, wherein $R_3$ is —$CH_3$ or —$CH_2CH_3$ or —$CH_2CH_2OH$.

For example, the compound of formula (I) has one of the following structures:

YK-301

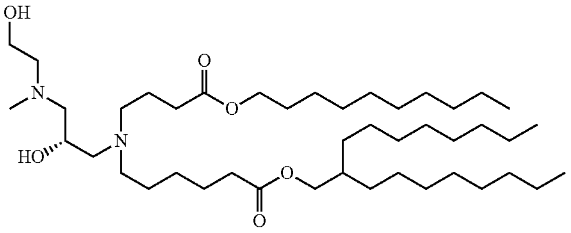,

YK-302

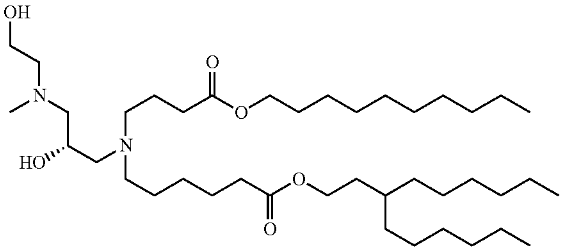,

YK-303

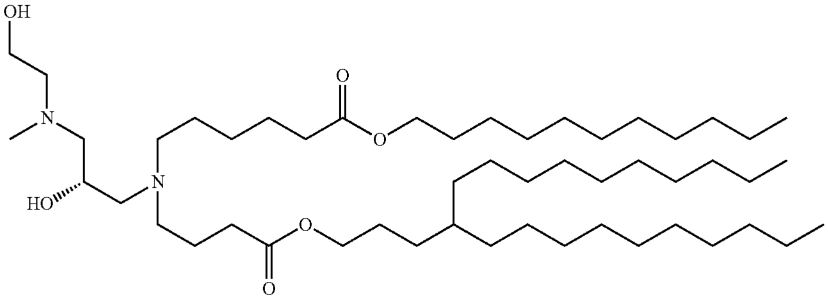,

-continued
YK-304
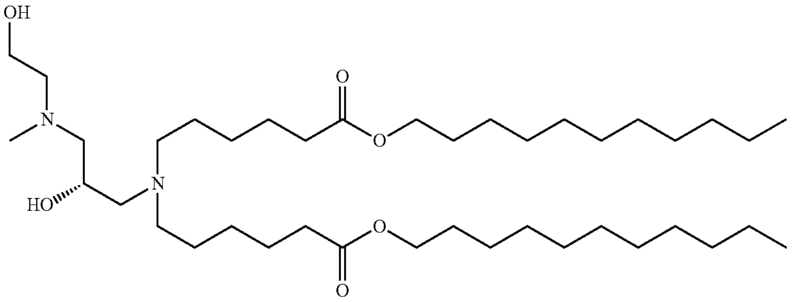
,
YK-305
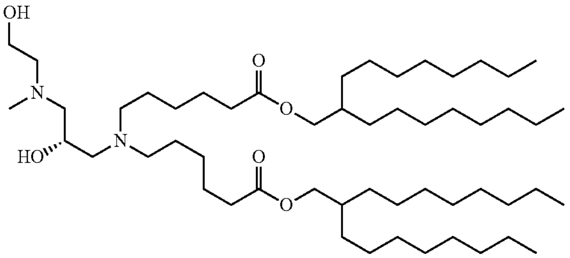
,
YK-306
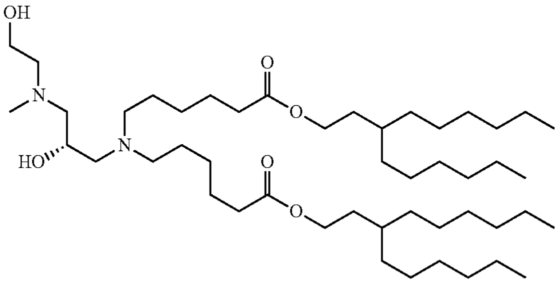
,
YK-307
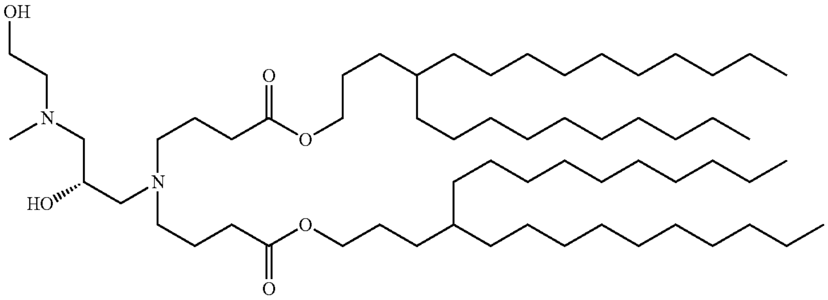
,
YK-308
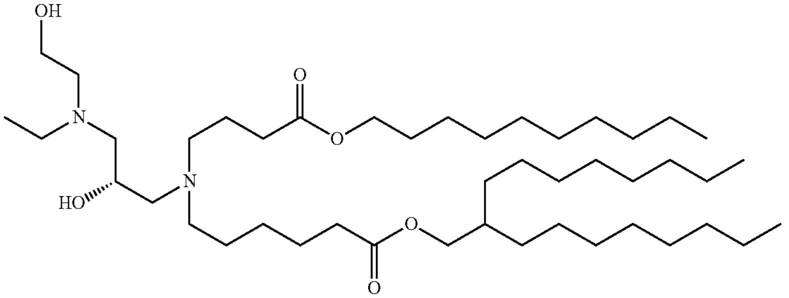
,
YK-309
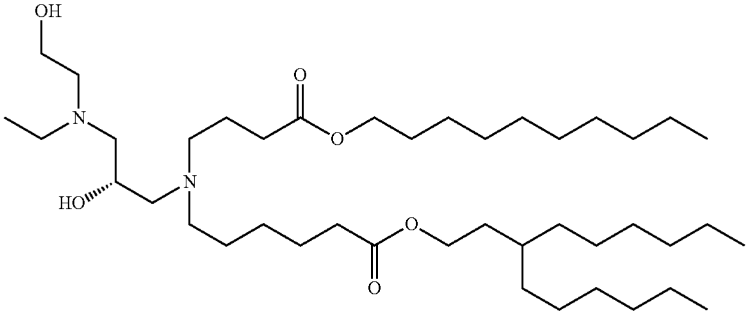
, -continued
YK-310
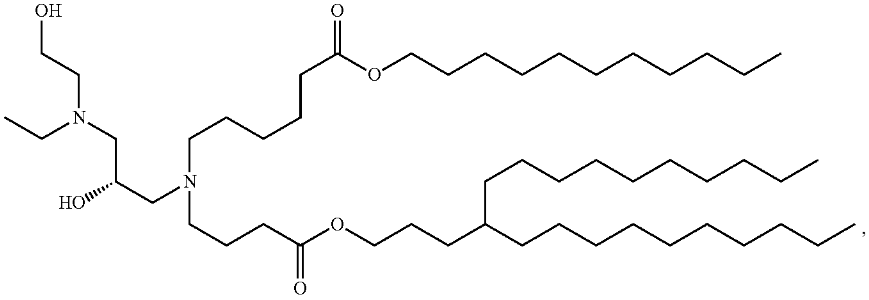
,
YK-311
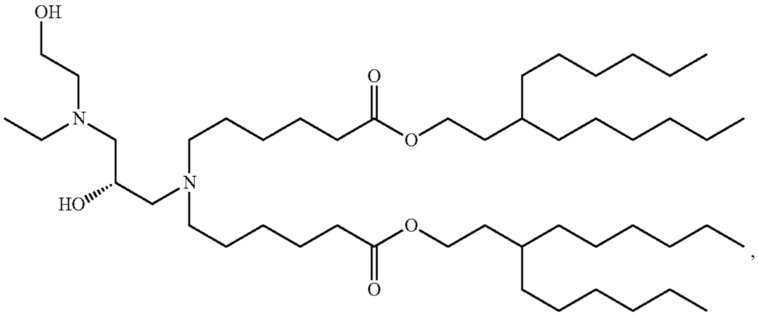
,
YK-312
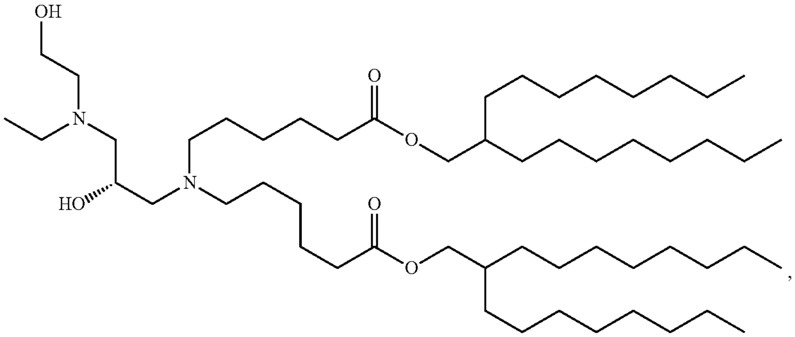
,
YK-313
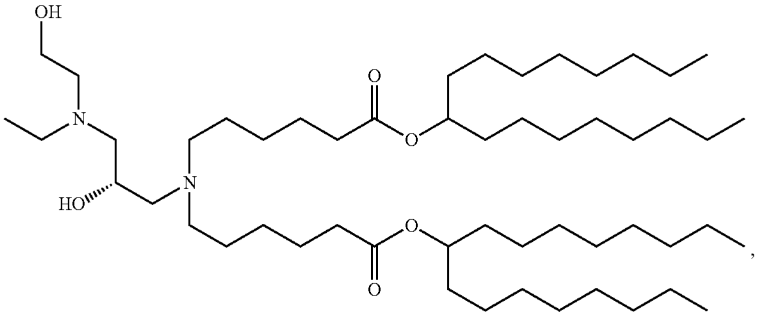
,
YK-314
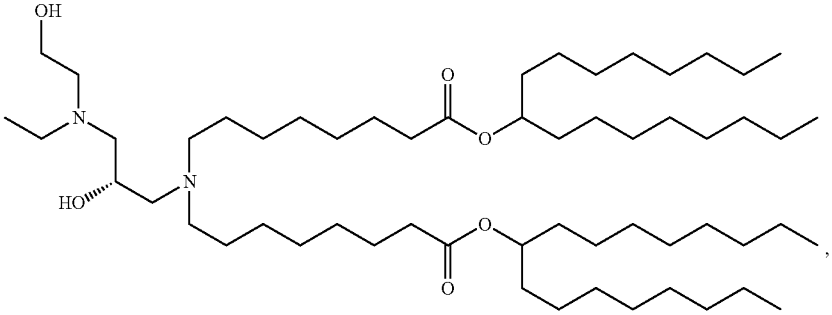
, -continued
YK-315
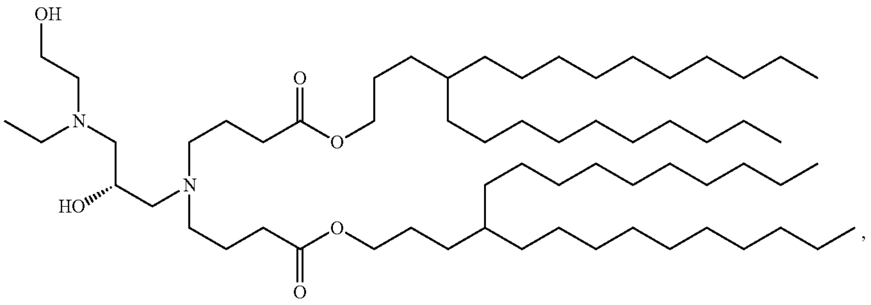
YK-316
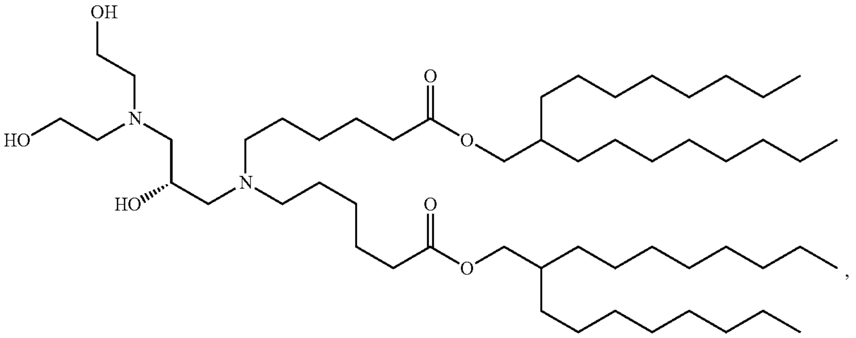
YK-317
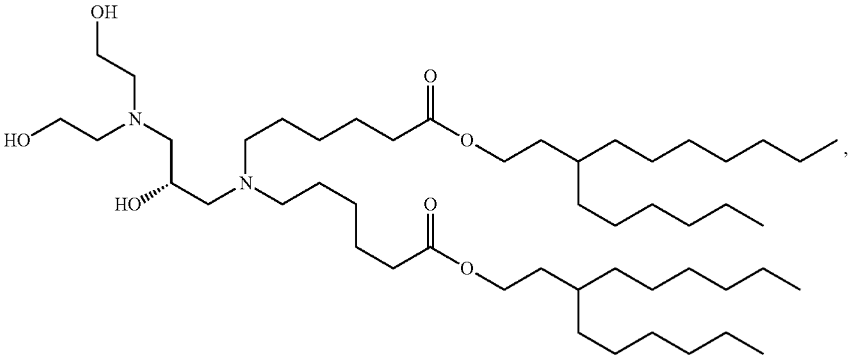
YK-318
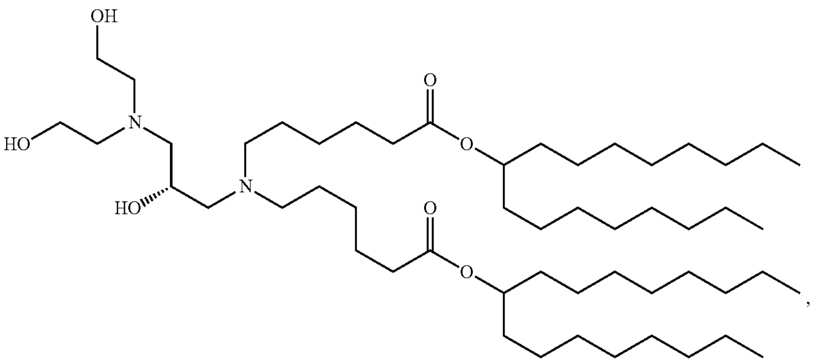

-continued

YK-319

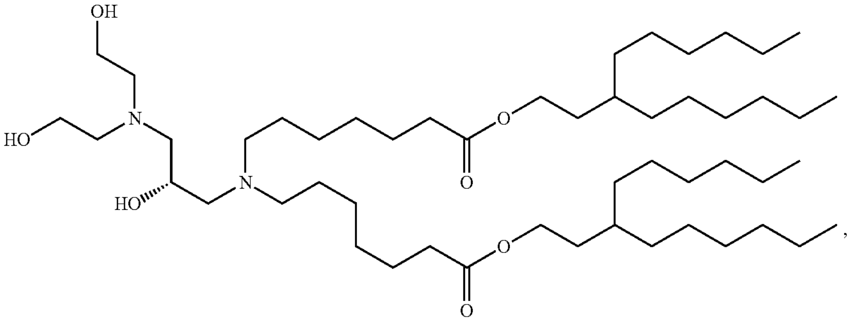

,

YK-320

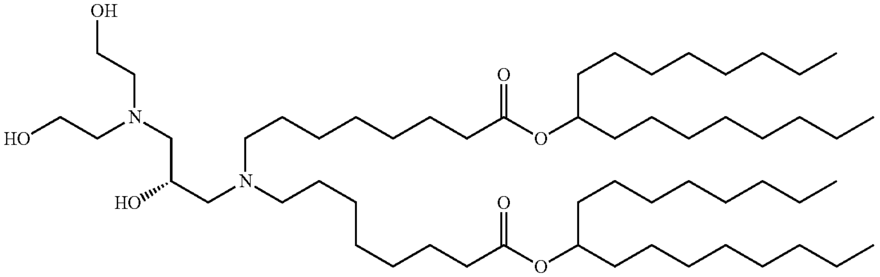

,

YK-321

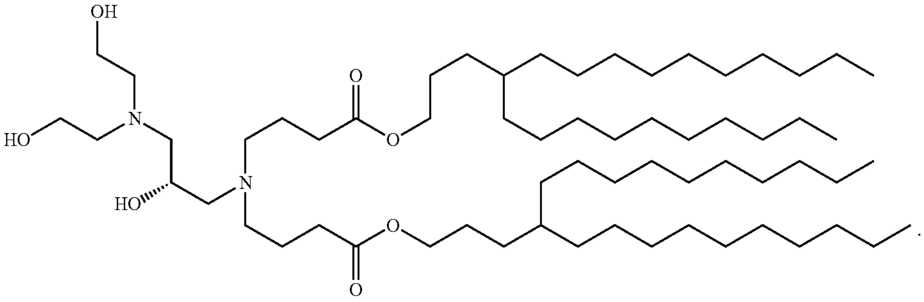

.

Another aspect of the present disclosure provides a composition, which comprises a carrier comprising a cationic lipid comprising the compound of formula (I) described above or an N-oxide, solvate, pharmaceutically acceptable salt or stereoisomer thereof.

Yet another aspect of the present disclosure provides use of the compound of formula (I) described above or an N-oxide, solvate, pharmaceutically acceptable salt or stereoisomer thereof or the composition described above in the manufacture of a nucleic acid drug, gene vaccine, small molecule drug, peptide or protein drug.

Yet another aspect of the present disclosure provides use of the compound of formula (I) described above or an N-oxide, solvate, pharmaceutically acceptable salt or stereoisomer thereof or the composition described above in the manufacture of a medicament for treating a disease or condition in a mammal in need thereof.

DETAILED DESCRIPTION

Figure 1:
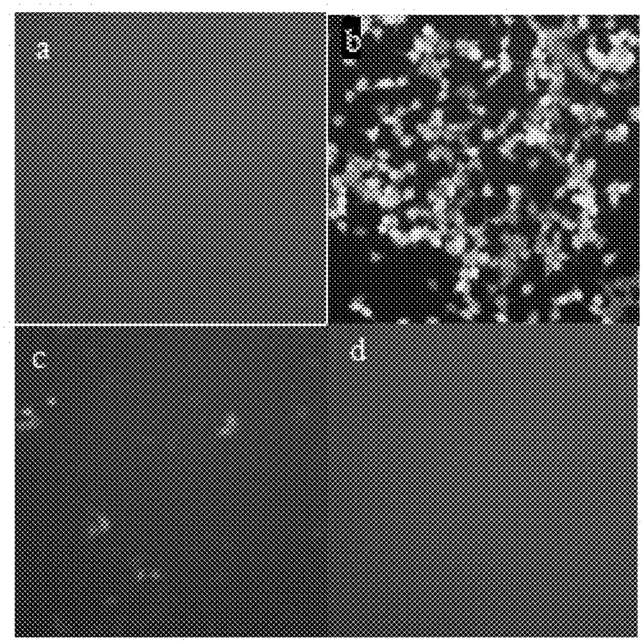
FIG. 1 shows the results of cell transfection tests with different weight ratios of the carrier to mRNA used in the preparation of LNP formulations, wherein a has carrier: mRNA of 5:1, b has carrier: mRNA of 15:1, c has carrier: mRNA of 35:1, and dis a blank control.

In order to make the purpose, technical solutions and advantages of the examples of the present disclosure clearer, the technical solutions of the examples of the present disclosure will be clearly and completely described below in conjunction with the drawings of the examples of the present disclosure. Apparently, the described examples are some of the examples of the present disclosure, not all of them. Based on the described examples of the present disclosure, all other examples obtained by persons of ordinary skill in the art without creative efforts shall fall within the protection scope of the present disclosure.

The present disclosure may be embodied in other specific forms without departing from essential attributes of the present disclosure. It should be understood that any and all embodiments of the present disclosure can be combined with technical features in any other embodiment(s) to obtain additional embodiments under the premise of no conflict. The present disclosure includes additional embodiments obtained from such combinations.

All publications and patents mentioned in this disclosure are incorporated herein by reference in their entirety. If usage or terminology used in any publications and patents incorporated by reference conflicts with usage or terminology used in the present disclosure, the usage and terminology in the present disclosure shall prevail.

The section headings used herein are for the purpose of organizing the article only and should not be construed as limitations on the subject matter described.

Unless defined otherwise, all technical and scientific terms used herein have their ordinary meanings in the art to which the claimed subject matter belongs. In the event that more than one definitions exist for a term, the definition herein prevails.

Except in the working examples or where otherwise indicated, all numbers stating quantitative properties such as dosages in the specification and claims are to be understood as modified in all instances by the term “about”. It is also to be understood that any numerical range recited herein is intended to include all sub-ranges within that range and any combination of various endpoints of such ranges or sub-ranges.

The words “including”, “comprising”, or “containing” and similar words used in the present disclosure mean that the element appearing before the word covers the elements listed after the word and their equivalents, and does not exclude unrecited elements. The terms “comprising” or “including (containing)” used herein can be open, semi-closed and closed. In other words, the terms also include “consisting essentially of”, or “consisting of”.

The term “pharmaceutically acceptable” in this application means that a compound or composition is chemically and/or toxicologically compatible with the other ingredients making up the formulation and/or with the human or mammal in which it is used to prevent or treat a disease or condition.

The term “subject” or “patient” as used herein includes human and mammals.

The term “treating” as used herein refers to the administration of one or more drug substances to a patient or subject suffering from a disease or symptoms of the disease in order to cure, alleviate, relieve, ameliorate or affect the disease or symptoms of the disease. In the context of this application, unless specifically stated to the contrary, the term “treating” may also include prophylaxis.

The term “solvate” in this application refers to a complex formed by combining a compound of formula (I) or a pharmaceutically acceptable salt thereof with a solvent (e.g., ethanol or water). It should be understood that any solvate of a compound of formula I for use in the treatment of a disease or condition may provide different properties including pharmacokinetic properties, however will result in the compound of formula I upon absorption into a subject, such that the use of the compound of formula I encompasses the use of any solvate of the compound of formula I respectively.

The term “hydrate” refers to the situation where the solvent in the above term “solvate” is water.

It should be further understood that a compound of formula I, or a pharmaceutically acceptable salt thereof may be isolated in the form of a solvate, and therefore any such solvate is included within the scope of the present disclosure. For example, a compound of formula I, or a pharmaceutically acceptable salt thereof may exist in an unsolvated form as well as a solvated form with a pharmaceutically acceptable solvent such as water, ethanol, or the like.

The term "pharmaceutically acceptable salt" refers to a relatively non-toxic, inorganic or organic acid addition salt of a compound of the present disclosure. For example, see S. M. Berge et al. "Pharmaceutical Salts", *J. Pharm. Sci.* 1977, 66, 1-19. The inorganic acid is for example hydrochloric, hydrobromic, hydroiodic, sulfuric, phosphoric, or nitric acid; and the organic acid is for example formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, or sulfosalicylic acid. For example, a pharmaceutically acceptable salt may be formed by using a compound of formula I and HCl (or hydrochloric acid), HBr (or hydrobromic acid solution), methanesulfonic acid, sulfuric acid, tartaric acid or fumaric acid.

The nitrogen-containing compounds of formula (I) of the present disclosure may be converted to N-oxides by treatment with an oxidizing agent (e.g., m-chloroperbenzoic acid, hydrogen peroxide, ozone). Therefore, under the conditions allowed by the valence state and structure, the compounds claimed in this application include not only the nitrogen-containing compounds shown in the structural formulas, but also their N-oxide derivatives.

Certain compounds of the present disclosure may exist as one or more stereoisomers. Stereoisomers include geometric isomers, diastereomers and enantiomers. Accordingly, the compounds claimed in this disclosure also include racemic mixtures, single stereoisomers, and optically active mixtures. It will be understood by those skilled in the art that one stereoisomer may have better efficacy and/or lower side effects than other stereoisomers. Single stereoisomers and optically active mixtures can be obtained by methods such as chiral source synthesis, chiral catalysis, and chiral resolution. The racemate can be chirally resolved by chromatographic resolution or chemical resolution. For example, chiral tartaric acid, chiral malic acid or other chiral acid resolution reagents may be added to form a salt with the compound of the present disclosure, and the product may be separated by utilizing the different physical and chemical properties of the product, such as solubility. For example, a single stereoisomer of cationic lipids can be obtained when the raw material for synthesizing the cationic lipids, 1-amino-3-chloropropan-2-ol, is (R)-1-amino-3-chloropropan-2-ol or (S)-1-amino-3-chloropropan-2-ol; and racemic cationic lipids can be obtained when the raw material for synthesizing the cationic lipids, 1-amino-3-chloropropan-2-ol, is a racemic mixture.

The present disclosure also includes all suitable isotopic variations of the disclosed compounds. An isotopic variant is defined as a compound in which at least one atom is replaced by an atom of the same atomic number but with an atomic mass different from that commonly found or predominantly found in nature. Examples of isotopes that may be incorporated into compounds of the present disclosure include isotopes of hydrogen, carbon, nitrogen, and oxygen, such as $^{2}H$ (deuterium), $^{3}H$ (tritium), $^{11}C$, $^{13}C$, $^{14}C$, $^{15}N$, $^{17}O$, and $^{18}O$, respectively.

The term "alkyl" is used in this disclosure to include branched and linear saturated aliphatic monovalent hydrocarbon groups having the specified number of carbon atoms. The term "alkylene" is used in this disclosure to include branched and linear saturated aliphatic divalent hydrocarbon groups having the specified number of carbon atoms. $C_{n-m}$ refers to groups having n to m carbon atoms. For example, $C_{2-5}$ alkylene includes $C_2$ alkylene, $C_3$ alkylene, $C_4$ alkylene, $C_5$ alkylene An alkyl (or alkylene) group can be unsubstituted, or an alkyl (or alkylene) group can be substituted wherein at least one hydrogen is replaced by another chemical group.

A "therapeutically effective amount" is an amount of a therapeutic agent being administered which will improve a disease or condition in a subject. A "prophylactically effective amount" is an amount of a prophylactic agent being administered which will prevent a disease or condition in a subject. The "therapeutically effective amount" for a therapeutic agent or the "prophylactically effective amount" for a prophylactic agent may vary with the therapeutic/prophylactic agent, the disease state and its severity, the age and weight of a patient/subject to be treated/prevented, etc. The therapeutically effective amount and the prophylactically effective amount can be routinely determined by one of ordinary skill in the art based on his knowledge and this disclosure.

In this application, when the name of the compound is inconsistent with the structural formula, the structural formula shall prevail.

It should be understood that the term "compound of the present disclosure" used in the present application may include the compound of formula (I), N-oxide thereof, solvate thereof, pharmaceutically acceptable salt thereof, stereoisomer thereof, or mixture thereof according to the context.

The term "cationic lipid" as used herein refers to a lipid that is positively charged at a selected pH value.

Cationic lipids are prone to bind to negatively charged nucleic acids, that is, to form lipid nanoparticles (LNPs) by interacting with negatively charged phosphate groups present in nucleic acids through electrostatic forces. LNP is one of the current mainstream delivery vehicles.

When screening a large number of compounds, the inventors found that it is very difficult to screen out suitable cationic lipid compounds that meet the following conditions: having huge differences in structure from the representative cationic lipids of the prior art, while having extremely high transfection efficiency and extremely low cytotoxicity, and having high and sustained expression in mice. The inventors have discovered some compounds, such as YK-305, YK-310, YK-312, YK-319 and YK-318, etc., which can deliver nucleic acid with significantly improved intracellular transfection efficiency, significantly reduced cytotoxicity, and significantly improved expression and duration in animals compared with cationic lipids with very different chemical structures in the prior art.

Briefly, the present disclosure is based on at least the following findings:

1. A series of designed compounds, including YK-305, YK-310, YK-312, YK-319 and YK-318, have huge structural difference compared with representative cationic lipids in the prior art, such as SM-102 (compound 25 disclosed in WO2017049245A2), ALC-0315 (compound 3 disclosed in CN108368028B), compound 21 and compound 23 disclosed in WO2021055833A1, HIMA (compound 1 disclosed in CN112979483B) and compound YK-009 disclosed in CN114044741B, in which the $G_3$ group is completely different, and other parts are also very different, so there are great differences in polarity, acidity and alkalinity, and hydrophilicity.

Therefore, it is impossible to infer the cell transfection efficiency, cytotoxicity, and expression in animals of LNP preparations prepared from this series of compounds based on the cationic lipid compounds disclosed in the above-mentioned prior art.

The chemical structures of SM-102, ALC-0315, compound 21, compound 23 and HMA are as follows:

SM-102

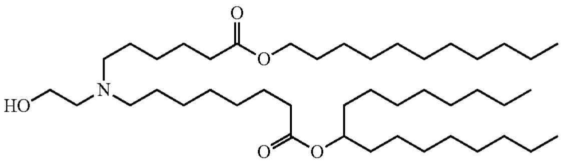

;

(WO2017049245A2, page 29 of the specification)

ALC-0315

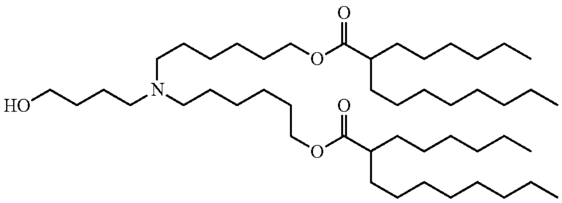

;

(CN108368028B, page 24 of the specification)

Compound 21

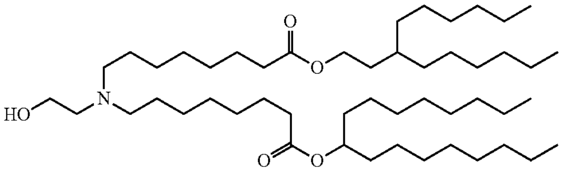

;

(WO2021055833A1, page 22 of the specification)

Compound 23

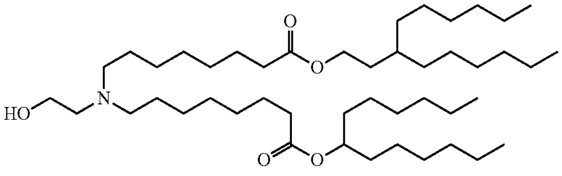

;

(WO2021055833A1, page 22 of the specification)

HHMA

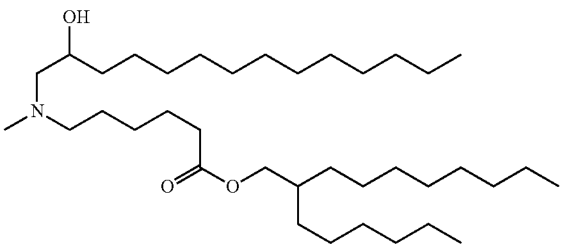

(CN112979483B, page 12 of the specification)

2. In this series of compounds designed, LNP formulations prepared from YK-305, YK-310, YK-312, YK-319 and YK-318 have significantly improved cell transfection efficiency, significantly reduced cytotoxicity, significantly increased expression amount and duration of mRNA in mice, and reduced or no toxicity to the liver compared with representative cationic lipids in the prior art.

For example, the cell transfection efficiency of YK-305 can be up to 17 times that of SM-102, 19 times that of compound 21, and 20 times that of compound 23; the cell survival rate of YK-305 and YK-310 can both be 30% higher than that of ALC-0315, 12% higher than that of SM-102 and 15% higher than that of HHMA; for the expression amount of mRNA in mice, both YK-305 and YK-310, can be up to 30 times that of SM-102, compound 21 and compound 23.

Among the series of compounds that we designed with little difference in chemical structure, LNP formulations prepared from YK-305, YK-310, YK-312, YK-319 and YK-318 have significantly improved cell transfection activity, significantly reduced cytotoxicity, and significantly increased expression amount and duration of mRNA in mice compared with other compounds.

Compared with YK-305, YK-310, YK-312, YK-319 and YK-318, this series of compounds are only slightly different in individual groups, but the cell transfection activity of YK-305 can be up to 1,300 times that of YK-304 and 900 times that of YK-302; the cytotoxicity of YK-305 and YK-310 can be reduced by 65% compared with YK-302; the expression amount of mRNA in mice of YK-305 can be up to above 1,000 times that of YK-302.

3. There is no obvious correspondence between the structure of cationic lipid compounds with intracellular transfection efficiency, toxicity to cells, and the high expression and sustained expression of mRNA in LNP formulations prepared from them in animals. Compounds with small structural differences are likely to have very large differences in transfection efficiency and/or toxicity to cells and intracellular expression.

For example, compared with YK-305, YK-302 only has 2 less C in the $G_1$ group; has a linear chain structure of the $R_1$ group, while YK-305 has a branched chain structure; has 1 more C in the single chain, and 2 less C in each single chain in the double chain of the $R_2$ group; other structures are identical, but the cell transfection efficiency of YK-305 is 900 times that of YK-302, and the toxicity to transfected cells of YK-305 is 65% lower than that of YK-302, the expression of YK-305 in mice can be up to 1,000 times that of YK-302; compared with YK-310, YK-303 only has 1 less C in the group connecting the $G_3$ group to N; other structures are identical, but the cell transfection efficiency of YK-310 is 40 times that of YK-303, and the toxicity to transfected cells of YK-310 is 18% lower than that of YK-303.

Therefore, it is very difficult and require a lot of creative work to screen out a suitable cationic lipid compound that can simultaneously have high transfection efficiency and low toxicity to cells, as well as high and sustained expression of mRNA in mice.

4. Through unique design and extensive screening, the present disclosure has discovered some compounds, such as YK-305, YK-310, YK-312, YK-319 and YK-318, which can deliver nucleic acids with significantly improved cell transfection efficiency, significantly reduced cytotoxicity, significantly improved expression and duration in animals and reduced or no toxicity to the liver, compared with other compounds in the prior art. Unexpected technical effects have been achieved.

In short, through unique design and extensive screening, the present disclosure discovered some compounds, such as YK-305, YK-310, YK-312, YK-319 and YK-318. These compounds are significantly different from representative cationic lipids in the prior art in chemical structures, which can deliver nucleic acids with significantly improved cell transfection efficiency, significantly reduced cytotoxicity, significantly improved expression and duration in animals and reduced or no toxicity to the liver compared with other compounds in the prior art. Unexpected technical effects have been achieved.

Details are as follows:

1. Compared with Representative Cationic Lipids in the Prior Art, Such as SM-102, ALC-0315, Compound 21, Compound 23, YK-009 and HHMA, the Chemical Structure is Significantly Different Representative cationic lipids in the prior art, such as SM-102, ALC-0315, compound 21, compound 23, YK-009 and HHMA, are compared with the designed series of compounds:

a. HHMA has the biggest difference in structure. It can be seen from the chemical structure that only one side chain of the group connected to the central N atom of HHMA is similar to one side chain of this series of structures, and the other parts are completely different.

b. Other cationic lipids in the prior art, such as SM-102, ALC-0315, compound 21, compound 23 and YK-009, have completely different $G_3$ groups. The $G_3$ group of this series of compounds has one more tertiary amine group and one to two more hydroxyl groups, so there are great differences in polarity, acidity-alkalinity and hydrophilicity.

c. There are also huge differences in the $G_1$, $G_2$, $R_1$ and $R_2$ groups compared with SM-102, ALC-0315, compound 21, compound 23 and YK-009.

2. In Vitro Cell Transfection Efficiency is Significantly Improved Compared to Representative Cationic Lipids in the Prior Art and Structurally Similar Compounds 1) The cell transfection efficiencies of LNP formulations prepared from YK-305, YK-310, YK-312, YK-319 and YK-318 are the highest, which are significantly improved in the activity compared to representative cationic lipids in the prior art. For example, YK-305 can be up to 17.09 times that of SM-102, 19.14 times that of compound 21, and 20.21 times that of compound 23.

2) Compared with compounds with similar structures and the $G_3$ group being $HO(CH_2)_2N(CH_3)CH_2CH(OH)CH_2—$, YK-305, YK-310, YK-312, YK-319 and YK-318 cells have the highest transfection efficiencies. YK-305 is 1,300 times higher than YK-304 and 9,00 times higher than YK-302.

3) Compared with compounds with similar structures and the $G_3$ group being $HO(CH_2)_2N(CH_2CH_3)CH_2CH(OH)CH_2—$, YK-305, YK-310, YK-312, YK-319 and YK-318 cells have the highest transfection efficiencies. YK-305 and YK-310 are 200 times higher than YK-309.

4) Compared with compounds with similar structures and the $G_3$ group being $(HO(CH_2)_2)_2NCH_2CH(OH)CH_2—$, YK-305, YK-310, YK-312, YK-319 and YK-318 cells have the highest transfection efficiencies. For example, YK-305 can be up to 20 times that of YK-321.

5) There is no correspondence between the structure of a compound and intracellular transfection efficiency. Compounds with small structural differences are likely to have very large differences in transfection efficiency. Therefore, screening out cationic lipid compounds with high transfection efficiency is very difficult and requires a lot of creative work.

3. Cytotoxicity is Significantly Reduced Compared to Representative Cationic Lipids in the Prior Art and Structurally Similar Compounds 1) LNP formulations prepared from YK-305, YK-310, YK-312, YK-319 and YK-318 have the lowest cytotoxicity and significantly increased cell survival rate compared with representative cationic lipids in the prior art. For example, the cell survival rates of both YK-305 and YK-310 are 30% higher than that of ALC-0315, 12% higher than that of SM-102, and 15% higher than that of HHMA.

2) Compared with compounds with similar structures and the $G_3$ group being $HO(CH_2)_2N(CH_3)CH_2CH(OH)CH_2—$, YK-305, YK-310, YK-312, YK-319 and YK-318 have the lowest cytotoxicity, and significantly improved cell survival rate. For example, YK-305 and YK-310 are both 65% higher than YK-302.

3) Compared with compounds with similar structures and the $G_3$ group being $HO(CH_2)_2N(CH_2CH_3)CH_2CH(OH)CH_2—$, YK-305, YK-310, YK-312, YK-319 and YK-318 have the lowest cytotoxicity, and significantly improved cell survival rate. For example, YK-305 and YK-310 are 50% higher than YK-302.

4) Compared with Compounds with Similar Structures and the $G_3$ Group being $(HO(CH_2)_2)_2NCH_2CH(OH)CH_2—$, YK-305, YK-310, YK-312, YK-319 and YK-318 have the Lowest Cytotoxicity, and Significantly Improved Cell Survival Rate. For Example, YK-305 and YK-310 are 20% Higher than YK-317.

5) There is no correspondence between the structure of a compound and its cytotoxicity. Even compounds with small structural differences are likely to have very large differences in cytotoxicity. Therefore, its cytotoxicity cannot be predicted based on its chemical structure, and it is very difficult to screen out cationic lipid compounds with low cytotoxicity, requiring a lot of creative work.

4. The Expression Amount and Duration of mRNA in Animals are Significantly Improved, and the Liver Toxicity is Reduced or Non-Toxic Compared with Those of Representative Cationic Lipids in the Prior Art and Structurally Similar Compounds.

1) For LNP formulations prepared from YK-305, YK-310, YK-312, YK-319 and YK-318, the mRNA expression amounts are the highest in mice and the mRNA sustains expressed, in which the expression amounts are significantly improved at 6 h, 24 h, 48 h and 7 d compared with the representative cationic lipids in the prior art. For example, YK-305 and YK-310 can be up to 30 times that of SM-102, compound 21 and compound 23.

2) Compared with compounds with similar structures and the $G_3$ group being $HO(CH_2)_2N(CH_3)CH_2CH(OH)CH_2—$, the LNP formulations prepared from YK-305, YK-310, YK-312, YK-319 and YK-318 have the highest mRNA expression intensity and longest duration in mice. For example, YK-305 can be up to more than 1000 times that of YK-302 in 48 hours, and can be up to more than 300 times in 7 days.

3) Compared with compounds with similar structures and the $G_3$ group being $HO(CH_2)_2N(CH_2CH_3)CH_2CH(OH)CH_2—$, the LNP formulations prepared from YK-305, YK-310, YK-312, YK-319 and YK-318 have the highest mRNA expression intensity and longest duration in mice. For example, YK-305 can be up to 160 times that of YK-309 in 48 hours, and can be up to 100 times in 7 days.

4) Compared with compounds with similar structures and the $G_3$ group being $(HO(CH_2)_2)_2NCH_2CH(OH)CH_2—$, the LNP formulations prepared from YK-305, YK-310, YK-312, YK-319 and YK-318 have the highest mRNA expression intensity and longest duration in mice. For example, YK-310 can be up to 29 times that of YK-321 in 24 hours, and can be up to 17 times in 7 days.

5) Compared with representative cationic lipids in the prior art, such as SM-102, ALC-0315, compound 21, Compound 23 and HHMA, the liposomes prepared from our designed compounds have reduced target protein expression amount in the liver, or unable to stay in the liver and express the target protein. Therefore, compared with existing cationic lipids, LNP formulations prepared from our designed compounds have reduced or no toxicity to the liver.

6) There is no correspondence between the structure of cationic lipids and the high expression and sustained expression of delivered mRNA in mice. Even if the structural differences of cationic lipid compounds are very small, the expression in vivo of mRNA in animals of the LNP formulations prepared from them are likely to be very different. It is impossible to predict whether mRNA will be highly and continuously expressed in animals based on the chemical structure of cationic lipids. Therefore, it is very difficult to screen out cationic lipid compounds with high and sustained expression of mRNA, which requires creative work.

One aspect of the present disclosure provides a novel cationic lipid compound for the delivery of a therapeutic or prophylactic agent. The cationic lipid compounds of the present disclosure can be used to deliver nucleic acid molecules, small molecule compounds, polypeptides or proteins. Compared with known cationic lipid compounds, the cationic lipid compounds of the present disclosure exhibit higher transfection efficiencies and less cytotoxicities, and thus improve delivery efficiencies and safeties.

The present disclosure provides a cationic lipid, which is a compound of formula (I)

I

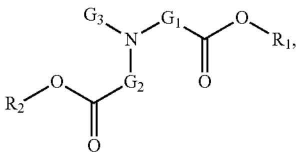

or an N-oxide, solvate, pharmaceutically acceptable salt or stereoisomer thereof, wherein

- $G_1$ is $C_{1-8}$ alkylene, preferably unsubstituted $C_{3-7}$ alkylene, more preferably unsubstituted $C_3$ alkylene or unsubstituted $C_5$ alkylene or unsubstituted $C_6$ alkylene;
- $G_2$ is $C_{2-8}$ alkylene, preferably unsubstituted $C_{3-7}$ alkylene, more preferably unsubstituted $C_3$ alkylene or $C_5$ alkylene or $C_6$ alkylene;
- $R_1$ is $C_{6-25}$ linear or branched alkyl, preferably unsubstituted $C_{11}$ linear alkyl or unsubstituted $C_{12-24}$ branched alkyl, wherein the unsubstituted $C_{12-24}$ branched alkyl is preferably unsubstituted $C_{18}$ branched alkyl or $C_{18}$ branched alkyl or $C_{24}$ branched alkyl or $C_{17}$ branched alkyl;
- $R_2$ is $C_{12-25}$ linear or branched alkyl, preferably unsubstituted $C_{11}$ linear alkyl or unsubstituted $C_{14-24}$ branched alkyl, wherein the unsubstituted $C_{14-24}$ branched alkyl is preferably unsubstituted $C_{18}$ branched alkyl or $C_{24}$ branched alkyl or $C_{15}$ branched alkyl or $C_{17}$ branched alkyl;
- $G_3$ is: $HO(CH_2)_2N(R_3)CH_2CH(OH)CH_2$—, wherein $R_3$ is —$CH_3$ or —$CH_2CH_3$ or —$CH_2CH_2OH$.

In one embodiment, $G_1$ is unsubstituted $C_3$ alkylene, e.g., —$(CH_2)_3$—.

In one embodiment, $G_1$ is unsubstituted $C_5$ alkylene, e.g., —$(CH_2)_5$—.

In one embodiment, $G_1$ is unsubstituted $C_6$ alkylene, e.g., —$(CH_2)_6$—.

In one embodiment, $G_2$ is unsubstituted $C_3$ alkylene, e.g., —$(CH_2)_3$—.

In one embodiment, $G_2$ is unsubstituted $C_5$ alkylene, e.g., —$(CH_2)_5$—.

In one embodiment, $G_2$ is unsubstituted $C_6$ alkylene, e.g., —$(CH_2)_6$—.

In one embodiment, $G_3$ is $HO(CH_2)_2N(CH_3)CH_2CH(OH)CH_2$—.

In one embodiment, $G_3$ is $HO(CH_2)_2N(CH_2CH_3)CH_2CH(OH)CH_2$—.

In one embodiment, $G_3$ is $(HO(CH_2)_2)_2NCH_2CH(OH)CH_2$—.

In one embodiment, $R_1$ is unsubstituted $C_{11}$ linear alkyl, i.e., —$(CH_2)_{10}CH_3$.

In one embodiment, $R_1$ is unsubstituted $C_{18}$ branched alkyl, $C_{15}$ branched alkyl, $C_{24}$ branched alkyl or $C_{17}$ branched alkyl. For example, $R_1$ is:

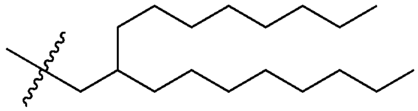

,

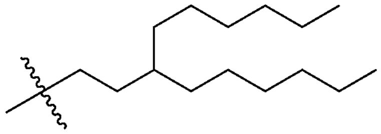

,

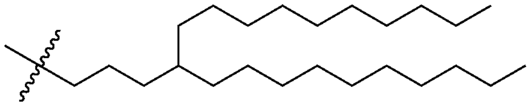

or

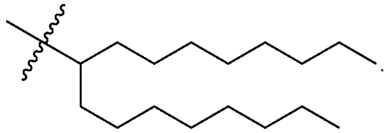

.

In one embodiment, $R_2$ is unsubstituted $C_{11}$ linear alkyl, i.e., —$(CH_2)_{10}CH_3$.

In one embodiment, $R_2$ is unsubstituted $C_{18}$ branched alkyl, $C_{24}$ branched alkyl, $C_{15}$ branched alkyl or $C_{17}$ branched alkyl. For example, $R_2$ is:

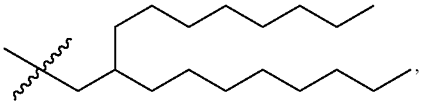

,

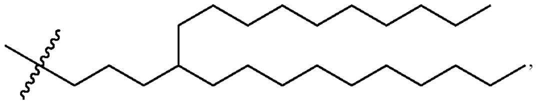

,

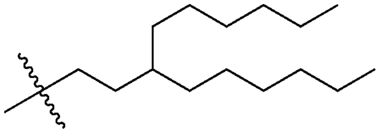

or

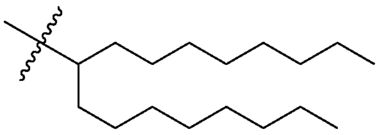

.

In one embodiment, $G_1$ is —$(CH_2)_5$—, $G_2$ is —$(CH_2)_5$—, $G_3$ is $HO(CH_2)_2N(CH_3)CH_2CH(OH)CH_2$—, $R_1$ is:

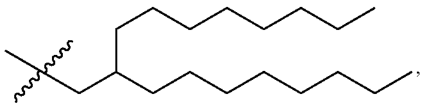 [SMILES: *CC(CCCCCCCC)CCCCCCCC]

$R_2$ is:

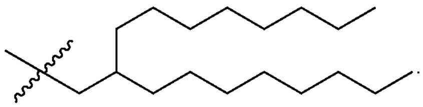 [SMILES: *CC(CCCCCCCC)CCCCCCCC]

In one embodiment, $G_1$ is $-(CH_2)_5-$, $G_2$ is $-(CH_2)_3-$, $G_3$ is $HO(CH_2)_2N(CH_2CH_3)CH_2CH(OH)CH_2-$, $R_1$ is $-(CH_2)_{10}CH_3$, $R_2$ is:

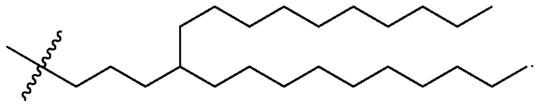 [SMILES: *CCCC(CCCCCCCCCC)CCCCCCCCCC]

In one embodiment, $G_1$ is $-(CH_2)_5-$, $G_2$ is $-(CH_2)_5-$, $G_3$ is $HO(CH_2)_2N(CH_2CH_3)CH_2CH(OH)CH_2-$, $R_1$ is:

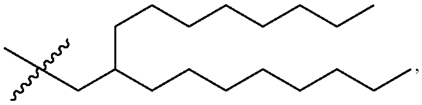 [SMILES: *CC(CCCCCCCC)CCCCCCCC]

$R_2$ is:

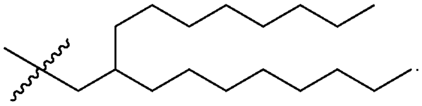 [SMILES: *CC(CCCCCCCC)CCCCCCCC]

In one embodiment, $G_1$ is $-(CH_2)_6-$, $G_2$ is $-(CH_2)_6-$, $G_3$ is $(HO(CH_2)_2)_2NCH_2CH(OH)CH_2-$, $R_1$ is:

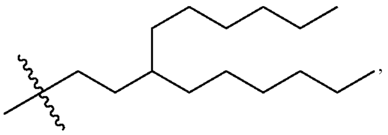 [SMILES: *CCC(CCCCCC)CCCCCC]

$R_2$ is:

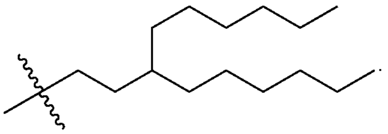 [SMILES: *CCC(CCCCCC)CCCCCC]

In one embodiment, $G_1$ is $-(CH_2)_5-$, $G_2$ is $-(CH_2)_5-$, G is $(HO(CH_2)_2)_2NCH_2CH(OH)CH_2-$, $R_1$ is:

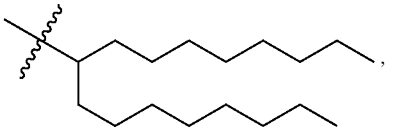 [SMILES: *C(CCCCCCCC)CCCCCCCC]

$R_2$ is:

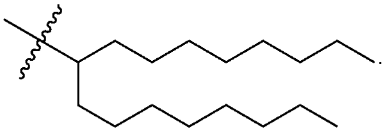 [SMILES: *C(CCCCCCCC)CCCCCCCC]

In an exemplary embodiment, the compound is selected from the following compounds or N-oxides, solvates, pharmaceutically acceptable salts or stereoisomers thereof:

YK-301

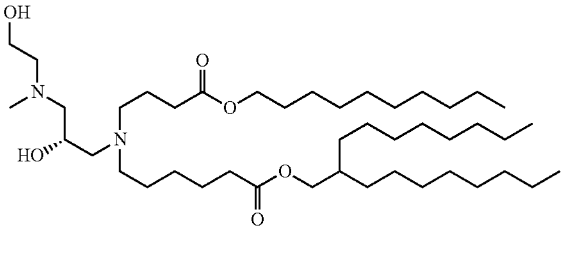

,

YK-302

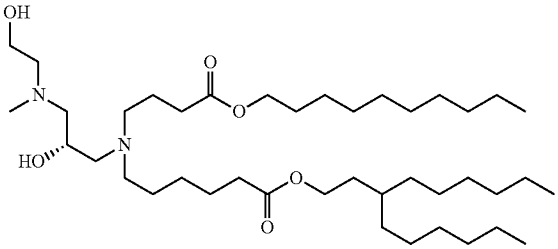

,

-continued
YK-303
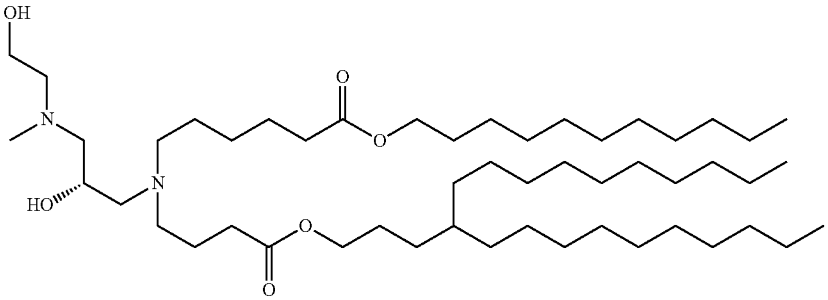
,
YK-304
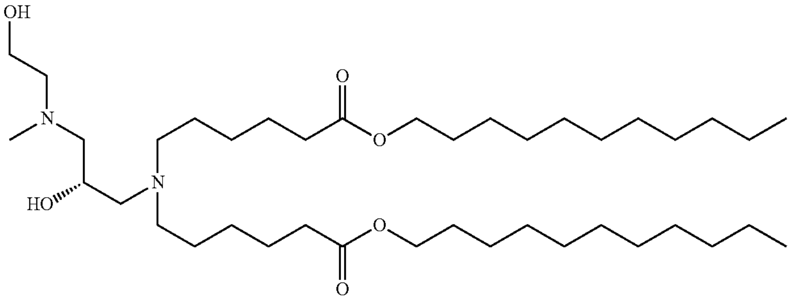
,
YK-305
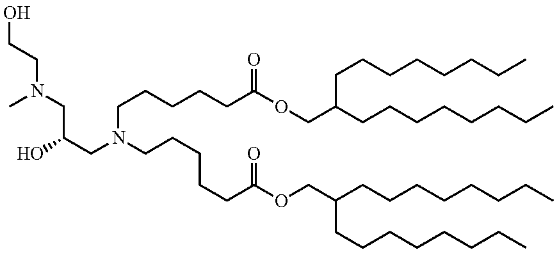
,
YK-306
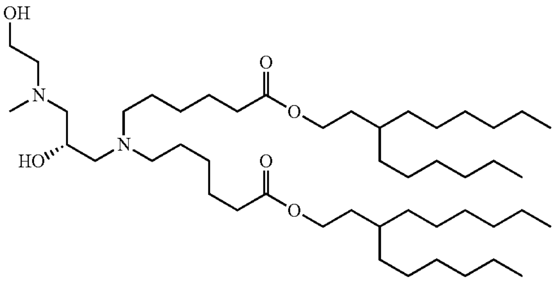
,
YK-307
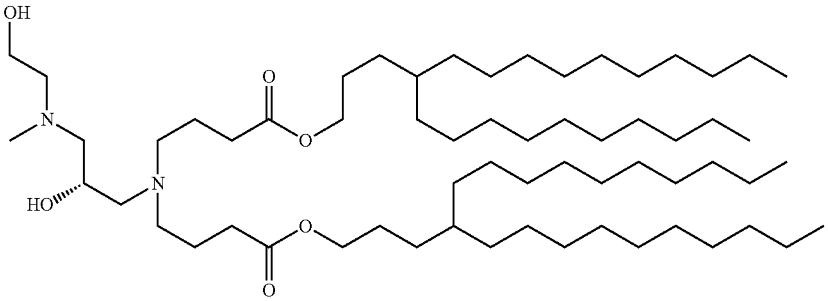
,
YK-308
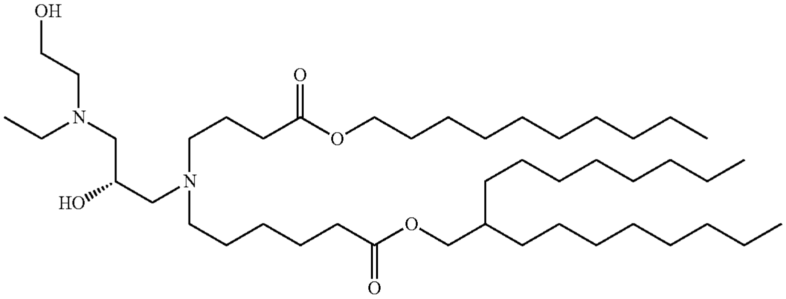
, -continued
YK-309
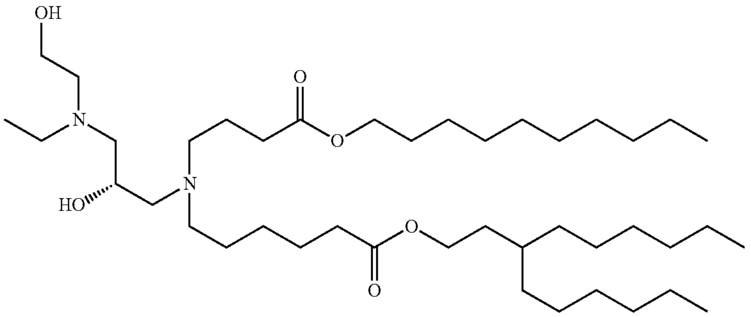
,
YK-310
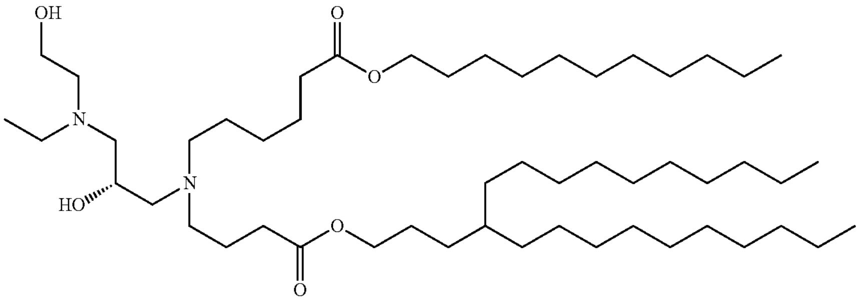
,
YK-311
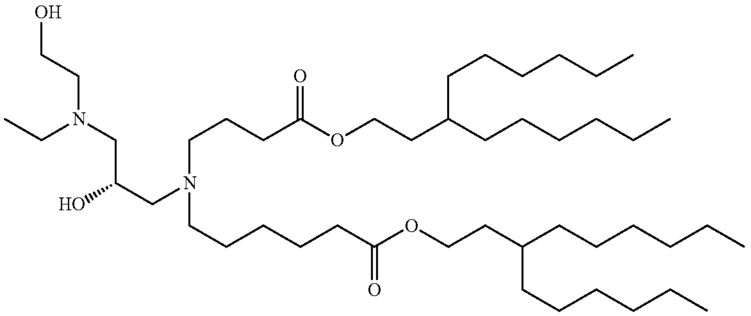
,
YK-312
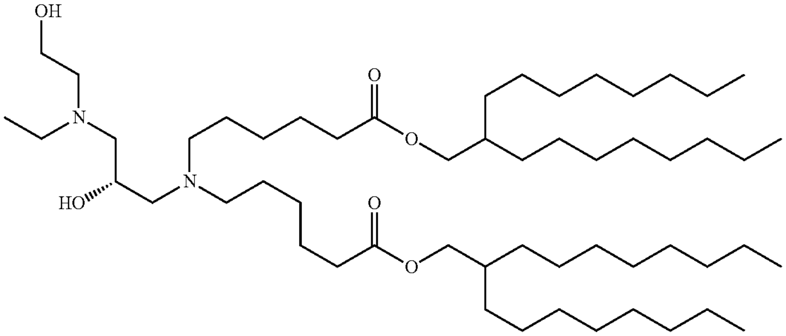
,
YK-313
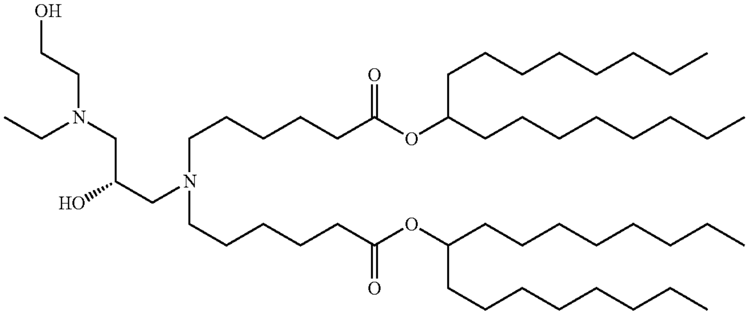
, -continued
YK-314
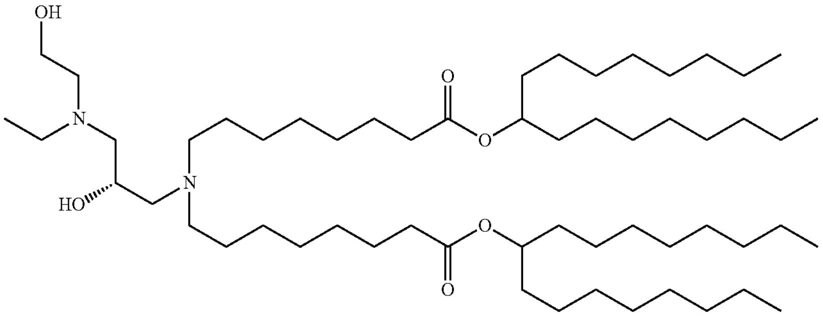
,
YK-315
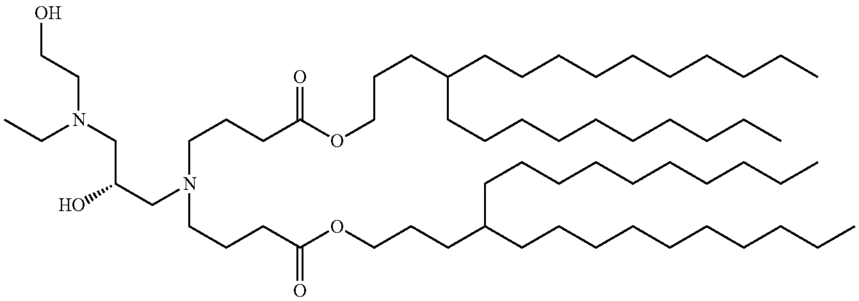
,
YK-316
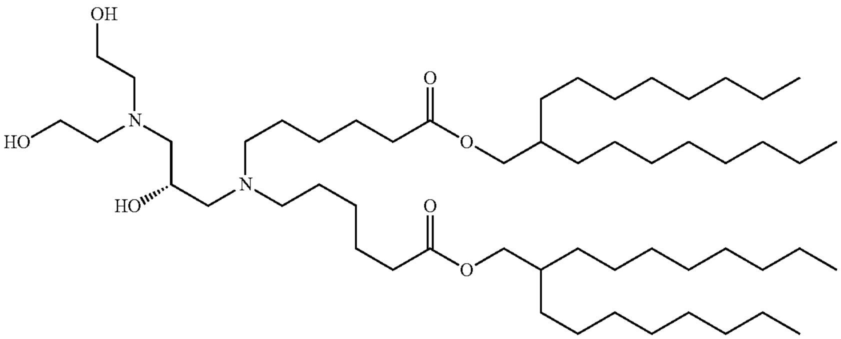
,
YK-317
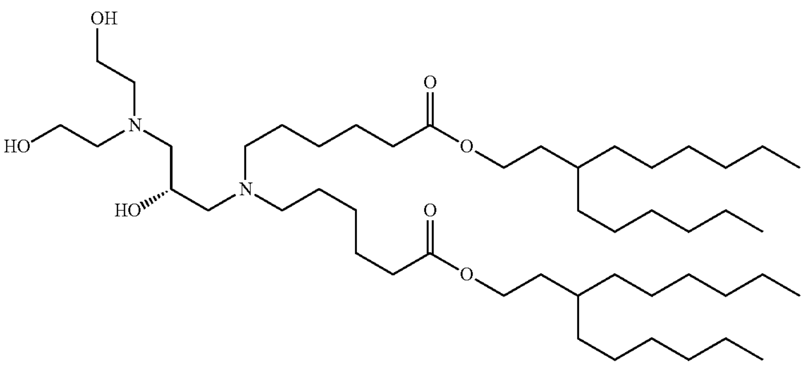
, -continued

YK-318

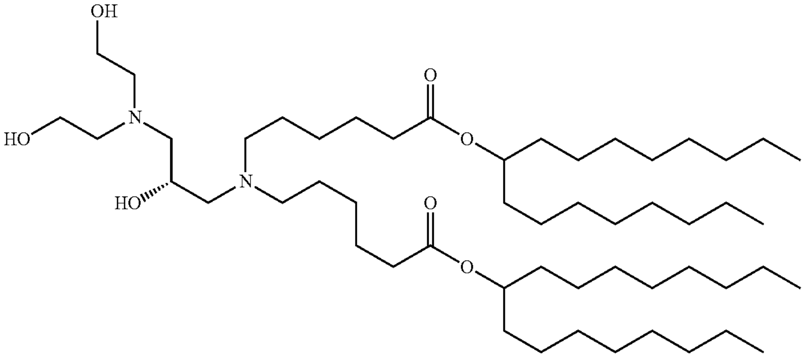

,

YK-319

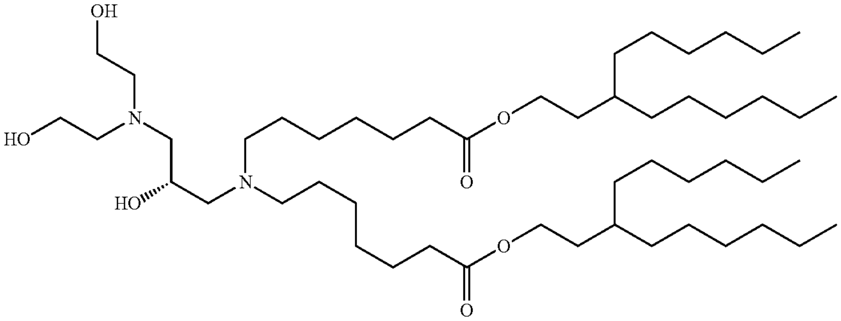

,

YK-320

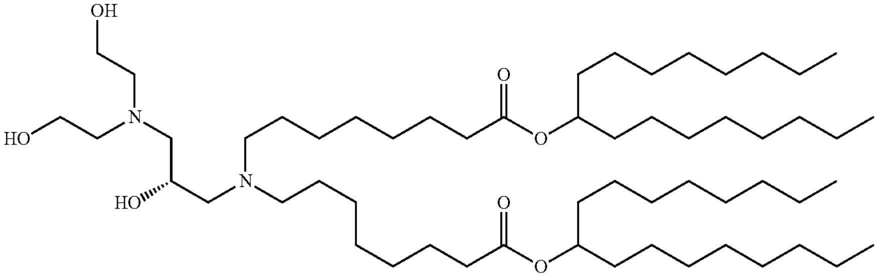

,

YK-321

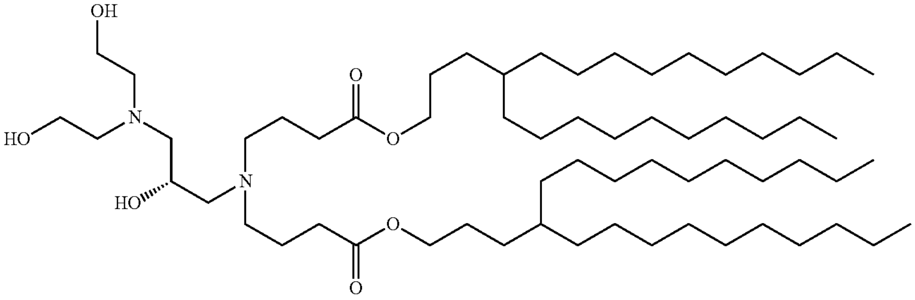

.

Another aspect of the present disclosure provides a composition comprising a carrier, which comprises a cationic lipid, and the cationic lipid includes the above compound of formula (I) or an N-oxide, solvate, pharmaceutically acceptable salt or stereoisomer thereof.

In one embodiment, the composition is a nanoparticle formulation, which has a average size of 10 nm to 300 nm, preferably 90 nm to 280 nm; and a polydispersity coefficient ≤50%, preferably ≤45%, more preferably ≤40%.

Cationic Lipid

In one embodiment of the composition/carrier of the present disclosure, the cationic lipid is one or more selected from the above compound of formula (I) or an N-oxide, solvate, pharmaceutically acceptable salt or stereoisomer thereof. In one embodiment, the cationic lipid is selected from the compounds of formula (I) described above. For example, the cationic lipid is compound YK-301, YK-302, YK-303, YK-304, YK-305, YK-306, YK-307, YK-308, YK-309, YK-310, YK-311, YK-312, YK-313, YK-314, YK-315, YK-316, YK-317, YK-318, YK-319, YK-320 and YK-321. In a preferred embodiment, the cationic lipid is compound YK-305. In another preferred embodiment, the cationic lipid is compound YK-310. In another preferred embodiment, the cationic lipid is compound YK-312. In another preferred embodiment, the cationic lipid is compound YK-319. In another preferred embodiment, the cationic lipid is compound YK-318.

In another embodiment of the composition/carrier of the present disclosure, the cationic lipid comprises (a) one or more selected from the above compound of formula (I) or an N-oxide, solvate, pharmaceutically acceptable salt or stereoisomer thereof and (b) one or more other ionizable lipid compound(s) different from (a). The cationic lipid compound (b) can be a commercially available cationic lipid, or a cationic lipid compound reported in literatures. For example, the cationic lipid compound (b) can be SM-102 (compound 25 in WO2017049245A2), and can also be compound 21 and compound 23 in WO2021055833, or HHMA (compound 1 in CN112979483B).

In one embodiment, the molar ratio of the cationic lipid to the carrier is 25%~75%, such as 30%, 40%, 49%, 55%, 60%, 65% or 70%.

The carrier can be used to deliver an active ingredient such as a therapeutic or prophylactic agent. The active ingredient can be sealed within the carrier or bound to the carrier.

For example, the therapeutic or prophylactic agent includes one or more of nucleic acid molecules, small molecule compounds, polypeptides or proteins. Such nucleic acids include, but are not limited to, single-chained DNA, double-chained DNA, and RNA. Suitable RNAs include, but are not limited to, small interfering RNA (siRNA), asymmetric interfering RNA (aiRNA), microRNA (miRNA), Dicer-substrate RNA (dsRNA), small hairpin RNA (shRNA), messenger RNA (mRNA) and mixtures thereof.

Neutral Lipid

The carrier may comprise a neutral lipid. Neutral lipid in this disclosure refers to an auxiliary lipid that is uncharged or exists in a zwitterionic form at a selected pH value. The neutral lipid may regulate the flow of nanoparticles into a lipid bilayer structure and improve efficiency by promoting lipid phase transition, while also possibly affecting target organ specificity.

In one embodiment, the molar ratio of the cationic lipid to the neutral lipid is about 1:1~15:1, for example about 14:1, 13:1, 12:1, 11:1, 10:1, 9:1, 8:1, 7:1, 6:1, 5:1, 4:1, 3:1 and 2:1. In a preferred embodiment, the molar ratio of the cationic lipid to the neutral lipid is about 4.5:1. In another preferred embodiment, the molar ratio of the cationic lipid to the neutral lipid is about 4.9:1.

For example, neutral lipids may include one or more of phosphatidylcholine, phosphatidylethanolamine, sphingomyelin, ceramide, sterol, and derivatives thereof.

The carrier component of a composition comprising the cationic lipid may comprise one or more neutral lipid-phospholipids, such as one or more (poly) unsaturated lipids. Phospholipids can be assembled into one or more lipid bilayers. In general, a phospholipid can comprise a phospholipid moiety and one or more fatty acid moieties.

The neutral lipid moiety may be selected from the non-limiting group consisting of phosphatidylcholine, phosphatidylethanolamine, phosphatidylglycerol, phosphatidylserine, phosphatidic acid, 2-lysophosphatidylcholine, and sphingomyelin. The fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Also contemplated are non-natural species which include natural species with modifications and substitutions such as branching, oxidation, cyclization and alkynes. For example, a phospholipid can be functionalized with or cross-linked with one or more alkynes (e.g., an alkenyl group in which one or more double bonds are replaced by a triple bond). Under appropriate reaction conditions, alkynyl groups may undergo copper-catalyzed cycloaddition reactions when exposed to azides. These reactions can be used to functionalize the lipid bilayer of the composition to facilitate membrane penetration or cell recognition, or to couple the composition to useful components such as targeting or imaging moieties (e.g., dyes).

Neutral lipids useful in these compositions can be selected from the non-limiting group consisting of: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

In some embodiments, the neutral lipid comprises DSPC. In certain embodiments, the neutral lipid comprises DOPE. In some embodiments, the neutral lipid comprises both DSPC and DOPE.

Structured Lipid

The carrier of the composition comprising the cationic lipid may also comprise one or more structured lipid(s). Structured lipids in this disclosure refer to lipids that enhance the stability of nanoparticles by filling the gaps between lipids.

In one embodiment, the molar ratio of the cationic lipid to the structured lipid is about 0.6:1~3:1, for example, about 1.0:1, 1.1:1, 1.2:1, 1.3:1, 1.4:1, 1.5:1, 1.6:1, 1.7:1, 1.8:1, 1.9:1, 2.0:1.

Structured lipids may be selected from, but are not limited to, the group consisting of cholesterol, nonsterol, sitosterol, ergosterol, campesterol, stigmasterol, brassicasterol, tomatine, tomatine, ursolic acid, alpha-tocopherol, corticosteroid and mixtures thereof. In some embodiments, the structured lipid is cholesterol. In some embodiments, the structured lipid comprises cholesterol, and corticosteroid (e.g., prednisolone, dexamethasone, prednisone, and hydrocortisone) or a combination thereof.

Polymer-Conjugated Lipid

The carrier of the composition comprising the cationic lipid may also comprise one or more polymer-conjugated lipid(s). Polymer-conjugated lipids mainly refer to lipids modified with polyethylene glycol (PEG). Hydrophilic PEG stabilizes LNPs, regulates nanoparticle size by limiting lipid fusion, and increases nanoparticle half-life by reducing nonspecific interactions with macrophages.

In one embodiment, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol. The molecular weight of PEG for the PEG modification is usually 350-5000 Da.

For example, the polymer-conjugated lipid is selected from one or more of distearoyl phosphatidylethanolamine polyethylene glycol 2000 (DSPE-PEG2000), dimyristoylglycero-3-methoxy polyethylene glycol 2000 (DMG-PEG2000) and methoxypolyethylene glycol ditetradecylacetamide (ALC-0159).

In one embodiment of the composition/carrier of the present disclosure, the polymer-conjugated lipid is DMG-PEG2000.

In one embodiment of the composition/carrier of the present disclosure, the carrier comprises a neutral lipid, a structured lipid and a polymer-conjugated lipid, wherein the molar ratio of the cationic lipid, the neutral lipid, the structured lipid, and the polymer-conjugated lipids is (25 to 75):(5 to 25):(15 to 65):(0.5 to 10), for example (35 to 49):(7.5 to 15):(35 to 55):(1 to 5).

In one embodiment of the composition/carrier of the present disclosure, the carrier comprises a neutral lipid, a structured lipid and a polymer-conjugated lipid, wherein the molar ratio of the cationic lipid, the neutral lipid, the structured lipid, and the polymer-conjugated lipid is 49:10:39.5:1.5 or 45:10:43.5:1.5 or 35:10:53.5:1.5.

Therapeutic and/or Prophylactic Agent

The composition may comprise one or more therapeutic and/or prophylactic agent(s). In one embodiment, the mass ratio of the carrier to the therapeutic or prophylactic agent is from 10:1 to 30:1, for example 12:1, 13:1, 14:1, 15:1, 16:1, 17:1, 18:1, 19:1, 20:1, 21:1, 22:1, 23:1, 24:1, 25:1.

In one embodiment, the mass ratio of the carrier to the therapeutic or prophylactic agent is from 12.5:1~20:1, preferably 15:1.

The therapeutic or prophylactic agent includes, but is not limited to, one or more of a nucleic acid molecule, a small molecule compound, a polypeptide or a protein.

For example, the therapeutic or prophylactic agent is a vaccine or compound capable of eliciting an immune response.

The carriers of the present disclosure can deliver therapeutic and/or prophylactic agents to mammalian cells or organs, and thus the present disclosure also provides a method of treating diseases or conditions in mammals in need thereof, which comprises administering to the mammal a composition comprising a therapeutic and/or prophylactic agent and/or contacting mammalian cells with the composition.

Therapeutic and/or prophylactic agents include biologically active substances and are referred to alternatively as "active agents." The therapeutic and/or prophylactic agent may be a substance that, after delivery to a cell or organ, causes a desired change in the cell or organ or in other tissues or systems of the body. Such species can be used to treat one or more diseases, disorders or conditions. In some embodiments, the therapeutic and/or prophylactic agent is a small molecule drug useful in the treatment of a particular disease, disorder or condition. Examples of drugs that can be used in the composition include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracycline, alkylating agents, platinum compounds, antimetabolites, and nucleoside analogs such as methotrexate and purine and pyrimidine analogs), anti-infectives, local anesthetics (e.g., dibucaine and chlorpromazine), beta-adrenergic blockers (e.g., propranolol, timolol and labetalol), antihypertensives (e.g., clonidine and hydralazine), antidepressants (e.g., imipramine, amitriptyline, and doxepin), anticonvulsants (e.g., phenytoin), antihistamines (e.g., diphenhydramine, chlorpheniramine, and promethazine), antibiotics/antibacterials (e.g., gentamycin, ciprofloxacin, and cefoxitin), antifungals (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma drugs, vitamins, sedatives, and imaging agents.

In some embodiments, the therapeutic and/or prophylactic agent is a cytotoxin, a radioactive ion, a chemotherapeutic agent, a vaccine, a compound that elicits an immune response, and/or another therapeutic agent and/or prophylactic agent. A cytotoxin or cytotoxic agent includes any agent that is harmful to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, maytansinoids such as maytansinol, rachelmycin (CC-1065), and their analogs or homologues. Radioactive ions include, but are not limited to, iodine (e.g., iodine 125 or iodine 131), strontium 89, phosphorus, palladium, cesium, iridium, phosphate, cobalt, yttrium 90, samarium 153, and praseodymium. Vaccines include compounds and formulations that confer immunity against one or more conditions associated with infectious diseases such as influenza, measles, human papillomavirus (HPV), rabies, meningitis, pertussis, tetanus, plague, hepatitis and tuberculosis, and may include mRNA encoding infectious disease-derived antigens and/or epitopes. Vaccines may also include compounds and formulations that lead to an immune response against cancer cells and may include mRNA encoding tumor cell-derived antigens, epitopes and/or neo-epitopes. Compounds that elicit an immune response may include vaccines, corticosteroids (e.g., dexamethasone), and other species. In some embodiments, vaccines and/or compounds capable of eliciting an immune response are administered by intramuscular administration of a composition comprising a compound according to formula (I), (IA), (IB), (II), (IIa), (IIb), (IIc), (IId), (IIe), (IIf), (IIg) or (III) (e.g., compound 3, 18, 20, 25, 26, 29, 30, 60, 108 to 112 or 122). Other therapeutic and/or prophylactic agents include, but are not limited to, antimetabolites (e.g., methotrexate, 6-mercaptopurine, 6-thioguanine, cytarabine, 5-fluorouracil, and dacarbazine), alkanes (e.g., mechlorethamine, thiotepa, chlorambucil, lazithromycin (CC-1065), melphalan, carmustine (BSNU), lomustine (CCNU), cyclophosphamide, busulfan, dibromomannitol, streptozotocin, mitomycin C, and cis-dichlorodiamino platinum (II) (DDP), cisplatin), anthracyclines (e.g., daunorubicin (formerly known as daunomycin) and doxorubicin), antibiotics (e.g., dactinomycin (formerly known as actinomycin), bleomycin, mithramycin, and anthramycin (AMC)) and antimitotic agents (e.g., vincristine, vinblastine, paclitaxel, and maytansinoid).

In other embodiments, the therapeutic and/or prophylactic agent is a protein. Therapeutic proteins that can be used in the nanoparticles of the present disclosure include, but are not limited to, gentamicin, amikacin, insulin, erythropoietin (EPO), granulocyte colony stimulating factor (G-CSF), granulocyte-macrophage colony-stimulating factor (GM-CSF), factor VIR, luteinizing hormone-releasing hormone (LIR) analogs, interferon, heparin, hepatitis B surface antigen, typhoid vaccines and cholera vaccines.

In some embodiments, the therapeutic agent is a polynucleotide or nucleic acid (e.g., ribonucleic acid or deoxyribonucleic acid). The term "polynucleotide" in its broadest sense includes any compound and/or substance which is an oligonucleotide chain or can be incorporated into an oligonucleotide chain. Exemplary polynucleotides for use in accordance with the present disclosure include, but are not limited to, one or more of deoxyribonucleic acid (DNA); ribonucleic acid (RNA), including messenger mRNA (mRNA), hybrids thereof; RNAi-inducing factors; RNAi factors; siRNA; shRNA; miRNA; antisense RNA; ribozyme; catalytic DNA; RNA that induces triple helix formation; aptamer, etc. In some embodiments, the therapeutic and/or prophylactic agent is RNA. RNAs useful in the compositions and methods described herein can be selected from the group consisting of, but not limited to, shortmer, antagomir, antisense RNA, ribozymes, small interfering RNA (siRNA), asymmetric interfering RNA (aiRNA), microRNA (miRNA), Dicer-substrate RNA (dsRNA), small hairpin RNA (shRNA), transfer RNA (tRNA), messenger RNA (mRNA) and mixtures thereof. In certain embodiments, the RNA is mRNA.

In certain embodiments, the therapeutic and/or prophylactic agent is mRNA. The mRNA can encode any polypeptide of interest, including any naturally or non-naturally occurring or otherwise modified polypeptide. The polypeptide encoded by the mRNA can be of any size and can have any secondary structure or activity. In some embodiments, the polypeptide encoded by an mRNA may have a therapeutic effect when expressed in a cell.

In other embodiments, the therapeutic and/or prophylactic agent is siRNA. The siRNA can selectively reduce the expression of a gene of interest or downregulate the expression of that gene. For example, the siRNA can be selected such that a gene associated with a particular disease, disorder or condition is silenced upon administration of a composition comprising the siRNA to a subject in need thereof. siRNA can comprise a sequence that is complementary to an mRNA sequence encoding a gene or protein of interest. In some embodiments, the siRNA can be an immunomodulatory siRNA.

In certain embodiments, the therapeutic and/or prophylactic agent is sgRNA and/or cas9 mRNA. sgRNA and/or cas9 mRNA can be used as gene editing tools. For example, sgRNA-cas9 complexes can affect mRNA translation of cellular genes.

In some embodiments, the therapeutic and/or prophylactic agent is shRNA or a vector or plasmid encoding shRNA. shRNA can be produced inside a target cell after an appropriate construct is delivered into the nucleus. The constructs and mechanisms associated with shRNA are well known in the related art.

Disease or Condition

The composition/carrier of the present disclosure can deliver a therapeutic or prophylactic agent to a subject or patient. The therapeutic or prophylactic agent includes, but is not limited to, one or more of nucleic acid molecules, small molecular compounds, polypeptides or proteins. Therefore, the composition of the present disclosure can be used to prepare nucleic acid medicine, gene vaccine, small molecule medicine, polypeptide or protein medicine. Due to the wide variety of therapeutic or prophylactic agents described above, the composition of the present disclosure can be used to treat or prevent a variety of diseases or conditions.

In one embodiment, the disease or condition is characterized by dysfunctional or abnormal protein or polypeptide activity.

For example, the disease or condition is selected from the group consisting of infectious diseases, cancer and proliferative diseases, genetic diseases, autoimmune diseases, diabetes, neurodegenerative diseases, cardiovascular and renovascular diseases, and metabolic diseases.

In one embodiment, the infectious disease is selected from diseases caused by coronavirus, influenza virus, or HIV virus, infantile pneumonia, Rift Valley fever, yellow fever, rabies, and various herpes.

Other Components

The composition may include one or more component(s) other than those described in the preceding sections. For example, the composition may comprise one or more small hydrophobic molecules, such as vitamins (e.g., vitamin A or vitamin E) or sterols.

The composition may also include one or more permeability enhancing molecules, carbohydrates, polymers, surface-altering agents or other components. The permeability enhancing molecule can be, for example, molecules described in US Patent Application Publication No. 2005/0222064. The carbohydrates can include simple sugars such as glucose and polysaccharides such as glycogen and derivatives and analogs thereof.

Surface-altering agents may include, but are not limited to, anionic proteins such as bovine serum albumin, surfactants for example cationic surfactants such as dimethyldioctadecylammonium bromide, sugars or sugar derivatives (e.g., cyclodextrins), nucleic acids, polymers (e.g., heparin, polyethylene glycol, and poloxamers), mucolytics (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine and erdosteine) and DNases (e.g., rhDNase). Surface-altering agents can be disposed within and/or on the surface of the nanoparticles of the composition (e.g., by coating, adsorption, covalent attachment, or other methods).

The composition may also comprise one or more functionalized lipids. For example, lipids can be functionalized with alkyne groups that may undergo cycloaddition reactions when exposed to azide under appropriate reaction conditions. Specifically, lipid bilayers can be functionalized in this way with one or more groups that effectively facilitate membrane penetration, cell recognition, or imaging. The surface of the composition may also be coupled to one or more useful antibodies. Functional groups and conjugates useful for targeted cell delivery, imaging and membrane penetration are well known in the art.

In addition to these components, the composition may include any material that can be used in pharmaceutical compositions. For example, a composition may include one or more pharmaceutically acceptable excipients or auxiliary ingredients, such as, but not limited to, one or more of solvents, dispersion media, diluents, dispersion aids, suspension aids, granulation aids, disintegrants, fillers, glidants, liquid vehicles, binders, surfactants, isotonic agents, thickeners, emulsifiers, buffering agents, lubricants, oils, preservatives, flavoring agents, colorants, etc. Excipients are, for example, starch, lactose or dextrin. Pharmaceutically acceptable excipients are well known in the art (see for example Remington's The Science and Practice of Pharmacy, 21st Edition, A. R. Gennaro; Lippincott, Williams & Wilkins, Baltimore, MD, 2006).

Examples of diluents may include, but are not limited to, calcium carbonate, sodium carbonate, calcium phosphate, dicalcium phosphate, calcium sulfate, calcium hydrogen phosphate, sodium phosphate, lactose, sucrose, cellulose, microcrystalline cellulose, kaolin, mannitol, sorbitol, inositol, sodium chloride, dry starch, corn starch, powdered sugar and/or a combination thereof.

In some embodiments, compositions comprising one or more lipids described herein may also comprise one or more adjuvants, such as glucopyranosyl lipid adjuvant (GLA), CpG oligodeoxyribonucleotide (e.g., class A or class B), poly(I:C), aluminum hydroxide, and Pam3CSK4.

The compositions of the present disclosure can be formulated into a preparation in solid, semi-solid, liquid or gaseous form, such as tablets, capsules, ointments, elixirs, syrups, solutions, emulsions, suspensions, injections, and aerosols. The compositions of the present disclosure can be prepared by methods well known in the art of pharmacy. For example, sterile injectable solutions can be prepared by incorporating the therapeutic or prophylactic agent in the required amount with various other ingredients enumerated above as required into an appropriate solvent such as sterile distilled water and then filtered sterilization. Surfactants may also be added to promote the formation of a uniform solution or suspension.

For example, compositions of the present disclosure may be administered intravenously, intramuscularly, intradermally, subcutaneously, intranasally, or by inhalation. In one embodiment, the composition is administered subcutaneously.

The compositions of the present disclosure are administered in therapeutically effective amounts which may vary not only with the particular agent chosen, but also with the route of administration, the nature of the disease being treated, and the age and condition of the patient, and may ultimately be at the discretion of the attending physician or clinician. For example, a dose of about 0.001 mg/kg to about 10 mg/kg of the therapeutic or prophylactic agent can be administered to a mammal (e.g., a human).

The present disclosure includes, but is not limited to, the following embodiments:

1. A compound of formula (I)

I

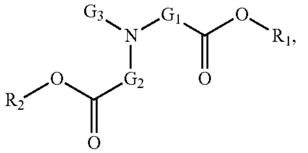

or an N-oxide, solvate, pharmaceutically acceptable salt or stereoisomer thereof, wherein $G_1$ is $C_{1-8}$ alkylene;

$G_2$ is $C_{2-8}$ alkylene;

$R_1$ is $C_{6-25}$ linear or branched alkyl;

$R_2$ is $C_{12-25}$ linear or branched alkyl;

$G_3$ is: $HO(CH_2)_2N(R_3)CH_2CH(OH)CH_2$—, wherein $R_3$ is —$CH_3$ or —$CH_2CH_3$ or —$CH_2CH_2OH$.

2. The compound of formula (I) or an N-oxide, solvate, pharmaceutically acceptable salt or stereoisomer thereof according to embodiment 1, wherein $G_1$ is unsubstituted $C_{3-7}$ alkylene.

3. The compound of formula (I) or an N-oxide, solvate, pharmaceutically acceptable salt or stereoisomer thereof according to embodiment 1 or 2, wherein $G_1$ is unsubstituted $C_3$ alkylene or $C_5$ alkylene or $C_6$ alkylene.

4. The compound of formula (I) or an N-oxide, solvate, pharmaceutically acceptable salt or stereoisomer thereof according to any one of the preceding embodiments, wherein $G_2$ is unsubstituted $C_{3-7}$ alkylene.

5. The compound of formula (I) or an N-oxide, solvate, pharmaceutically acceptable salt or stereoisomer thereof according to any one of the preceding embodiments, wherein $G_2$ is unsubstituted $C_3$ alkylene or $C_5$ alkylene or $C_6$ alkylene.

6. The compound of formula (I) or an N-oxide, solvate, pharmaceutically acceptable salt or stereoisomer thereof according to any one of the preceding embodiments, wherein $R_1$ is unsubstituted $C_{11}$ linear alkyl or unsubstituted $C_{12-24}$ branched alkyl.

7. The compound of formula (I) or an N-oxide, solvate, pharmaceutically acceptable salt or stereoisomer thereof according to embodiment 6, wherein $R_1$ is unsubstituted $C_{18}$ branched alkyl or $C_{15}$ branched alkyl or $C_{24}$ branched alkyl or $C_{17}$ branched alkyl.

8. The compound of formula (I) or an N-oxide, solvate, pharmaceutically acceptable salt or stereoisomer thereof according to embodiment 7, wherein $R_1$ is:

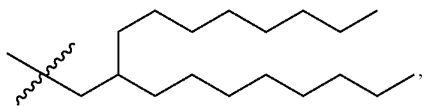

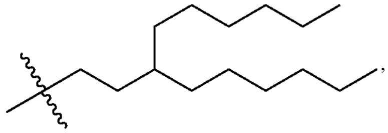

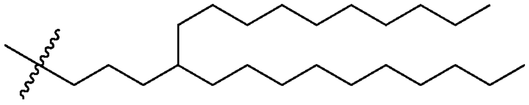

or

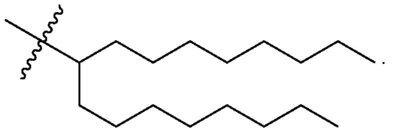

9. The compound of formula (I) or an N-oxide, solvate, pharmaceutically acceptable salt or stereoisomer thereof according to any one of the preceding embodiments, wherein $R_2$ is unsubstituted $C_{11}$ linear alkyl or unsubstituted $C_{14-24}$ branched alkyl.

10. The compound of formula (I) or an N-oxide, solvate, pharmaceutically acceptable salt or stereoisomer thereof according to embodiment 9, wherein $R_2$ is unsubstituted $C_{18}$ branched alkyl or $C_{24}$ branched alkyl or $C_{15}$ branched alkyl or $C_{17}$ branched alkyl.

11. The compound of formula (I) or an N-oxide, solvate, pharmaceutically acceptable salt or stereoisomer thereof according to embodiment 10, wherein $R_2$ is:

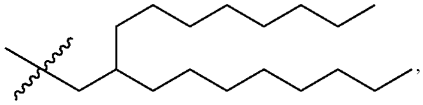

,

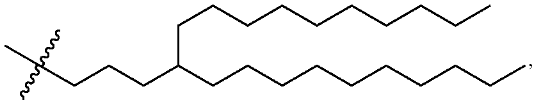

,

-continued

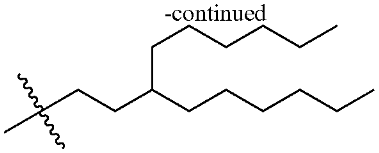

or

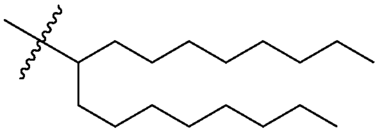

.

12. The compound of formula (I) or an N-oxide, solvate, pharmaceutically acceptable salt or stereoisomer thereof according to any one of the preceding embodiments, wherein the compound of formula (I) has one of the following structures:

YK-301

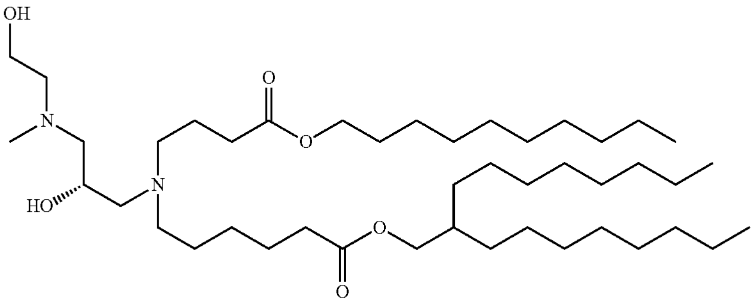

,

YK-302

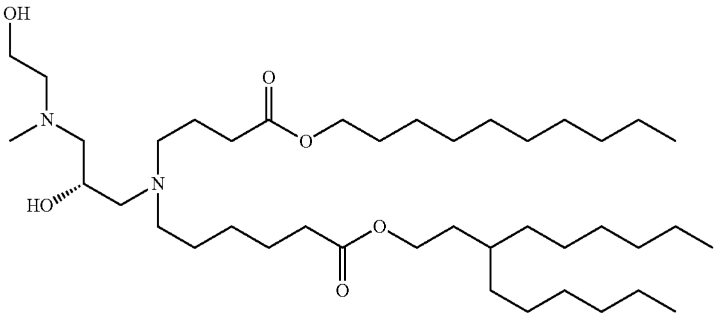

,

YK-303

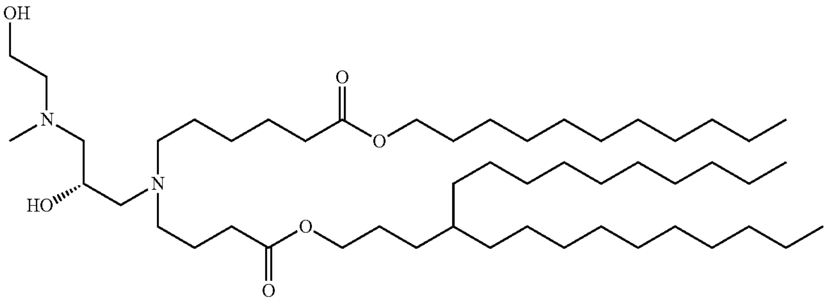

,

-continued
YK-304
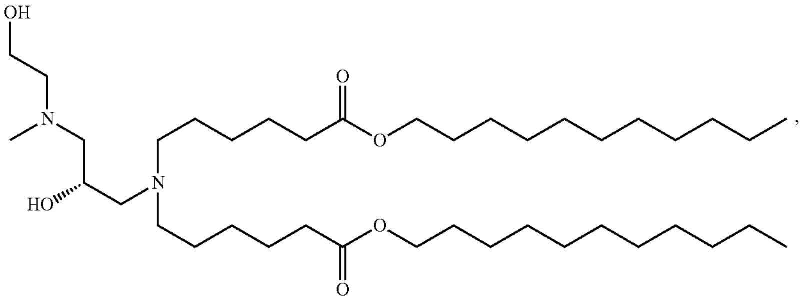
YK-305
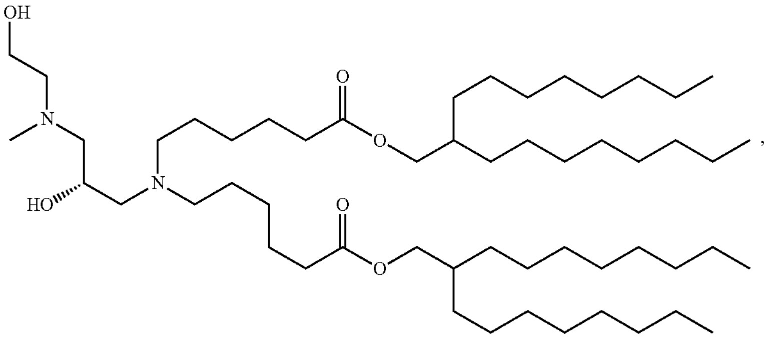
YK-306
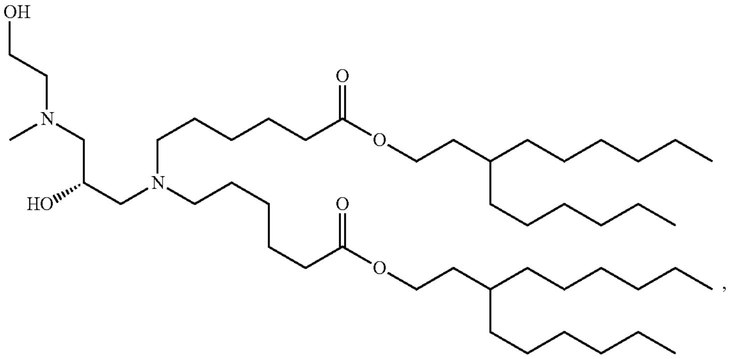
YK-307
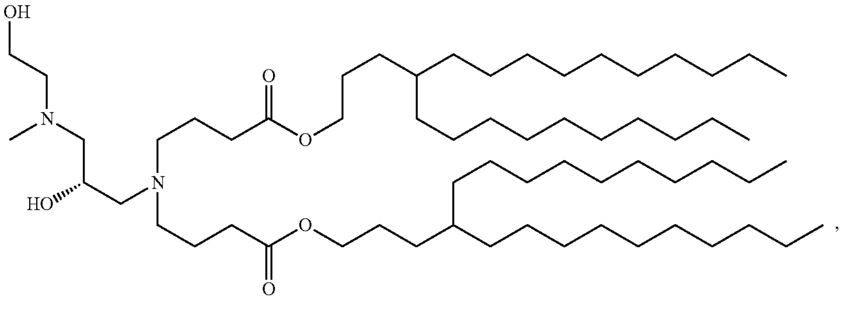
YK-308
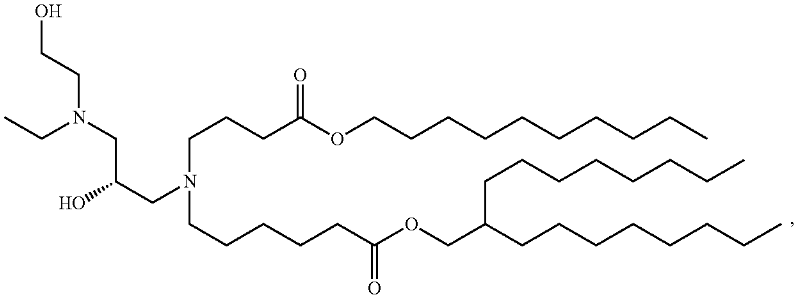

-continued
YK-309
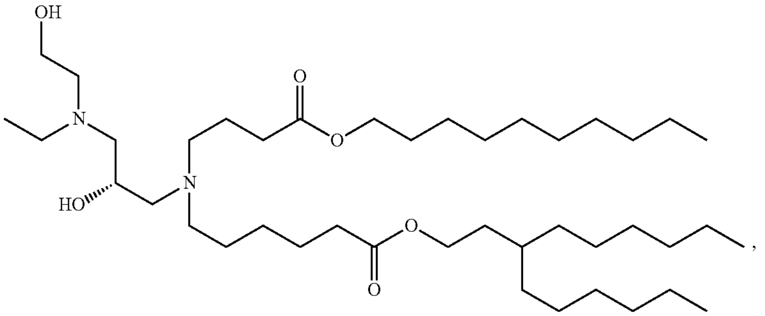
YK-310
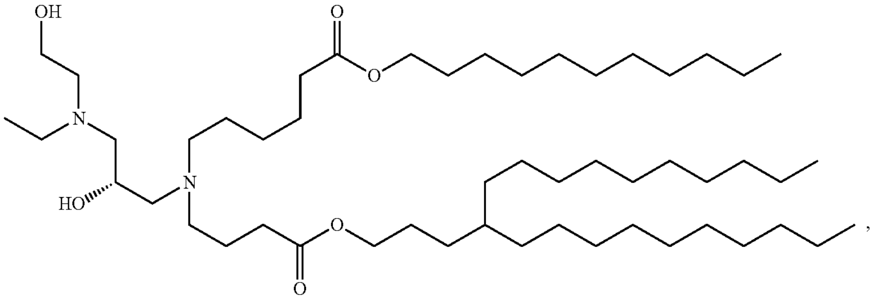
YK-311
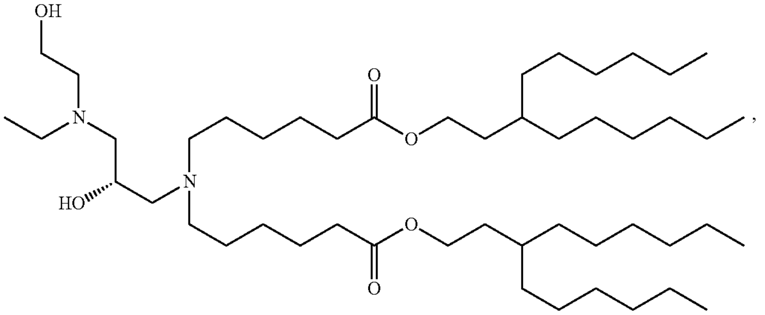
YK-312
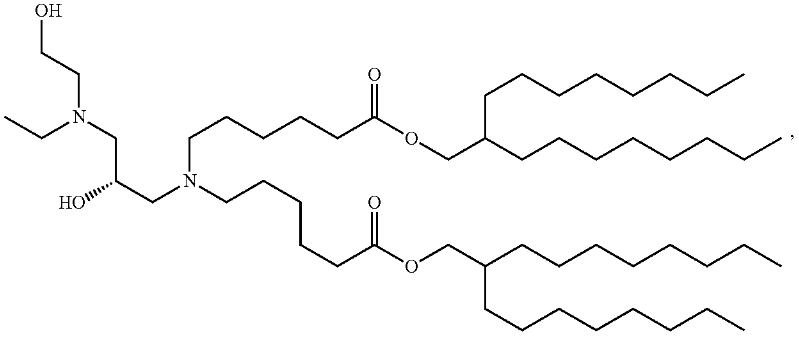
YK-313
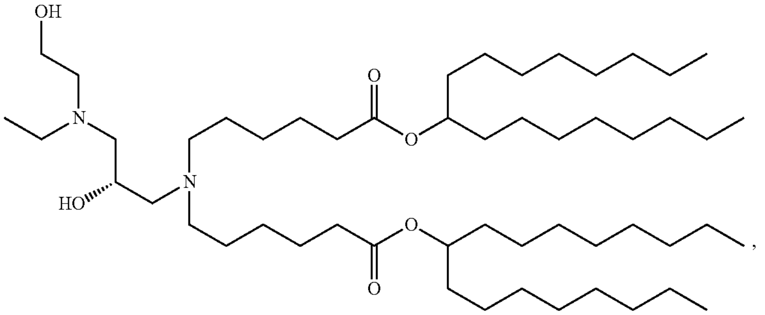

-continued
YK-314
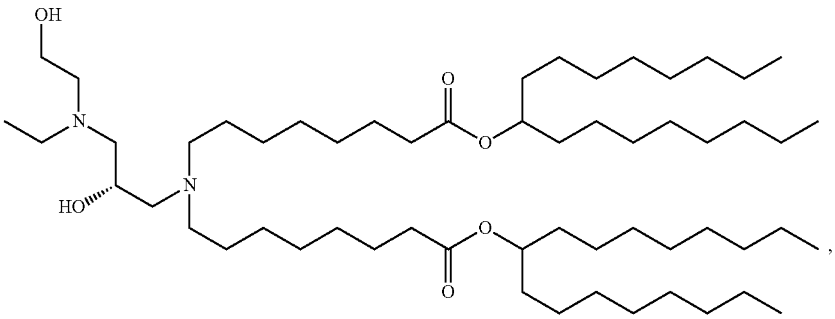
,
YK-315
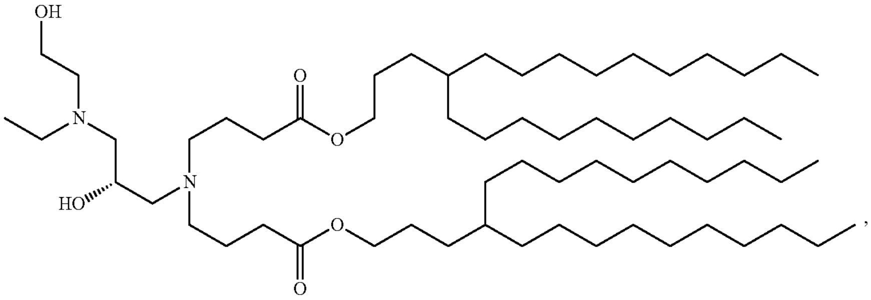
,
YK-316
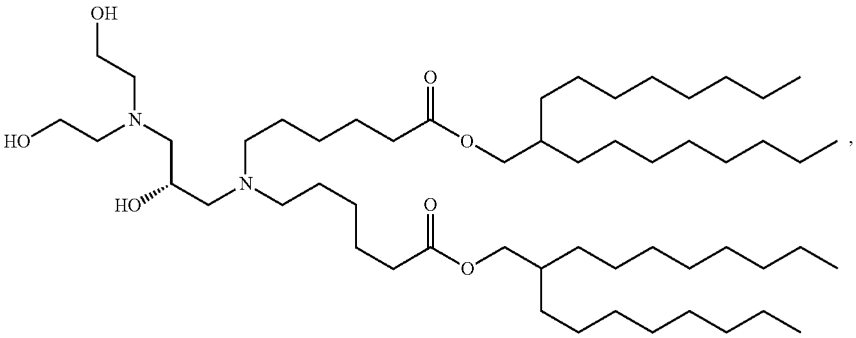
,
YK-317
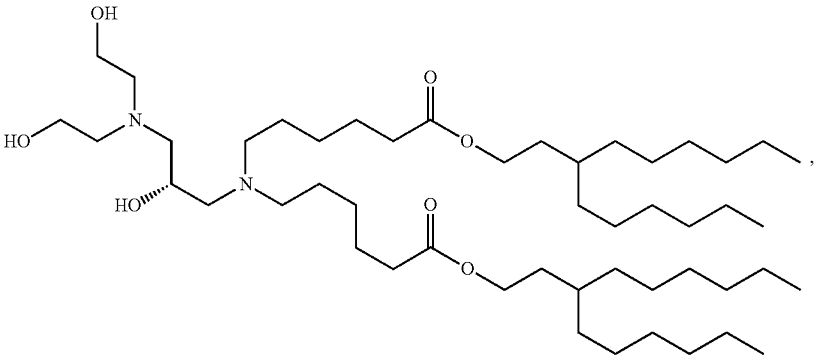
, -continued
YK-318
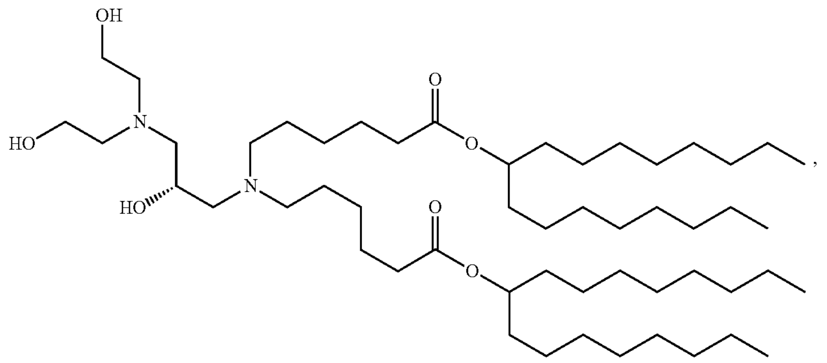
YK-319
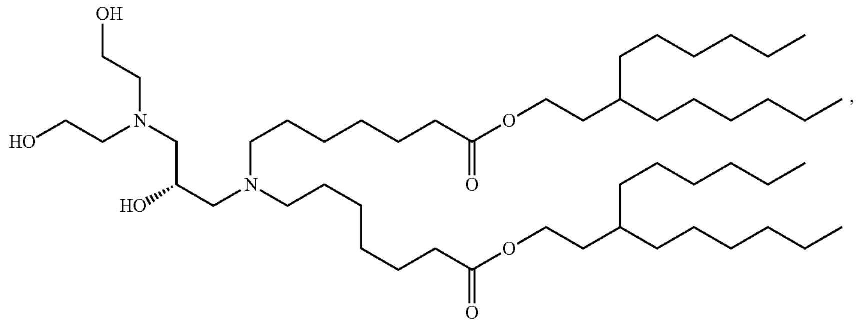
YK-320
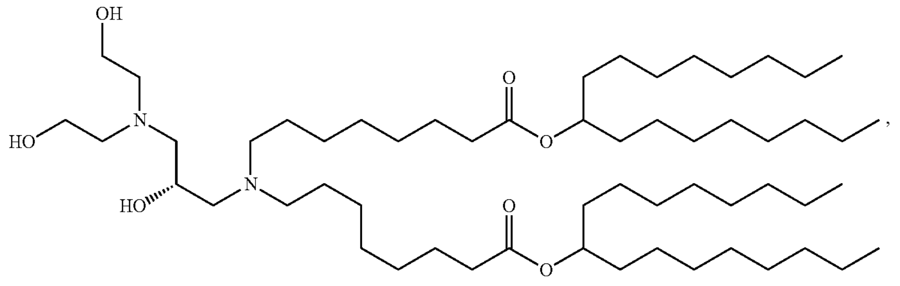
YK-321
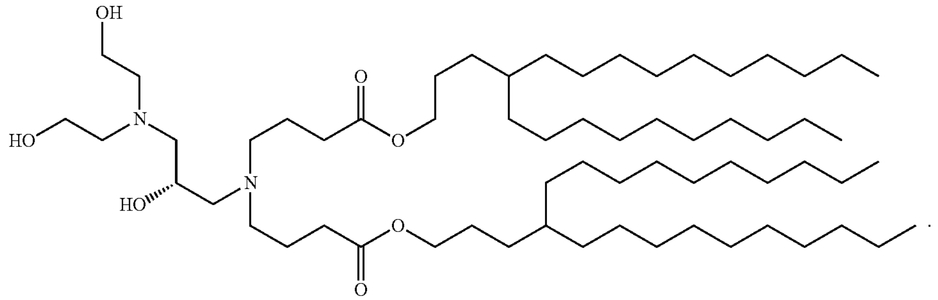

13. The compound of formula (I) or an N-oxide, solvate, pharmaceutically acceptable salt or stereoisomer thereof according to any one of the preceding embodiments, wherein the compound of formula (I) is compound YK-305 with the following structure:

YK-305

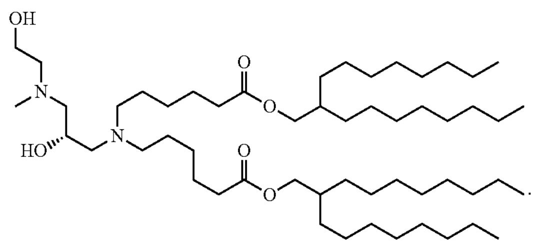

14. The compound of formula (I) or an N-oxide, solvate, pharmaceutically acceptable salt or stereoisomer thereof according to any one of embodiments 1 to 12, wherein the compound of formula (I) is compound YK-310 with the following structure:

YK-310

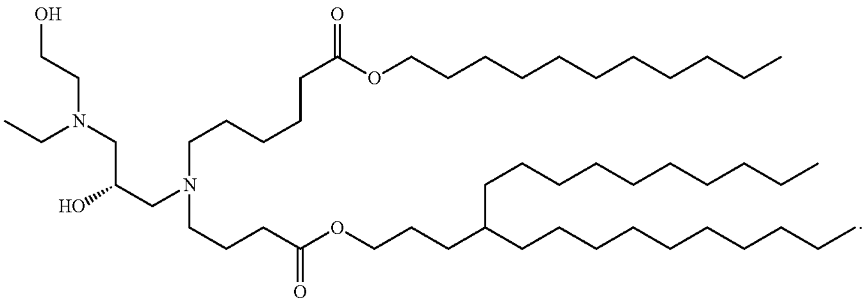

15. The compound of formula (I) or an N-oxide, solvate, pharmaceutically acceptable salt or stereoisomer thereof according to any one of embodiments 1 to 12, wherein the compound of formula (I) is compound YK-312 with the following structure:

YK-312

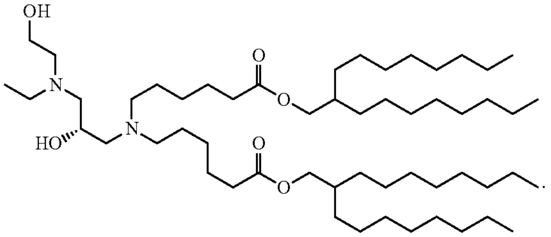

16. The compound of formula (I) or an N-oxide, solvate, pharmaceutically acceptable salt or stereoisomer thereof according to any one of embodiments 1 to 12, wherein the compound of formula (I) is compound YK-319 with the following structure:

YK-319

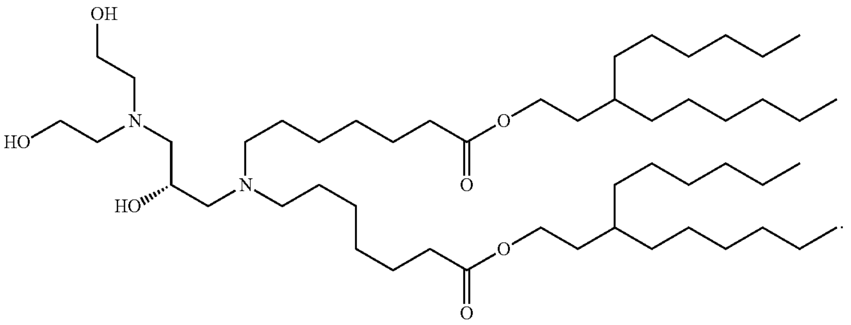

17. The compound of formula (I) or an N-oxide, solvate, pharmaceutically acceptable salt or stereoisomer thereof according to any one of embodiments 1 to 12, wherein the compound of formula (I) is compound YK-318 with the following structure:

YK-318

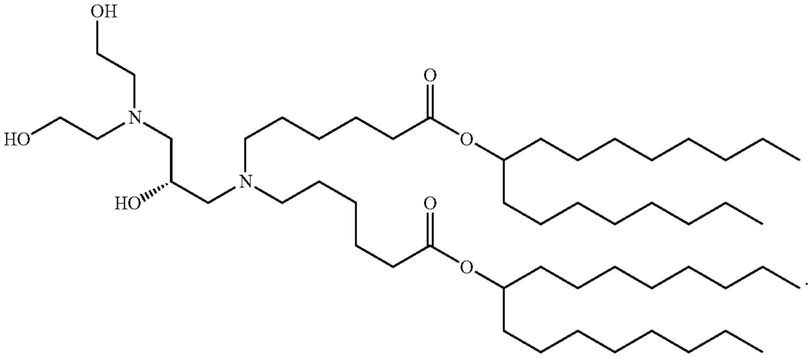

18. A composition comprising a carrier, wherein the carrier comprises a cationic lipid, and the cationic lipid comprises the compound of formula (I) according to any one of the preceding embodiments or an N-oxide, solvate, pharmaceutically acceptable salt or stereoisomer thereof.

19. The composition according to embodiment 18, wherein the molar ratio of the cationic lipid to the carrier is from 25% to 75%.

20. The composition according to any one of embodiments 18 to 19, wherein the carrier further comprises a neutral lipid.

21. The composition according to embodiment 20, wherein the molar ratio of the cationic lipid to the neutral lipid is from 1:1 to 15:1, preferably 4.5:1.

22. The composition according to any one of embodiments 20 to 21, wherein the neutral lipid comprises one or more of phosphatidylcholine, phosphatidylethanolamine, sphingomyelin, ceramide, sterol and a derivative thereof.

23. The composition according to any one of embodiments 20 to 22, wherein the neutral lipid is selected from one or more of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

24. The composition according to any one of embodiment 23, wherein the neutral lipid is DOPE and/or DSPC.

25. The composition according to any one of embodiments 18 to 24, wherein the carrier further comprises a structured lipid.

26. The composition according to embodiment 25, wherein the molar ratio of the cationic lipid to the structured lipid is from 0.6:1 to 3:1.

27. The composition according to any one of embodiments 25 to 26, wherein the structured lipid is selected from one or more of cholesterol, nonsterol, sitosterol, ergosterol, campesterol, stigmasterol, brassicasterol, tomatine, tomatine, ursolic acid, alpha-tocopherol, and corticosteroid.

28. The composition according to embodiment 27, wherein the structured lipid is cholesterol.

29. The composition according to any one of embodiments 18 to 28, wherein the carrier further comprises a polymer-conjugated lipid.

30. The composition according to embodiment 29, wherein the molar ratio of the polymer-conjugated lipid to the carrier is from 0.5% to 10%, preferably 1.5%.

31. The composition according to any one of embodiments 29-30, wherein the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol.

32. The composition according to embodiment 31, wherein the polymer-conjugated lipid is selected from one or more of distearoyl phosphatidylethanolamine polyethylene glycol 2000 (DSPE-$PEG_2$000), dimyristoylglycero-3-methoxy polyethylene glycol 2000 (DMG-$PEG_2$000) and methoxypolyethylene glycol ditetradecylacetamide (ALC-0159).

33. The composition according to any one of embodiments 18-32, wherein the carrier comprises a neutral lipid, a structured lipid and a polymer-conjugated lipid, and the molar ratio of the cationic lipid, the neutral lipid, the structured lipid and the polymer-conjugated lipid is (25 to 75):(5 to 25):(15 to 65):(0.5 to 10).

34. The composition according to embodiment 33, wherein the molar ratio of the cationic lipid, the neutral lipid, the structured lipid, and the polymer-conjugated lipid is (35 to 49):(7.5 to 15):(35 to 55):(1 to 5).

35. The composition according to embodiment 34, wherein the molar ratio of the cationic lipid, the neutral lipid, the structured lipid, and the polymer-conjugated lipid is 45:10:43.5:1.5.

36. The composition according to any one of embodiments 18 to 35, wherein the composition is a nanoparticle formulation which has an average particle size of 10 nm to 300 nm and a polydispersity coefficient less than or equal to 50%.

37. The composition according to embodiment 36, wherein the composition is a nanoparticle formulation, which has an average particle size of 90 nm to 280 nm and a polydispersity coefficient less than or equal to 45%.

38. The composition according to any one of embodiments 18 to 37, wherein the cationic lipid further comprises one or more other ionizable lipid compound(s).

39. The composition according to any one of embodiments 18 to 38, further comprising a therapeutic or prophylactic agent.

40. The composition according to embodiment 39, wherein the mass ratio of the carrier to the therapeutic agent or prophylactic agent is from 10:1 to 30:1.

41. The composition according to embodiment 40, wherein the mass ratio of the carrier to the therapeutic agent or prophylactic agent is from 12.5:1 to 20:1.

42. The composition according to embodiment 41, wherein the mass ratio of the carrier to the therapeutic agent or prophylactic agent is 15:1.

43. The composition according to any one of embodiments 39 to 42, wherein the therapeutic or prophylactic agent comprises one or more of a nucleic acid molecule, a small molecule compound, a polypeptide or a protein.

44. The composition according to any one of embodiments 39 to 42, wherein the therapeutic or prophylactic agent is a vaccine or compound capable of eliciting an immune response.

45. The composition according to any one of embodiments 39 to 44, wherein the therapeutic or prophylactic agent is a nucleic acid.

46. The composition according to embodiment 45, wherein the therapeutic or prophylactic agent is ribonucleic acid (RNA).

47. The composition according to embodiment 45, wherein the therapeutic or prophylactic agent is deoxyribonucleic acid (DNA).

48. The composition according to embodiment 46, wherein the RNA is selected from the group consisting of a small interfering RNA (siRNA), an asymmetric interfering RNA (aiRNA), a microRNA (miRNA), a Dicer-substrate RNA (dsRNA), a small hairpin RNA (shRNA), a messenger RNA (mRNA), and a mixture thereof.

49. The composition according to embodiment 48, wherein the RNA is mRNA.

50. The composition according to any one of embodiments 18 to 49, wherein the composition further comprises one or more of pharmaceutically acceptable excipients or diluents.

51. Use of the compound of formula (I), or an N-oxide, solvate, pharmaceutically acceptable salt or stereoisomer thereof according to any one of embodiments 1 to 17, or the composition according to any one of embodiments 18 to 50 in the manufacture of nucleic acid medicine, gene vaccine, small molecule medicine, polypeptide or protein medicine.

52. Use of the compound of formula (I), or an N-oxide, solvate, pharmaceutically acceptable salt or stereoisomer thereof according to any one of embodiments 1 to 17, or the composition according to any one of embodiments 18 to 50 in the manufacture of a medicament for treating a disease or condition in a mammal in need thereof.

53. The use according to embodiment 52, wherein the disease or condition is characterized by dysfunctional or abnormal protein or polypeptide activity.

54. The use according to any one of embodiments 52 to 53, wherein the disease or condition is selected from the group consisting of infectious diseases, cancer and proliferative diseases, genetic diseases, autoimmune diseases, diabetes, neurodegenerative diseases, cardiovascular and renovascular diseases, and metabolic diseases.

55. The use according to embodiment 54, wherein the infectious disease is selected from: diseases caused by coronavirus, influenza virus or HIV virus, infantile pneumonia, Rift Valley fever, yellow fever, rabies, and various herpes.

56. The use according to any one of embodiments 52 to 55, wherein the mammal is a human.

57. The use according to any one of embodiments 51 to 56, wherein the composition is administered intravenously, intramuscularly, intradermally, subcutaneously, intranasally or by inhalation.

58. The use according to embodiment 57, wherein the composition is administered subcutaneously.

59. The use according to any one of embodiments 51 to 58, wherein the therapeutic or prophylactic agent is administered to the mammal at a dose of about 0.001 mg/kg to about 10 mg/kg.

EXAMPLES

The present disclosure will be further described below in conjunction with examples. However, the present disclosure is not limited to the following examples. The implementation conditions used in the examples can be further adjusted according to different requirements for specific use. Unspecified implementation conditions are conventional conditions in the industry. In the specific examples of the present disclosure, the raw materials used are all commercially available. Unless otherwise stated, percentages in this context are by weight and all temperatures are given in degrees Celsius. The technical features involved in the various embodiments of the present disclosure can be combined with each other as long as they do not conflict with each other.

Example 1: Synthesis of Cationic Lipid Compounds

1. Synthesis of YK-301 and YK-305

The synthesis route is as follows:

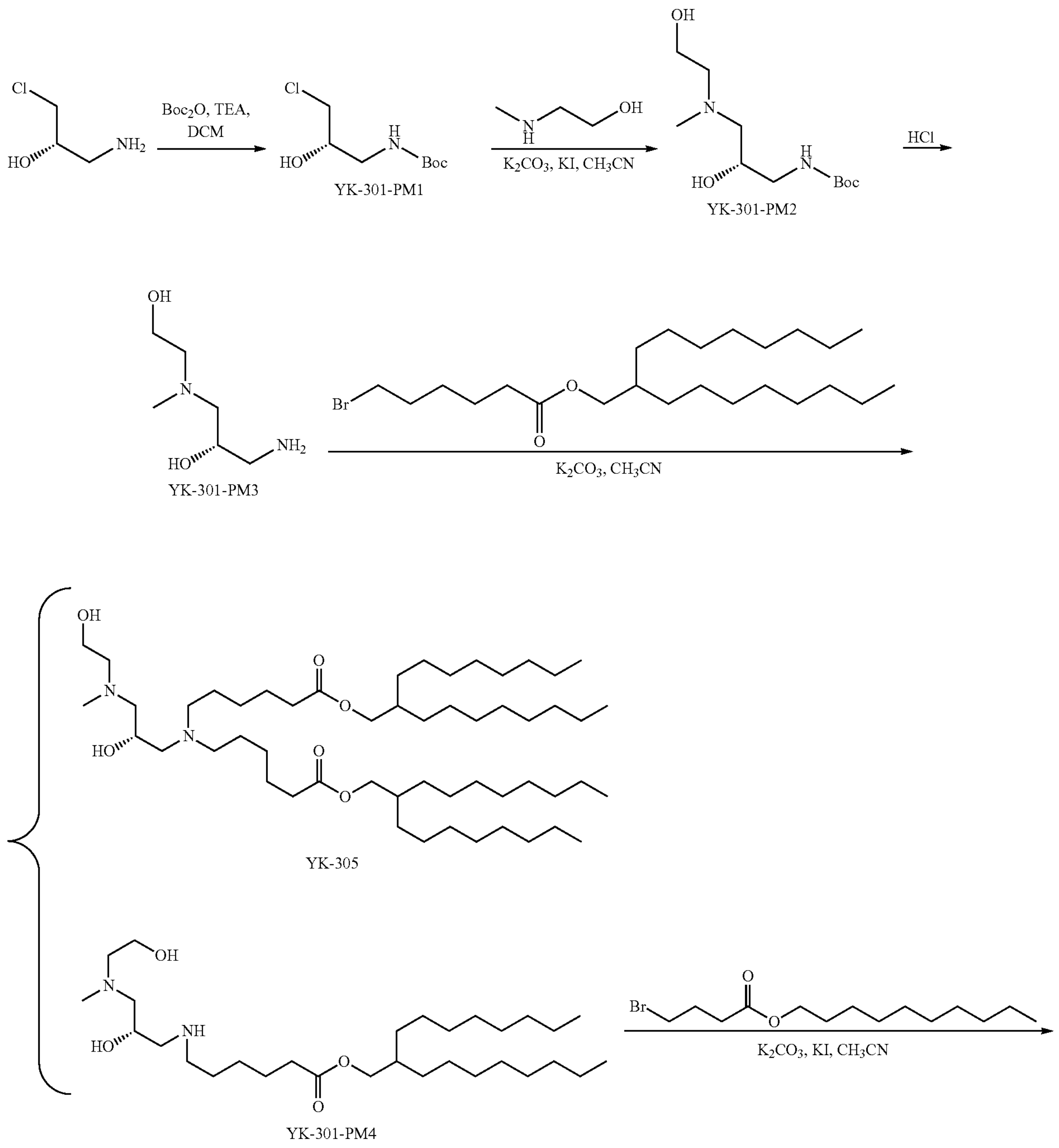

-continued

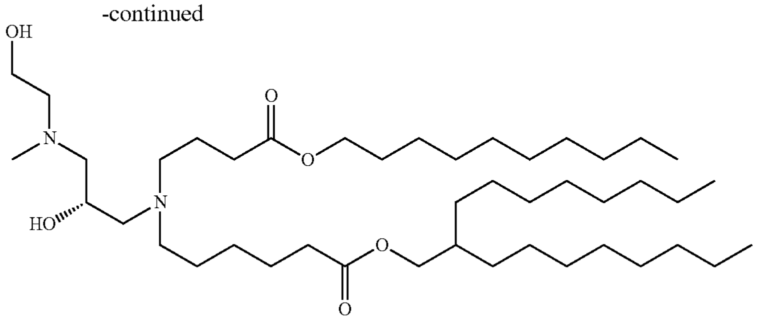

YK-301

Step 1: Synthesis of tert-butyl (S)-(3-chloro-2-hydroxypropyl)carbamate ester (YK-301-PM1)

(S)-1-amino-3-chloropropan-2-ol (5.0 g, 45.6 mmol) and triethylamine (5.1 g, 50.4 mmol) were dissolved in dichloromethane (50 mL). Di-tert-butyl carbonate (10.9 g, 49.9 mmol) was dissolved in dichloromethane (20 mL) was slowly added dropwise into the above solution, and the reaction was stirred at room temperature for 5 hours. After the reaction was completed, 100 mL of water was added to the reaction solution, and the mixture was extracted with dichloromethane (200 mL×2). The organic phases were combined, washed with brine (50 mL×3), dried over anhydrous sodium sulfate, and filtered. The filtrate was concentrated under vacuum. The residue was purified by silica gel chromatography (ethyl acetate/n-hexane) to obtain YK-301-PM1 (7.0 g, 33.4 mmol, 73.2%). $C_8H_{16}ClNO_3$, MS(ES): m/z(M+H$^+$)210.1.

Step 2: Synthesis of tert-butyl (S)-2-hydroxy-3-(((2-hydroxyethyl)(methyl)amino)propyl) carbamate (YK-301-PM2)

YK-301-PM1 (300 mg, 1.43 mmol) and 2-(methylamino) ethanol (108 mg, 1.44 mmol) were dissolved in acetonitrile (3 mL). Potassium carbonate (594 mg, 4.30 mmol) and potassium iodide (48 mg, 0.29 mmol) were added to the above system, and the mixture was heated to 70° C. and stirred to react for 5 hours. After the reaction was completed, the reaction mixture was filtered, and the filtrate was concentrated under vacuum. The residue was purified by silica gel chromatography (methanol/dichloromethane) to obtain YK-301-PM2 (350 mg, 1.41 mmol, 98.6%). $C_{11}H_{24}N_2O_4$, MS(ES): m/z(M+H$^+$)249.2.

Step 3: Synthesis of (S)-1-amino-3-((2-hydroxyethyl)(methyl)amino)propan-2-ol (YK-301-PM3)

YK-301-PM2 (350 mg, 1.41 mmol) prepared above was added to 4M hydrochloric acid/1,4-dioxane (2 mL), and the mixture was stirred to react at room temperature for 10 hours. After the reaction was completed, the mixture was concentrated. 100 mL dichloromethane and 100 mL saturated aqueous sodium bicarbonate solution were added, and the mixture was stirred. The layers were separated, then extracted with dichloromethane (100 mL×2). The organic phases were combined and then washed with brine (50 mL×2), dried over anhydrous sodium sulfate and filtered. The filtrate was concentrated under reduced pressure to obtain YK-301-PM3 (200 mg, 1.35 mmol, 95.7%). $C_6H_{16}N_2O_2$, MS(ES): m/z(M+H$^+$)149.1.

Step 4: Synthesis of 2-octyldecyl (S)-6-(2-hydroxy-3-((2-hydroxyethyl)(methyl)amino)propyl)hexanoate (YK-301-PM4) and (R)-Bis(2-octyldecyl)-6,6'-((2-hydroxy-3-((2-hydroxyethyl)(methyl)amino)propyl) azanediyl)dihexanoate (YK-305)

YK-301-PM3 (200 mg, 1.35 mmol) and 2-octyldecyl 6-bromohexanoate (604 mg, 1.35 mmol) prepared above were dissolved in acetonitrile (2 mL). Potassium carbonate (583 mg, 4.22 mmol) was added to the above system, and the mixture was heated to 70° C. and stirred to react for 7 hours. After the reaction was completed, 20 mL of water was added to the reaction solution, and the mixture was extracted with ethyl acetate (20 mL×2). The organic phases were combined and then washed with brine (20 mL×2), dried over anhydrous sodium sulfate, and filtered. The filtrate was concentrated under vacuum to remove the solvent. The residue was purified by silica gel chromatography (dichloromethane/methanol) to obtain YK-301-PM4 (210 mg, 0.41 mmol, 30.2%). $C_{30}H_{62}N_2O_4$, MS(ES): m/z(M+H$^+$)515.4; to obtain YK-305 (160 mg, 0.18 mmol, 13.4%). $C_{54}H_{108}N_2O_6$, MS(ES): m/z(M+H$^+$)881.8.

Step 5: Synthesis of (R)-2-octyldecyl-6-((4-(decyloxy)-4-oxobutyl)((2-hydroxy-3-(2-hydroxyethyl) (methyl)amino)propyl)amino)hexanoate (YK-301)

YK-301-PM4 (210 mg, 0.41 mmol) and n-decyl 4-bromobutyrate (150 mg, 0.49 mmol) prepared above were dissolved in acetonitrile (2 mL). Potassium carbonate (169 mg, 1.22 mmol) and potassium iodide (14 mg, 0.084 mmol) were added to the above system, and the mixture was heated to 70° C. and stirred for 10 hours. After the reaction was completed, 20 mL of water was added to the reaction solution, and the mixture was extracted with ethyl acetate (20 mL×2). The organic phases were combined and then washed with brine (20 mL×2), dried over anhydrous sodium sulfate, and filtered. The filtrate was concentrated under vacuum to remove the solvent. The residue was purified by silica gel chromatography (dichloromethane/methanol) to obtain the target compound (93 mg, 0.12 mmol, 30.2%). $C_{44}H_{88}N_2O_6$, MS(ES): m/z(M+H$^+$)741.6.

YK-301: $^1$H NMR (400 MHz, Chloroform-d) δ 4.06 (t, J=6.8 Hz, 2H), 3.96 (d, J=5.8 Hz, 2H), 3.90 (s, 1H), 3.81-3.76 (m, 1H), 3.70 (t, J=4.7 Hz, 4H), 2.76 (s, 2H), 2.63-2.41 (m, 10H), 2.31 (q, J=7.3, 6.3 Hz, 4H), 1.79 (dp, J=13.5, 6.9 Hz, 2H), 1.63 (q, J=7.2 Hz, 5H), 1.54-1.43 (m, 2H), 1.28 (d, J=14.3 Hz, 44H), 0.88 (t, J=6.6 Hz, 9H).

YK-305: $^1$H NMR (400 MHz, Chloroform-d) δ 4.07 (s, 2H), 3.96 (d, J=5.8 Hz, 4H), 3.76-3.69 (m, 1H), 2.87-2.55 (m, 10H), 2.51 (s, 3H), 2.31 (t, J=7.4 Hz, 4H), 1.62 (dq, J=15.5, 7.7 Hz, 10H), 1.27 (s, 62H), 0.88 (t, J=6.7 Hz, 12H).

2. Synthesis of YK-302 and YK-306

The synthesis route is as follows:

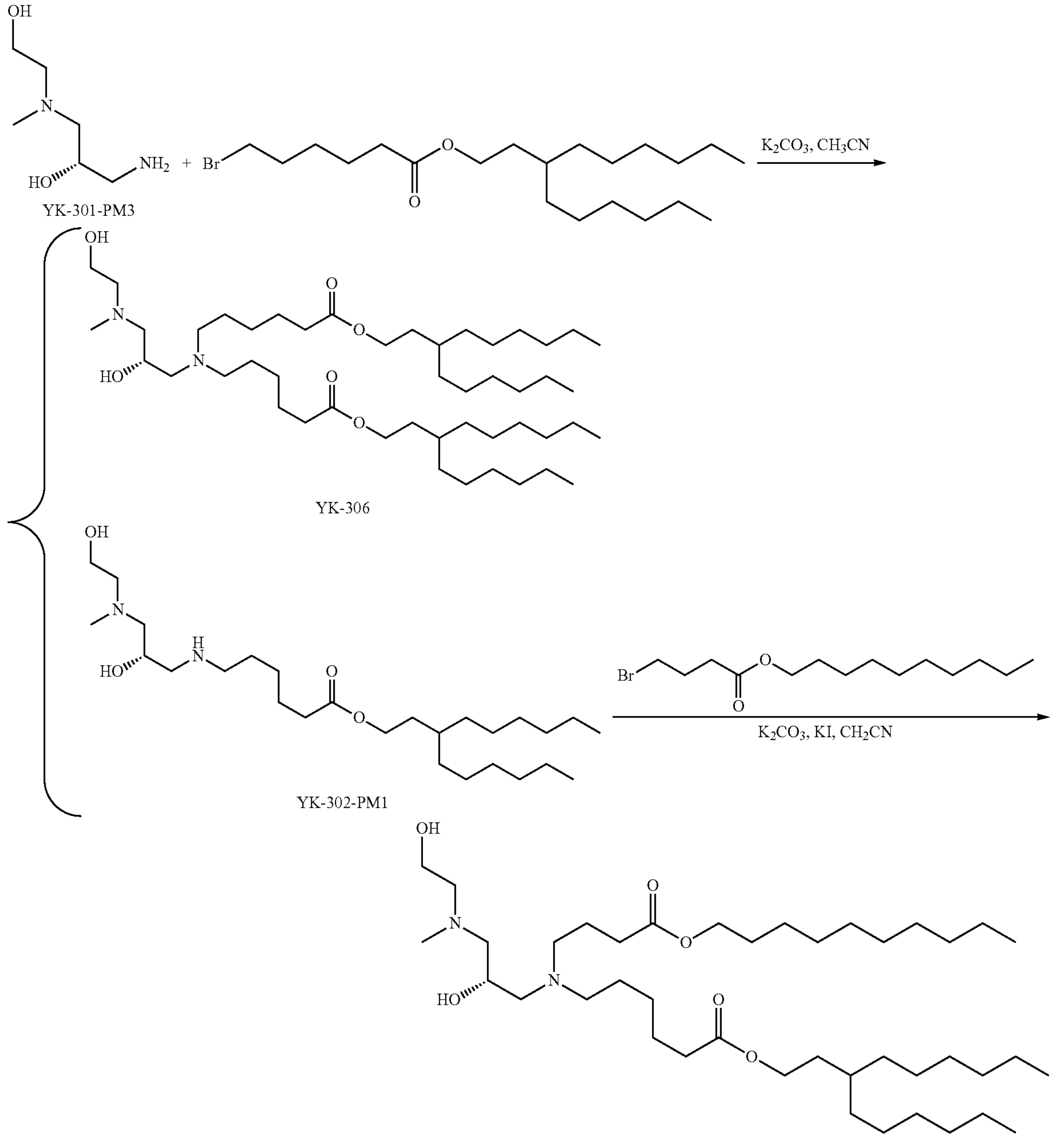

YK-302

Step 1: Synthesis of 3-hexylnonyl (S)-6-(2-hydroxy-3-((2-hydroxyethyl)(methyl)amino)propyl) hexanoate (YK-302-PM1) and (R)-bis(3-hexylnonyl)-6,6'-((2-hydroxy-3-((2-hydroxyethyl)(methyl) amino)propyl)azanediyl)dihexanoate (YK-306)

According to the method for preparing YK-301-PM4, YK-301-PM3 (221 mg, 0.99 mmol) and 3-hexylnonyl 6-bromohexanoate (400 mg, 1.49 mmol) were used as raw materials, to obtain YK-302-PM1 (160 mg, 0.34 mmol, 35.2%), $C_{27}H_{56}N_2O_4$, MS(ES): m/z(M+H$^+$)473.4; to obtain YK-306 (35 mg, 0.04 mmol, 4.4%). $C_{48}H_{96}N_2O_6$, MS(ES): m/z(M+H$^+$)797.7.

Step 2: Synthesis of (R)-3-hexylnonyl-6-(4-(decyloxy)-4-oxobutyl)((2-hydroxy-3-(2-hydroxyethyl) (methyl)amino)propyl)amino)hexanoate (YK-302)

According to the method for preparing YK-301, YK-302-PM1 (160 mg, 0.34 mmol) and n-decyl 4-bromobutyrate (114 mg, 0.37 mmol) were used as raw materials, to obtain YK-302 (120 mg, 0.17 mmol, 50.5%), $C_{41}H_{82}N_2O_6$, MS(ES): m/z(M+H$^+$)699.6.

YK-302: $^1$H NMR (400 MHz, Chloroform-d) δ 4.12-3.85 (m, 8H), 3.75 (t, J=4.9 Hz, 2H), 2.86 (t, J=4.8 Hz, 2H), 2.73-2.50 (m, 9H), 2.31 (dt, J=15.1, 7.2 Hz, 4H), 1.90-1.75 (m, 2H), 1.65-1.54 (m, 6H), 1.28 (d, J=18.9 Hz, 40H), 0.88 (t, J=6.5 Hz, 9H).

YK-306: $^1$H NMR (400 MHz, Chloroform-d) δ 4.37 (s, 1H), 4.08 (t, J=7.1 Hz, 4H), 3.82 (t, J=4.5 Hz, 2H), 3.48 (s, 4H), 3.04-2.80 (m, 8H), 2.64 (s, 3H), 2.31 (t, J=7.2 Hz, 4H), 1.67 (dq, J=15.1, 7.5 Hz, 7H), 1.60-1.53 (m, 4H), 1.25 (s, 48H), 0.88 (t, J=6.4 Hz, 12H).

3. Synthesis of YK-303 and YK-304

The synthesis route is as follows:

Step 1: Synthesis of n-undecyl (S)-6-(2-hydroxy-3-((2-hydroxyethyl)(methyl)amino)propyl)hexanoate (YK-303-PM1) and (R)-bis(undecyl)-6,6'-((2-hydroxy-3-((2-hydroxyethyl)(methyl)amino)propyl) azanediyl)dihexanoate (YK-304)

According to the method for preparing YK-301-PM4, YK-301-PM3 (160 mg, 1.08 mmol) and n-undecyl 6-bromohexanoate (251 mg, 0.72 mmol) were used as raw materials, to obtain YK-303-PM1 (114 mg, 0.27 mmol, 38.0%), $C_{23}H_{48}N_2O_4$, MS(ES): m/z(M+H$^+$)417.4; to obtain YK-304 (50 mg, 0.07 mmol, 10.1%). $C_{40}H_{80}N_2O_6$, MS(ES): m/z(M+H$^+$)685.6.

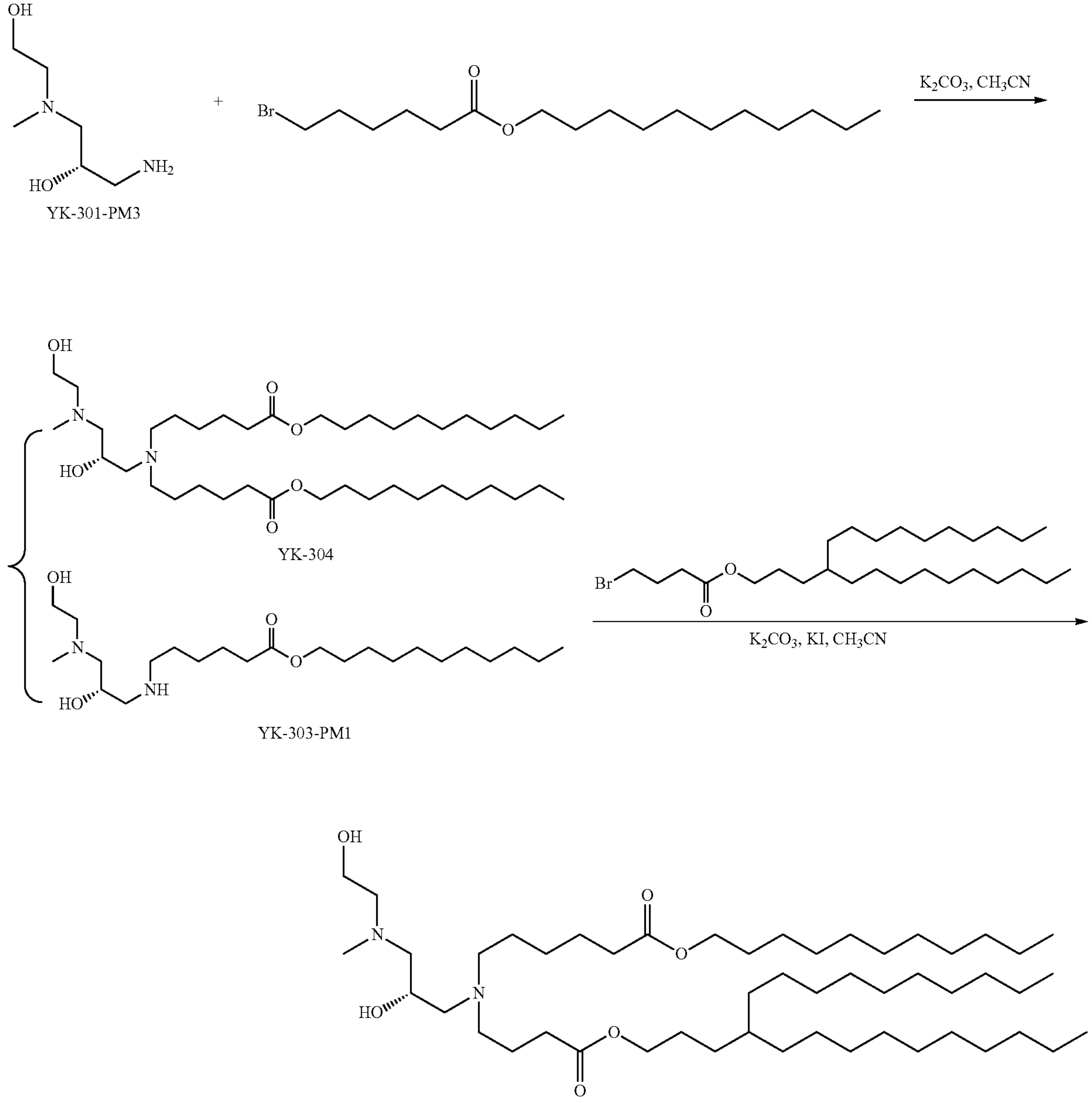

YK-303

Step 2: Synthesis of (R)-undecyl-6-(4-(4-decyltetradecyloxy)-4-oxobutyl)((2-hydroxy-3-((2-hydroxyethyl)(methyl)amino)propyl)amino)hexanoate (YK-303)

According to the method for preparing YK-301, YK-303-PM1 (114 mg, 0.27 mmol) and 4-decyltetradecyl 4-bromobutyrate (156 mg, 0.31 mmol) were used as raw materials, to obtain YK-303 (75 mg, 0.09 mmol, 33.1%), $C_{51}H_{102}N_2O_6$, MS(ES): m/z(M+H$^+$)839.8.

YK-303: $^1$H NMR (400 MHz, Chloroform-d) δ 4.42 (s, 1H), 4.08-4.00 (m, 4H), 3.91 (s, 2H), 3.49 (s, 1H), 3.14 (s, 3H), 2.82 (d, J=10.5 Hz, 10H), 2.39 (t, J=6.6 Hz, 2H), 2.31 (t, J=7.2 Hz, 2H), 1.95 (s, 3H), 1.63 (dt, J=15.4, 7.3 Hz, 8H), 1.25 (d, J=11.9 Hz, 62H), 0.88 (t, J=6.6 Hz, 9H).

YK-304: $^1$H NMR (400 MHz, Chloroform-d) δ 5.30 (s, 1H), 4.80 (s, 2H), 4.16-4.02 (m, 4H), 3.75 (q, J=7.6, 6.4 Hz, 2H), 3.02-2.61 (m, 9H), 2.56 (s, 3H), 2.31 (t, J=7.4 Hz, 4H), 1.71-1.54 (m, 12H), 1.40-1.22 (m, 36H), 0.88 (t, J=6.6 Hz, 6H).

4. Synthesis of YK-307

The synthesis route is as follows:

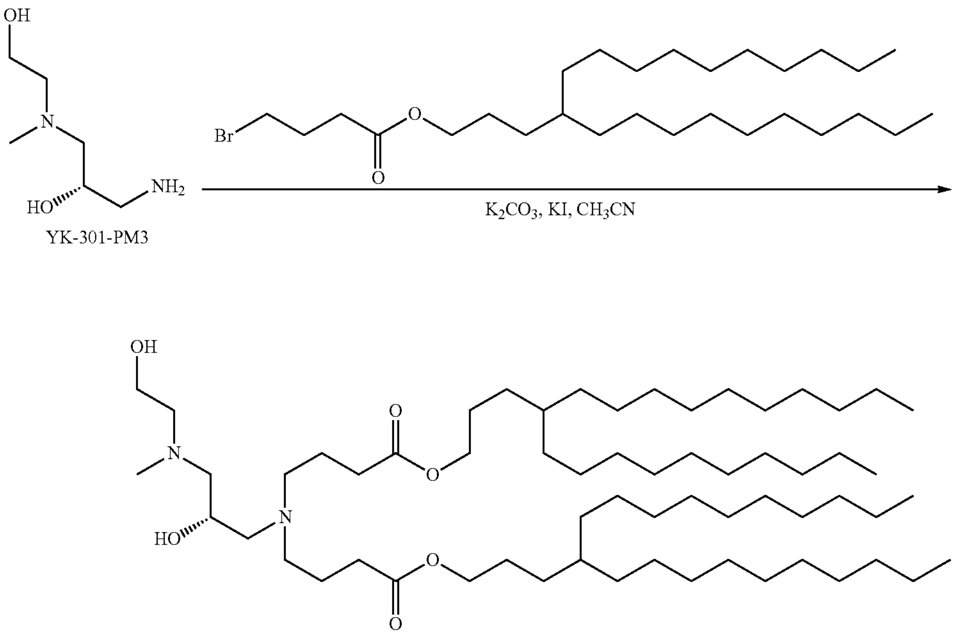

YK-307

Synthesis of (R)-bis(4-decyltetradecyl)-4,4'-(2-hydroxy-3-((2-hydroxyethyl)(methyl)amino)propyl)azanediyl)dibutyrate (YK-307)

According to the method for preparing YK-301-PM4, YK-301-PM3 (160 mg, 1.08 mmol) and 4-decyltetradecyl 4-bromobutyrate (362 mg, 0.72 mmol) were used as raw materials, to obtain YK-307 (75 mg, 0.08 mmol, 20.9%). $C_{62}H_{124}N_2O_6$, MS(ES): m/z(M+H$^+$)993.9.

$^1$H NMR (400 MHz, Chloroform-d) δ 5.30 (s, 1H), 4.04 (t, J=6.8 Hz, 4H), 3.89-3.74 (m, 2H), 3.03 (d, J=4.1 Hz, 4H), 2.60 (dd, J=16.6, 9.7 Hz, 7H), 2.32 (t, J=6.8 Hz, 4H), 1.87-1.74 (m, 4H), 1.63-1.55 (m, 4H), 1.25 (d, J=12.2 Hz, 80H), 0.88 (t, J=6.7 Hz, 12H).

5. Synthesis of YK-308 and YK-312
The synthesis route is as follows:
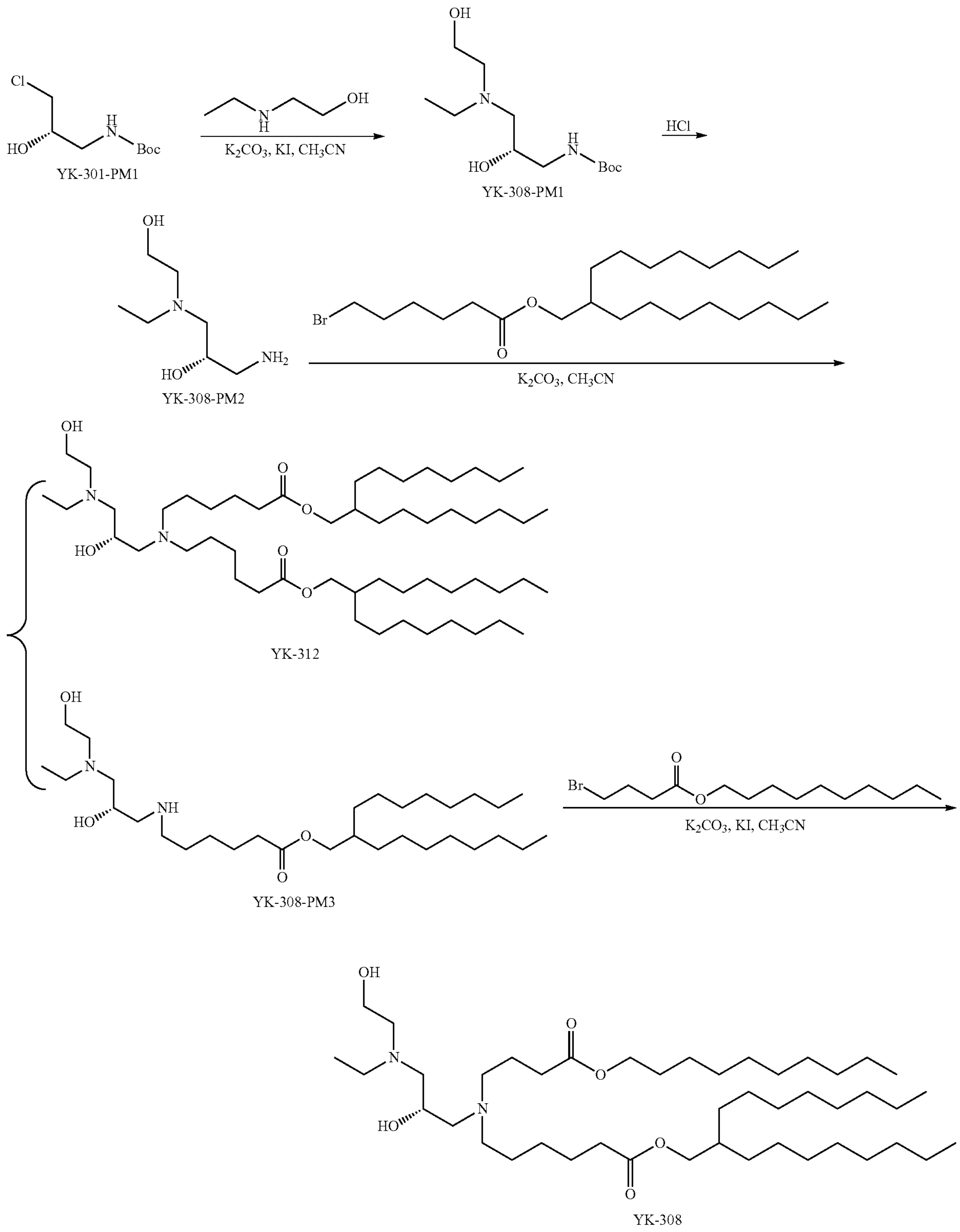

Step 1: Synthesis of tert-butyl (S)-2-hydroxy-3-(((2-hydroxyethyl)(ethyl)amino)propyl)carbamate (YK-308-PM1)

According to the method for preparing YK-301-PM2, YK-301-PM1 (600 mg, 2.87 mmol) and 2-(ethylamino) ethanol (256 mg, 2.87 mmol) were used as raw materials, to obtain YK-308-PM1 (300 mg, 1.14 mmol, 39.8%), $C_{12}H_{26}N_2O_4$, MS(ES): m/z(M+H$^+$)263.2.

Step 2: Synthesis of (S)-1-amino-3-((2-hydroxyethyl)(ethyl)amino)propan-2-ol (YK-308-PM2)

According to the method for preparing YK-301-PM3, YK-308-PM1 (200 mg, 0.76 mmol) was used as raw materials, to obtain YK-308-PM2 (120 mg, 0.74 mmol, 97.3%), $C_7H_{18}N_2O_2$, MS(ES): m/z(M+H$^+$)163.1.

Step 3: Synthesis of 2-octyldecyl (S)-6-(2-hydroxy-3-(((2-hydroxyethyl)(ethyl)amino)propyl)hexanoate (YK-308-PM3) and (S)-bis(2-octyldecyl)-6,6'-((2-hydroxy-3-((2-hydroxyethyl)(ethyl)amino)propyl) azanediyl)dihexanoate (YK-312)

According to the method for preparing YK-301-PM4, YK-308-PM2 (185 mg, 1.14 mmol) and 2-octyldecyl 6-bromohexanoate (349 mg, 1.14 mmol) were used as raw materials, to obtain YK-308-PM3 (150 mg, 0.28 mmol, 24.9%), $C_{31}H_{64}N_2O_4$, MS(ES): m/z(M+H$^+$)529.5; to obtain YK-312 (71 mg, 0.08 mmol, 7.0%). $C_{55}H_{110}N_2O_6$, MS(ES): m/z(M+H$^+$)895.8.

Step 4: Synthesis of (S)-2-octyldecyl-6-(4-(decyloxy)-4-oxobutyl)((2-hydroxy-3-(2-hydroxyethyl) (ethyl)amino)propyl)amino)hexanoate (YK-308)

According to the method for preparing YK-301, YK-308-PM3 (150 mg, 0.28 mmol) and n-decyl 4-bromobutyrate (104 mg, 0.34 mmol) were used as raw materials, to obtain YK-308 (90 mg, 0.12 mmol, 42.6%), $C_{45}H_{90}N_2O_6$, MS(ES): m/z(M+H$^+$)755.7.

YK-308: $^1$H NMR (400 MHz, Chloroform-d) δ 4.06 (t, J=6.7 Hz, 2H), 3.96 (d, J=5.8 Hz, 2H), 3.74 (s, 1H), 2.90 (s, 3H), 2.84-2.38 (m, 10H), 2.31 (q, J=7.1, 6.6 Hz, 4H), 1.80 (s, 2H), 1.69-1.58 (m, 5H), 1.49 (s, 2H), 1.26 (s, 48H), 0.88 (t, J=6.6 Hz, 9H).

YK-312: $^1$H NMR (400 MHz, Chloroform-d) δ 3.96 (d, J=5.8 Hz, 4H), 3.84 (s, 2H), 2.91 (d, J=94.1 Hz, 12H), 2.32 (t, J=7.3 Hz, 4H), 1.72-1.54 (m, 10H), 1.27 (s, 66H), 0.88 (t, J=6.7 Hz, 12H).

6. Synthesis of YK-309 and YK-311

The synthesis route is as follows:

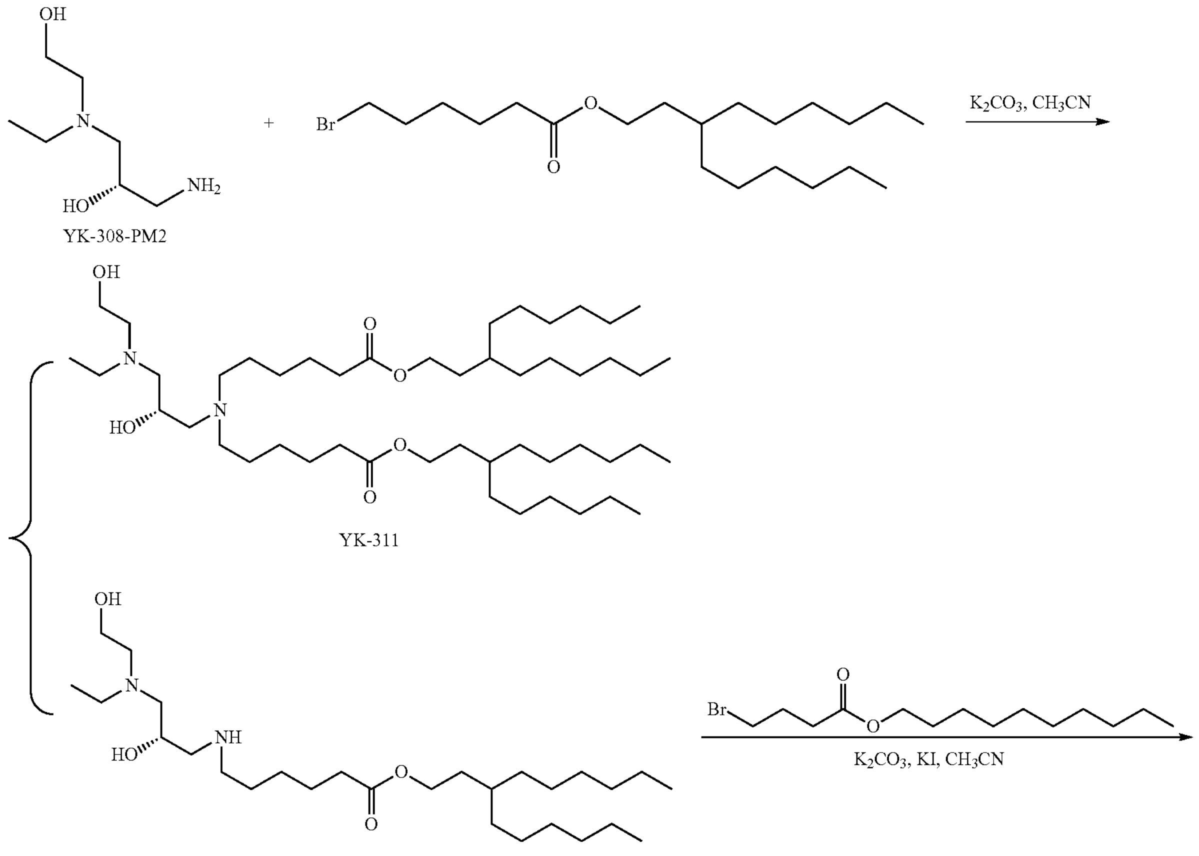

YK-308-PM2
YK-311
YK-309-PM1

-continued

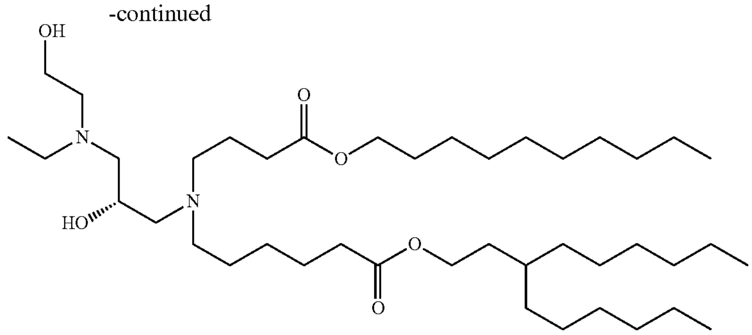

YK-309

Step 1: Synthesis of 3-hexylnonyl (S)-4-(2-hydroxy-3-((2-hydroxyethyl)(ethyl)amino)propyl) hexanoate (YK-309-PM1) and (S)-bis(3-hexylnonyl)-6,6'-((((2-hydroxyethyl)(ethyl)amino)propyl) azanediyl)dihexanoate (YK-311)

According to the method for preparing YK-301-PM4, YK-308-PM2 (247 mg, 1.52 mmol) and 3-hexylnonyl 6-bromohexanoate (680 mg, 1.67 mmol) were used as raw materials, to obtain YK-309-PM1 (260 mg, 0.53 mmol, 35.1%), $C_{28}H_{58}N_2O_4$, MS(ES): m/z(M+H$^+$)487.4; to obtain YK-311 (160 mg, 0.20 mmol, 13.0%). $C_{49}H_{98}N_2O_6$, MS(ES): m/z(M+H$^+$)811.7.

Step 2: Synthesis of (S)-3-hexylnonyl-6-(4-(decyloxy)-4-oxobutyl)(2-hydroxy-3-(((2-hydroxyethyl) (ethyl)amino)propyl)amino)hexanoate (YK-309)

According to the method for preparing YK-301, YK-309-PM1 (160 mg, 0.33 mmol) and 3-n-decyl 4-bromobutyrate (101 mg, 0.33 mmol) were used as raw materials, to obtain YK-309 (160 mg, 0.22 mmol, 68.0%), $C_{42}H_{84}N_2O_6$, MS(ES): m/z(M+H$^+$)713.6.

YK-309: $^1$H NMR (400 MHz, Chloroform-d) δ 4.07 (q, J=7.2 Hz, 4H), 3.86 (dt, J=8.3, 4.3 Hz, 1H), 3.68 (t, J=5.0 Hz, 2H), 2.80 (q, J=7.0 Hz, 4H), 2.70-2.37 (m, 8H), 2.34-2.27 (m, 3H), 1.78 (tt, J=13.8, 7.1 Hz, 2H), 1.60 (dp, J=20.9, 7.2 Hz, 6H), 1.51-1.23 (m, 40H), 1.13 (t, J=7.1 Hz, 3H), 0.88 (t, J=6.7 Hz, 9H).

YK-311: $^1$H NMR (400 MHz, Chloroform-d) δ 4.08 (t, J=7.1 Hz, 4H), 3.87 (s, 1H), 3.66 (t, J=5.1 Hz, 2H), 2.82-2.71 (m, 4H), 2.69-2.37 (m, 8H), 2.29 (t, J=7.4 Hz, 4H), 1.69-1.44 (m, 12H), 1.39 (s, 2H), 1.26 (s, 44H), 1.11 (t, J=7.1 Hz, 3H), 0.88 (t, J=6.7 Hz, 12H).

7. Synthesis of YK-310 and YK-315

The synthesis route is as follows:

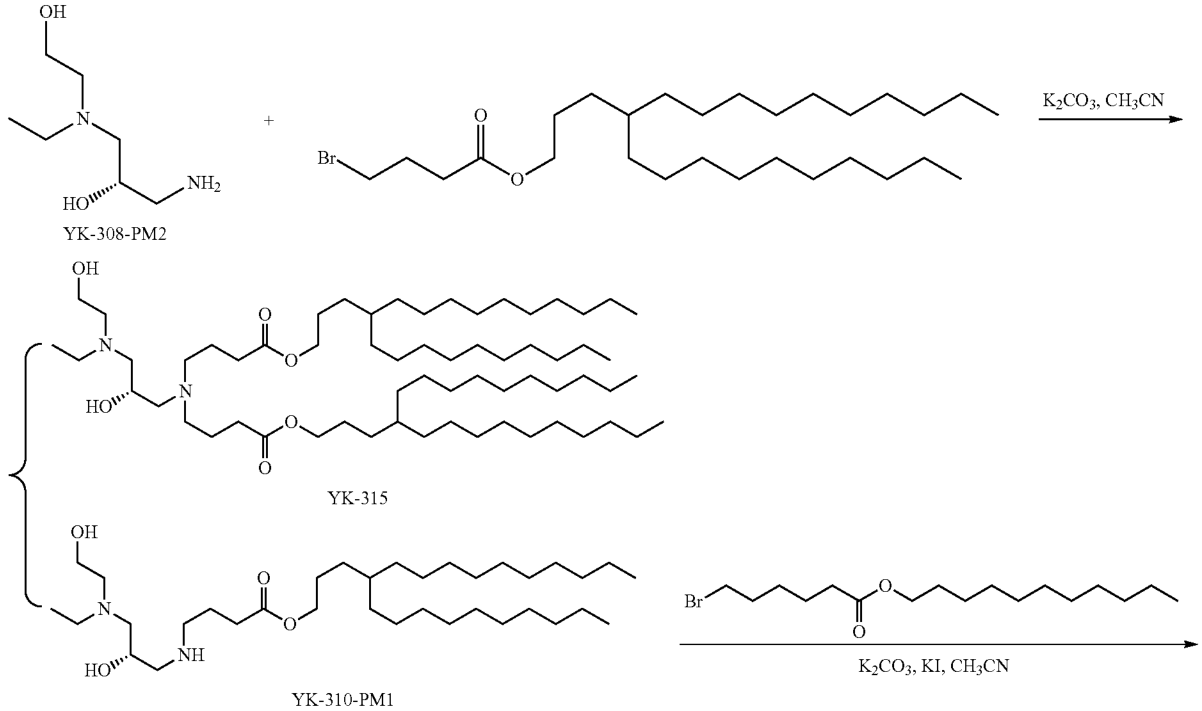

-continued

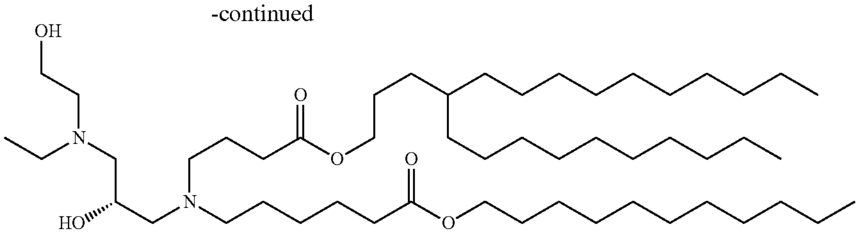

YK-310

Step 1: Synthesis of 4-decyltetradecyl (S)-4-(2-Hydroxy-3-((2-hydroxyethyl)(ethyl)amino)propyl) butyrate (YK-310-PM 1) and (S)-bis(4-decyltetradecyl)-4,4'-(((2-hydroxyethyl)(ethyl)amino)propyl) azanediyl)dibutyrate (YK-315)

According to the method for preparing YK-301-PM4, YK-308-PM2 (124 mg, 0.76 mmol) and 4-decyltetradecyl 4-bromobutyrate (385 mg, 0.76 mmol) were used as raw materials, to obtain YK-310-PM1 (142 mg, 0.24 mmol, 31.9%), $C_{35}H_{72}N_2O_4$, MS(ES): m/z(M+H$^+$)585.6; to obtain YK-315 (30 mg, 0.03 mmol, 3.9%). $C_{63}H_{126}N_2O_6$, MS(ES): m/z(M+H$^+$)1008.0.

Step 2: Synthesis of (S)-4-decyltetradecyl-4-(6-(undecyloxy)-6-oxohexyl)(2-hydroxy-3-(2-hydroxyethyl)(ethyl)amino)propyl)amino)butyrate (YK-310)

According to the method for preparing YK-301, YK-310-PM1 (142 mg, 0.24 mmol) and undecyl 6-bromohexanoate (153 mg, 0.44 mmol) were used as raw materials, to obtain YK-310 (90 mg, 0.11 mmol, 43.9%), $C_{52}H_{104}N_2O_6$, MS(ES): m/z(M+H$^+$)853.8.

YK-310: $^1$H NMR (400 MHz, Chloroform-d) δ 4.10-3.94 (m, 5H), 3.75 (q, J=6.2, 5.6 Hz, 2H), 2.95-2.80 (m, 4H), 2.74-2.46 (m, 6H), 2.36-2.23 (m, 4H), 1.81 (q, J=7.7 Hz, 2H), 1.68-1.56 (m, 6H), 1.49 (d, J=7.3 Hz, 2H), 1.25 (d, J=12.2 Hz, 62H), 0.88 (t, J=6.7 Hz, 9H).

YK-315: $^1$H NMR (400 MHz, Chloroform-d) δ 4.39 (s, 1H), 4.08-3.96 (m, 6H), 3.27 (d, J=7.1 Hz, 4H), 2.72 (s, 5H), 2.35 (t, J=6.8 Hz, 4H), 1.85 (d, J=6.9 Hz, 4H), 1.59 (s, 4H), 1.42 (t, J=7.1 Hz, 4H), 1.25 (d, J=12.1 Hz, 80H), 0.88 (t, J=6.6 Hz, 12H).

8. Synthesis of YK-313

The synthesis route is as follows:

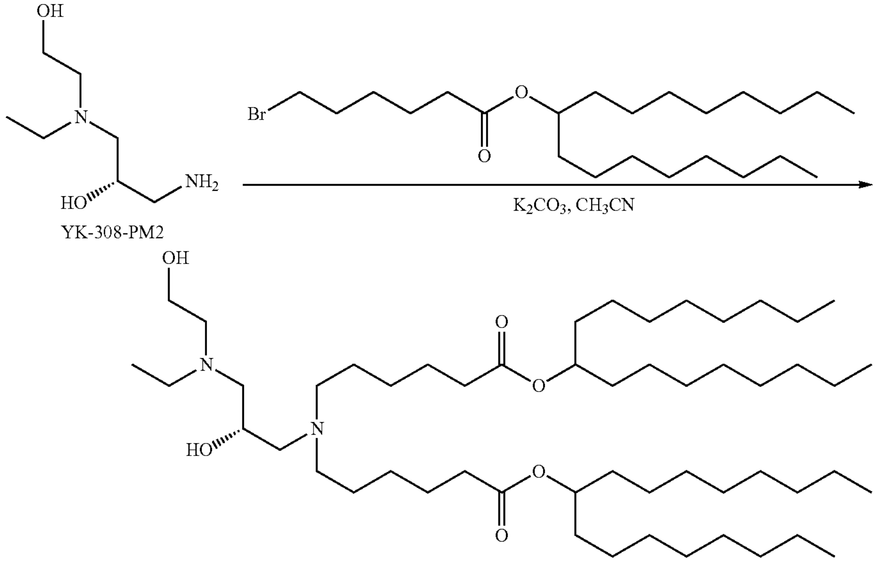

YK-313

Synthesis of (S)-Bis(heptadecan-9-yl)-6,6'-(((2-hydroxyethyl)(ethyl)amino)propyl)azanediyl)dihexanoate (YK-313)

According to the method for preparing YK-301-PM4, YK-308-PM2 (62 mg, 0.38 mmol) and heptadecan-9-yl 6-bromohexanoate (330 mg, 0.76 mmol) were used as raw materials, to obtain YK-313 (170 mg, 0.20 mmol, 51.6%). $C_{53}H_{106}N_2O_6$, MS(ES): m/z(M+H$^+$)867.8.

$^1$H NMR (400 MHz, Chloroform-d) δ 4.86 (p, J=6.2 Hz, 2H), 3.84 (s, 1H), 3.65 (t, J=5.1 Hz, 2H), 2.80-2.69 (m, 4H), 2.64-2.35 (m, 8H), 2.28 (t, J=7.5 Hz, 4H), 1.63 (p, J=7.6 Hz, 4H), 1.56-1.44 (m, 12H), 1.28 (d, J=15.2 Hz, 54H), 1.09 (t, J=7.1 Hz, 3H), 0.88 (t, J=6.8 Hz, 12H).

9. Synthesis of YK-314

The synthesis route is as follows:

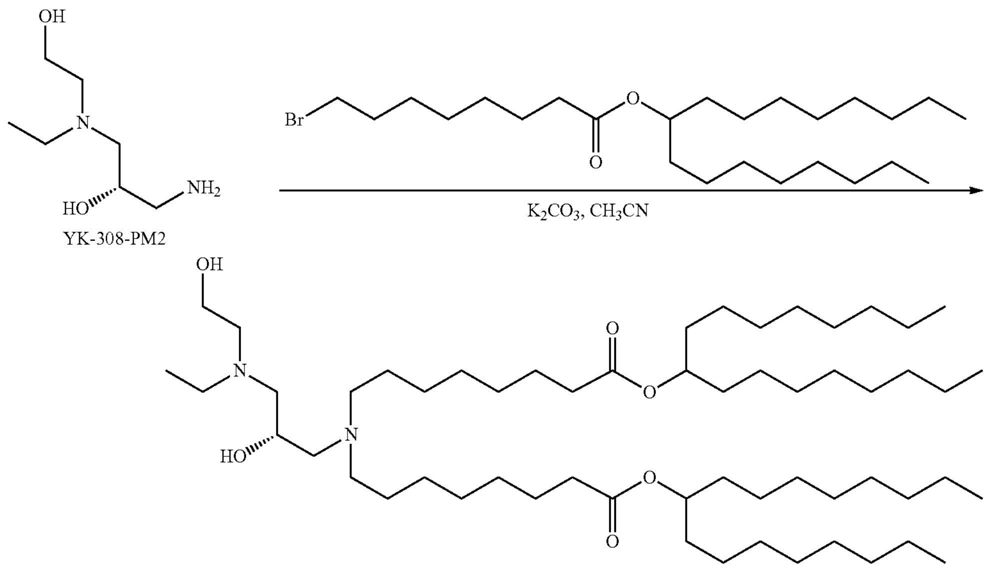

YK-308-PM2

YK-314

Synthesis of (S)-bis(heptadecan-9-yl)-8,8'-(((2-hydroxyethyl)(ethyl)amino)propyl) azanediyl)dioctanoate (YK-314)

According to the method for preparing YK-301-PM4, YK-308-PM2 (60 mg, 0.37 mmol) and heptadecan-9-yl 8-bromooctanoate (512 mg, 1.11 mmol) were used as raw materials, to obtain YK-314 (120 mg, 0.13 mmol, 35.1%). $C_{57}H_{114}N_2O_6$, MS(ES): m/z(M+H$^+$)923.9.

$^1$H NMR (400 MHz, Chloroform-d) δ 4.86 (p, J=6.1 Hz, 2H), 3.87 (s, 1H), 3.64 (t, J=5.1 Hz, 2H), 2.78-2.68 (m, 4H), 2.66-2.35 (m, 8H), 2.27 (t, J=7.5 Hz, 4H), 1.65-1.57 (m, 4H), 1.50 (s, 12H), 1.29 (d, J=22.9 Hz, 62H), 1.09 (t, J=7.0 Hz, 3H), 0.88 (t, J=6.6 Hz, 12H).

10. Synthesis of YK-316

The synthesis route is as follows:

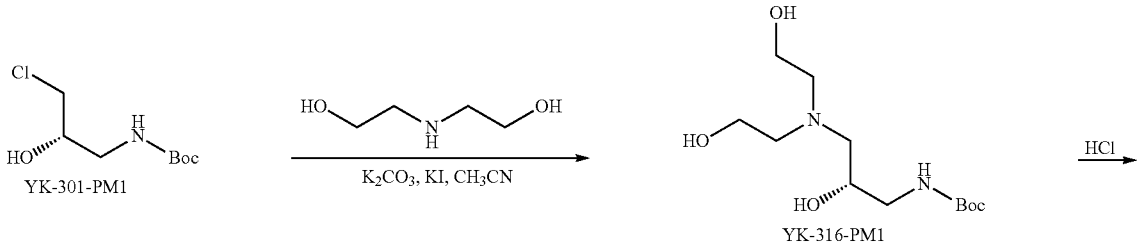

YK-301-PM1

YK-316-PM1

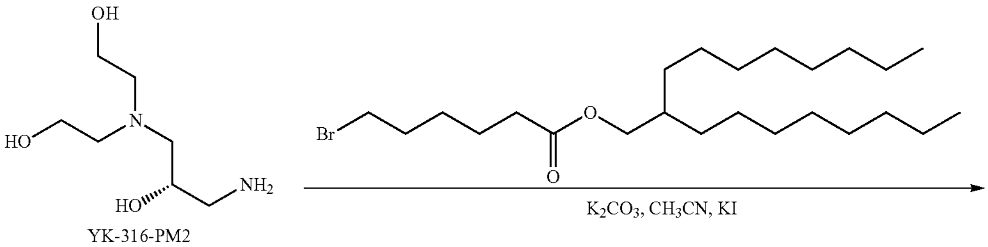

YK-316-PM2

-continued

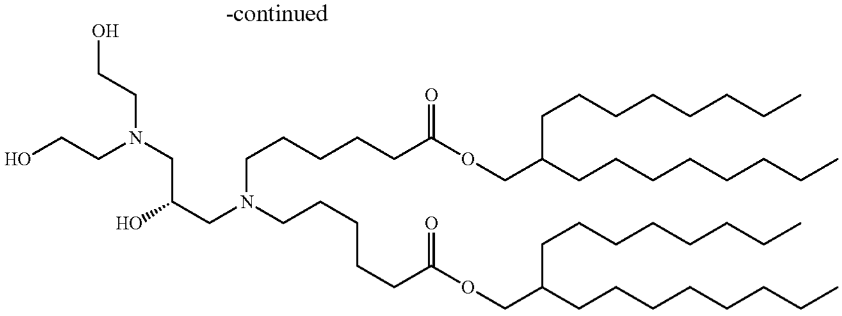

YK-316

Step 1: Synthesis of tert-butyl (S)-((3-(bis(2-hydroxyethyl)amino)-2-hydroxypropyl)carbamate (YK-316-PM1)

According to the method for preparing YK-301-PM2, YK-301-PM1 (1.0 g, 4.78 mmol) and bishydroxyethylamine (452 mg, 4.30 mmol) were used as raw materials, to obtain YK-316-PM1 (550 mg, 1.98 mmol, 46.0%), $C_{12}H_{26}N_2O_5$, MS(ES): m/z(M+H$^+$)279.2.

Step 2: Synthesis of (S)-1-amino-3-(bis(2-hydroxyethyl)amino)-2-propanol (YK-316-PM2)

According to the method for preparing YK-301-PM3, YK-316-PM1 (200 mg, 0.72 mmol) was used as raw materials, to obtain YK-316-PM2 (128 mg, 0.72 mmol, 100%), $C_7H_{18}N_2O_3$, MS(ES): m/z(M+H$^+$)179.1.

Step 3: Synthesis of (S)-bis(2-octyldecyl)-6,6'-(((3-(bis(2-hydroxyethyl)amino)-2-hydroxypropyl) azanediyl))dihexanoate (YK-316)

According to the method for preparing YK-301, YK-316-PM2 (64 mg, 0.36 mmol) and 2-octyldecyl 6-bromohexanoate (160 mg, 0.36 mmol) were used as raw materials, to obtain YK-316 (90 mg, 0.10 mmol, 27.4%). $C_{55}H_{110}N_2O_7$, MS(ES): m/z(M+H$^+$)911.8.

$^1$H NMR (400 MHz, Chloroform-d) δ 3.96 (d, J=5.8 Hz, 4H), 3.71 (s, 4H), 3.09-2.77 (m, 10H), 2.33 (t, J=7.2 Hz, 4H), 1.66 (dd, J=15.3, 7.5 Hz, 6H), 1.27 (s, 69H), 0.88 (t, J=6.8 Hz, 12H).

11. Synthesis of YK-317

The synthesis route is as follows:

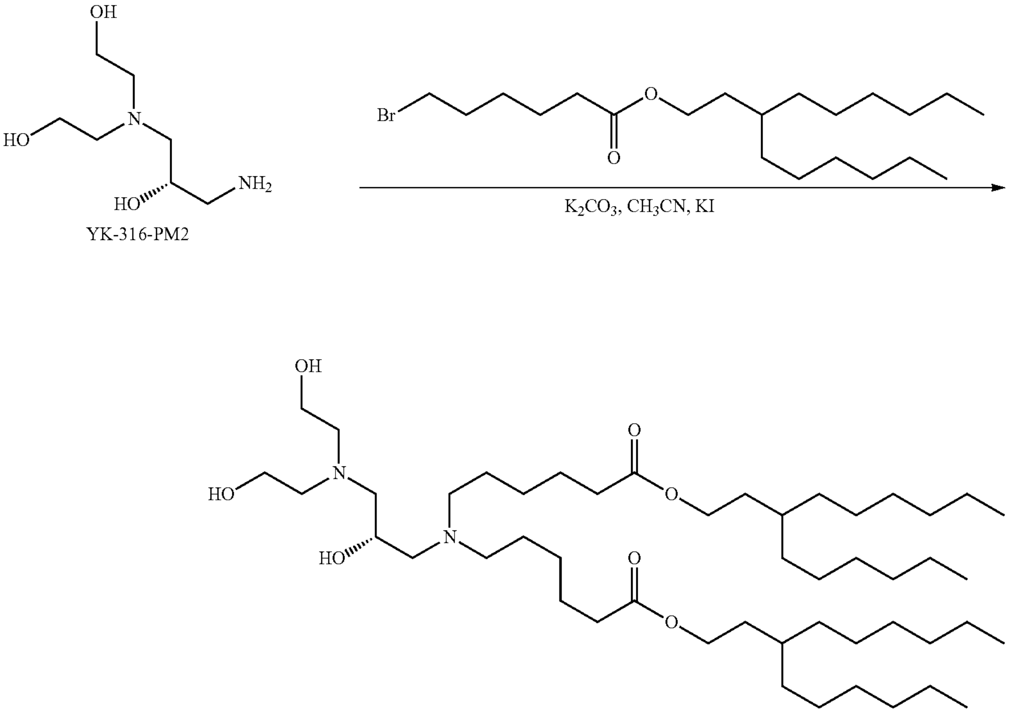

YK-317

Synthesis of (S)-Bis(3-hexylnonyl)-6,6'-((3-(bis(2-hydroxyethyl)amino)-2-hydroxypropyl)azanediyl) dihexanoate (YK-317)

According to the method for preparing YK-301, YK-316-PM2 (105 mg, 0.59 mmol) and 3-hexylnonyl 6-bromo-hexanoate (500 mg, 1.23 mmol) were used as raw materials, to obtain YK-317 (270 mg, 0.33 mmol, 55.3%). $C_{49}H_{98}N_2O_7$, MS(ES): m/z(M+H$^+$)827.7.

$^1$H NMR (400 MHz, Chloroform-d) δ 4.08 (t, J=6.9 Hz, 4H), 3.67 (s, 4H), 3.48 (s, 2H), 2.64 (dd, J=34.4, 20.4 Hz, 12H), 2.30 (t, J=7.2 Hz, 4H), 1.60 (dt, J=31.5, 6.9 Hz, 12H), 1.28 (d, J=19.3 Hz, 48H), 0.88 (t, J=6.2 Hz, 12H).

12. Synthesis of YK-318

The synthesis route is as follows:

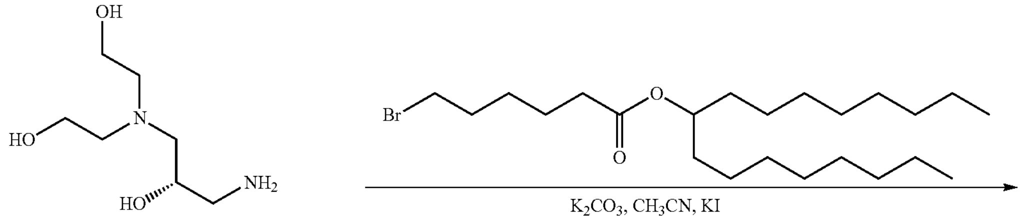

YK-316-PM2

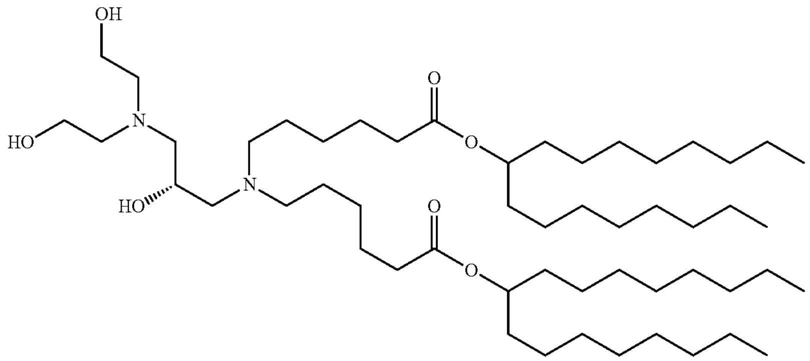

YK-318

Synthesis of (S)-bis(heptadecan-9-yl)-6,6'-((3-(bis(2-hydroxyethyl)amino)-2-hydroxypropyl)azanediyl) dihexanoate (YK-318)

According to the method for preparing YK-301, YK-316-PM2 (125 mg, 0.70 mmol) and heptadecan-9-yl 6-bromo-hexanoate (666 mg, 1.54 mmol) were used as raw materials, to obtain YK-318 (300 mg, 0.34 mmol, 48.5%). $C_{53}H_{106}N_2O_7$, MS(ES): m/z(M+H$^+$)883.8.

$^1$H NMR (400 MHz, Chloroform-d) δ 4.92-4.80 (m, 2H), 3.90 (s, 4H), 3.71-3.62 (m, 2H), 3.62-3.53 (m, 2H), 2.81-2.72 (m, 2H), 2.72-2.48 (m, 9H), 2.29 (t, J=7.3 Hz, 4H), 1.68-1.60 (m, 4H), 1.59-1.44 (m, 12H), 1.26 (s, 53H), 0.88 (t, J=5.5 Hz, 12H).

13. Synthesis of YK-319

The synthesis route is as follows:

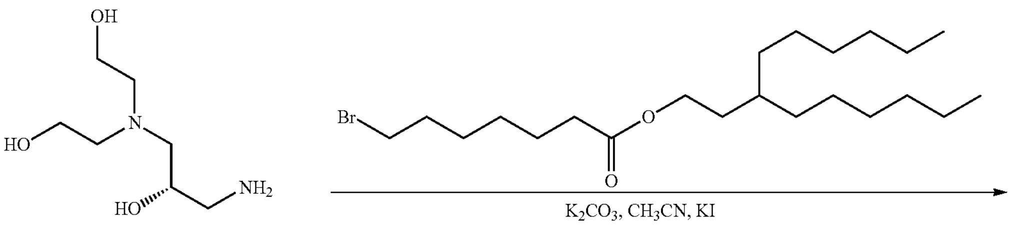

YK-316-PM2

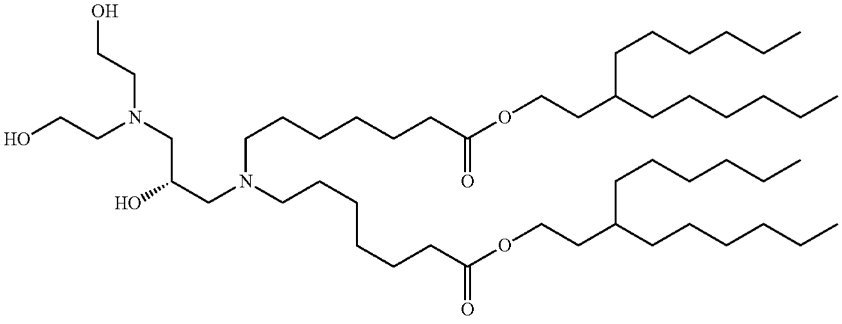

YK-319

Synthesis of (S)-bis(3-hexylnonyl)-7,7'-(((3-(bis(2-hydroxyethyl)amino)-2-hydroxypropyl)azanediyl) diheptanoate (YK-319)

According to the method for preparing YK-301, YK-316-PM2 (34 mg, 0.19 mmol) and 3-hexylnonyl 7-bromoheptanoate (160 mg, 0.38 mmol) were used as raw materials, to obtain YK-319 (40 mg, 0.05 mmol, 24.6%). $C_{51}H_{102}N_2O_7$, MS(ES): m/z(M+H$^+$)855.8.

$^1$H NMR (400 MHz, Chloroform-d) δ 4.08 (t, J=7.1 Hz, 4H), 3.65 (s, 4H), 2.76 (t, J=45.6 Hz, 12H), 2.29 (t, J=7.3 Hz, 4H), 1.74-1.51 (m, 12H), 1.25 (s, 54H), 0.88 (t, J=6.4 Hz, 12H).

14. Synthesis of YK-320

The synthesis route is as follows:

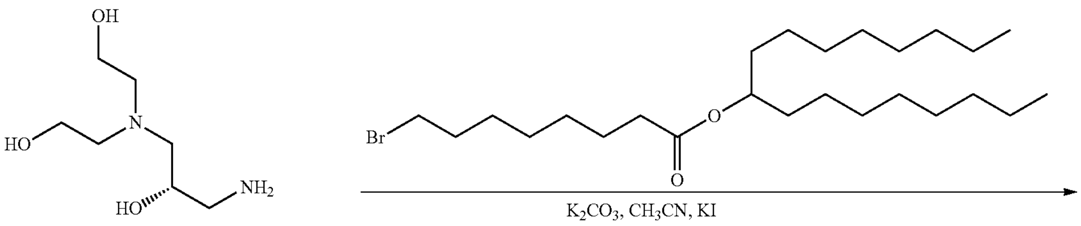

YK-316-PM2

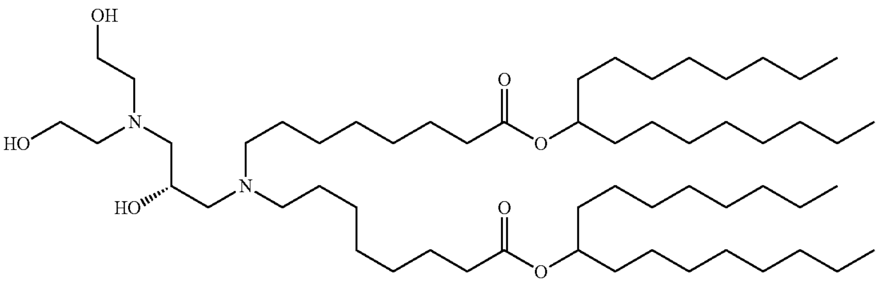

YK-320

Synthesis of (S)-Bis(heptadecan-9-yl)-8,8'-((3-(bis (2-hydroxyethyl)amino)-2-hydroxypropyl)azanediyl) dicaprylate (YK-320)

According to the method for preparing YK-301, YK-316-PM2 (41 mg, 0.23 mmol) and heptadecan-9-yl 8-bromooctanoate (244 mg, 0.53 mmol) were used as raw materials, to obtain YK-320 (150 mg, 0.16 mmol, 69.4%). $C_{57}H_{114}N_2O_7$, MS(ES): m/z(M+H$^+$)939.9.

$^1$H NMR (400 MHz, Chloroform-d) δ 5.30 (s, 1H), 4.85 (p, J=6.0 Hz, 2H), 4.19 (s, 2H), 3.76-3.55 (m, 5H), 2.98-2.60 (m, 10H), 2.28 (t, J=7.4 Hz, 4H), 1.64 (dd, J=15.8, 7.4 Hz, 8H), 1.55-1.46 (m, 8H), 1.30 (d, J=31.6 Hz, 60H), 0.88 (t, J=6.7 Hz, 12H).

15. Synthesis of YK-321

The synthesis route is as follows:

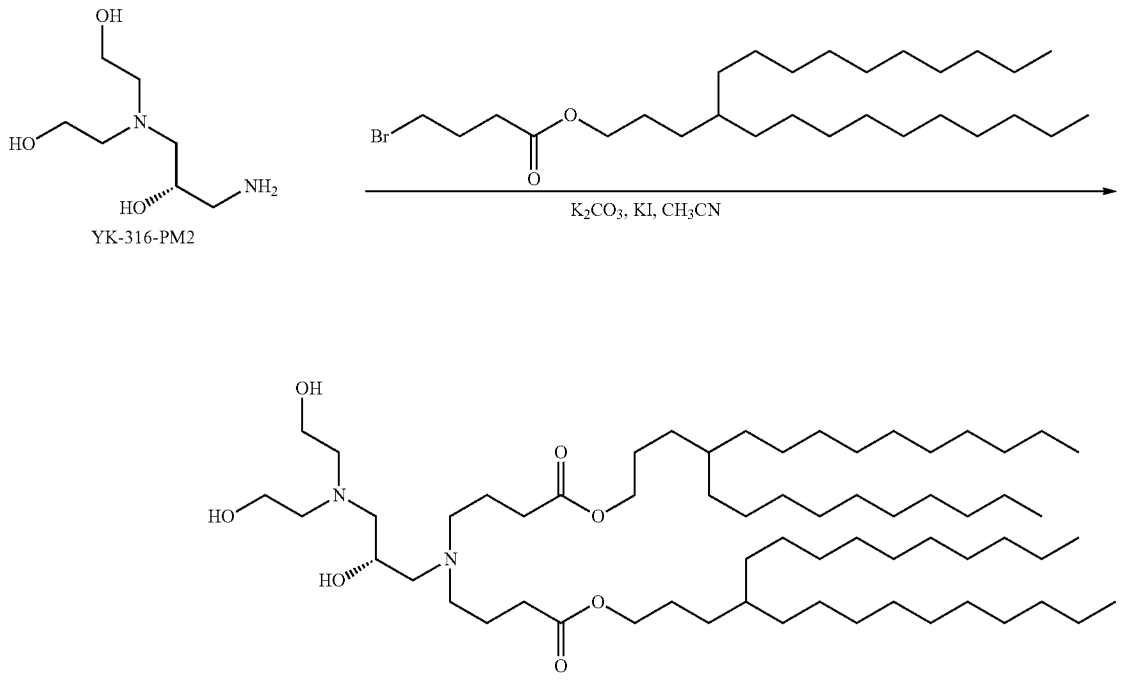

YK-321

Synthesis of (S)-bis(4-decyltetradecyl)-4,4'-((3-(bis (2-hydroxyethyl)amino)-2-hydroxypropyl)azanediyl) dibutyrate (YK-321)

According to the method for preparing YK-301, YK-316-PM2 (41 mg, 0.23 mmol) and 4-decyltetradecyl 4-bromobutyrate (266 mg, 0.53 mmol) were used as raw materials, to obtain YK-321 (85 mg, 0.08 mmol, 36.1%). $C_{63}H_{126}N_2O_7$, MS(ES): m/z(M+H$^+$)1024.0.

$^1$H NMR (400 MHz, Chloroform-d) δ 5.30 (s, 1H), 4.04 (t, J=6.8 Hz, 4H), 3.71 (s, 4H), 2.72 (s, 10H), 2.35 (t, J=6.8 Hz, 4H), 1.89 (s, 4H), 1.63-1.55 (m, 4H), 1.25 (d, J=12.2 Hz, 80H), 0.88 (t, J=6.6 Hz, 12H).

16. Synthesis of YK-009

According to the method in CN114044741B, YK-009 105 mg was obtained.

17. Synthesis of heptadecan-9-yl 8-(8-((3-hexylnonyl)oxy)-8-oxooctyl)-((2-hydroxyethyl)amino) octanoate (compound 21)

The synthesis route is as follows:

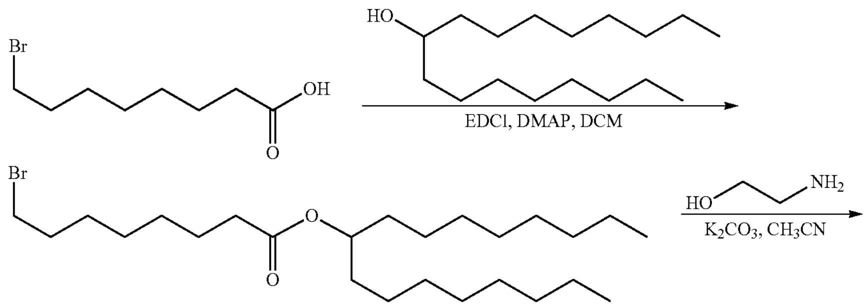

compound21-PM1

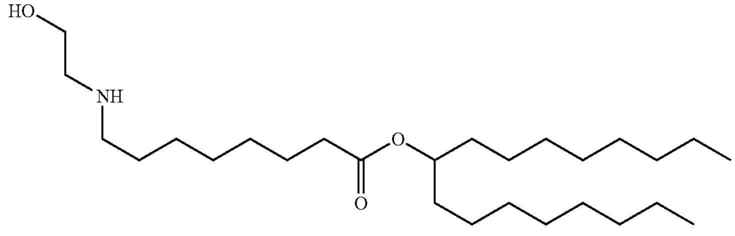

compound21-PM2

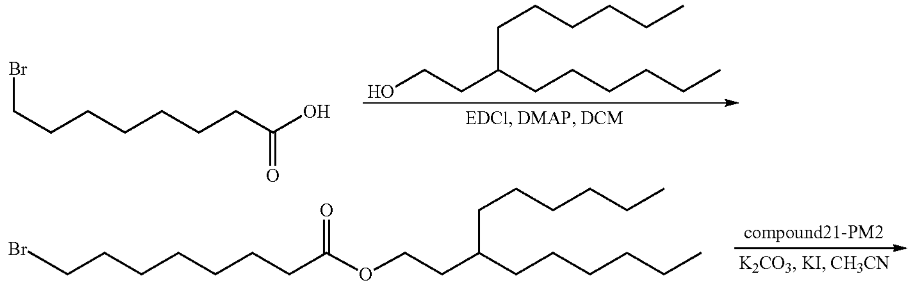

compound21-PM3

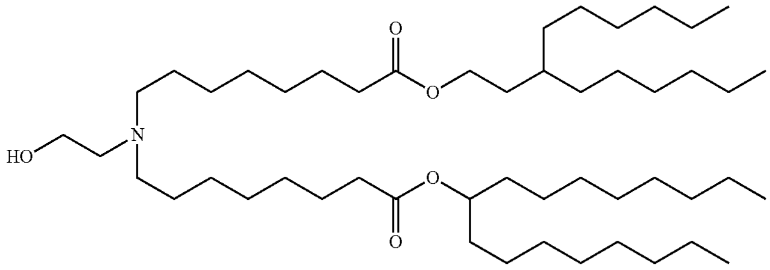

compound21

Step 1: Synthesis of heptadecan-9-yl 8-bromooctanoate (compound 21-PM1)

9-Heptadecanol (1.00 g, 3.90 mmol) and 8-bromooctanoic acid (1.04 g, 4.66 mmol) were dissolved in dichloromethane (10 mL), and 1-(3-dimethylaminopropyl)-3-ethylcarbodiimide hydrochloride (0.90 g, 4.68 mmol) and 4-dimethylaminopyridine (24 mg, 0.20 mmol) were added. The mixture was stirred and reacted at 30-35° C. for 8 hours. After the reaction was completed, the reaction solution was washed with saturated sodium carbonate, saturated brine, and dried over $Na_2SO_4$. The mixture was filtered. The filtrate was concentrated under reduced pressure in vacuo and purified by silica gel chromatography (ethyl acetate/n-hexane) to obtain heptadecan-9-yl 8-bromooctanoate (1.20 g, 2.60 mmol, 66.7%).

Step 2: Synthesis of heptadecan-9-yl 8-((2-hydroxyethyl)amino)octanoate (compound 21-PM2)

Heptadecan-9-yl 8-bromooctanoate (500 mg, 1.08 mmol) and ethanolamine (119 mg, 3.25 mmol) were dissolved in acetonitrile (5 mL), and potassium carbonate (149 mg, 1.08 mmol) was added. The mixture was heated to 70° C. and stirred to react for 2 hours. After the reaction was completed, the reaction solution was cooled to room temperature and then filtered. The filtrate was concentrated under reduced pressure in vacuo to remove the solvent. The residue was purified by silica gel chromatography (methanol/dichloromethane) to give heptadecan-9-yl 8-((2-hydroxyethyl) amino)octanoate (372 mg, 0.84 mmol, 78.0%), $C_{27}H_{55}NO_3$, MS(ES): m/z(M+H$^+$)442.3.

Step 3: Synthesis of 3-hexylnonyl 8-bromooctanoate (compound 21-PM3)

According to the method for preparing compound 21-PM1, 3-hexylnonanol (1.00 g, 4.38 mmol) and 8-bromooctanoic acid (1.17 g, 5.25 mmol) were used as raw materials and purified by silica gel chromatography (ethyl acetate/n-hexane) to give 3-hexylnonyl 8-bromooctanoate (1.62 g, 3.74 mmol, 85.3%).

Step 4: Synthesis of heptadecan-9-yl 8-(8-((3-hexylnonyl)oxy)-8-oxooctyl)-((2-hydroxyethyl)amino) octanoate (compound 21)

Heptadecan-9-yl 8-((2-hydroxyethyl)amino)octanoate (200 mg, 0.46 mmol) and 3-hexylnonyl 8-bromooctanoate (336 mg, 0.82 mmol) were dissolved in acetonitrile (6 mL), and potassium carbonate (254 mg, 1.84 mmol) and potassium iodide (8.3 mg, 0.05 mmol) were added. The mixture was heated to 70° C. and stirred to react for 20 hours. The reaction solution was cooled to room temperature and then filtered. The filtrate was concentrated under reduced pressure in vacuo to remove the solvent. The residue was purified by silica gel chromatography (ethyl acetate/n-hexane) to obtain the target compound (213 mg, 0.27 mmol, 58.4%). $C_{50}H_{99}NO_5$, MS(ES): m/z(M+H$^+$)794.8.

$^1$H NMR (400 MHz, $CDCl_3$) δ 4.90 (p, J=6.3 Hz, 1H), 4.21-4.02 (m, 2H), 3.66 (s, 2H), 2.73 (s, 2H), 2.60 (s, 4H), 2.43-2.20 (m, 4H), 2.12-1.99 (m, 1H), 1.75-1.49 (m, 13H), 1.48-1.39 (m, 2H), 1.42-1.15 (m, 56H), 0.92 (td, J=6.8, 2.2 Hz, 12H).

18. Synthesis of bis(3-hexylnonyl)-8,8'-((2-hydroxyethyl)azanediyl)dioctanoate (compound 23)

The synthesis route is as follows:

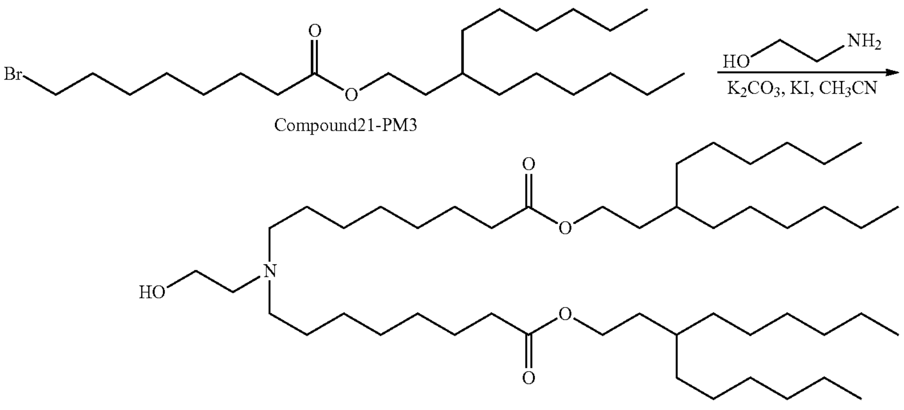

Compound23

3-Hexylnonyl 8-bromooctanoate (710 mg, 1.64 mmol) and ethanolamine (40 mg, 0.66 mmol) were dissolved in acetonitrile (10 mL). Potassium carbonate (1.09 g, 7.92 mmol) and potassium iodide (66 mg, 0.39 mmol) were added to the above system and the mixture was heated to 70° C. and stirred to react for 2 hours. After the reaction was completed, the reaction solution was cooled to room temperature and then filtered. The filtrate was concentrated under reduced pressure in vacuum to remove the solvent. The residue was purified by silica gel chromatography (methanol/dichloromethane) to obtain bis(3-hexylnonyl)-8,8'-((2-hydroxyethyl)azanediyl)dioctanoate (150 mg, 0.20 mmol, 29.7%), $C_{48}H_{95}NO_5$, MS(ES): m/z(M+H$^+$)766.5.

$^1$H NMR (400 MHz, $CDCl_3$) δ 4.12 (t, J=7.1 Hz, 4H), 3.62 (s, 2H), 2.68 (s, 2H), 2.51 (d, J=25.8 Hz, 4H), 2.32 (t, J=7.5 Hz, 4H), 1.72-1.57 (m, 8H), 1.55-1.40 (m, 6H), 1.40-1.17 (m, 55H), 0.92 (t, J=6.8 Hz, 12H).

Example 2: Optimization of Preparation Conditions for Lipid Nanoparticles (LNP Formulations)

1. Optimization of the Ratio of Carrier (Liposome) to mRNA

YK-305

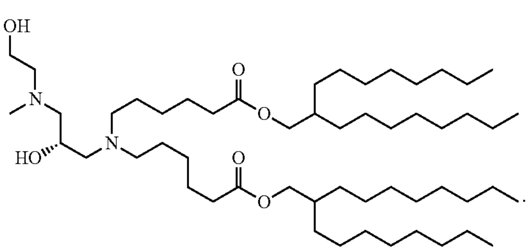

The cationic lipid compound YK-305 synthesized in Example 1 was dissolved in ethanol with DSPC (AVT (Shanghai) Pharmaceutical Technology Co., Ltd.), cholesterol (AVT (Shanghai) Pharmaceutical Technology Co., Ltd.) and DMG-PEG2000 according to a molar ratio of 49:10:39.5:1.5, respectively, to prepare an ethanol lipid solution. The ethanol lipid solution was quickly added to citrate buffer (pH=4-5) by ethanol injection method, and vortexed for 30 s for later use. eGFP-mRNA was diluted in citrate buffer (pH=4-5) to give an aqueous mRNA solution. A certain volume of liposome solution and mRNA aqueous solution were used to prepare liposomes at weight ratios of total lipids to mRNA of 5:1, 10:1, 15:1, 20:1, 30:1 and 35:1, respectively. The mixtures were sonicated at 25° C. for 15 min (with an ultrasonic frequency of 40 kHz and an ultrasonic power of 800 W). The resulting liposomes were diluted to 10 times volume with PBS, and then ultrafiltered with a 300 KDa ultrafiltration tube to remove ethanol. Then the volume was fixed to a certain volume with PBS to give an LNP formulation encapsulating eGFP-mRNA using cationic lipid YK-305/DSPC/cholesterol/DMG-PEG2000 (49:10:39.5:1.5 in molar percentage).

The results of the cell transfection test showed that when the weight ratio of carrier to mRNA was in the range of 10:1-30:1, all the transfection effects were good, wherein the ratio of 15:1 had the best transfection effect, and when the weight ratio of carrier to mRNA was 5:1 and 35:1, the transfection effect was poor, which could not be used to carry mRNA. (FIG. 1)

The same results were obtained with LNP formulations prepared from YK-310, YK-312, YK-319 and YK-318, which are not shown in the figures.

2. Optimization of the Ratio of Cationic Lipid to Neutral Lipid

The LNP formulation encapsulating eGFP-mRNA was prepared according to the method in 1, wherein the molar ratios of cationic lipid YK-305 and neutral lipid DSPC were 1:1, 3:1, 3.5:1, 4:1, 4.5:1, 4.9:1, 10:1, 15:1 and 20:1, respectively.

Figure 2:
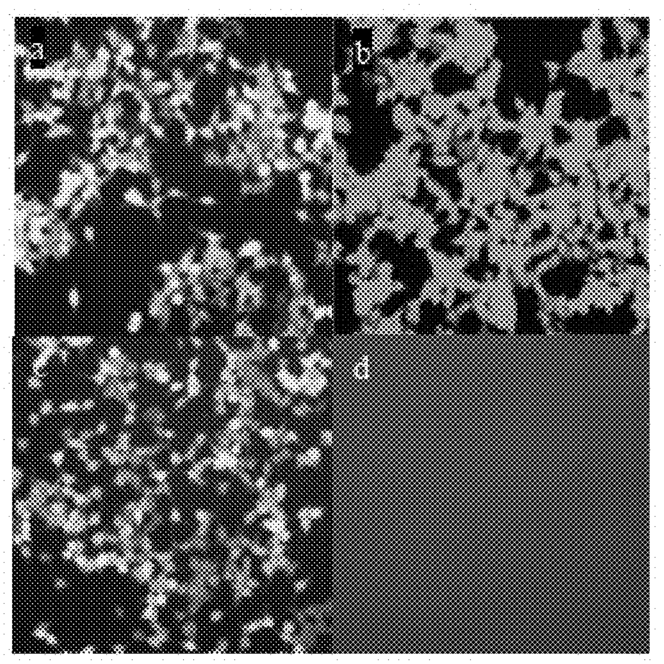
FIG. 2 shows the results of cell transfection tests with different molar ratios of the cationic lipid to the neutral lipid DSPC used in the preparation of LNP formulations, wherein a is 3.5:1, b is 4.5:1, c is 4.9:1, and d is a blank control.

It can be seen from the cell transfection test that when the molar ratio of cationic lipid to neutral lipid was 1:1 to 15:1, the transfection effect could all be achieved, wherein the transfection efficiency was the highest at the molar ratio of cationic lipid to neutral lipid of 4.5:1, and the ratio of 3.5:1 and 4.9:1 also had good transfection efficiency. (FIG. 2)

The same results were obtained with LNP formulations prepared from YK-310, YK-312, YK-319 and YK-318, which are not shown in the figures.

3. Optimization of the Ratio of Polymer-Conjugated Lipid to Carrier (Liposome)

The LNP formulation encapsulating eGFP-mRNA was prepared according to the method in 1, wherein the cationic lipid in the carrier was YK-305, and the molar ratios of the polymer-conjugated lipid DMG-PEG2000 to the carrier were 0.5%, 1.5%, 3.5%, 5%, 10% and 15%, respectively.

Figure 3:
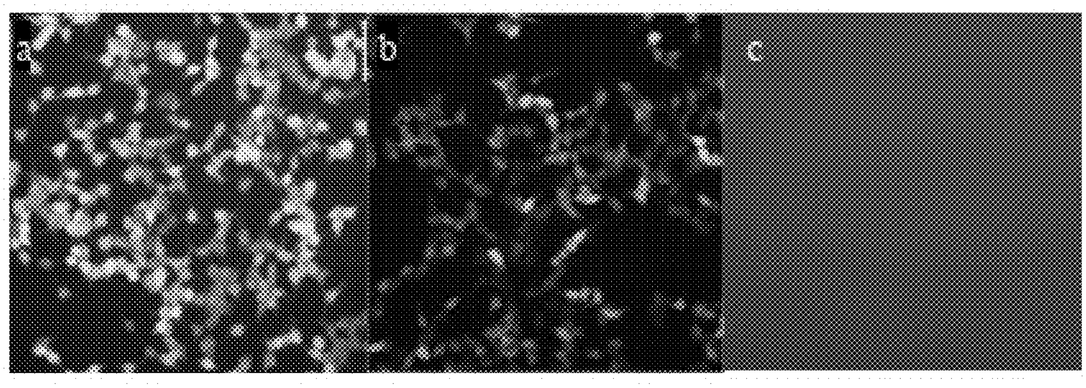
FIG. 3 shows the results of cell transfection tests with different molar ratios of polymer-conjugated lipid to carrier in the preparation of LNP formulations, wherein a is 1.5%, b is 10%, and c is a blank control.

The results of the cell transfection test showed that when the molar ratio of the polymer-conjugated lipid to the carrier was in the range of 0.5% to 5%, the transfection effect could be achieved, wherein the transfection efficiency was the highest when the molar ratio was 1.5%, and the lowest when the molar ratio was 10%. (FIG. 3)

The same results were obtained with LNP formulations prepared from YK-310, YK-312, YK-319 and YK-318, which are not shown in the figures.

4. Optimization of the Proportion of Components in the Carrier (Liposome)

The LNP formulation encapsulating eGFP-mRNA was prepared according to the method in 1, wherein the molar ratios of cationic lipid YK-305, neutral lipid DSPC, structured lipid cholesterol and polymer-conjugated lipid DMG-PEG2000 were 75:5:15:5, 49:10:39.5:1.5, 45:10:43.5:1.5, 45:25:20:10, 40:10:48.5:1.5, 35:10:53.5:1.5 and 25:5:65:5, respectively.

Figure 4:
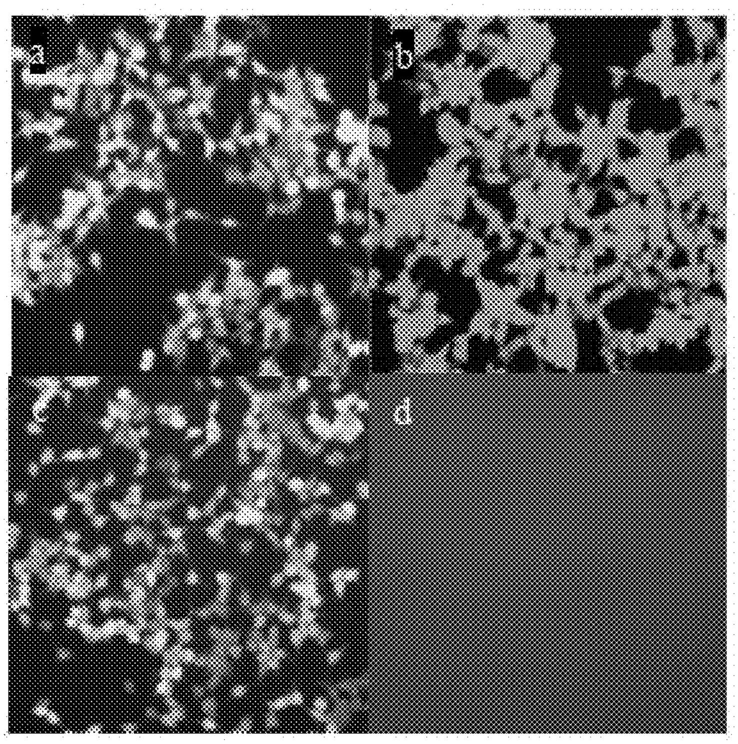
FIG. 4 shows the results of cell transfection tests with different ratios of the cationic lipid, the neutral lipid DSPC, the structural lipid cholesterol and the polymer-conjugated lipid DMG-PEG2000 in the carrier in the preparation of LNP formulations, wherein a is 35:10:53.5:1.5, b is 45:10:43.5:1.5, c is 49:10:39.5:1.5, and dis a blank control.

It can be seen from the cell transfection test that transfection was accessible when the molar ratios of cationic lipid, neutral lipid, structured lipid and polymer-conjugated lipid were 75:5:15:5, 49:10:39.5:1.5, 45:10:43.5:1.5, 45:25:20:10, 40:10:48.5:1.5, 35:10:53.5:1.5 and 25:5:65:5. It has good transfection effect within the ratio of (35 to 49):(7.5 to 15):(35 to 55):(1 to 5), among which the ratio of 45:10:43.5:1.5 has the best transfection effect (FIG. 4), showing that it is available to prepare LNP formulations when the molar ratio of cationic lipid, neutral lipid, structured lipid and polymer conjugated lipid is within the range of (25~75):(5~25):(15~65):(0.5~10), and the preferred ratio is (35 to 49):(7.5 to 15):(35 to 55):(1 to 5), among which the optimal ratio is 45:10:43.5:1.5.

The same results were obtained with LNP formulations prepared from YK-310, YK-312, YK-319 and YK-318, which are not shown in the figures.

Examples 3: Cell Transfection Test of LNP Formulation of eGFP-mRNA

Cell recovery and passage: 293T cells were recovered, cultured in a culture dish, and passaged to the required number of cells.

Seeding plate: The cells in the culture dish were digested and counted. Cells were spread in a 96-well plate at 10,000 cells per well and in a 12-well plate at 150,000 cells per well. Cells were cultured overnight until the cells adhered to the wall.

Cell transfection test: The LNP formulation containing 1.5 g of eGFP-mRNA prepared in Example 2 (the cationic lipid in the carrier was YK-305) and the Lipofectamin 3000 formulation of eGFP-mRNA were added respectively to the cell culture medium of the 12-well plate, and further incubated for 24 hours. The transfection efficiency of different samples was then investigated according to the fluorescence intensity by observing with a fluorescence microscope.

According to the results of the test, the preparation conditions of lipid nanoparticles (LNP formulation) were finally determined: the weight ratio of carrier to mRNA was 15:1; the molar ratio of cationic lipid to neutral lipid was 4.9:1; the molar ratio of polymer-conjugated lipid to liposome is 1.5%; the molar ratio of cationic lipid, neutral lipid, structured lipid and polymer-conjugated lipid was 49:10:39.5:1.5, at which various cationic lipids designed in this application and the cationic lipids used in the prior art all had good transfection effects (determined by Example 2, some test results are not shown). This condition was used to prepare lipid nanoparticles (LNP formulation) in subsequent tests.

Example 4: Preparation of Lipid Nanoparticles (LNP Formulation) (Optimal Ratio)
TABLE 1
| The structure of cationic lipids | | |
|---|---|---|
| Name | Structure | Remark |
| YK-301 | 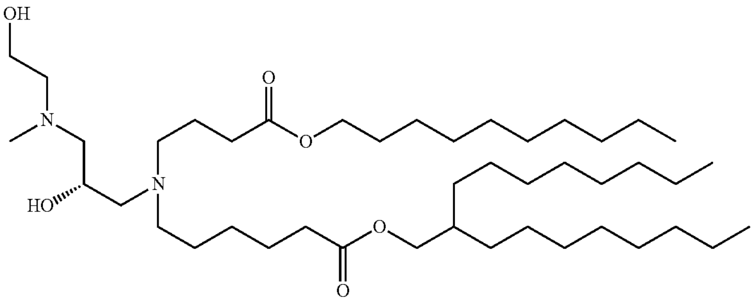 [SMILES: CCCCCCCCCCOC(=O)CCCN(CCCCCC(=O)OCC(CCCCCCCC)CCCCCCCC)C[C@H](O)CN(C)CCO] YK-301 | Synthesized in Example 1 |
| YK-302 | 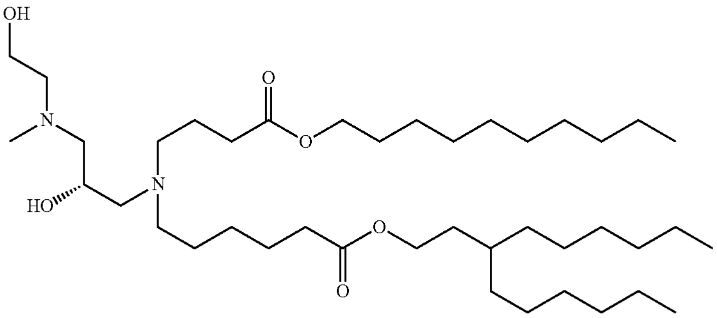 [SMILES: CCCCCCCCCCOC(=O)CCCN(CCCCCC(=O)OCCC(CCCCCC)CCCCCC)C[C@H](O)CN(C)CCO] YK-302 | Synthesized in Example 1 |
| YK-303 | 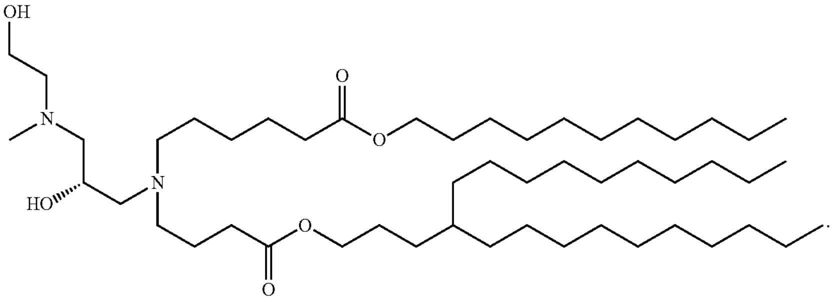 [SMILES: CCCCCCCCCCCOC(=O)CCCCCN(CCCC(=O)OCCCC(CCCCCCCCCC)CCCCCCCCCC)C[C@H](O)CN(C)CCO] YK-303 | Synthesized in Example 1 |
| YK-304 | 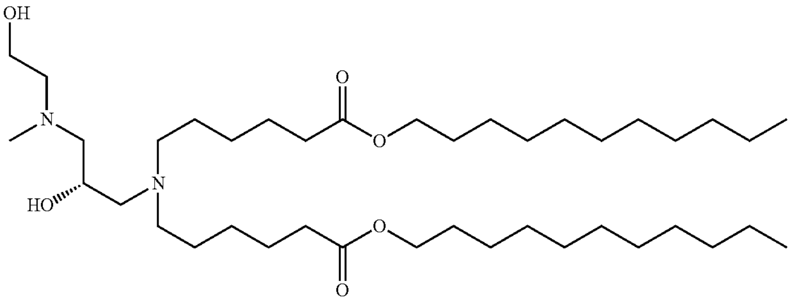 [SMILES: CCCCCCCCCCCOC(=O)CCCCCN(CCCCCC(=O)OCCCCCCCCCCC)C[C@H](O)CN(C)CCO] YK-304 | Synthesized in Example 1 |

TABLE 1-continued
| The structure of cationic lipids | | |
|---|---|---|
| Name | Structure | Remark |
| YK-305 | 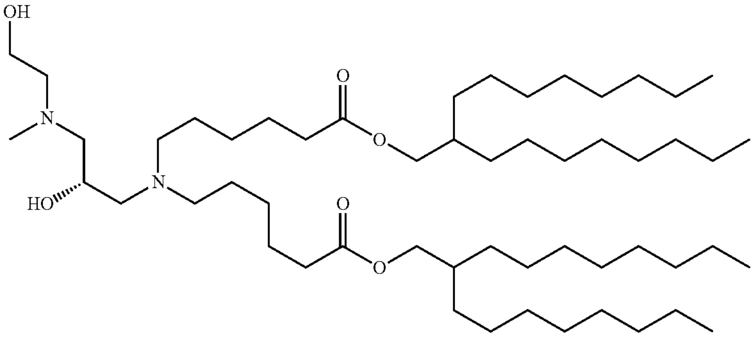 [SMILES: CCCCCCCCC(CCCCCCCC)COC(=O)CCCCCN(CCCCCC(=O)OCC(CCCCCCCC)CCCCCCCC)C[C@H](O)CN(C)CCO] YK-305 | Synthesized in Example 1 |
| YK-306 | 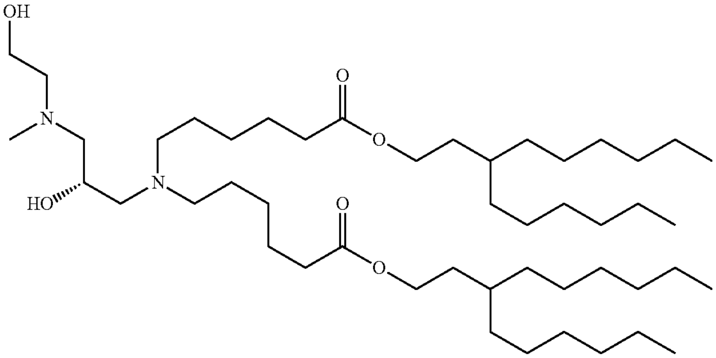 [SMILES: CCCCCCC(CCCCCC)CCOC(=O)CCCCCN(CCCCCC(=O)OCCC(CCCCCC)CCCCCC)C[C@H](O)CN(C)CCO] YK-306 | Synthesized in Example 1 |
| YK-307 | 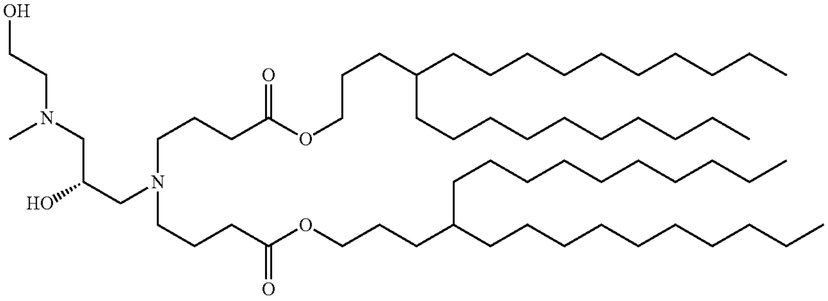 [SMILES: CCCCCCCCCCC(CCCCCCCCCC)CCCOC(=O)CCCN(CCCC(=O)OCCCC(CCCCCCCCCC)CCCCCCCCCC)C[C@H](O)CN(C)CCO] YK-307 | Synthesized in Example 1 |
| YK-308 | 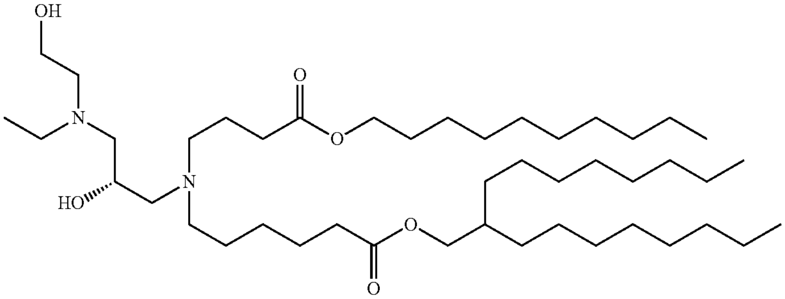 [SMILES: CCCCCCCCCCOC(=O)CCCN(CCCCCC(=O)OCC(CCCCCCCC)CCCCCCCC)C[C@H](O)CN(CC)CCO] YK-308 | Synthesized in Example 1 |

TABLE 1-continued
| The structure of cationic lipids | | |
|---|---|---|
| Name | Structure | Remark |
| YK-309 | 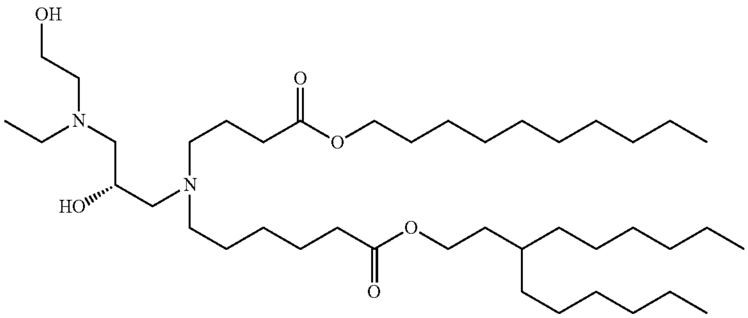 [SMILES: CCCCCCCCCCOC(=O)CCCN(CCCCCC(=O)OCCC(CCCCCC)CCCCCC)C[C@H](O)CN(CC)CCO] YK-309 | Synthesized in Example 1 |
| YK-310 | 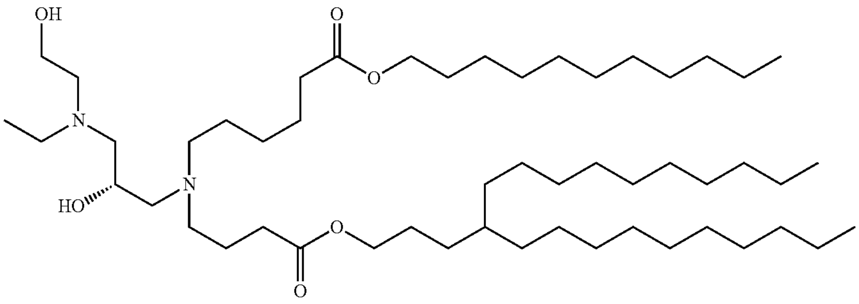 [SMILES: CCCCCCCCCCCOC(=O)CCCCCN(CCCC(=O)OCCCC(CCCCCCCCCC)CCCCCCCCCC)C[C@H](O)CN(CC)CCO] YK-310 | Synthesized in Example 1 |
| YK-311 | 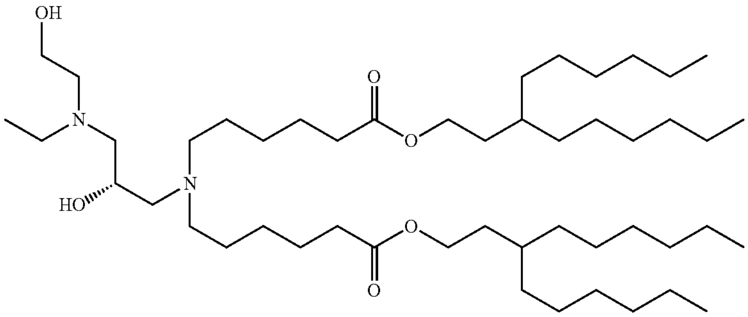 [SMILES: CCCCCCC(CCCCCC)CCOC(=O)CCCCCN(CCCCCC(=O)OCCC(CCCCCC)CCCCCC)C[C@H](O)CN(CC)CCO] YK-311 | Synthesized in Example 1 |
| YK-312 | 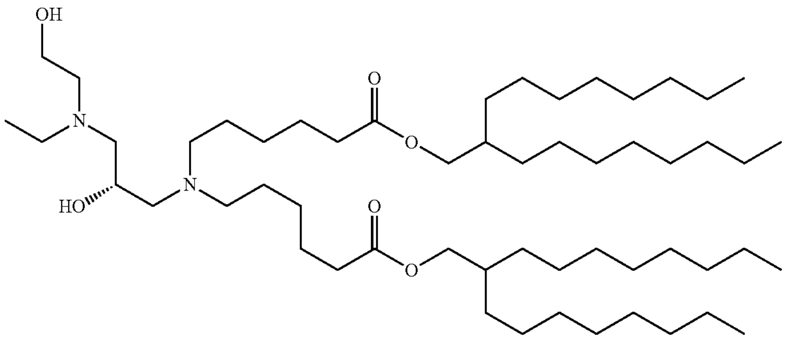 [SMILES: CCCCCCCCC(CCCCCCCC)COC(=O)CCCCCN(CCCCCC(=O)OCC(CCCCCCCC)CCCCCCCC)C[C@H](O)CN(CC)CCO] YK-312 | Synthesized in Example 1 |

TABLE 1-continued
| The structure of cationic lipids | | |
|---|---|---|
| Name | Structure | Remark |
| YK-313 | 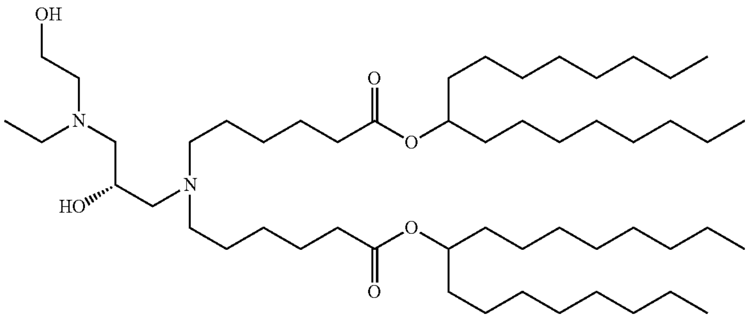 [SMILES: CCCCCCCCC(CCCCCCCC)OC(=O)CCCCCN(CCCCCC(=O)OC(CCCCCCCC)CCCCCCCC)C[C@H](O)CN(CC)CCO] YK-313 | Synthesized in Example 1 |
| YK-314 | 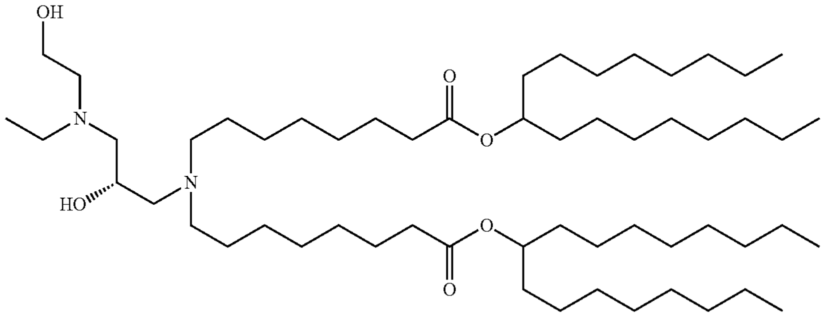 [SMILES: CCCCCCCCC(CCCCCCCC)OC(=O)CCCCCCCN(CCCCCCCC(=O)OC(CCCCCCCC)CCCCCCCC)C[C@H](O)CN(CC)CCO] YK-314 | Synthesized in Example 1 |
| YK-315 | 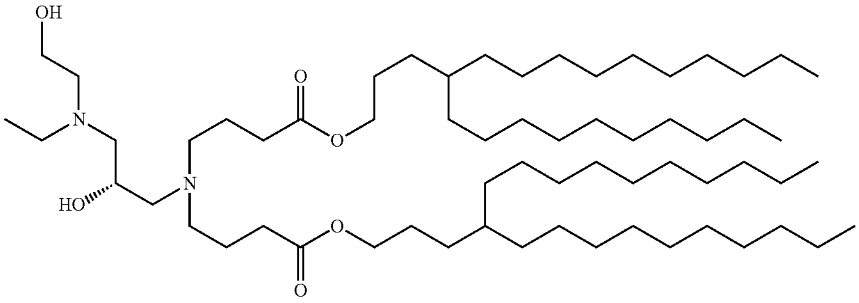 [SMILES: CCCCCCCCCCC(CCCCCCCCCC)CCCOC(=O)CCCN(CCCC(=O)OCCCC(CCCCCCCCCC)CCCCCCCCCC)C[C@H](O)CN(CC)CCO] YK-315 | Synthesized in Example 1 |
| YK-316 | 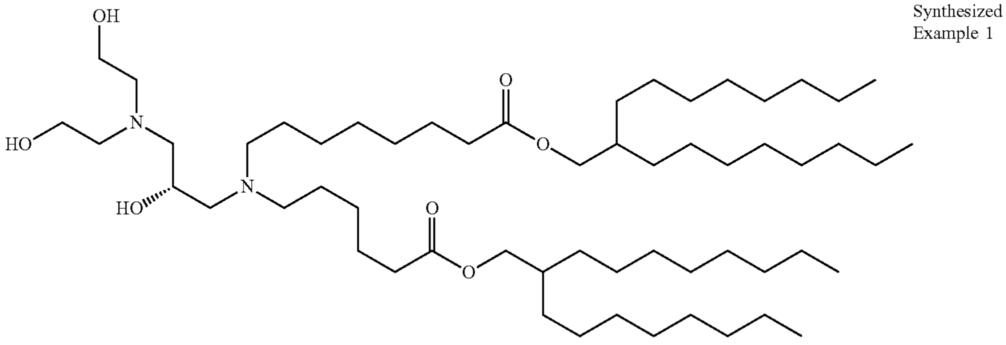 YK-316 | Synthesized in Example 1 |

TABLE 1-continued
| The structure of cationic lipids | | |
|---|---|---|
| Name | Structure | Remark |
| YK-317 | 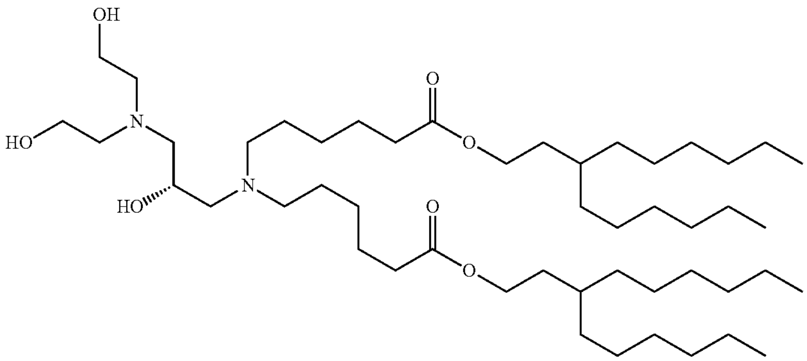 [SMILES: CCCCCCC(CCCCCC)CCOC(=O)CCCCCN(CCCCCC(=O)OCCC(CCCCCC)CCCCCC)C[C@H](O)CN(CCO)CCO] YK-317 | Synthesized in Example 1 |
| YK-318 | 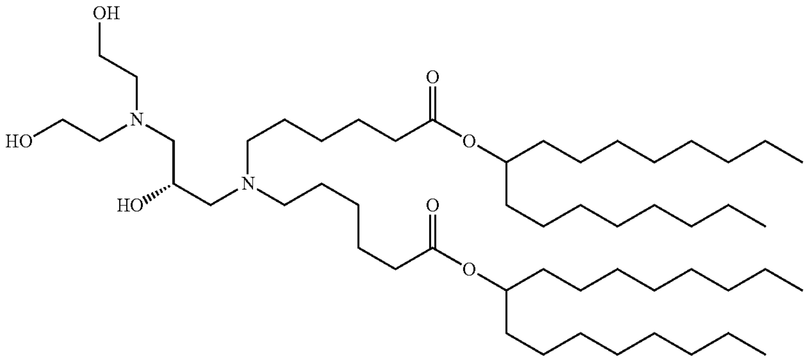 [SMILES: CCCCCCCCC(CCCCCCCC)OC(=O)CCCCCN(CCCCCC(=O)OC(CCCCCCCC)CCCCCCCC)C[C@H](O)CN(CCO)CCO] YK-318 | Synthesized in Example 1 |
| YK-319 | 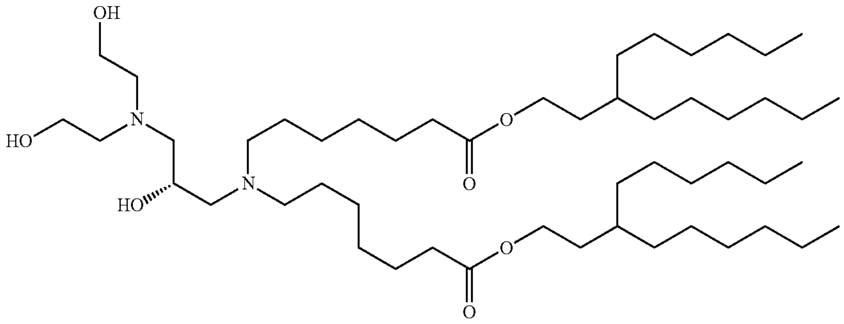 [SMILES: CCCCCCC(CCCCCC)CCOC(=O)CCCCCCN(CCCCCCC(=O)OCCC(CCCCCC)CCCCCC)C[C@H](O)CN(CCO)CCO] YK-319 | Synthesized in Example 1 |
| YK-320 | 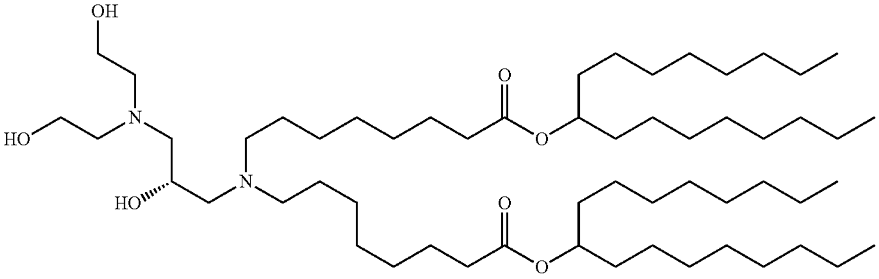 [SMILES: CCCCCCCCC(CCCCCCCC)OC(=O)CCCCCCCN(CCCCCCCC(=O)OC(CCCCCCCC)CCCCCCCC)C[C@H](O)CN(CCO)CCO] YK-320 | Synthesized in Example 1 |

TABLE 1-continued
| The structure of cationic lipids | | |
|---|---|---|
| Name | Structure | Remark |
| YK-321 | 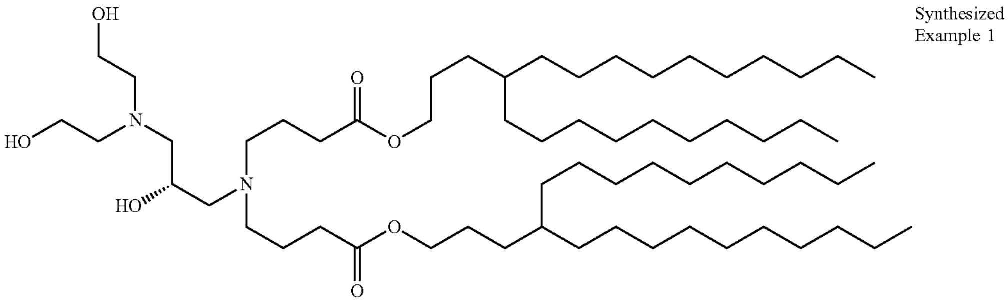 YK-321 | Synthesized in Example 1 |
| YK-009 | 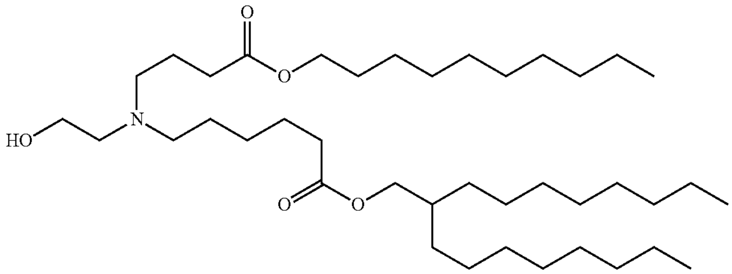 [SMILES: CCCCCCCCCCOC(=O)CCCN(CCO)CCCCCC(=O)OCC(CCCCCCCC)CCCCCCCC] YK-009 | Synthesized in Example 1, which is YK-009 in CN114044741B |
| Compound 21 | 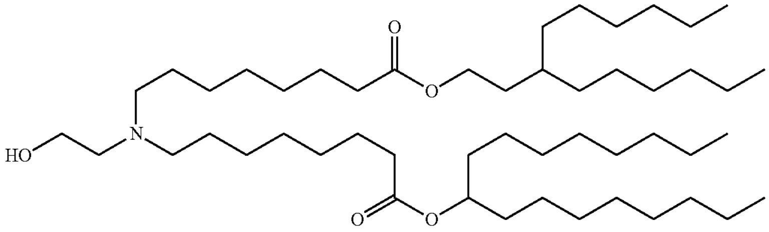 [SMILES: CCCCCCCCC(CCCCCCCC)OC(=O)CCCCCCCN(CCO)CCCCCCCC(=O)OCCC(CCCCCC)CCCCCC] Compound 21 | Synthesized in Example 1, which is compound 21 in WO2021055833 A1 |
| Compound 23 | 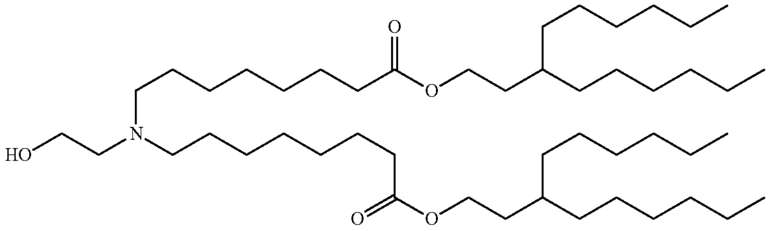 [SMILES: CCCCCCC(CCCCCC)CCOC(=O)CCCCCCCN(CCO)CCCCCCCC(=O)OCCC(CCCCCC)CCCCCC] Compound 23 | Synthesized in Example 1, which is compound 23 in WO2021055833 A1 |
| SM-102 | 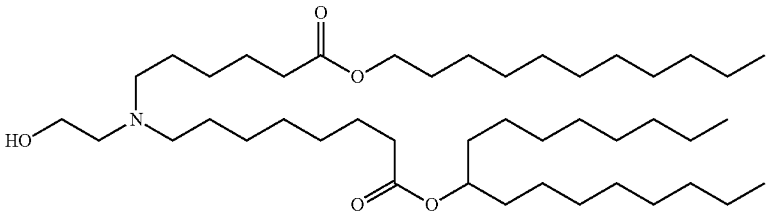 [SMILES: CCCCCCCCCCCOC(=O)CCCCCN(CCO)CCCCCCCC(=O)OC(CCCCCCCC)CCCCCCCC] SM-102 | Purchased from XiaMen Sinopeg Biotech Co., LTD, which is compound 25 in WO2017049245 A2 |

TABLE 1-continued

| The structure of cationic lipids | | |
|---|---|---|
| Name | Structure | Remark |
| ALC-0315 | 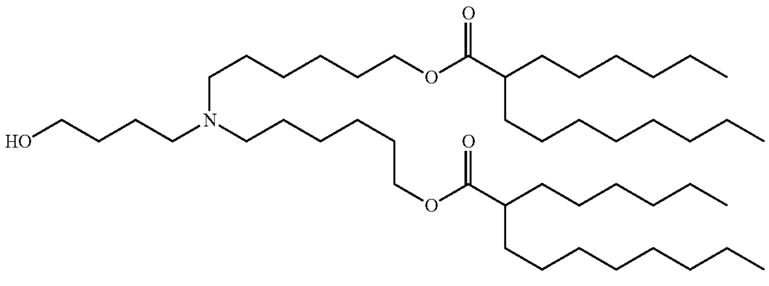 [SMILES: CCCCCCCCC(CCCCCC)C(=O)OCCCCCCN(CCCCO)CCCCCCOC(=O)C(CCCCCC)CCCCCCCC] ALC-0315 | Purchased from XiaMen Sinopeg Biotech Co., LTD- which is compound 3 in CN108368028B |
| HHMA | 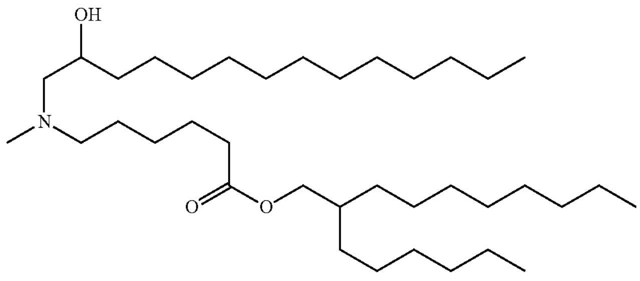 [SMILES: CCCCCCCCCCCCC(O)CN(C)CCCCCC(=O)OCC(CCCCCC)CCCCCCCC] HHMA | Purchased from XiaMen Sinopeg Biotech Co., LTD- which is compound 1 in CN112979483B |

The cationic lipids listed in Table 1 were dissolved in ethanol with DSPC (AVT (Shanghai) Pharmaceutical Technology Co., Ltd.), cholesterol (AVT (Shanghai) Pharmaceutical Technology Co., Ltd.) and DMG-PEG2000 according to a molar ratio of 49:10:39.5:1.5, respectively, to prepare ethanol lipid solution. The ethanol lipid solution was quickly added to citrate buffer (pH=4-5) by ethanol injection method, and vortexed for 30 s for later use. eGFP-mRNA (from Shanghai Biohub International Trade Co., Ltd) or Fluc-mRNA (from Shanghai Biohub International Trade Co., Ltd) was diluted in citrate buffer (pH=4 to 5) to give an aqueous mRNA solution. A certain volume of liposome solution and mRNA aqueous solution were used to prepare liposomes at a weight ratio of total lipids to mRNA of 15:1. The mixtures were sonicated at 25° C. for 15 min (with an ultrasonic frequency of 40 kHz and an ultrasonic power of 800 W). The resulting liposomes were diluted to 10 times volume with PBS, and then ultrafiltered with a 300 KDa ultrafiltration tube to remove ethanol. Then the volume was fixed to a certain volume with PBS to give an LNP formulation encapsulating eGFP-mRNA or Fluc-mRNA using cationic lipid/DSPC/cholesterol/DMG-PEG2000 (49:10:39.5:1.5 in molar percentage).

Lipofectamine 3000 transfection reagent is currently widely used for cell transfection. It has very good transfection performance and excellent transfection efficiency, which can improve cell activity, and is suitable for difficult-to-transfect cell types. We selected Lipofectamine 3000 transfection reagent as a control, and prepared Lipofectamin 3000 formulations of eGFP-mRNA or Fluc-mRNA according to the instructions of Lipofectamine 3000 (Invitrogen (Shanghai) Trading Co., Ltd.).

Example 5: Determination of Particle Size and Polydispersity Index (PDI) of Lipid Nanoparticles The particle size and polydispersity index (PDI) were determined by dynamic light scattering using Malvern laser particle size analyzer.

10 μL of the liposome solution was weighed, diluted to 1 mL with RNase-free deionized water, and added to the sample pool. Each sample was measured in triplicate. The measurement conditions were: 900 scattering angle, and 25° C. The test results were as follows:

TABLE 2

| Particle size and polydispersity index (PDI) | | |
|---|---|---|
| Name | Particle size (nm) | PDI (%) |
| YK-301 | 192 | 7.0 |
| YK-302 | 186 | 13.4 |
| YK-303 | 167 | 8.3 |
| YK-304 | 149 | 19.8 |
| YK-305 | 191 | 10.7 |
| YK-306 | 228 | 13.6 |
| YK-307 | 210 | 32.2 |
| YK-308 | 211 | 13.4 |
| YK-309 | 232 | 27.6 |
| YK-310 | 192 | 12.4 |
| YK-311 | 209 | 31.1 |
| YK-312 | 184 | 33.4 |
| YK-313 | 241 | 17.7 |
| YK-314 | 235 | 24.6 |
| YK-315 | 181 | 34.9 |
| YK-316 | 188 | 17.5 |
| YK-317 | 255 | 16.4 |
| YK-318 | 173 | 14.8 |
| YK-319 | 200 | 11.7 |
| YK-320 | 212 | 19.6 |
| YK-321 | 182 | 39.1 |

TABLE 2-continued

| Particle size and polydispersity index (PDI) | | |
|---|---|---|
| Name | Particle size (nm) | PDI (%) |
| YK-009 | 192 | 18.1 |
| SM-102 | 177 | 28.2 |
| ALC-0315 | 231 | 21.2 |
| Compound 21 | 175 | 24.3 |
| Compound 23 | 147 | 15.2 |
| HMMA | 150 | 19.3 |

The particle size of the nanolipid particles prepared in Example 4 was between 140 and 280 nm, and they can all be used to deliver mRNA. Among them, the particles prepared from Compound 23 and YK-304 had the smallest particle sizes, which were 147 nm and 149 nm respectively, and the particles prepared from YK-317 had the largest particle size, which is 255 nm. The polydispersity index of all nanolipid particles ranges from 5% to 45%, among which the smallest was 7.0% of YK-301, and the largest was 39.1% of YK-321.

Example 6: In Vitro Verification of the Performance of LNP Delivery Carriers

Cell recovery and passage: the method was the same as in Example 3.

Seeding plate: the method was the same as in Example 3.

1. Fluorescent Detection of Fluc-mRNA

An LNP formulation containing 0.3 g of Fluc-mRNA (the carrier components of the LNP formulation were cationic lipid, neutral lipid, structured lipid and polymer-conjugated lipid with a molar ratio of 49:10:39.5:1.5, wherein the cationic lipid was listed in Table 1) was added to the cell culture medium of a 96-well plate, and further incubated for 24 hours. The corresponding reagent was added according to the instructions of the *Gaussia* Luciferase Assay Kit, and the fluorescence expression intensity of each well was detected by an IVIS fluorescence detection system. This test verified the transfection efficiencies of LNP formulations in cells, see Tables 4-7 for specific test results.

Assay Results:

(1) the Compounds of this Application, Including YK-305, YK-310, YK-312, YK-319 and YK-318, are Very Different in Chemical Structure from the Cationic Lipids in the Prior Art.

A series of compounds designed in this application, including YK-305, YK-310, YK-312, YK-319 and YK-318, are very different in chemical structure from the cationic lipids in the prior art. For example, these compounds have completely different structures from HHMA; compared with SM-102, compound 21, compound 23 and YK-009, the $G_3$ group is completely different, and the $G_1$, $G_2$, $R_1$ and $R_2$ groups are also very different. See Table 3 for specific structural comparison.

TABLE 3

| Designed compounds and representative cationic lipids in the prior art | |
|---|---|
| Name | Structure |
| YK-305 | 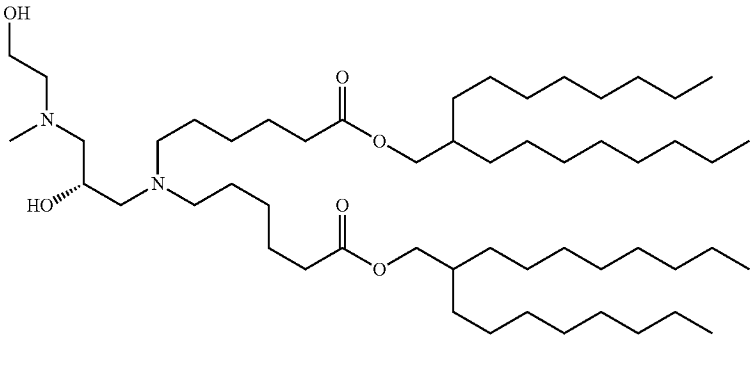 [SMILES: CCCCCCCCC(CCCCCCCC)COC(=O)CCCCCN(CCCCCC(=O)OCC(CCCCCCCC)CCCCCCCC)C[C@H](O)CN(C)CCO] YK-305 |
| YK-310 | 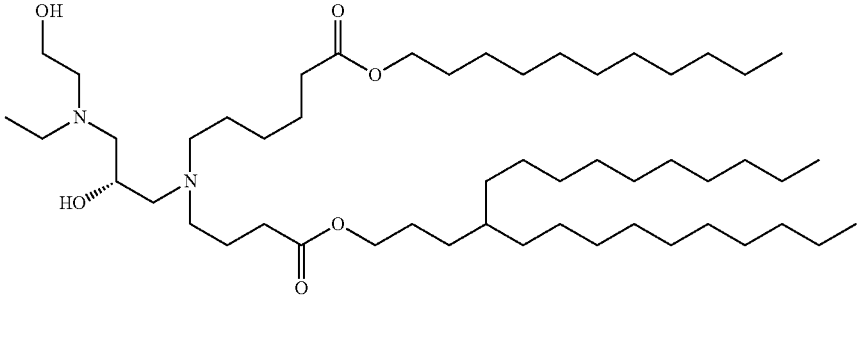 [SMILES: CCCCCCCCCCCOC(=O)CCCCCN(CCCC(=O)OCCCC(CCCCCCCCCC)CCCCCCCCCC)C[C@H](O)CN(CC)CCO] YK-310 |

TABLE 3-continued
| Designed compounds and representative cationic lipids in the prior art | |
|---|---|
| Name | Structure |
| YK-312 | 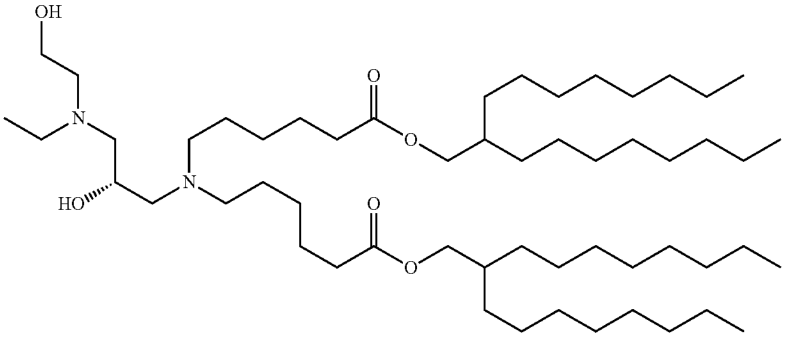 [SMILES: CCCCCCCCC(CCCCCCCC)COC(=O)CCCCCN(CCCCCC(=O)OCC(CCCCCCCC)CCCCCCCC)C[C@H](O)CN(CC)CCO] YK-312 |
| YK-319 | 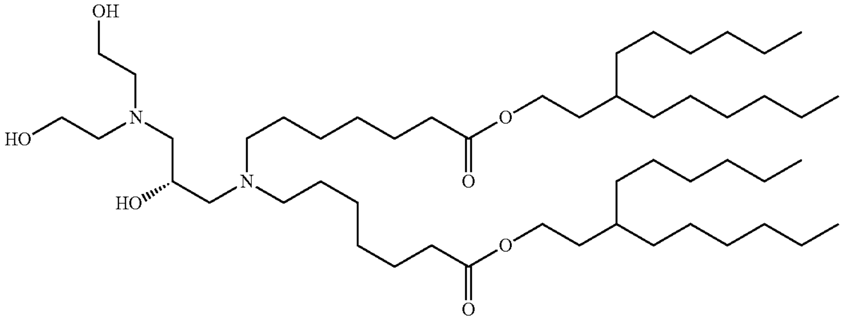 [SMILES: CCCCCCC(CCCCCC)CCOC(=O)CCCCCCN(CCCCCCC(=O)OCCC(CCCCCC)CCCCCC)C[C@H](O)CN(CCO)CCO] YK-319 |
| YK-318 | 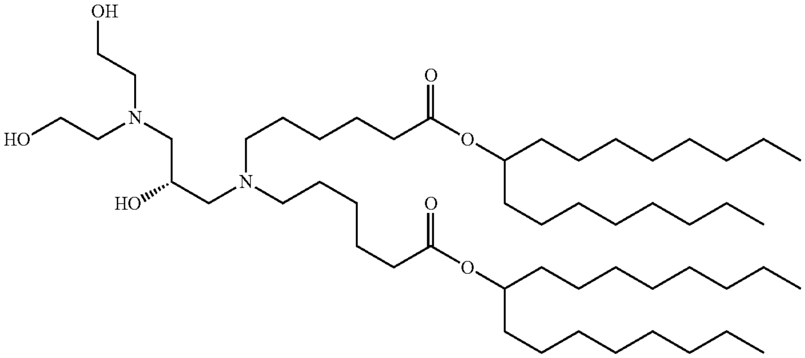 [SMILES: CCCCCCCCC(CCCCCCCC)OC(=O)CCCCCN(CCCCCC(=O)OC(CCCCCCCC)CCCCCCCC)C[C@H](O)CN(CCO)CCO] YK-318 |
| YK-009 | 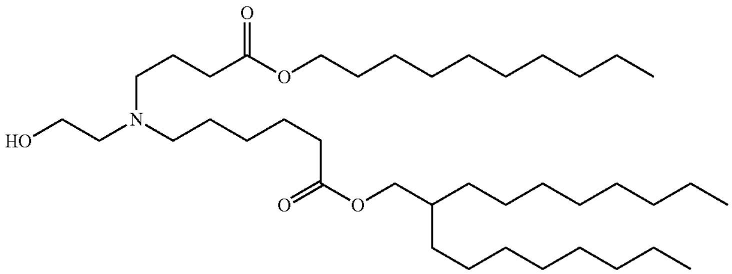 [SMILES: CCCCCCCCCCOC(=O)CCCN(CCO)CCCCCC(=O)OCC(CCCCCCCC)CCCCCCCC] YK-009 |

TABLE 3-continued
| Designed compounds and representative cationic lipids in the prior art | |
|---|---|
| Name | Structure |
| SM-102 | 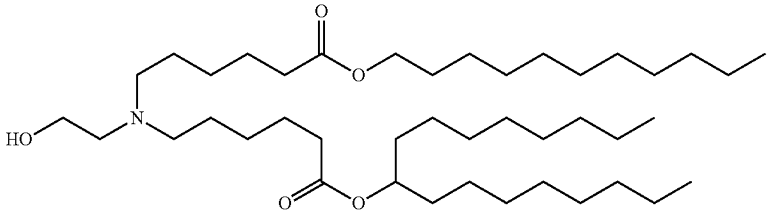 [SMILES: CCCCCCCCCCCOC(=O)CCCCCN(CCO)CCCCCC(=O)OC(CCCCCCCC)CCCCCCCC] SM-102 |
| ALC-0315 | 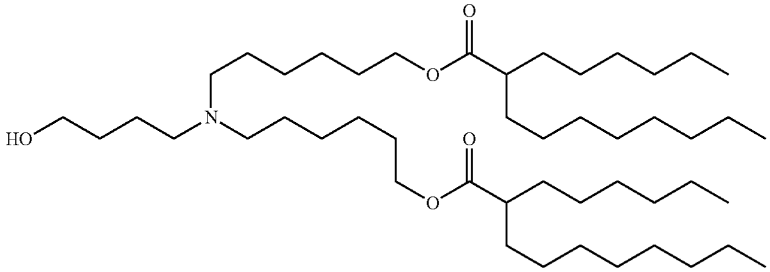 ALC-0315 |
| Compound 21 | 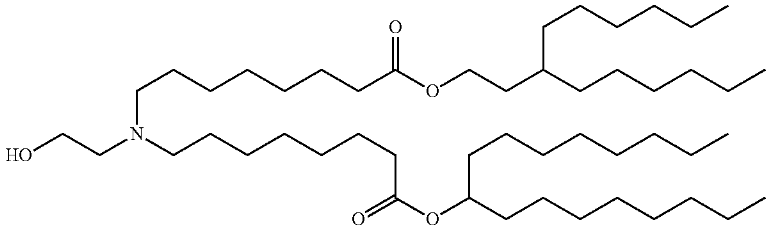 Compound 21 |
| Compound 23 | 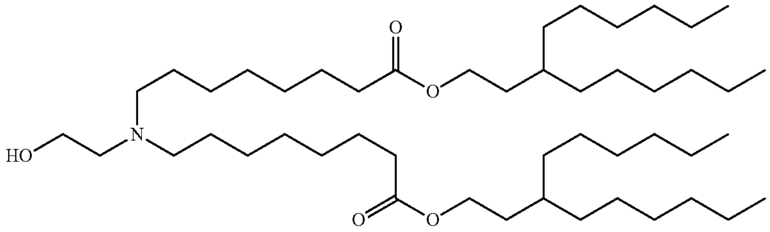 Compound 23 |
| HHMA | 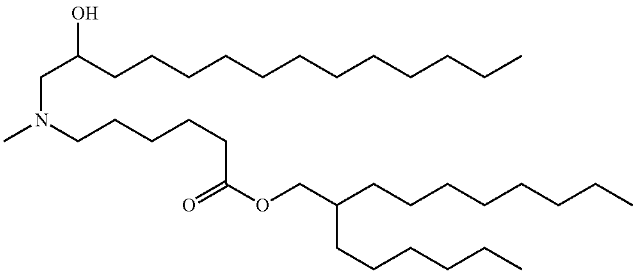 HHMA |

As can be seen from Table 3, the designed series of compounds, including YK-305, YK-310, YK-312, YK-319 and YK-318, are significantly different from the chemical structures of representative cationic lipids in the prior art. YK-009 is disclosed in CN114044741B (claim 1), compound 21 and compound 23 are disclosed in WO2021055833A1 (page 22 of the specification), SM-102 is compound 25 disclosed in WO2017049245A2 (page 29 of the specification), ALC-0315 is compound 3 disclosed in CN108368028B (page 24 of the specification), and HHMA is compound 1 disclosed in CN112979483B (page 12 of the specification).

Compared to this series of compounds:

a. HHMA has the biggest difference in structure. It can be seen from the chemical structure that only one side chain of the group connected to the central N atom of HHMA is similar to one side chain of this series of structures, and the other parts are completely different.

b. Other cationic lipids in the prior art, such as SM-102, ALC-0315, compound 21, compound 23 and YK-009, have completely different $G_3$ groups. The $G_3$ group of this series of compounds has one more tertiary amine group and one to two more hydroxyl groups, so there are great differences in polarity, acidity-alkalinity and hydrophilicity.

c. There are also huge differences in the $G_1$, $G_2$, $R_1$ and $R_2$ groups compared with SM-102, ALC-0315, compound 21, compound 23 and YK-009.

Details are as follows:

I. YK-305

YK-305 has a huge structural difference compared with the cationic lipids in the prior art, such as SM-102, compound 21, compound 23, YK-009 and HHMA.

Compared with SM-102, YK-305 has a branched chain structure of the $R_1$ group, while SM-102 has a linear chain structure; has 2 less C in the $G_2$ group; has 1 more C in the single chain of the $R_2$ group; the $G_3$ group is completely different, being $HO(CH_2)_2N(CH_3)CH_2CH(OH)CH_2$—, while in SM-102 it is $HO(CH_2)_2$—.

Compared with ALC-0315, YK-305 has 1 less C in the $G_1$ group; has 1 more C in the single chain, and has 2 more C in one single chain in the double chain of the $R_1$ group; has 1 less C in the $G_2$ group; has one more C in the single chain, and 2 more C in one single chain of the double chain in the $R_2$ group; the $G_3$ group is completely different, being $HO(CH_2)_2N(CH_3)CH_2CH(OH)CH_2$—, while in ALC-0315 it is $HO(CH_2)_4$—. Furthermore, the directions of the ester bonds between the $G_1$ group and the $R_1$ group and between the $G_2$ group and the $R_2$ group are also different between YK-305 and ALC-0315.

Compared with compound 21, YK-305 has 2 less C in the $G_1$ group; has 1 C less in the single chain, and has 2 more C in each single chain in the double chain of the $R_1$ group; has 2 less C in the $G_2$ group; has one more C in the single chain of the $R_2$ group; the $G_3$ group is completely different, being $HO(CH_2)_2N(CH_3)CH_2CH(OH)CH_2$—, while in compound 21 it is $HO(CH_2)_2$—.

Compared with compound 23, YK-305 has 2 less C in the $G_1$ group; has 1 less C in the single chain, and has 2 more C in each single chain in the double chain of the $R_1$ group; has 2 less C in the $G_2$ group; has 1 less C in the single chain and 2 more C in each single chain in the double chain of the $R_2$ group; the $G_3$ group is completely different, being $HO(CH_2)_2N(CH_3)CH_2CH(OH)CH_2$—, while in compound 23 it is $HO(CH_2)_2$—.

Compared with YK-009, YK-305 has 2 more C in the $G_1$ group; has a branched chain structure of the $R_1$ group, while YK-009 has a linear chain structure; the $G_3$ group is completely different, being $HO(CH_2)_2N(CH_3)CH_2CH(OH)CH_2$—, while in YK-009 it is $HO(CH_2)_2$—.

Compared with HHMA, the structure of YK-305 is completely different. Only one side chain of HHMA connected to the N atom is similar to the structure of one side chain of YK-305, and the other parts are very different.

II. YK-310

YK-310 has a huge structural difference compared with the cationic lipids in the prior art, such as SM-102, compound 21, compound 23, YK-009 and HHMA.

Compared with SM-102, YK-310 has 4 less C in the $G_2$ group; has 3 more C in the single chain, and has 2 more C in each single chain of the double chain in the $R_2$ group; the $G_3$ group is completely different, being $HO(CH_2)_2N(CH_2CH_3)CH_2CH(OH)CH_2$—, while in SM-102 it is $HO(CH_2)_2$—.

Compared with ALC-0315, YK-310 has 1 less C in the $G_1$ group; has a linear chain structure in the $R_1$ group, while ALC-0315 has a branched chain structure; has 3 less C in the $G_2$ group; has 3 more C in the single chain, has 2 more C in one single chain of the double chains, and 4 more C in the other single chain in the $R_2$ group; the $G_3$ group is completely different, being $HO(CH_2)_2N(CH_2CH_3)CH_2CH(OH)CH_2$—, while in ALC-0315 it is $HO(CH_2)_4$—. Furthermore, the directions of the ester bonds between the $G_1$ group and the $R_1$ group and between the $G_2$ group and the $R_2$ group are also different between YK-310 and ALC-0315.

Compared with compound 21, YK-310 has 2 less C in the $G_1$ group; has a linear structure, while compound 21 has a branched chain structure in the $R_1$ group; has 4 less C in the $G_2$ group; has 3 more C in the single chain, and has 2 more C in each single chain of the double chain in the $R_2$ group; the $G_3$ group is completely different, being $HO(CH_2)_2N(CH_2CH_3)CH_2CH(OH)CH_2$—, while in compound 21 it is $HO(CH_2)_2$—.

Compared with compound 23, YK-310 has 2 less C in the $G_1$ group; has a linear structure, while in compound 23 it has a branched structure in the $R_1$ group; has 4 less C in the $G_2$ group; has 1 more C in the single chain, and 4 more C in each single chain of the double chain in the $R_2$ group; the $G_3$ group is completely different, being $HO(CH_2)_2N(CH_2CH_3)CH_2CH(OH)CH_2$—, while in compound 23 it is $HO(CH_2)_2$—.

Compared with YK-009, YK-310 has 2 more C in the $G_1$ group; has 1 more C in the $R_1$ group; has 2 less C in the $G_2$ group; has 2 more C in the single chain, and 2 more C in each single chain of the double chain in the $R_2$ group; the $G_3$ group is completely different, being $HO(CH_2)_2N(CH_2CH_3)CH_2CH(OH)CH_2$—, while in YK-009 it is $HO(CH_2)_2$—.

Compared with HHMA, the structure of YK-310 is completely different. Only one side chain of HHMA connected to the N atom is similar to the structure of one side chain of YK-310, and the other parts are very different.

III. YK-312

YK-312 has a huge structural difference compared with the cationic lipids in the prior art, such as SM-102, compound 21, compound 23, YK-009 and HHMA.

Compared with SM-102, YK-312 has a branched chain structure in the $R_1$ group, while SM-102 has a linear chain structure; has 2 less C in the $G_2$ group; has 1 more C in the single chain of the $R_2$ group; the $G_3$ group is completely different, being $HO(CH_2)_2N(CH_2CH_3)CH_2CH(OH)CH_2$—, while in SM-102 it is $HO(CH_2)_2$—.

Compared with ALC-0315, YK-312 has 1 less C in the $G_1$ group; has 1 more C in the single chain, and has 2 more C in one single chain of the double chain in the $R_1$ group; has 1 less C in the $G_2$ group; has one more C in the single chain, and 2 more C in one single chain of the double chain in the $R_2$ group; the $G_3$ group is completely different, being $HO(CH_2)_2N(CH_2CH_3)CH_2CH(OH)CH_2$—, while in ALC-0315 is $HO(CH_2)_4$—. Furthermore, the directions of the ester bonds between the $G_1$ group and the $R_1$ group and between the $G_2$ group and the $R_2$ group are also different between YK-312 and ALC-0315.

Compared with compound 21, YK-312 has 2 less C in the $G_1$ group; has 1 less C in the single chain, and has 2 more C in each single chain of the double chain in the $R_1$ group; has 2 less C in the $G_2$ group; has one more C in the single chain of the $R_2$ group; the $G_3$ group is completely different, being $HO(CH_2)_2N(CH_2CH_3)CH_2CH(OH)CH_2$—, while in compound 21 it is $HO(CH_2)_2$—.

Compared with compound 23, YK-312 has 2 less C in the $G_1$ group; has 1 less C in the single chain, and has 2 more C in each single chain of the double chain in the $R_1$ group; has 2 C less of the $G_2$ group; has 1 less C in the single chain and 2 more C in each single chain of the double chain in the $R_2$ group; the $G_3$ group is completely different, being $HO(CH_2)_2N(CH_2CH_3)CH_2CH(OH)CH_2$—, while in compound 23 it is $HO(CH_2)_2$—.

Compared with YK-009, YK-312 has 2 more C in the $G_1$ group; has a branched chain structure in the $R_1$ group, while YK-009 has a linear chain structure; the $G_3$ group is completely different, being $HO(CH_2)_2N(CH_2CH_3)CH_2CH(OH)CH_2$—, while in YK-009 it is $HO(CH_2)_2$—.

Compared with HHMA, the structure of YK-312 is completely different. Only one side chain of HHMA connected to the N atom is similar to the structure of one side chain of YK-312, and the other parts are very different.

IV. YK-319

YK-319 has a huge structural difference compared with the cationic lipids in the prior art, such as SM-102, compound 21, compound 23, YK-009 and HHMA.

Compared with SM-102, YK-319 has 1 more C in the $G_1$ group; has a branched chain structure in the $R_1$ group, while SM-102 has a linear chain structure; has 1 less C in the $G_2$ group; has 2 more C in the single chain, and 2 less C in each single chain of the double chain in the $R_2$ group; the $G_3$ group is completely different, being $(HO(CH_2)_2)_2NCH_2CH(OH)CH_2$—, while in SM-102 it is $HO(CH_2)_2$—.

Compared with ALC-0315, YK-319 has 2 more C in the single chain and 2 less C in one single chain of the double chain in the $R_1$ group; has 2 more C in the single chain and 2 less C in one single chain of the double chain in the $R_2$ group; the $G_3$ group is completely different, being $(HO(CH_2)_2)_2NCH_2CH(OH)CH_2$—, while in ALC-0315 it is $HO(CH_2)_4$—. Furthermore, the directions of the ester bonds between the $G_1$ group and the $R_1$ group and between the $G_2$ group and the $R_2$ group are also different between YK-319 and ALC-0315.

Compared with compound 21, YK-319 has 1 less C in the $G_1$ group; has 1 less C in the $G_2$ group; has 2 more C in the single chain, and 2 less C in each single chain of the double chain in the $R_2$ group; the $G_3$ group is completely different, being $(HO(CH_2)_2)_2NCH_2CH(OH)CH_2$—, while in compound 21 it is $HO(CH_2)_2$—.

Compared with compound 23, YK-319 has 1 less C in the $G_1$ group; has 1 less C in the $G_2$ group; the $G_3$ group is completely different, being $(HO(CH_2)_2)_2NCH_2CH(OH)CH_2$—, while in compound 23 it is $HO(CH_2)_2$—.

Compared with YK-009, YK-319 has 3 more C in the $G_1$ group; has a branched chain structure in the $R_1$ group, while YK-009 has a linear chain structure; has 1 more C of the $G_2$ group; has 1 more C in the single chain, and 2 less C in each single chain of the double chain in the $R_2$ group; the $G_3$ group is completely different, being $(HO(CH_2)_2)_2NCH_2CH(OH)CH_2$—, while in YK-009 it is $HO(CH_2)_2$—.

Compared with HHMA, the structure of YK-319 is completely different. Only one side chain of HHMA connected to the N atom is similar to the structure of one side chain of YK-319, and the other parts are very different.

V. YK-318

YK-318 has a huge structural difference compared with the cationic lipids in the prior art, such as SM-102, compound 21, compound 23, YK-009 and HHMA.

Compared with SM-102, YK-318 has a branched chain structure in the $R_1$ group, while SM-102 has a linear chain structure; has 2 less C in the $G_2$ group; the $G_3$ group is completely different, being $(HO(CH_2)_2)_2NCH_2CH(OH)CH_2$—, while in SM-102 it is $HO(CH_2)_2$—.

Compared with ALC-0315, YK-318 has 1 less C in the $G_1$ group; has 2 more C in one single chain in the double chain of the $R_1$ group; has 1 less C in the $G_2$ group; has 2 more C in one single chain in the double chain of the $R_2$ group; the $G_3$ group is completely different, being $(HO(CH_2)_2)_2NCH_2CH(OH)CH_2$—, while in ALC-0315 it is $HO(CH_2)_4$—. Furthermore, the directions of the ester bonds between the $G_1$ group and the $R_1$ group and between the $G_2$ group and the $R_2$ group are also different between YK-318 and ALC-0315.

Compared with compound 21, YK-318 has 2 less C in the $G_1$ group; has 2 less C in the single chain, and 2 more C in each single chain of the double chain in the $R_1$ group; has 2 less C in the $G_2$ group; the $G_3$ group is completely different, being $(HO(CH_2)_2)_2NCH_2CH(OH)CH_2$—, while in compound 21 it is $HO(CH_2)_2$—.

Compared with compound 23, YK-318 has 2 less C in the $G_1$ group; has 2 less C in the single chain, and has 2 more C in each single chain of the double chain in the $R_1$ group; has 1 less C in the $G_2$ group; the $R_2$ group has 2 less C in the single chain and 2 more C in each single chain of the double chain; the $G_3$ group is completely different, being $(HO(CH_2)_2)_2NCH_2CH(OH)CH_2$—, while in compound 23 it is $HO(CH_2)_2$—.

Compared with YK-009, YK-318 has 2 more C in the $G_1$ group; has a branched chain structure in the $R_1$ group, while YK-009 has a linear chain structure; has 1 less C in the single chain of the $R_2$ group; the $G_3$ group is completely different, being $(HO(CH_2)_2)_2NCH_2CH(OH)CH_2$—, while in YK-009 it is $HO(CH_2)_2$—.

Compared with HIMA, the structure of YK-318 is completely different. Only one side chain of HHMA connected to the N atom is similar to the structure of one side chain of YK-318, and the other parts are very different.

From the above comparison, it can be seen that the designed series of compounds, including YK-305, YK-310, YK-312, YK-319 and YK-318, are very different from the cationic lipid compounds in the prior art, such as SM-102, ALC-0315, compound 21, compound 23, HHMA and YK-009 in chemical structure. This series of compounds have completely different structures from HHMA; and completely different from SM-102, ALC-0315, compound 21, compound 23 and YK-009 in the $G_3$ group. The $G_3$ group of this series of compounds has one more tertiary amine group, and has 1-2 more hydroxyl groups, and the $G_1$, $G_2$, $R_1$ and $R_2$ groups are also very different.

Due to the huge difference in chemical structure, the physical and chemical properties, such as polarity, acidity and alkalinity, and hydrophilicity, of this series of compounds are also very different from those of SM-102, ALC-0315, compound 21, compound 23, HHMA and YK-009. Therefore, it is impossible to infer the cell transfection efficiency, cytotoxicity, and expression in animals of LNP formulations prepared from this series of compounds based on the above-mentioned cationic lipid compounds disclosed in the prior art.

(2) Among a Series of Designed Compounds, the LNP Formulations Prepared from YK-305, YK-310, YK-312, YK-319 and YK-318 had the Highest Cell Transfection Efficiencies, which were Significantly Improved Compared with the Representative Cationic Lipid Compounds in the Prior Art. For Example, YK-305 can be Up to 17 Times that of SM-102, 19 Times that of Compound 21, and 20 Times that of Compound 23.

TABLE 4

The chemical structures of the designed compounds and representative cationic lipid in the prior art

| Name | Structure |
|---|---|
| YK-305 | 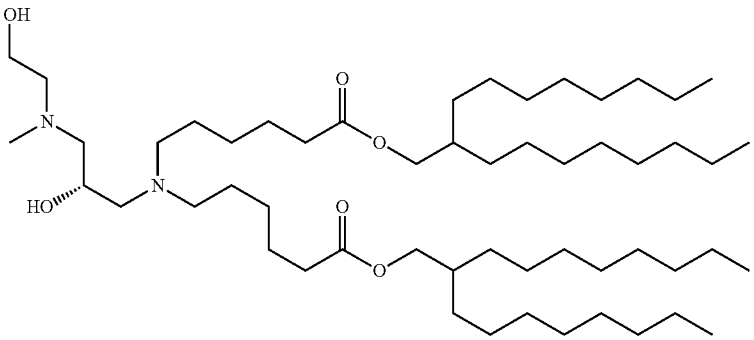 YK-305 |
| YK-310 | 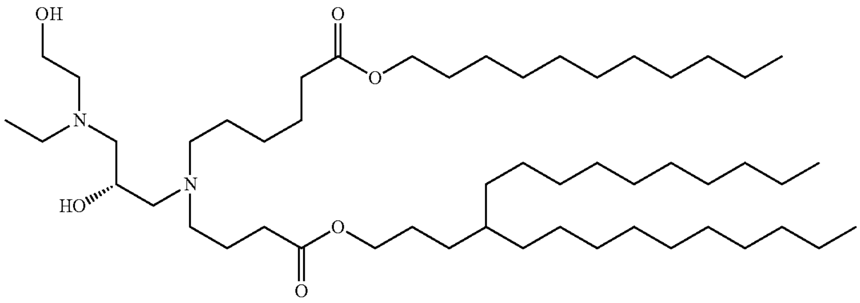 [SMILES: CCCCCCCCCCCOC(=O)CCCCCN(CCCC(=O)OCCCC(CCCCCCCCCC)CCCCCCCCCC)C[C@H](O)CN(CC)CCO] YK-310 |
| YK-312 | 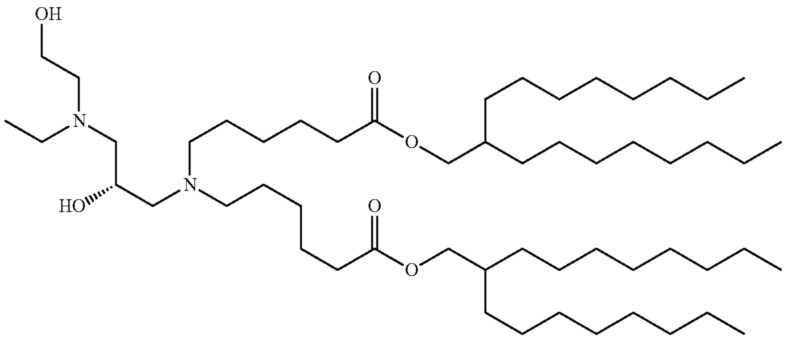 [SMILES: CCCCCCCCC(CCCCCCCC)COC(=O)CCCCCN(CCCCCC(=O)OCC(CCCCCCCC)CCCCCCCC)C[C@H](O)CN(CC)CCO] YK-312 |

TABLE 4-continued
| The chemical structures of the designed compounds and representative cationic lipid in the prior art | |
|---|---|
| Name | Structure |
| YK-319 | 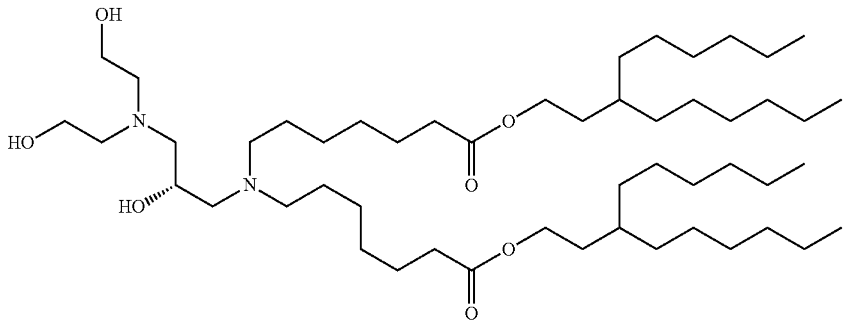 [SMILES: CCCCCCC(CCCCCC)CCOC(=O)CCCCCCN(CCCCCCC(=O)OCCC(CCCCCC)CCCCCC)C[C@H](O)CN(CCO)CCO] YK-319 |
| YK-318 | 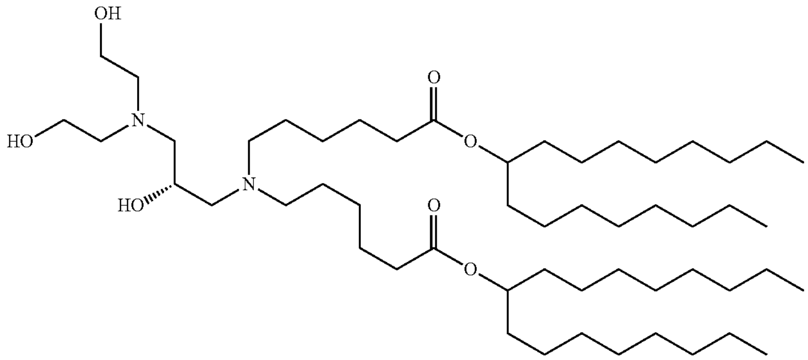 YK-318 |
| YK-009 | 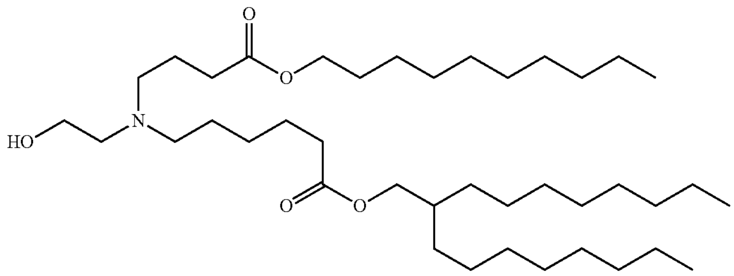 YK-009 |
| SM-102 | 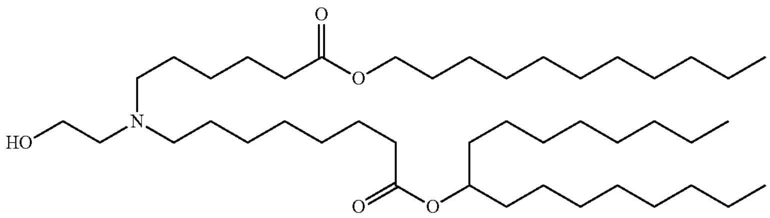 SM-102 |

TABLE 4-continued

| The chemical structures of the designed compounds and representative cationic lipid in the prior art | |
|---|---|
| Name | Structure |
| Compound 21 | 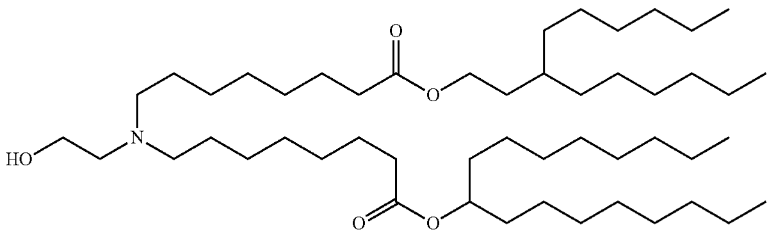 Compound 21 |
| Compound 23 | 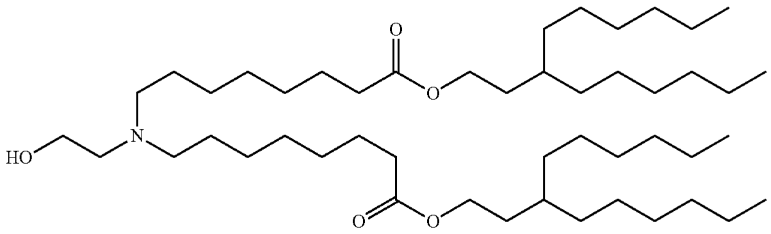 Compound 23 |
| HHMA | 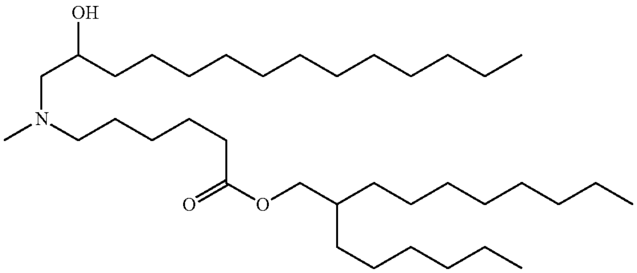 HHMA |

TABLE 5

Fluorescence detection results of Fluc-mRNA - 1

| No. | Name | Relative light unit (RLU) | Ratio relative to SM-102 | Multiples (YK-305) | Multiples (YK-310) | Multiples (YK-312) | Multiples (YK-319) | Multiples (YK-318) |
|---|---|---|---|---|---|---|---|---|
| 1 | YK-305 | 27408734 | 17.09 | 1.00 | 0.94 | 0.74 | 0.89 | 0.41 |
| 2 | XK-310 | 25797040 | 16.08 | 1.06 | 1.00 | 0.78 | 0.95 | 0.43 |
| 3 | YK-312 | 20148450 | 12.56 | 1.36 | 1.28 | 1.00 | 1.21 | 0.56 |
| 4 | YK-319 | 24467760 | 15.25 | 1.12 | 1.05 | 0.82 | 1.00 | 0.46 |
| 5 | YK-318 | 11190068 | 6.98 | 2.45 | 2.31 | 1.80 | 2.19 | 1.00 |
| 6 | YK-009 | 5118942 | 3.19 | 5.35 | 5.04 | 3.94 | 4.78 | 2.19 |
| 7 | SM-102 | 1604013 | 1.00 | 17.09 | 16.08 | 12.56 | 15.25 | 6.98 |
| 8 | ALC-0315 | 2033550 | 1.27 | 13.48 | 12.69 | 9.91 | 12.03 | 5.50 |
| 9 | Compound 21 | 1432170 | 0.89 | 19.14 | 18.01 | 14.07 | 17.08 | 7.81 |
| 10 | Compound 23 | 1356022 | 0.85 | 20.21 | 19.02 | 14.86 | 18.04 | 8.25 |
| 11 | HHMA | 2006110 | 1.25 | 13.66 | 12.86 | 10.04 | 12.20 | 5.58 |
| 12 | Lipofectamine 3000 | 1185743 | 0.74 | 23.12 | 21.76 | 16.99 | 20.63 | 9.44 |

Differences in Cell Transfection Efficiency

Table 4 shows the chemical structural differences between the designed compounds and representative cationic lipids in the prior art.

Table 5 lists the fluorescence detection results of LNP formulations containing Fluc-mRNA prepared from different cationic lipids. Wherein, YK-009 is disclosed in CN114044741B (claim 1), compound 21 and compound 23 are disclosed in WO2021055833A1 (page 22 of the specification), SM-102 is compound 25 disclosed in WO2017049245A2 (page 29 of the specification), ALC-0315 is compound 3 disclosed in CN108368028B (page 24 of the specification), and HHMA is compound 1 disclosed in CN112979483B (page 12 of the specification); Lipofectamine 3000 is a currently widely used cell transfection reagent. These cationic lipids are representative cationic lipids in the prior art and have good transfection performance.

Figure 5:
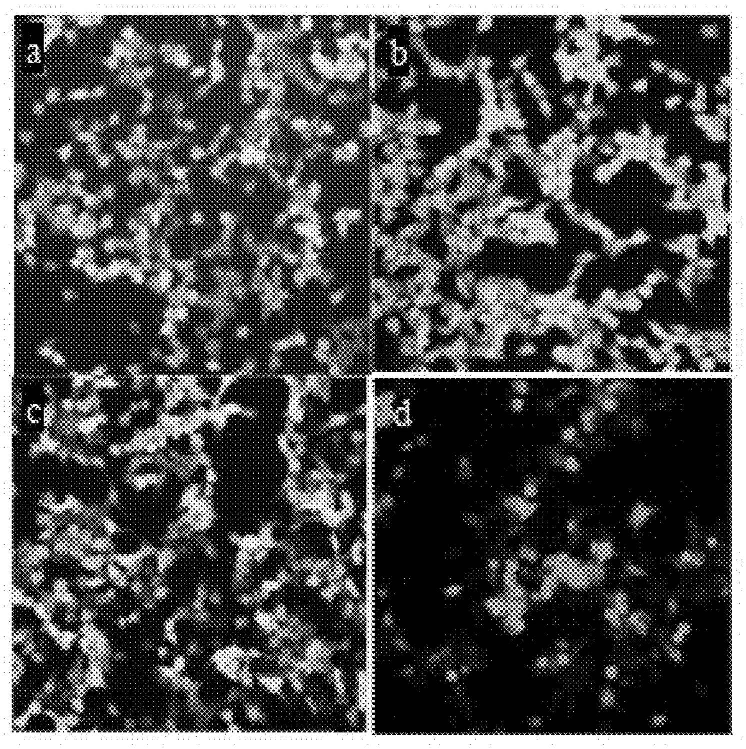
FIG. 5 shows the fluorescence absorption intensity of LNP formulations of Fluc-mRNA prepared from different cationic lipids (a: YK-305; b: YK-310; c: YK-319; d: SM-102).

It can be seen from Table 5 and FIG. 5 that the LNP formulations containing Fluc-mRNA prepared from YK-305, YK-310, YK-312, YK-319 and YK-318 had the strongest fluorescence absorption, and the RLU values were 27408734, 25797040, 20148450, 24467760 and 11190068 respectively.

YK-305 can be up to 17.09 times that of SM-102, 13.48 times that of ALC-0315, 19.14 times that of compound 21, 20.21 times that of compound 23, 13.66 times that of HHMA, 23.12 times that of Lipofectamine 3000 and 5.35 times that of YK-009.

YK-310 can be up to 16.08 times that of SM-102, 12.69 times that of ALC-0315, 18.01 times that of compound 21, 19.02 times that of compound 23, 12.86 times that of HHMA, 21.76 times that of Lipofectamine 3000 and 5.04 times that of YK-009.

YK-312 can be up to 12.56 times that of SM-102, 9.91 times that of ALC-0315, 14.07 times that of compound 21, 14.86 times that of compound 23, 10.04 times that of HHMA, 16.99 times that of Lipofectamine 3000 and 3.94 times that of YK-009.

YK-319 can be up to 15.25 times that of SM-102, 12.03 times that of ALC-0315, 17.08 times that of compound 21, 18.04 times that of compound 23, 12.20 times that of HHMA, 20.63 times that of Lipofectamine 3000 and 4.78 times that of YK-009.

YK-318 can be up to 6.98 times that of SM-102, 5.50 times that of ALC-0315, 7.81 times that of compound 21, 8.25 times that of compound 23, 5.58 times that of HHMA, 9.44 times that of Lipofectamine 3000 and 2.19 times that of YK-009.

The data were analyzed using GraphPad Prism software. Any one of YK-305, YK-310, YK-312, YK-319 and YK-318 was significantly different from SM-102, ALC-0315, compound 21, compound 23, HHMA, Lipofectamine 3000 and YK-009, and the transfection efficiency was significantly improved.

Brief Summary:

In terms of chemical structure, a series of designed compounds, including YK-305, YK-310, YK-312, YK-319 and YK-318, are very different from representative cationic lipids in the prior art. For example, the structures are completely different HHMA; compared with SM-102, ALC-0315, compound 21, compound 23 and YK-009, the $G_3$ group is completely different, and the $G_1$, $G_2$, $R_1$ and $R_2$ groups are also very different.

LNP formulations prepared from YK-305, YK-310, YK-312, YK-319 and YK-318 had the highest cell transfection efficiencies, and their activities were significantly improved compared to representative cationic lipids in the prior art, for example, YK-305 can be up to 17 times that of SM-102, 19 times that of compound 21 and 20 times that of compound 23.

At the same time, the present application has designed for the first time a compound that is significantly different in chemical structure from the cationic lipids in the prior art, and the LNP formulations prepared therefrom had significantly improved transfection efficiency and significantly enhanced cell transfection activity.

(3) YK-305, YK-310, YK-312, YK-319 and YK-318 had the Highest Cell Transfection Efficiencies Compared with a Series of Compounds with Similar Structures, and the $G_3$ Group being $HO(CH_2)_2N(CH_3)CH_2CH(OH)CH_2$—. For Example, YK-305 can be Up to 1300 Times that of YK-304 and 900 Times that of YK-302.

A series of compounds with similar structures and the $G_3$ group being $HO(CH_2)_2N(CH_3)CH_2CH(OH)CH_2$— were compared with YK-305, YK-310, YK-312, YK-319 and YK-318. The only structural difference between these compounds is that the $G_1$, $G_2$, $G_3$, $R_1$ or $R_2$ groups are slightly different (Table 6). The results show that the activities of this series of compounds vary greatly. Among them, YK-305, YK-310, YK-312, YK-319 and YK-318 had the highest cell transfection efficiencies, which can be up to 1300 times, 1200 times, 900 times, 1100 times and 400 times that of YK-304 which had the lowest activity, showing significantly improved transfection efficiencies.

TABLE 6

The chemical structures of the designed compounds

| Name | Structure |
| --- | --- |
| YK-305 | 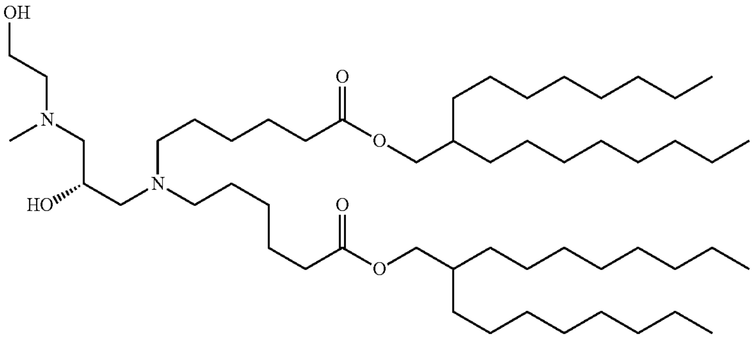 YK-305 |

TABLE 6-continued
| The chemical structures of the designed compounds | |
|---|---|
| Name | Structure |
| YK-310 | 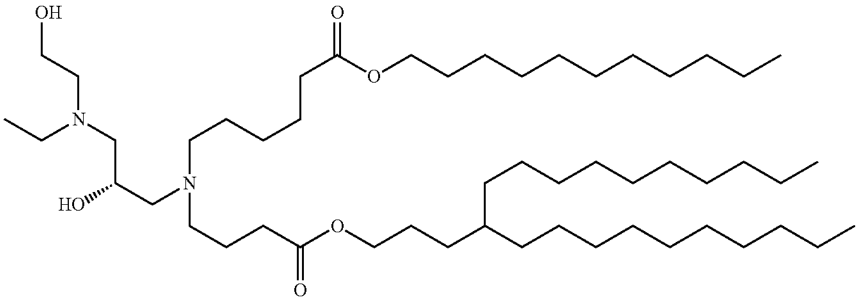 YK-310 |
| YK-312 | 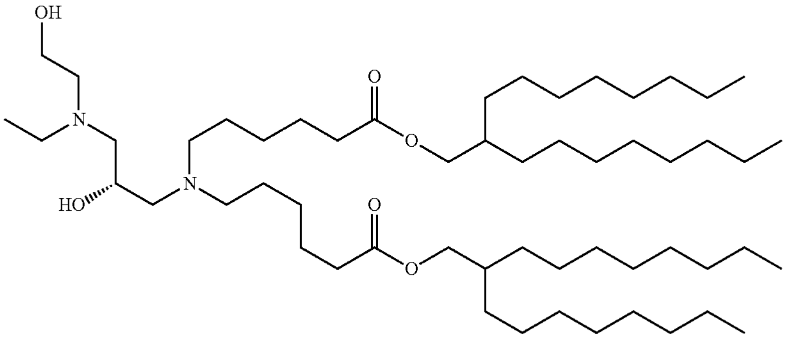 YK-312 |
| YK-319 | 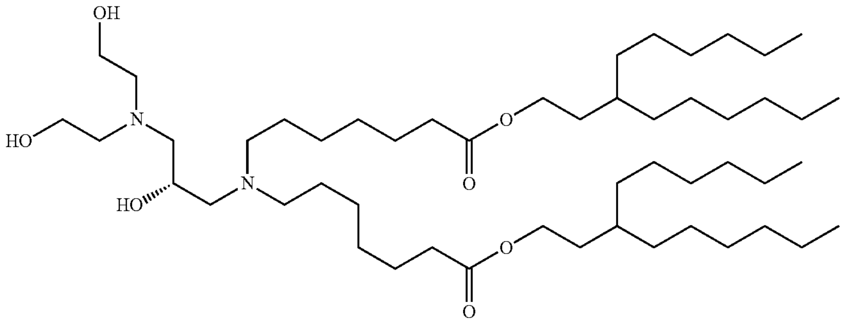 YK-319 |
| YK-318 | 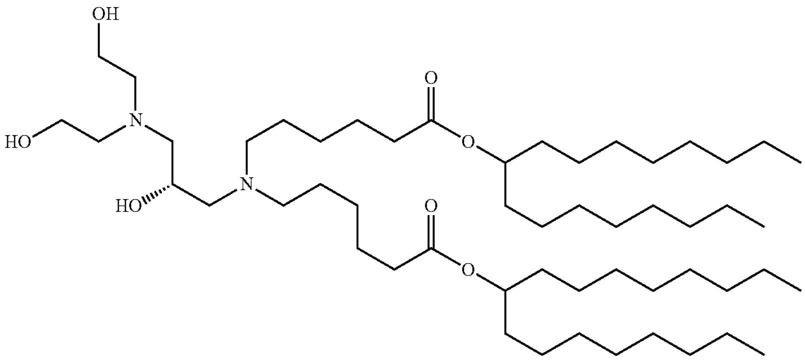 [SMILES: CCCCCCCCC(CCCCCCCC)OC(=O)CCCCCN(CCCCCC(=O)OC(CCCCCCCC)CCCCCCCC)C[C@H](O)CN(CCO)CCO] YK-318 |

TABLE 6-continued
The chemical structures of the designed compounds
| Name | Structure |
| --- | --- |
| YK-301 | 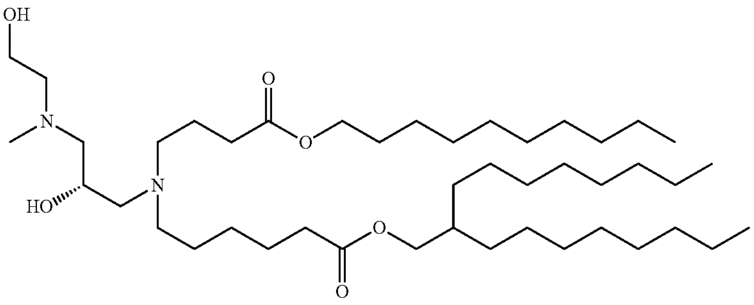 [SMILES: CCCCCCCCCCOC(=O)CCCN(CCCCCC(=O)OCC(CCCCCCCC)CCCCCCCC)C[C@H](O)CN(C)CCO] YK-301 |
| YK-302 | 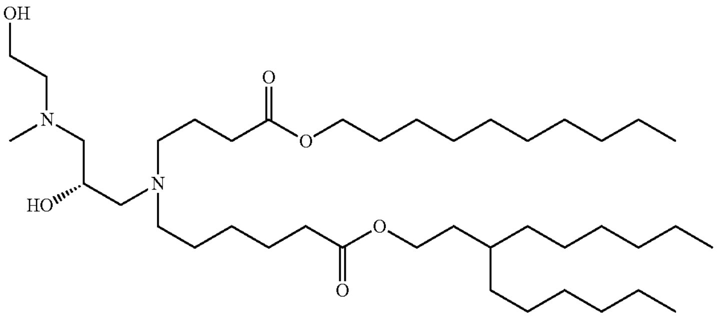 [SMILES: CCCCCCCCCCOC(=O)CCCN(CCCCCC(=O)OCCC(CCCCCC)CCCCCC)C[C@H](O)CN(C)CCO] YK-302 |
| YK-303 | 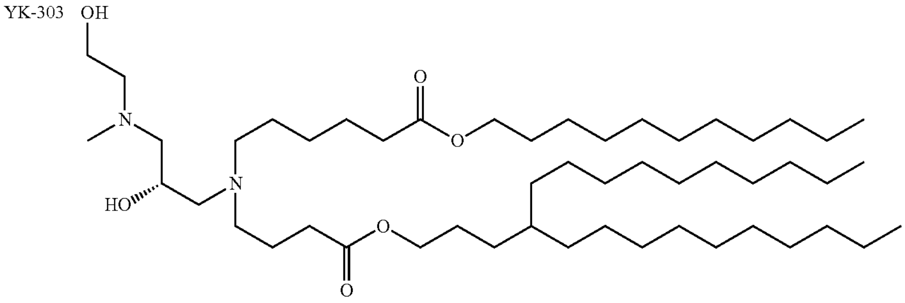 YK-303 |
| YK-304 | 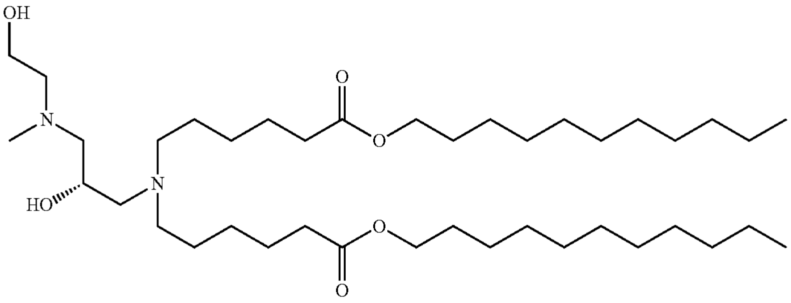 [SMILES: CCCCCCCCCCCOC(=O)CCCCCN(CCCCCC(=O)OCCCCCCCCCCC)C[C@H](O)CN(C)CCO] YK-304 |

TABLE 6-continued
The chemical structures of the designed compounds
| Name | Structure |
|---|---|
| YK-306 | 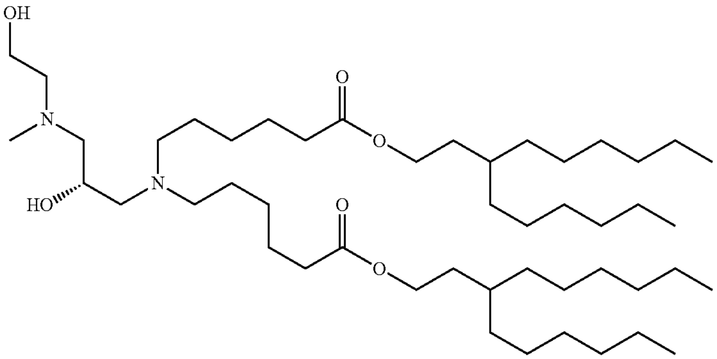 [SMILES: CCCCCCC(CCCCCC)CCOC(=O)CCCCCN(CCCCCC(=O)OCCC(CCCCCC)CCCCCC)C[C@H](O)CN(C)CCO] YK-306 |
| YK-307 | 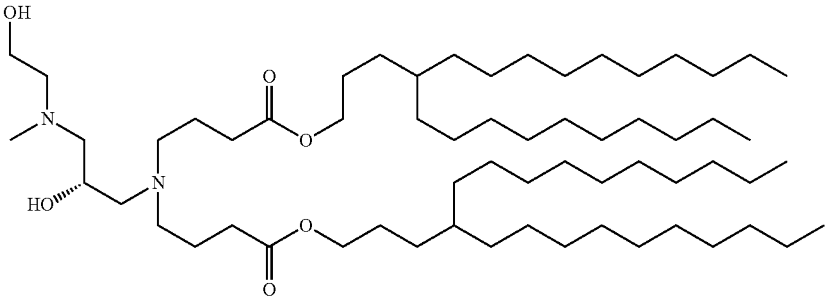 [SMILES: CCCCCCCCCCC(CCCCCCCCCC)CCCOC(=O)CCCN(CCCC(=O)OCCCC(CCCCCCCCCC)CCCCCCCCCC)C[C@H](O)CN(C)CCO] YK-307 |
TABLE 7
Fluorescence detection results of Fluc-mRNA - 2
| No. | Name | Relative light unit (RLU) | Ratio relative to SM-102 | Multiples (YK-305) | Multiples (YK-310) | Multiples (YK-312) | Multiples (YK-319) | Multiples (YK-318) |
|---|---|---|---|---|---|---|---|---|
| 1 | YK-305 | 27408734 | 17.09 | 1.00 | 0.94 | 0.74 | 0.89 | 0.41 |
| 2 | YK-310 | 25797040 | 16.08 | 1.06 | 1.00 | 0.78 | 0.95 | 0.43 |
| 3 | YK-312 | 20148450 | 12.56 | 1.36 | 1.28 | 1.00 | 1.21 | 0.56 |
| 4 | YK-319 | 24467760 | 15.25 | 1.12 | 1.05 | 0.82 | 1.00 | 0.46 |
| 5 | YK-318 | 11190068 | 6.98 | 2.45 | 2.31 | 1.80 | 2.19 | 1.00 |
| 6 | YK-301 | 842452 | 0.16 | 32.53 | 30.62 | 23.92 | 29.04 | 13.28 |
| 7 | YK-302 | 27778 | 0.005 | 936.71 | 928.69 | 725.34 | 880.83 | 402.84 |
| 8 | YK-303 | 626314 | 0.12 | 43.76 | 41.19 | 32.17 | 39.07 | 17.87 |
| 9 | YK-304 | 20686 | 0.004 | 1324.99 | 1247.08 | 974.01 | 1182.82 | 540.95 |
| 10 | YK-306 | 2197174 | 0.43 | 12.47 | 11.14 | 9.17 | 11.14 | 5.09 |
| 11 | YK-307 | 4557420 | 0.89 | 6.01 | 5.66 | 4.42 | 5.37 | 2.46 |
| 12 | SM-102 | 1604015 | 1.00 | 17.00 | 16.08 | 12.56 | 15.25 | 6.98 |
| 13 | ALC-0315 | 2033550 | 1.27 | 13.48 | 12.69 | 9.91 | 12.03 | 5.50 |
| 14 | Compound 21 | 1432170 | 0.89 | 19.14 | 18.01 | 14.07 | 17.08 | 7.81 |
| 15 | Compound 23 | 1356022 | 0.85 | 20.21 | 19.02 | 14.86 | 18.04 | 8.25 |
| 16 | HHMA | 2006110 | 1.25 | 13.66 | 12.86 | 10.04 | 12.20 | 5.58 |
| 17 | Lipofectamine 3000 | 1185743 | 0.74 | 23.12 | 21.76 | 16.99 | 20.63 | 9.44 |

a. Differences in Cell Transfection Efficiency

Figure 6:
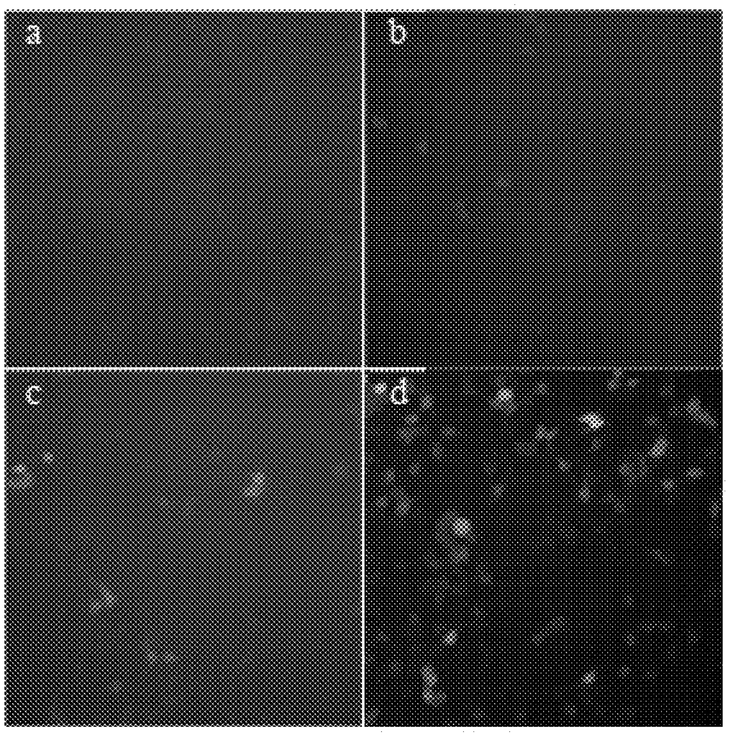
FIG. 6 shows the fluorescence absorption intensity of LNP formulations of Fluc-mRNA prepared from different cationic lipids (a: YK-301; b: YK-302; c: YK-304; d: compound 21).

It can be seen from Table 7 and FIG. 6 that the fluorescence absorption values of LNP formulations prepared from these compounds were very different from those of YK-305, YK-310, YK-312, YK-319 and YK-318.

YK-305 can be up to 32.53 times that of YK-301, 986.71 times that of YK-302, 43.76 times that of YK-303, 1324.99 times that of YK-304, 12.47 times that of YK-306 and 6.01 times that of YK-307.

YK-310 can be up to 30.62 times that of YK-301, 928.69 times that of YK-302, 41.19 times that of YK-303, 1247.08 times that of YK-304, 11.74 times that of YK-306 and 5.66 times that of YK-307.

YK-312 can be up to 23.92 times that of YK-301, 725.34 times that of YK-302, 32.17 times that of YK-303, 974.01 times that of YK-304, 9.17 times that of YK-306 and 4.42 times that of YK-307.

YK-319 can be up to 29.04 times that of YK-301, 880.83 times that of YK-302, 39.07 times that of YK-303, 1182.82 times that of YK-304, 11.14 times that of YK-306 and 5.37 times that of YK-307.

YK-318 can be up to 13.28 times that of YK-301, 402.84 times that of YK-302, 17.87 times that of YK-303, 540.95 times that of YK-304, 5.09 times that of YK-306 and 2.46 times that of YK-307.

The activity differences between YK-301, YK-302, YK-303, YK-304, YK-306 and YK-307 are also large. The cell transfection efficiencies of YK-306 and YK-307 were stronger than that of SM-102, which can be up to 1.37 times and 2.84 times that of SM-102 respectively; YK-301 and YK-303 were not much different from SM-102, which were slightly lower, and were 0.53 times and 0.39 times that of SM-102 respectively; YK-302 and YK-304 had the lowest cell transfection efficiencies, only 0.017 times and 0.013 times that of SM-102.

The data were analyzed using GraphPad Prism software. Any one of YK-305, YK-310, YK-312, YK-319 and YK-318 was significantly different from YK-301, YK-302, YK-303, YK-304, YK-306 and YK-307, and the transfection efficiency was significantly improved.

b. Differences in Chemical Structure

This series of compounds are very similar to YK-305, YK-310, YK-312, YK-319 and YK-318 in structure, except that the $G_1$, $G_2$, $G_3$, $R_1$ or $R_2$ groups are slightly different. This series of compounds are also very similar to each other (see Table 6).

I. Differences in Structure from YK-305

Compared with YK-305, YK-304 only has a linear structure of the $R_1$ group and $R_2$ group, while YK-305 has a branched chain structure; other structures are identical, but regarding cell transfection efficiency YK-305 can be up to 1324.99 times that of YK-304.

Compared with YK-305, YK-302 has 2 less C in the $G_1$ group, and has a linear chain structure in the $R_1$ group, while YK-305 has a branched chain structure; has 1 more C in the single chain, and 2 less C in each single chain of the double chain in the $R_2$ group; other structures are identical, but regarding cell transfection efficiency, YK-305 was 986.71 times that of YK-302.

Compared with YK-305, YK-303 has a linear chain structure in the $R_1$ group, while YK-305 has a branched chain structure; has 2 less C in the $G_2$ group; has 2 more C in the single chain, and has 2 more C in each single chain of the double chain in the $R_2$ group; other structures are identical, but regarding cell transfection efficiency, YK-305 was 43.76 times that of YK-303.

II. Differences in Structure from YK-310

Compared with YK-310, YK-304 has 2 more C in the $G_2$ group; has a linear chain structure in the $R_2$ group, while in YK-310 it has a branched chain structure in the $R_2$ group; the group connected to N in the $G_3$ group has one less C; other structures are identical, but regarding cell transfection efficiency YK-310 was 1247.08 times that of YK-304.

Compared with YK-310, YK-302 only has 2 less C in the $G_1$ group; 1 less C in the $R_1$ group; 2 more C in the $G_2$ group; and 1 less C in the single chain of the $R_2$ group, and has 4 less C in each single chain of the double chain in the $R_2$ group; 1 less C in the group connected to N in the $G_3$ group; other structures are identical, but regarding cell transfection efficiency YK-310 was 928.69 times that of YK-302.

Compared with YK-310, YK-303 only has one less C in the group of $G_3$ group connected to N; other structures are identical, but regarding cell transfection efficiency, YK-310 was 41.19 times that of YK-303.

III. Differences in Structure from YK-312

Compared with YK-312, YK-304 only has a linear structure of the $R_1$ group and the $R_2$ group, while YK-312 has a branched chain structure; the group connected to N in the $G_3$ group has 1 less C; other structures are identical, but regarding cell transfection efficiency YK-312 was 974.01 times that of YK-304.

Compared with YK-312, YK-302 has 2 less C in the $G_1$ group; has a linear chain structure in the $R_1$ group, while YK-312 has a branched chain structure; has 1 more C in the single chain, and 2 less C in each single chain of the double chain in the $R_2$ group; the group connected to N in the $G_3$ group has 1 less C; other structures are identical, but regarding cell transfection efficiency, YK-312 was 725.34 times that of YK-302.

Compared with YK-312, YK-303 has a linear structure in the $R_1$ group, while YK-312 has a branched chain structure; has 2 less C in the $G_2$ group; has 2 more C in each single chain of the double chain in the $R_2$ group; the group connected to N in the $G_3$ group has 1 less C; other structures are identical, but regarding cell transfection efficiency, YK-312 was 32.17 times that of YK-303.

IV. Differences in Structure from YK-319

Compared with YK-319, YK-304 has one less C in the $G_1$ group and $G_2$ group; the $R_1$ group and $R_2$ group have linear structures, while YK-319 has branched chain structures in the $R_1$ group and $R_2$ group; the group connected to N in the $G_3$ group has one less hydroxymethyl group; other structures are identical, but regarding cell transfection efficiency, YK-319 was 1182.82 times that of YK-304.

Compared with YK-319, YK-302 has 3 less C in the $G_1$ group; has a linear chain structure in the $R_1$ group, while YK-319 has a branched chain structure; has 1 less C in the $G_2$ group; has one less hydroxymethyl group in the group connected to N in the $G_3$ group; other structures are identical, but regarding cell transfection efficiency, YK-319 was 880.83 times that of YK-302.

Compared with YK-319, YK-306 has 1 less C in $G_1$ group and 1 less C in $G_2$ group; 1 less hydroxymethyl group in the group connected to N in the $G_3$ group; other structures are identical, but regarding cell transfection efficiency, YK-319 was 11.14 times that of YK-306.

V. Differences in Structure from YK-318

Compared with YK-318, YK-304 has a linear structure in the $R_1$ group and $R_2$ group, while YK-318 has a branched chain structure; has one less hydroxylmethyl group in the group connected to N in the $G_3$ group; other structures are identical, but regarding cell transfection efficiency, YK-318 was 540.95 times that of YK-304.

Compared with YK-318, YK-302 has 2 less C in the $G_1$ group; has a linear chain structure in the $R_1$ group, while YK-318 has a branched chain structure; has one less hydroxylmethyl group in the group connected to N in the $G_3$ group; other structures are identical, but regarding cell transfection efficiency, YK-318 was 402.84 times that of YK-302.

Compared with YK-318, YK-303 has a linear structure of the $R_1$ group, while YK-318 has a branched chain structure; has 2 less C in the $G_2$ group; has 3 more C in the single chain, and has 2 more C in each single chain of the double chain in the $R_2$ group; has one less hydroxylmethyl group in the group connected to N in the $G_3$ group; other structures are identical, but regarding cell transfection efficiency, YK-318 was 17.87 times that of YK-303.

Brief Summary:

In a series of compounds with very similar structures that we designed, compared with compounds with similar structures and the $G_3$ group being $HO(CH_2)_2N(CH_3)CH_2CH(OH)CH_2$—, YK-305, YK-310, YK-312, YK-319 and YK-318 have the highest cell transfection efficiencies. For example, YK-305 can be 1,300 times higher than YK-304 and 9,000 times better than YK-302.

At the same time, it is found that there is no correspondence between the structure of compounds and intracellular transfection efficiency. Even a group of compounds with very similar structures are very likely to have very different cell transfection efficiencies.

Therefore, screening out cationic lipid compounds with high transfection efficiencies from a series of compounds with very similar structures is very difficult and requires a lot of creative work.

(4) YK-305, YK-310, YK-312, YK-319 and YK-318 had the Highest Cell Transfection Efficiencies Compared with a Series of Compounds with Similar Structures and the $G_3$ Group being $HO(CH_2)_2N(CH_2CH_3)CH_2CH(OH)CH_2$—. For Example, YK-305 can be Up to More than 200 Times that of YK-309.

A series of compounds with similar structures and the $G_3$ group being $HO(CH_2)_2N(CH_2CH_3)CH_2CH(OH)CH_2$— were compared with YK-305, YK-310, YK-312, YK-319 and YK-318. The only structural difference between these compounds is that the $G_1$, $G_2$, $G_3$, $R_1$ or $R_2$ groups are slightly different (see Table 8). The results show that the activities of this series of compounds varied greatly. Among them, YK-305, YK-310, YK-312, YK-319 and YK-318 had the highest cell transfection efficiencies, which can be up to 210 times, 200 times, 160 times, 190 times and 90 times that of YK-309 which had the lowest activity, showing significantly improved transfection efficiency.

TABLE 8

The chemical structures of the designed compounds

| Name | Structure |
| --- | --- |
| YK-305 | 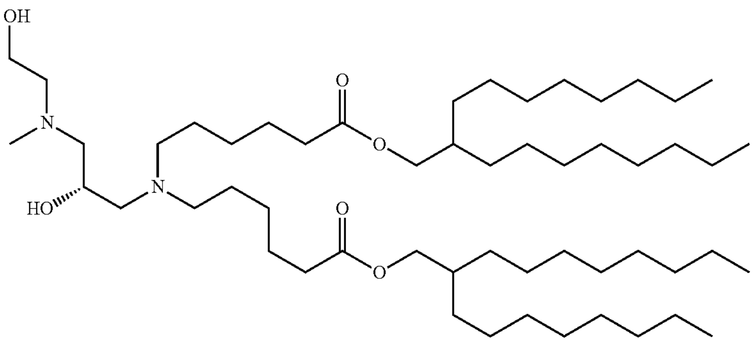 [SMILES: CCCCCCCCC(CCCCCCCC)COC(=O)CCCCCN(CCCCCC(=O)OCC(CCCCCCCC)CCCCCCCC)C[C@H](O)CN(C)CCO] YK-305 |
| YK-310 | 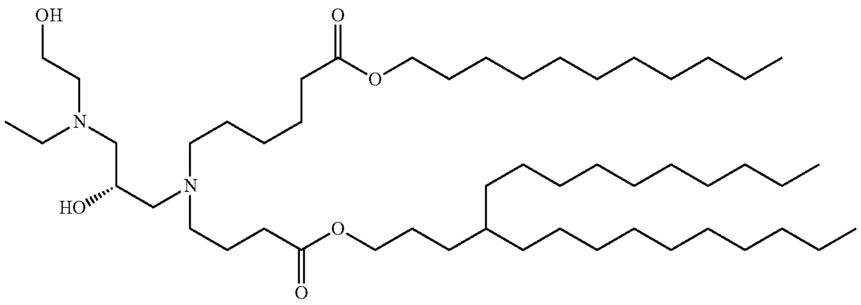 [SMILES: CCCCCCCCCCCOC(=O)CCCCCN(CCCC(=O)OCCCC(CCCCCCCCCC)CCCCCCCCCC)C[C@H](O)CN(CC)CCO] YK-310 |

TABLE 8-continued
| The chemical structures of the designed compounds | |
|---|---|
| Name | Structure |
| YK-312 | 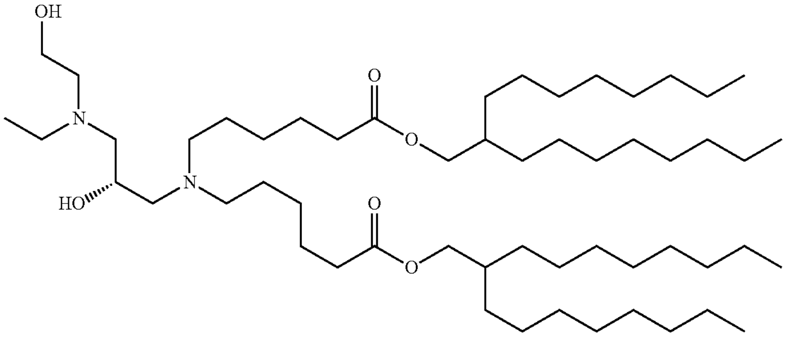 [SMILES: CCCCCCCCC(CCCCCCCC)COC(=O)CCCCCN(CCCCCC(=O)OCC(CCCCCCCC)CCCCCCCC)C[C@H](O)CN(CC)CCO] YK-312 |
| YK-319 | 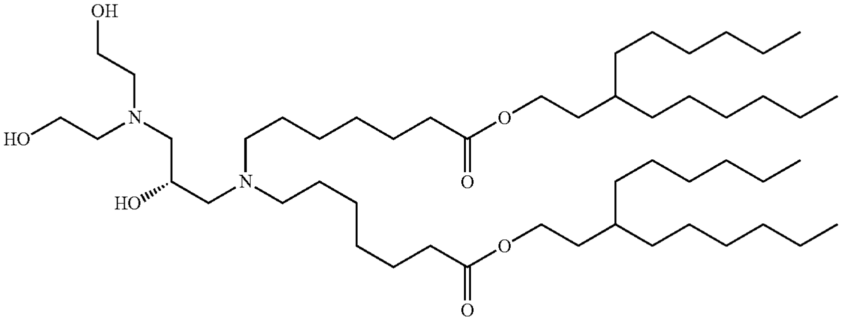 [SMILES: CCCCCCC(CCCCCC)CCOC(=O)CCCCCCN(CCCCCCC(=O)OCCC(CCCCCC)CCCCCC)C[C@H](O)CN(CCO)CCO] YK-319 |
| YK-318 | 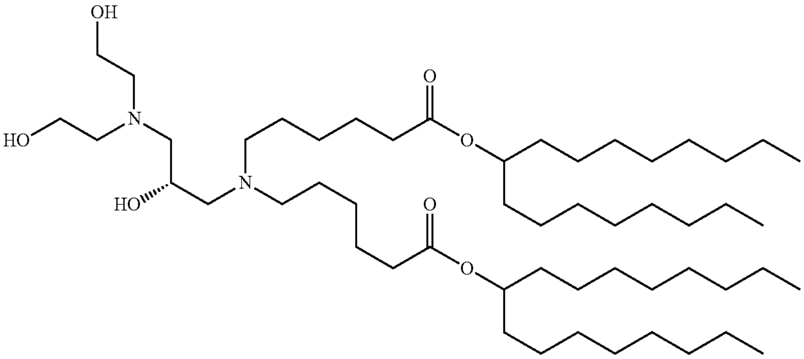 [SMILES: CCCCCCCCC(CCCCCCCC)OC(=O)CCCCCN(CCCCCC(=O)OC(CCCCCCCC)CCCCCCCC)C[C@H](O)CN(CCO)CCO] YK-318 |
| YK-308 | 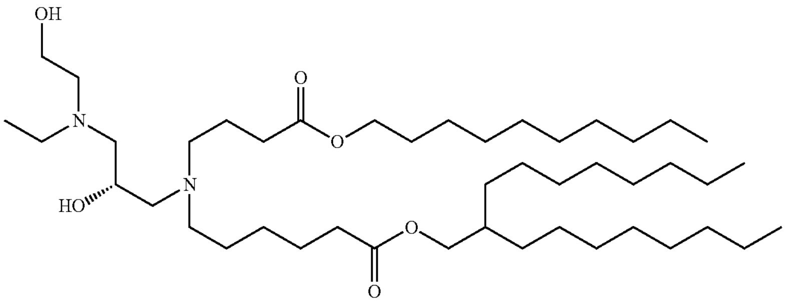 YK-308 |

TABLE 8-continued
| The chemical structures of the designed compounds | |
|---|---|
| Name | Structure |
| YK-309 | 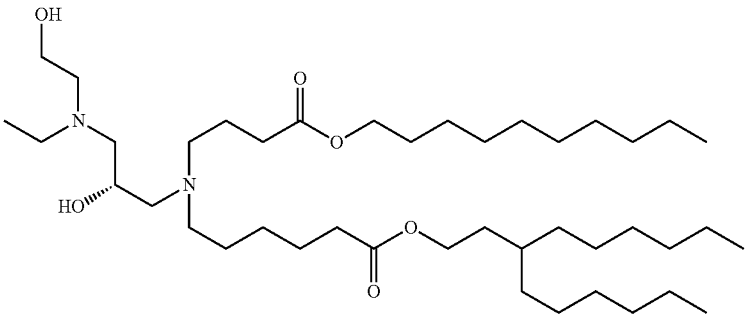 YK-309 |
| YK-311 | 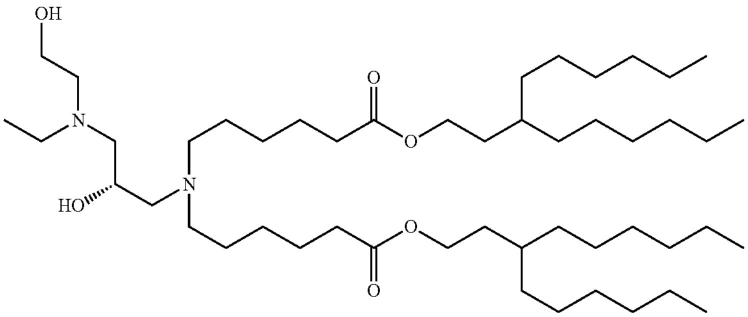 YK-311 |
| YK-313 | 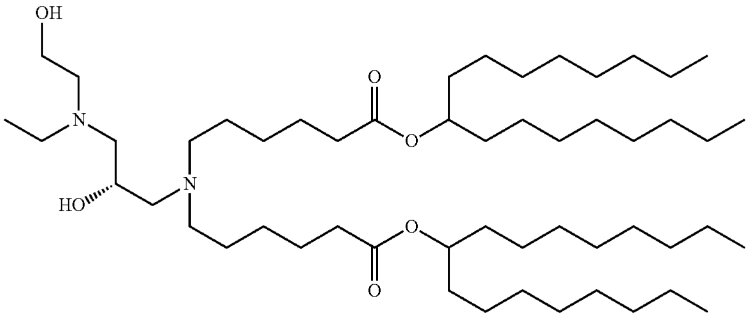 YK-313 |
| YK-314 | 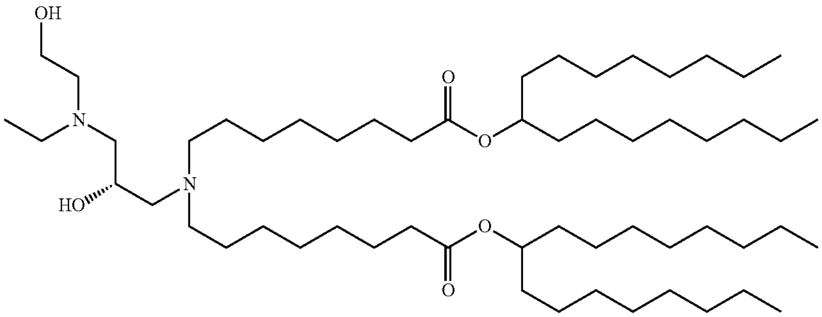 YK-314 |

TABLE 8-continued

| The chemical structures of the designed compounds | |
|---|---|
| Name | Structure |
| YK-315 | 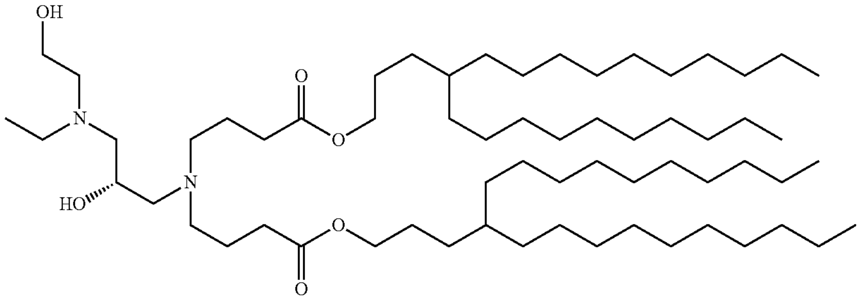 YK-315 |

TABLE 9

| Fluorescence detection results of Fluc-mRNA - 3 | | | | | | | | |
|---|---|---|---|---|---|---|---|---|
| No. | Name | Relative light unit (RLU) | Ratio relative to SM-102 | Multiples (YK-305) | Multiples (YK-310) | Multiples (YK-312) | Multiples (YK-319) | Multiples (YK-318) |
| 1 | YK-305 | 27408734 | 17.09 | 1.00 | 0.94 | 0.74 | 0.41 | 0.89 |
| 2 | YK-310 | 25797040 | 16.08 | 1.06 | 1.00 | 0.78 | 0.43 | 0.95 |
| 3 | YK-312 | 20148450 | 12.56 | 1.36 | 1.28 | 1.00 | 0.56 | 1.21 |
| 4 | YK-319 | 24467760 | 15.25 | 1.12 | 1.05 | 0.82 | 0.46 | 1.00 |
| 5 | YK-318 | 11190068 | 6.98 | 2.45 | 2.31 | 1.80 | 1.00 | 2.19 |
| 6 | YK-308 | 5036582 | 3.14 | 5.44 | 5.12 | 4.00 | 2.22 | 4.86 |
| 7 | YK-309 | 125370 | 0.08 | 218.62 | 205.77 | 160.71 | 89.26 | 195.16 |
| 8 | YK-311 | 1963636 | 1.22 | 13.96 | 13.14 | 10.26 | 5.70 | 12.46 |
| 9 | YK-313 | 866536 | 0.54 | 31.63 | 29.77 | 23.25 | 12.91 | 28.24 |
| 10 | YK-314 | 547434 | 0.34 | 50.07 | 47.12 | 36.81 | 20.44 | 44.70 |
| 11 | YK-315 | 1587188 | 0.99 | 17.27 | 16.25 | 12.69 | 7.03 | 15.42 |
| 12 | SM-102 | 1604015 | 1.00 | 17.09 | 16.08 | 12.56 | 6.98 | 15.25 |
| 13 | ALC-0315 | 2033550 | 1.27 | 13.48 | 12.69 | 9.91 | 12.03 | 5.50 |
| 14 | Compound 21 | 1432170 | 0.89 | 19.14 | 18.01 | 14.07 | 7.81 | 17.08 |
| 15 | Compound 23 | 1356022 | 0.85 | 20.21 | 19.02 | 14.86 | 8.25 | 18.04 |
| 16 | HHMA | 2006110 | 1.25 | 13.66 | 12.86 | 10.04 | 5.58 | 12.20 |
| 17 | Lipofectamine 3000 | 1183743 | 0.74 | 23.12 | 21.76 | 16.99 | 9.44 | 20.63 |

a. Difference in Cell Transfection Efficiency

Although compared with YK-305, YK-310, YK-312, YK-319 and YK-318, other compounds only have some minor differences in the $G_1$, $R_1$, $G_2$, $R_2$ or $G_3$ group (See Table 8), but the impact on cell transfection efficiency is very large, where the difference can be up to more than 200 times.

Specifically, it can be seen from Table 9 that the fluorescence absorption value of the LNP formulation prepared from YK-309 was very different from those of YK-305, YK-310, YK-312, YK-319 and YK-318.

YK-305, YK-310, YK-312, YK-319 and YK-318 can be up to 218.62 times, 205.77 times, 160.71 times, 195.16 times and 89.26 times that of YK-309 respectively.

Fluorescence absorbance values of LNP formulations prepared from YK-311, YK-313, YK-314 and YK-315 show a big difference in transfection efficiency compared with those of YK-305, YK-310, YK-312, YK-319 and YK-318.

YK-305 was 13.96 times that of YK-311, 31.63 times that of YK-313, 50.07 times that of YK-314, and 17.27 times that of YK-315.

YK-310 was 13.14 times that of YK-311, 29.77 times that of YK-313, 47.12 times that of YK-314 and 16.25 times that of YK-315.

YK-312 was 10.26 times that of YK-311, 23.25 times that of YK-313, 36.81 times that of YK-314 and 12.69 times that of YK-315.

YK-319 was 12.46 times that of YK-311, 28.24 times that of YK-313, 44.70 times that of YK-314 and 15.42 times that of YK-315.

YK-318 was 5.70 times that of YK-311, 12.91 times that of YK-313, 20.44 times that of YK-314 and 7.05 times that of YK-315.

The fluorescence absorbance value of an LNP formulation prepared from YK-308 shows a big difference in transfection efficiency compared with those of YK-305, YK-310, YK-312, YK-319 and YK-318.

YK-305, YK-310, YK-312, YK-318 and YK-319 were 5.44 times, 5.12 times, 4.00 times, 4.86 times and 2.22 times that of YK-308 respectively.

The data were analyzed using GraphPad Prism software. Any one of YK-305, YK-310, YK-312, YK-319 and YK-318 was significantly different from other compounds, and the cell transfection efficiency was significantly improved.

b. Differences in Chemical Structure

This series of compounds are very similar to YK-305, YK-310, YK-312, YK-319 and YK-318 in structure, except that the $G_1$, $G_2$, $G_3$, $R_1$ or $R_2$ group is slightly different. This series of compounds are also very similar to each other (see Table 8).

I. Differences in Structure from YK-305

Compared with YK-305, YK-309 only has 2 less C in the $G_1$ group; has a linear chain structure in the $R_1$ group, while YK-305 has a branched chain structure; has 1 more C in the single chain, and 2 less C in each single chain of the double chain in the $R_2$ group; has 1 more C in the group connected to N in the $G_3$ group; other structures are identical, but regarding cell transfection efficiency, YK-305 was 218.62 times that of YK-309.

Compared with YK-305, YK-314 only has 2 more C in the $G_1$ and $G_2$ groups; 1 less C in the single chain in the $R_1$ and $R_2$ groups; has 1 more C in the group connected to N in the $G_3$ group; other structures are identical, but regarding cell transfection efficiency, YK-305 was 50.07 times that of YK-314.

Compared with YK-305, YK-313 has one less C in each single chain in the $R_1$ and $R_2$ groups; has 1 more C in the group connected to N in the $G_3$ group; other structures are identical, but regarding cell transfection efficiency, YK-305 was 31.63 times that of YK-313.

II. Differences in Structure from YK-310

Compared with YK-310, YK-309 has 2 less C in the $G_1$ group; 1 less C in the $R_1$ group; 2 more C in the $G_2$ group; and has 1 less C in the single chain, and 4 less C in each single chain of the double chain in the $R_2$ group; other structures are identical, but regarding cell transfection efficiency, YK-310 was 205.77 times that of YK-309.

Compared with YK-310, YK-314 has 2 more C in the $G_1$ group; has a branched chain structure in the $R_1$ group, while YK-310 has a linear chain structure; has 4 more C in the $G_2$ group; and has 3 less C in the single chain, and 2 less C in each single chain of the double chain in the $R_2$ group; other structures are identical, but regarding cell transfection efficiency, YK-310 was 47.12 times that of YK-314.

Compared with YK-310, YK-313 has a branched chain structure in the $R_1$ group, while YK-310 has a linear chain structure; has 2 more C in the $G_2$ group; has 3 less C in the single chain, and 2 less C in each single chain of the double chain in the $R_2$ group; other structures are identical, but regarding cell transfection efficiency, YK-310 was 29.77 times that of YK-313.

III. Differences in Structure from YK-312

Compared with YK-312, YK-309 has 2 less C in the $G_1$ group; has a linear chain structure in the $R_1$ group, while YK-312 has a branched chain structure; has 1 more C in the single chain, and 2 less C in each single chain of the double chain in the $R_2$ group; other structures are identical, but regarding cell transfection efficiency, YK-312 was 160.71 times that of YK-309.

Compared with YK-312, YK-314 has 2 more C in the $G_1$ and $G_2$ groups; has 1 less C in the single chain in the $R_1$ and $R_2$ groups; other structures are identical, but regarding cell transfection efficiency, YK-312 was 36.81 times that of YK-314.

Compared with YK-312, YK-313 has one less C in the single chain in the $R_1$ and $R_2$ groups; other structures are identical, but regarding cell transfection efficiency, YK-312 was 23.25 times that of YK-313.

IV. Differences in Structure from YK-319

Compared with YK-319, YK-309 has 3 less C in the $G_1$ group; has a linear chain structure in the $R_1$ group, while YK-319 has a branched chain structure; has 1 less C in the $G_2$ group; has one less hydroxyl group in the group connected to N in the $G_3$ group; other structures are identical, but regarding cell transfection efficiency, YK-319 was 195.16 times that of YK-309.

Compared with YK-319, YK-314 has 1 more C in the $G_1$ and $G_2$ groups; 2 less C in each single chain, and 2 more C in each single chain of the double chain in the $R_1$ and $R_2$ groups; has one less hydroxyl group in the group connected to N in the $G_3$ group; other structures are identical, but regarding cell transfection efficiency, YK-319 was 44.70 times that of YK-314.

Compared with YK-319, YK-313 has 1 less C in the $G_1$ and $G_2$ groups; 2 less C in each single chain, and 2 more C in each single chain of the double chain in the $R_1$ and $R_2$ groups; has one less hydroxyl group in the group connected to N in the $G_3$ group; other structures are identical, but regarding cell transfection efficiency, YK-319 was 28.24 times that of YK-313.

V. Differences in Structure from YK-318

Compared with YK-318, YK-309 has 2 less C in the $G_1$ group; has a linear chain structure in the $R_1$ group, while YK-318 has a branched chain structure; 1 less hydroxyl group in the group connected to N in the $G_3$ group; other structures are identical, but regarding cell transfection efficiency, YK-318 was 89.26 times that of YK-309.

Compared with YK-318, YK-314 has 2 less C in the $G_1$ and $G_2$ groups; has 1 less hydroxyl group in the group connected to N in the $G_3$ group; other structures are identical, but regarding cell transfection efficiency, YK-318 was 20.44 times that of YK-314.

Compared with YK-318, YK-313 has one less hydroxyl group in the group connected to N in the $G_3$ group; other structures are identical, but regarding cell transfection efficiency, YK-318 was 12.91 times that of YK-313.

Brief Summary:

In a series of compounds that we designed with very similar structures, compared with compounds with similar structures and the $G_3$ group being $HO(CH_2)_2N(CH_2CH_3)CH_2CH(OH)CH_2—$, YK-305, YK-310, YK-312, YK-319 and YK-318 have the highest dell transfection efficiencies. For example, YK-305 and YK-310 can be 200 times higher than YK-309.

At the same time, it is found that there is no correspondence between the structure of compounds and intracellular transfection efficiency. Even a group of compounds with very similar structures are very likely to have very different cell transfection efficiencies.

Therefore, screening out cationic lipid compounds with high transfection efficiency from a series of compounds with very similar structures is very difficult and requires a lot of creative work.

(5) YK-305, YK-310, YK-312, YK-319 and YK-318 had the Highest Cell Transfection Efficiencies Compared with a Series of Compounds with Similar Structures and the $G_3$ Group being $(HO(CH_2)_2)_2NCH_2CH(OH)CH_2—$. For Example, YK-305 can be Up to 20 Times that of YK-321.

YK-305, YK-310, YK-312, YK-319 and YK-318 had the highest cell transfection efficiencies compared with compounds with similar structures and the $G_3$ group being $(HO(CH_2)_2)_2NCH_2CH(OH)CH_2—$. For example, YK-305 can be up to 20 times that of YK-321.

TABLE 10
| The chemical structures of the designed compounds | |
|---|---|
| Name | Structure |
| YK-305 | 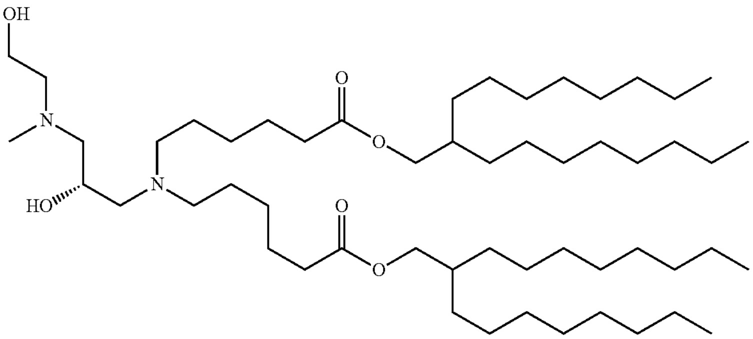 YK-305 |
| YK-310 | 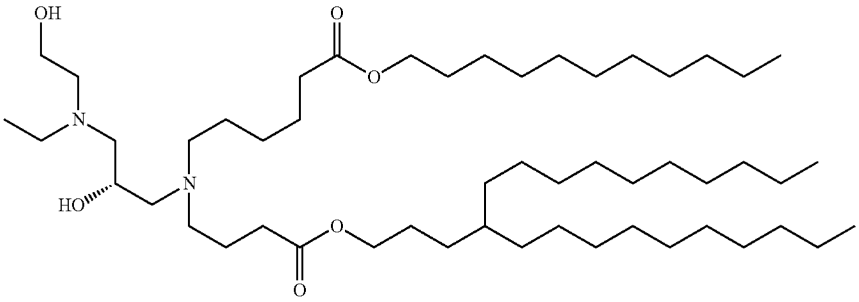 YK-310 |
| YK-312 | 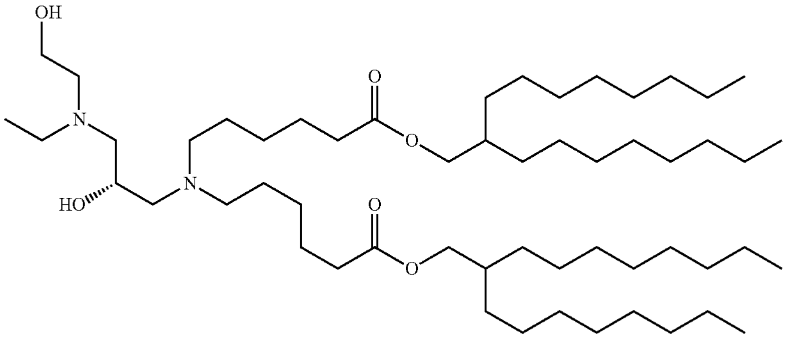 YK-312 |
| YK-319 | 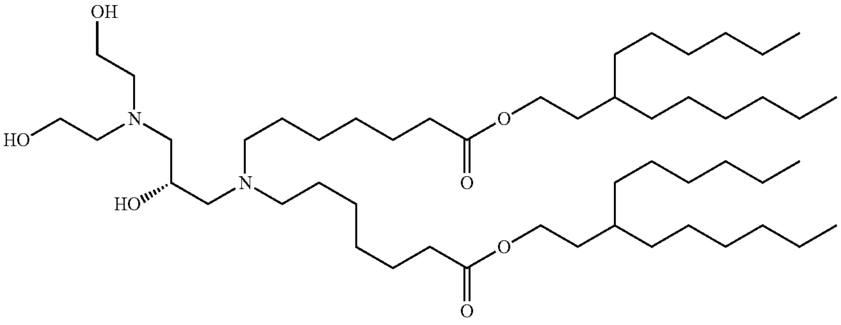 YK-319 |

TABLE 10-continued
| The chemical structures of the designed compounds | |
|---|---|
| Name | Structure |
| YK-318 | 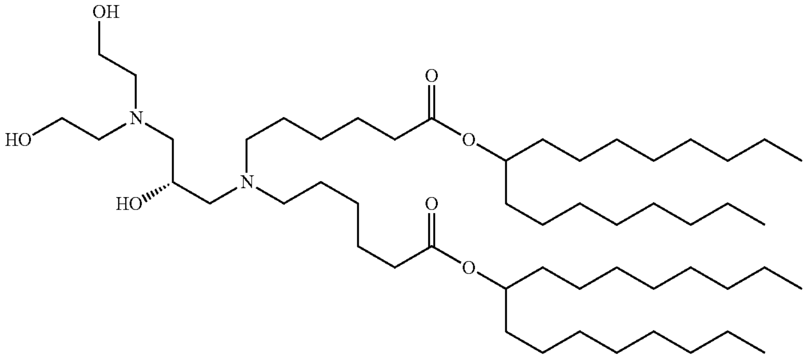 YK-318 |
| YK-316 | 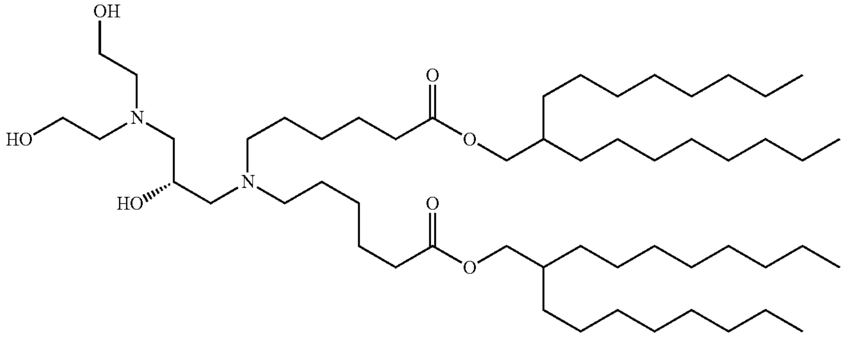 YK-316 |
| YK-317 | 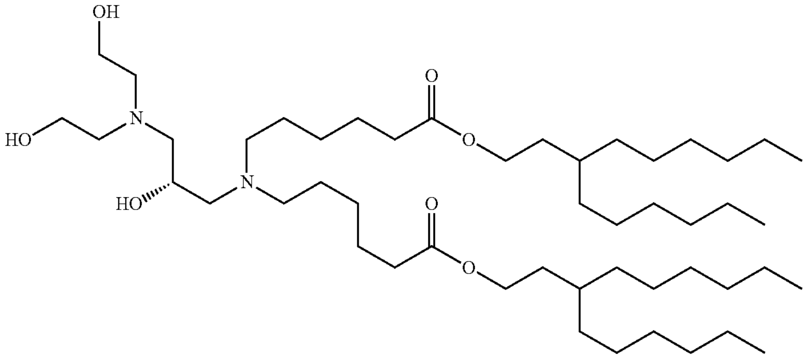 YK-317 |
| YK-320 | 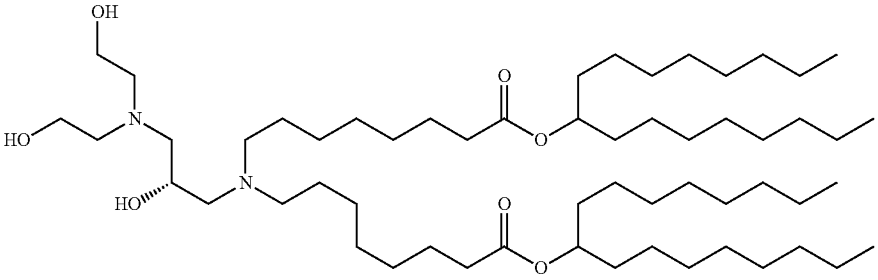 YK-320 |

TABLE 10-continued

| The chemical structures of the designed compounds | |
|---|---|
| Name | Structure |
| YK-321 | 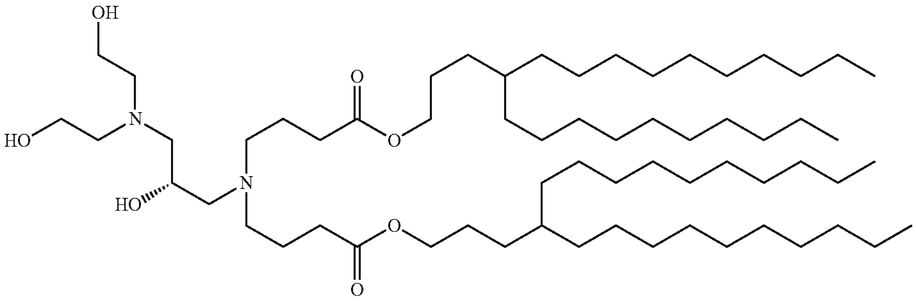 YK-321 |

TABLE 11

| Fluorescence detection results of Fluc-mRNA - 4 | | | | | | | | |
|---|---|---|---|---|---|---|---|---|
| No. | Name | Relative light unit (RLU) | Ratio relative to SM-102 | Multiples (YK-305) | Multiples (YK-310) | Multiples (YK-312) | Multiples (YK-319) | Multiples (YK-318) |
| 1 | YK-305 | 27408734 | 17.09 | 1.00 | 0.94 | 0.74 | 0.89 | 0.41 |
| 2 | YK-310 | 25797040 | 16.08 | 1.06 | 1.00 | 0.78 | 0.95 | 0.43 |
| 3 | YK-312 | 20148450 | 12.56 | 1.36 | 1.28 | 1.00 | 1.21 | 0.56 |
| 4 | YK-319 | 24467760 | 15.25 | 1.12 | 1.05 | 0.82 | 1.00 | 0.46 |
| 5 | YK-318 | 11190068 | 6.98 | 2.45 | 2.31 | 1.80 | 2.19 | 1.00 |
| 6 | YK-316 | 4810210 | 3.00 | 5.70 | 5.36 | 4.19 | 5.09 | 2.33 |
| 7 | YK-317 | 3605054 | 2.25 | 7.60 | 7.16 | 5.59 | 6.79 | 3.10 |
| 8 | YK-320 | 2702966 | 1.69 | 10.14 | 9.54 | 7.45 | 9.05 | 4.14 |
| 9 | YK-321 | 1403416 | 0.87 | 18.33 | 18.38 | 14.36 | 17.43 | 7.97 |
| 10 | SM-102 | 1604015 | 1.00 | 17.09 | 16.08 | 12.56 | 15.25 | 6.98 |
| 11 | ALC-0315 | 2033350 | 1.27 | 13.48 | 12.69 | 9.91 | 12.03 | 5.50 |
| 12 | Compound 21 | 1432170 | 0.89 | 19.14 | 18.01 | 14.07 | 17.08 | 7.81 |
| 13 | Compound 23 | 1356022 | 0.85 | 20.21 | 19.02 | 14.86 | 18.04 | 8.25 |
| 14 | HHMA | 2006110 | 1.25 | 13.66 | 12.86 | 10.04 | 12.20 | 5.58 |
| 15 | Lipofectamine 3000 | 1185743 | 0.74 | 23.12 | 21.76 | 16.99 | 20.63 | 9.44 |

a. Difference in Cell Transfection Efficiency

Compared with compounds with similar structures and the $G_3$ group being $(HO(CH_2)_2)_2NCH_2CH(OH)CH_2$— (see Table 10), YK-305, YK-310, YK-312, YK-319 and YK-318 had the highest cell transfection efficiencies. For example, YK-305 can be up to 20 times that of YK-321.

Details are as follows:

It can be seen from Table 11, YK-321 was very different from YK-305, YK-310, YK-312, YK-318 and YK-319.

YK-305, YK-310, YK-312, YK-319 and YK-318 were 19.53 times, 18.38 times, 14.36 times, 17.43 times and 7.97 times that of YK-321 respectively.

In addition, YK-316, YK-317 and YK-320 were quite different from YK-305, YK-310, YK-312, YK-319 and YK-318.

YK-305 can be up to 5.70 times that of YK-316, 7.60 times that of YK-317 and 10.14 times that of YK-320.

YK-310 can be up to 5.36 times that of YK-316, 7.16 times that of YK-317, and 9.54 times that of YK-320.

YK-312 can be up to 4.19 times that of YK-316, 5.59 times that of YK-317 and 7.45 times that of YK-320.

YK-319 can be up to 5.09 times that of YK-316, 6.79 times that of YK-317, and 9.05 times that of YK-320.

YK-318 can be up to 2.33 times that of YK-316, 3.10 times that of YK-317 and 4.14 times that of YK-320.

Figure 7:
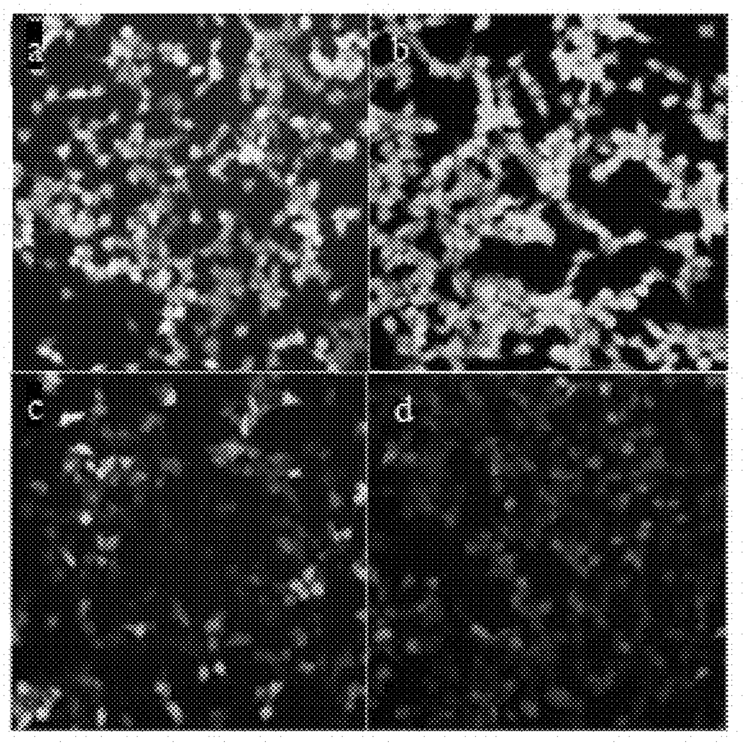
FIG. 7 shows the fluorescence absorption intensity of LNP formulations of Fluc-mRNA prepared from different cationic lipids (a: YK-305; b: YK-310; c: YK-320; d: YK-321).

FIG. 7 shows the fluorescence absorption images of LNP formulations prepared from YK-305, YK-310, YK-320 and YK-321. It can be seen that compared with YK-305 and YK-310, YK-320 and YK-321 had very weak fluorescence absorptions.

The data were analyzed using GraphPad Prism software. Any one of YK-305, YK-310, YK-312, YK-319 and YK-318 was significantly different from other compounds, and the transfection efficiency was significantly improved.

b. Differences in Chemical Structure

This series of compounds are very similar to YK-305, YK-310, YK-312, YK-319 and YK-318, except that the $G_1$, $G_2$, $G_3$, $R_1$ or $R_2$ groups is slightly different. The structures of this series of compounds are also very similar. (See Table 10)

I. Differences in Structure from YK-305

Compared with YK-305, YK-321 has 2 less C in the $G_1$ and $G_2$ groups; has 2 more C in each single chain, and 2 more C in each single chain of the double chain in the $R_1$ and $R_2$ groups; has one more hydroxymethyl group in the group connected to N in the $G_3$ group; other structures are identical, but regarding cell transfection efficiency, YK-305 was 19.53 times that of YK-321.

Compared with YK-305, YK-320 has 2 more C in the $G_1$ and $G_2$ groups; 1 less C in the single chain of the $R_1$ and $R_2$ groups; has one more hydroxymethyl group in the group connected to N in the $G_3$ group; other structures are identical, but regarding cell transfection efficiency, YK-305 was 10.14 times that of YK-320.

Compared with YK-305, YK-316 has one more hydroxymethyl group in the group connected to N in the $G_3$ group; other structures are identical, but regarding cell transfection efficiency, YK-305 was 5.70 times that of YK-316.

II. Differences in Structure from YK-310

Compared with YK-310, YK-321 has 2 less C in the $G_1$ group; has a branched chain structure in the $R_1$ group, while YK-310 has a linear chain structure; has 1 more hydroxyl group in the group connected to N in the $G_3$ group; other structures are identical, but regarding cell transfection efficiency, YK-310 was 18.38 times that of YK-321.

Compared with YK-310, YK-320 has 2 more C in the $G_1$ group; has a branched chain structure in the $R_1$ group, while YK-310 has a linear chain structure; has 4 more C in the $G_2$ group; has 3 less C in the single chain, and has 2 less C in each single chain of the double chain in the $R_2$ group; has 1 more hydroxyl group in the group connected to N in the $G_3$ group; other structures are identical, but regarding cell transfection efficiency, YK-310 was 9.54 times that of YK-320.

Compared with YK-310, YK-317 has a branched chain structure in the $R_1$ group, while YK-310 has a linear chain structure; has 2 more C in the $G_2$ group; has 1 less C in the single chain, and has 4 less C in each single chain of the double chain in the $R_2$ group; has 1 more hydroxyl group in the group connected to N in the $G_3$ group; other structures are identical, but regarding cell transfection efficiency, YK-310 was 7.16 times that of YK-317.

III. Differences in Structure from YK-312

Compared with YK-312, YK-321 has 2 less C in $G_1$ and $G_1$ groups; 2 more C in each single chain, and 2 more C in each single chain of the double chain in the $R_1$ and $R_2$ groups; has 1 more hydroxyl group in the group connected to N in the $G_3$ group; other structures are identical, but regarding cell transfection efficiency, YK-312 was 14.36 times that of YK-321.

Compared with YK-312, YK-320 has 2 more C in the $G_1$ and $G_1$ groups; 1 less C in the single chain in the $R_1$ and $R_2$ groups; has 1 more hydroxyl group in the group connected to N in the $G_3$ group; other structures are identical, but regarding cell transfection efficiency, YK-312 was 7.45 times that of YK-320.

Compared with YK-312, YK-316 has 1 more hydroxyl group in the group connected to N in the $G_3$ group; other structures are identical, but regarding cell transfection efficiency, YK-312 was 4.19 times that of YK-316.

IV. Differences in Structure from YK-319

Compared with YK-319, YK-321 has 3 less C in the $G_1$ and $G_1$ groups; has 1 more C in each single chain, and 4 more C in each single chain of the double chain in the $R_1$ and $R_2$ groups; other structures are identical, but regarding cell transfection efficiency, YK-319 was 17.43 times that of YK-321.

Compared with YK-319, YK-320 has 1 more C in the $G_1$ and $G_1$ groups; has 2 less C in each single chain, and 2 more C in each single chain of the double chain in the $R_1$ and $R_2$ groups; other structures are identical, but regarding cell transfection efficiency, YK-319 was 9.05 times that of YK-320.

Compared with YK-319, YK-317 has one less C in $G_1$ and $G_1$ groups; other structures are identical, but regarding cell transfection efficiency YK-319 was 6.79 times that of YK-317.

V. Differences in Structure from YK-318

Compared with YK-318, YK-321 has 2 less C in the $G_1$ and $G_2$ groups; 3 more C in each single chain, and 2 more C in each single chain of the double chain in the $R_1$ and $R_2$ groups; other structures are identical, but regarding cell transfection efficiency, YK-318 was 7.97 times that of YK-321.

Compared with YK-318, YK-320 has 2 more C in $G_1$ and $G_2$ groups; other structures are identical, but regarding cell transfection efficiency YK-318 was 4.14 times that of YK-320.

Compared with YK-318, YK-316 has one more C in the single chain in the $R_1$ and $R_2$ groups; other structures are identical, but regarding cell transfection efficiency, YK-318 was 2.33 times that of YK-316.

Brief Summary:

In a series of compounds with very similar structures we designed, compared with compounds with similar structures and the $G_3$ group being $(HO(CH_2)_2)_2NCH_2CH(OH)CH_2$—, YK-305, YK-310, YK-312, YK-319 and YK-318 have the highest cell transfection efficiencies. For example, YK-305 can be up to 20 times that of YK-321.

At the same time, it is found that it is impossible to predict the difference in cell transfection efficiency between different compounds (no matter whether they have similar or very different structures) based on structural differences. Even a group of compounds with small structural differences are likely to have very different cell transfection efficiencies.

Therefore, it is very difficult and requires a lot of creative work to screen out cationic lipid compounds with high transfection efficiencies from a series of compounds with similar chemical structures.

Summary:

1) Through various designs of compound structures and a lot of creative work, cationic lipid compounds with high cell transfection efficiencies, such as YK-305, YK-310, YK-312, YK-319 and YK-318, were designed and screened out.

The designed series of compounds are very different from the representative cationic lipids in the prior art, such as SM-102, ALC-0315, compound 21, compound 23, HHMA and YK-009. The $G_3$ group is completely different, and other parts are also different, so there are great differences in terms of polarity, acidity and alkalinity, and hydrophilicity. It is impossible to predict the cell transfection efficiency, cytotoxicity, and expression in animals of LNP formulations prepared from this series of compounds based on the above-mentioned cationic lipid compounds disclosed in the prior art.

2) The cell transfection efficiencies of LNP formulations prepared from YK-305, YK-310, YK-312, YK-319 and YK-318 were the highest, and the activity was significantly improved compared to the representative cationic lipids in the prior art. For example, YK-305 can be up to 17 times that of SM-102, 19 times that of compound 21, and 20 times that of compound 23.

Compared with compounds with similar structures and the $G_3$ group being $HO(CH_2)_2N(CH_3)CH_2CH(OH)CH_2$—, YK-305, YK-310, YK-312, YK-319 and YK-318 have the highest cell transfection efficiencies. For example, YK-305 can be 1,300 times higher than YK-304 and 9,000 times higher than YK-302.

Compared with compounds with similar structures and the $G_3$ group being $HO(CH_2)_2N(CH_2CH_3)CH_2CH(OH)CH_2$—, YK-305, YK-310, YK-312, YK-319 and YK-318 have the highest cell transfection efficiencies. For example, both YK-305 and YK-310 are 200 times higher than YK-309.

Compared with compounds with similar structures and the $G_3$ group being $(HO(CH_2)_2)_2NCH_2CH(OH)CH_2$—, YK-305, YK-310, YK-312, YK-319 and YK-318 have the highest cell transfection efficiencies. For example, YK-305 can be up to 20 times that of YK-321.

3) There is no correspondence between the structure of a compound and intracellular transfection efficiency. Compounds with small structural differences are very likely to have very large differences in transfection efficiency. Therefore, screening out cationic lipid compounds with high transfection efficiency requires multiple designs and a lot of creative work.

2. Cell Survival Rate Determination

An LNP formulation containing 1.5 g of Fluc-mRNA (the carrier components of the LNP formulation were cationic lipid, neutral lipid, structured lipid and polymer-conjugated lipid with a molar ratio of 49:10:39.5:1.5, wherein the cationic lipid was listed in Table 1) and the formulation of Lipofectamine 3000 were added to the cell culture medium of a 96-well plate, and further cultivated for 24 hours. 10 μL of CCK-8 solution was then added to each well, and the culture plate was incubated in an incubator for 1 hour. The absorbance at 450 nm was measured by a microplate reader. The results are shown in Tables 12 to 15.

Cell survival rate can represent the toxicity of cationic lipids to cells. The higher the cell survival rate, the lower the toxicity to cells.

Assay Results:

(1) Among a Series of Designed Compounds, LNP Formulations Prepared from YK-305, YK-310, YK-312, YK-319 and YK-318 had Significantly Decreased Cytotoxicity and Significantly Improved Cell Survival Rate Compared with the Representative Cationic Lipids in the Prior Art. For Example, the Cell Survival Rates of YK-305 and YK-310 were 12.73% and 12.65% Higher than SM-102, Respectively, and 15.71% and 15.63% Higher than HHMA, Respectively.

TABLE 12

| Cell survival rate - 1 | | |
|---|---|---|
| Serial No. | Cationic lipid | Cell survival rate (%) |
| 1 | YK-305 | 82.18 |
| 2 | YK-310 | 82.10 |
| 3 | YK-312 | 76.96 |
| 4 | YK-319 | 75.21 |
| 5 | YK-318 | 75.56 |
| 6 | YK-009 | 72.55 |
| 7 | SM-102 | 69.45 |
| 8 | ALC-0315 | 51.03 |
| 9 | Compound 21 | 70.21 |
| 10 | Compound 23 | 71.50 |
| 11 | HHMA | 66.47 |
| 12 | Lipofectamine 3000 | 25.01 |

a. Difference in Cell Survival Rate

Table 12 lists the cytotoxicity test results of LNP formulations prepared from different cationic lipid compounds. Among them, YK-009 is disclosed in CN114044741B (claim 1), SM-102 is compound 25 disclosed in WO2017049245A2 (page 29 of the specification), ALC-0315 is compound 3 disclosed in CN108368028B (page 24 of the specification), compound 21 and compound 23 are disclosed in WO2021055833A1 (page 22 of the specification), and HHMA is compound 1 disclosed in CN112979483B (page 12 of the specification); Lipofectamine 3000 is a currently widely used cell transfection reagent with good transfection performance.

Figure 8:
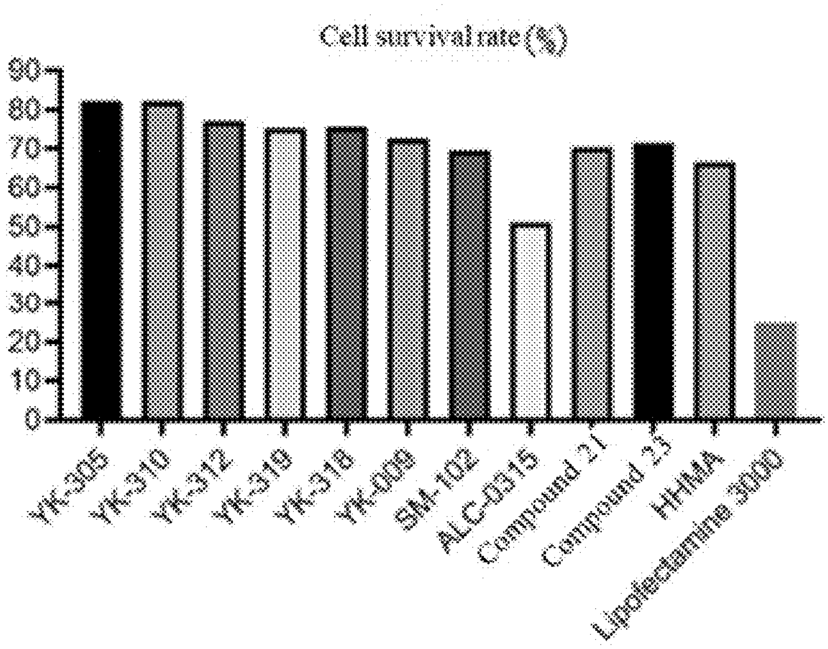
FIG. 8 shows the cell survival rate after introducing the LNP formulations of Fluc-mRNA prepared from different cationic lipids (YK-305, YK-310, YK-312, YK-319, YK-318, YK-009, SM-102, ALC-0315, compound 21, compound 23 and HHMA) and a Lipofectamine 3000 formulation containing Fluc-mRNA into the cell culture medium and culturing for 24 hours.

It can be seen from Table 12, the LNP formulations of Fluc-mRNA prepared from YK-305, YK-310, YK-312, YK-319 and YK-318 had the lowest cytotoxicities, with cell survival rates of 82.18% and 82.10%, 76.96%, 75.21% and 75.56%, respectively. (FIG. 8)

YK-305 was 12.73% higher than SM-102, 31.15% higher than ALC-0315, 11.97% higher than compound 21, 10.68% higher than compound 23, 15.71% higher than HIMA, and 57.17% higher than Lipofectamine 3000.

YK-310 was 12.65% higher than SM-102, 31.07% higher than ALC-0315, 11.89% higher than compound 21, 10.60% higher than compound 23, 15.63% higher than HIMA, and 57.09% higher than Lipofectamine 3000.

YK-312 was 7.51% higher than SM-102, 25.93% higher than ALC-0315, 6.75% higher than compound 21, 5.46% higher than compound 23, 10.49% higher than HIMA, and 51.95% higher than Lipofectamine 3000.

YK-319 was 5.76% higher than SM-102, 24.18% higher than ALC-0315, 5.00% higher than compound 21, 3.71% higher than compound 23, 8.74% higher than HHMA, and 50.20% higher than Lipofectamine 3000.

YK-318 was 6.11% higher than SM-102, 24.53% higher than ALC-0315, 5.35% higher than compound 21, 4.06% higher than compound 23, 9.09% higher than HHMA, and 50.55% higher than Lipofectamine 3000.

The data were analyzed using GraphPad Prism software, in which any one of YK-305, YK-310, YK-312, YK-319 and YK-318 was significantly different from SM-102, ALC-0315, compound 21, compound 23, HHMA and Lipofectamine 3000, and the cytotoxicity was significantly reduced.

b. Differences in Chemical Structure

Compared with the cationic lipids in the prior art, YK-305, YK-310, YK-312, YK-319 and YK-318 have very different chemical structures. Among them, HHMA has the biggest difference in structure. It can be seen from the chemical structure that only one side chain of the group connected to the central N atom of HHMA is similar to one side chain of this series of structures, and the other parts are completely different; Compared with SM-102, ALC-0315, compound 21, compound 23 and YK-009, the $G_3$ group is completely different, and the $G_1$, $R_1$, $G_2$ and $R_2$ groups are also greatly different.

Brief Summary:

Among a series of designed compounds, LNP formulations prepared from YK-305, YK-310, YK-312, YK-319 and YK-318 had the lowest cytotoxicities and had improved cell survival rates compared with the representative cationic lipids in the prior art. For example, the cell survival rates of both YK-305 and YK-310 were 30% higher than that of ALC-0315, 12% higher than that of SM-102, and 15% higher than that of HHMA.

Compared with representative cationic lipids in the prior art, YK-305, YK-310, YK-312, YK-319 and YK-318 have huge differences in chemical structure. The $G_3$ group is completely different, and $G_1$, $R_1$, $G_2$ and $R_2$ groups also have great differences.

The LNP formulation prepared from compounds designed for the first time in this application with a huge chemical structure differences from the cationic lipids in the prior art had significantly reduced cytotoxicities and significantly improved cell survival rates compared to those prepared from the cationic lipids in the prior art.

(2) YK-305, YK-310, YK-312, YK-319 and YK-318 had the lowest cytotoxicity and significantly improved cell survival rate compared with a series of compounds with similar structures and the $G_3$ group being $HO(CH_2)_2N(CH_3)CH_2CH(OH)CH_2$—. For example, YK-305 and YK-310 both had increased cell survival rates by 65% compared with YK-302.

YK-305, YK-310, YK-312, YK-319 and YK-318 were compared with a series of compounds with similar structures and the $G_3$ group being $HO(CH_2)_2N(CH_3)CH_2CH(OH)CH_2$—, and these compounds are different only slightly in the $G_1$, $G_2$, $G_3$, $R_1$ or $R_2$ group.

The results showed that the cytotoxicity difference of this series of compounds was very significant. Among them, YK-305, YK-310, YK-312, YK-319 and YK-318 had the highest cell survival rates. For example, YK-305 and YK-310 were both higher by 65% than YK-302.

TABLE 13

Cell survival rate - 2

| Serial No. | Cationic lipid | Cell survival rate (%) |
|---|---|---|
| 1 | YK-305 | 82.18 |
| 2 | YK-310 | 82.10 |
| 3 | YK-312 | 76.96 |
| 4 | YK-319 | 75.21 |
| 5 | YK-318 | 75.56 |
| 6 | YK-301 | 52.96 |
| 7 | YK-302 | 16.43 |
| 8 | YK 303 | 63.32 |
| 9 | YK-304 | 34.16 |
| 10 | YK-306 | 42.19 |
| 11 | YK-307 | 61.14 |
| 12 | SM-102 | 69.45 |
| 13 | ALC-0315 | 51.03 |
| 14 | Compound 21 | 70.21 |
| 15 | Compound 23 | 71.50 |
| 16 | HHMA | 66.47 |
| 17 | Lipofectamine 3000 | 25.01 |

a. Difference in Cell Survival Rate

Figure 9:
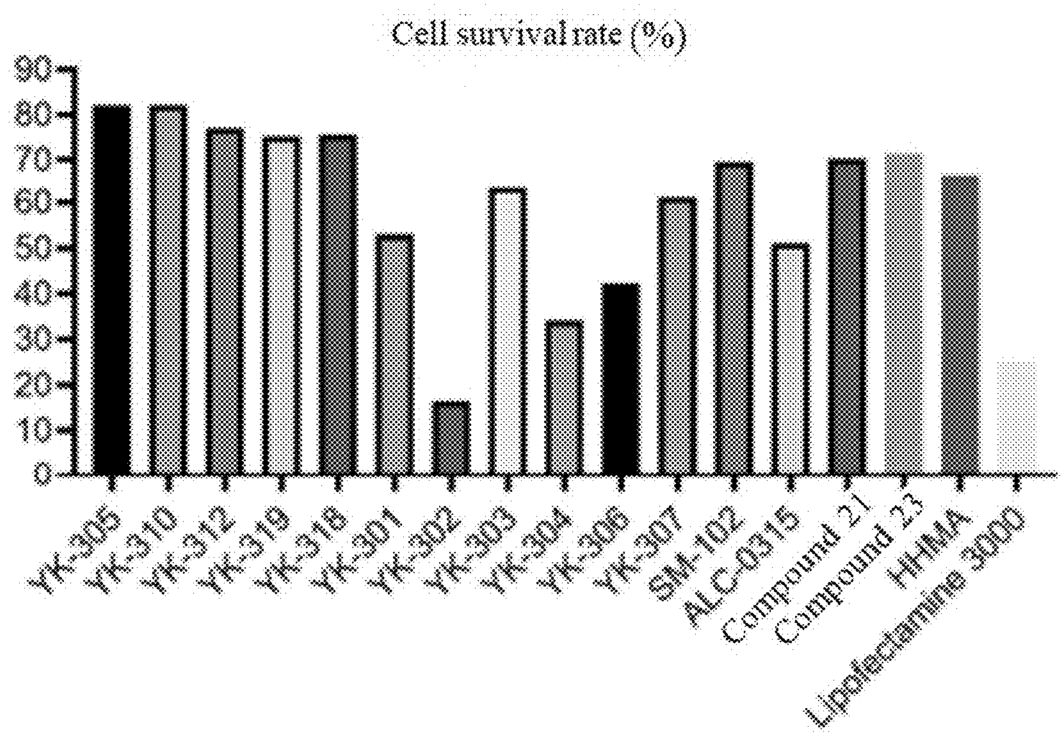
FIG. 9 shows the cell survival rate after introducing the LNP formulations of Fluc-mRNA prepared from different cationic lipids (YK-305, YK-310, YK-312, YK-319, YK-318, YK-301, YK-302, YK-303, YK-304, YK-306, YK-307, SM-102, ALC-0315, compound 21, compound 23 and HHMA) and a Lipofectamine 3000 formulation containing Fluc-mRNA into the cell culture medium and culturing for 24 hours.

It can be seen from Table 13, the cytotoxicity of LNP formulations prepared from these compounds varied greatly, among which YK-302 had the highest toxicity and the lowest cell survival rate of only 16.43%. (FIG. 9)

The cell survival rates of YK-305, YK-310, YK-312, YK-319 and YK-318 were increased by 65.75%, 65.67%, 60.53%, 58.78% and 59.13% respectively compared with YK-302.

Compared with YK-305, YK-310, YK-312, YK-319 and YK-318, the cell survival rates of other compounds were also quite different.

The cell survival rate of YK-305 was 29.22% higher than YK-301, 18.86% higher than YK-303, 48.02% higher than YK-304, 39.99% higher than YK-306, and 21.04% higher than YK-307.

The cell survival rate of YK-310 was 29.14% higher than YK-301, 18.78% higher than YK-303, 47.94% higher than YK-304, 39.91% higher than YK-306, and 20.96% higher than YK-307.

The cell survival rate of YK-312 was 24.00% higher than YK-301, 13.64% higher than YK-303, 42.80% higher than YK-304, 34.77% higher than YK-306, and 15.82% higher than YK-307.

The cell survival rate of YK-319 was 22.25% higher than YK-301, 11.89% higher than YK-303, 41.05% higher than YK-304, 33.02% higher than YK-306, and 14.07% higher than YK-307.

The cell survival rate of YK-318 was 22.60% higher than YK-301, 12.24% higher than YK-303, 41.40% higher than YK-304, 33.37% higher than YK-306, and 14.42% higher than YK-307.

The data were analyzed using GraphPad Prism software, in which, any one of YK-305, YK-310, YK-312, YK-319 and YK-318 had a significant difference in cytotoxicity from other compounds, the cytotoxicity was significantly reduced, and the cell survival rate was significantly improved.

b. Differences in Chemical Structure

The structures of this series of compounds are very similar, with only slight differences in individual groups. YK-305, YK-310, YK-312, YK-319 and YK-318 are very close in structure to other compounds; other compounds are also very similar to each other.

Brief Summary:

In a series of compounds with very similar structures that we designed, compared with compounds with similar structures and the $G_3$ group being $HO(CH_2)_2N(CH_3)CH_2CH(OH)CH_2$—, YK-305, YK-310, YK-312, YK-319 and YK-318 have the lowest cytotoxicity, and significantly improved cell survival rate. For example, YK-305 and YK-310 are both 65% improved compared with YK-302.

At the same time, it is found that there is no correspondence between the structure of a compound and its cytotoxicity. Even a group of compounds with the most similar structures may have very different cytotoxicities.

Therefore, screening out cationic lipid compounds with low cytotoxicity from a series of compounds with only small differences in chemical structure is very difficult and requires a lot of creative work.

(3) YK-305, YK-310, YK-312, YK-319 and YK-318 had the Lowest Cytotoxicity and Significantly Improved Cell Survival Rate Compared with a Series of Compounds with Similar Structures and the $G_3$ Group being $HO(CH_2)_2N(CH_2CH_3)CH_2CH(OH)CH_2$—. For Example, the Cell Survival Rates of YK-305 and YK-310 can be Increased by 50% Compared with YK-309.

YK-305, YK-310, YK-312, YK-319 and YK-318 were compared with a series of compounds with similar structures and the $G_3$ group being $HO(CH_2)_2N(CH_2CH_3)CH_2CH(OH)CH_2$—. These compounds are different only slightly in the $G_1$, $G_2$, $G_3$, $R_1$ or $R_2$ groups.

The results showed that the cytotoxicity difference of this series of compounds was very significant. Among them, YK-305, YK-310, YK-312, YK-319 and YK-318 had the highest cell survival rates. For example, YK-305 and YK-310 can both increase by 50% compared to YK-309.

TABLE 14

Cell survival rate - 3

| Serial No. | Cationic lipid | Cell survival rate (%) |
|---|---|---|
| 1 | YK-305 | 82.18 |
| 2 | YK-310 | 82.10 |
| 3 | YK-312 | 76.96 |
| 4 | YK-319 | 25.21 |
| 5 | YK-318 | 75.56 |
| 6 | YK-308 | 70.99 |
| 7 | YK-309 | 31.61 |
| 8 | YK-311 | 70.06 |

TABLE 14-continued

| Cell survival rate - 3 | | |
|---|---|---|
| Serial No. | Cationic lipid | Cell survival rate (%) |
| 9 | YK-313 | 68.93 |
| 10 | YK-314 | 67.88 |
| 11 | YK-315 | 71.28 |
| 12 | SM-102 | 69.45 |
| 13 | ALC-0315 | 51.03 |
| 14 | Compound 21 | 70.21 |
| 15 | Compound 23 | 71.50 |
| 16 | CHMA | 66.47 |
| 17 | Lipofectamine 3000 | 25.01 |

a. Difference in Cell Survival Rate

Although compared with YK-305, YK-310, YK-312, YK-319 and YK-318, other compounds only have some minor differences in the $G_1$, $G_2$, $G_3$, $R_1$ or $R_2$ groups, the impact on cytotoxicity is very large. The cell survival rates of YK-305, YK-310, YK-312, YK-319 and YK-318 can be at most 50% higher than those of other compounds.

As can be seen from Table 14, among this series of compounds, the LNP formulation prepared from YK-309 had the highest cytotoxicity, with a cell survival rate of only 31.61%.

The cell survival rates of YK-305, YK-310, YK-312, YK-319 and YK-318 were increased by 50.57%, 50.49%, 45.35%, 43.60% and 43.95% respectively compared with YK-309.

Other compounds were also quite different from YK-305, YK-310, YK-312, YK-319 and YK-318.

The cell survival rate of YK-305 were 11.19% higher than YK-308, 12.12% higher than YK-311, 13.25% higher than YK-313, 14.30% higher than YK-314, and 10.90% higher than YK-315.

The cell survival rate of YK-310 was 11.11% higher than YK-308, 12.04% higher than YK-311, 13.17% higher than YK-313, 14.22% higher than YK-314, and 10.82% higher than YK-315.

The cell survival rate of YK-312 was 5.97% higher than YK-308, 6.90% higher than YK-311, 8.03% higher than YK-313, 9.08% higher than YK-314, and 5.68% higher than YK-315.

The cell survival rate of YK-319 was 4.22% higher than YK-308, 5.15% higher than YK-311, 6.28% higher than YK-313, 7.33% higher than YK-314, and 3.93% higher than YK-315.

Figure 10:
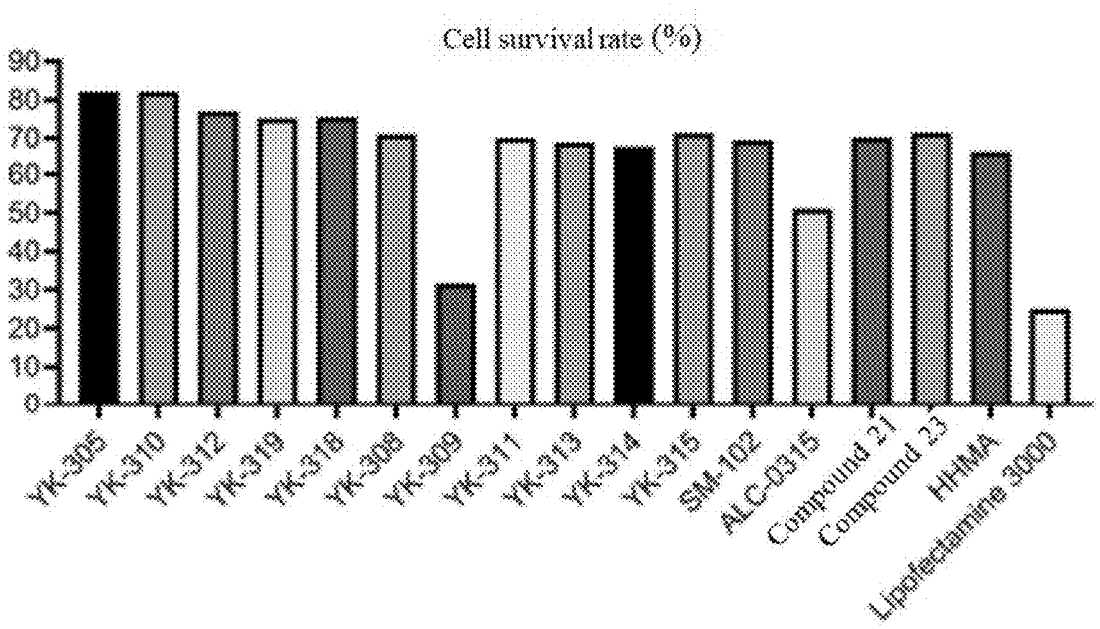
FIG. 10 shows the cell survival rate after introducing the LNP formulations of Fluc-mRNA prepared from different cationic lipids (YK-305, YK-310, YK-312, YK-319, YK-318, YK-308, YK-309, YK-311, YK-313, YK-314, YK-315, SM-102, ALC-0315, compound 21, compound 23 and HHMA) and a Lipofectamine 3000 formulation containing Fluc-mRNA into the cell culture medium and culturing for 24 hours.

The cell survival rate of YK-318 was 4.57% higher than YK-308, 5.50% higher than YK-311, 6.63% higher than YK-313, 7.68% higher than YK-314, and 4.28% higher than YK-315. (FIG. 10)

The data were analyzed using GraphPad Prism software, where any one of YK-305, YK-310, YK-312, YK-319 and YK-318 was significantly different in cytotoxicity with YK-308, YK-309, YK-311, YK-313, YK-314 and YK-315, and the cytotoxicity was significantly reduced and the cell survival rate was significantly increased.

b. Differences in Chemical Structure

The structures of this series of compounds are very similar, with only slight differences in individual groups. YK-305, YK-310, YK-312, YK-319 and YK-318 are very close in structure to other compounds; other compounds are also very similar to each other.

Brief Summary:

In a series of compounds designed with very similar structures, compared with compounds with similar structures and the $G_3$ group being $HO(CH_2)_2N(CH_2CH_3)CH_2CH(OH)CH_2$—, YK-305, YK-310, YK-312, YK-319 and YK-318 had the lowest cytotoxicity, and significantly improved cell survival rate. For example, YK-305 and YK-310 can be improved by 50% compared to YK-302.

At the same time, it is found that there is no correspondence between the structure of a compound and its cytotoxicity. Compounds with only small differences in structure are very likely to have very large differences in cytotoxicity.

Therefore, screening out cationic lipid compounds with low cytotoxicities from a series of compounds with only minor differences in individual groups is very difficult and requires a lot of creative effort.

(4) YK-305, YK-310, YK-312, YK-319 and YK-318 had Significantly Reduced Cytotoxicity Compared with a Series of Compounds with Similar Structures and the $G_3$ Group being $(HO(CH_2)_2)_2NCH_2CH(OH)CH_2$—. For Example, the Cell Survival Rates of YK-305 and YK-310 were 20% Higher than that of YK-317.

YK-305, YK-310, YK-312, YK-319 and YK-318 were compared with a series of compounds having similar structures and the $G_3$ group being $(HO(CH_2)_2)_2NCH_2CH(OH)CH_2$—. These compounds are different only slightly in the $G_1$, $G_2$, $G_3$, $R_1$ or $R_2$ groups. The results showed that the cytotoxicity difference of this series of compounds was very significant. Among them, YK-305, YK-310, YK-312, YK-319 and YK-318 had the highest cell survival rates. For example, YK-305 and YK-310 were both increased by 20% than YK-317.

TABLE 15

| Cell survival rate - 4 | | |
|---|---|---|
| Serial No. | Cationic lipid | Cell survival rate (%) |
| 1 | YK-303 | 82.18 |
| 2 | YK-310 | 82.10 |
| 3 | YK-312 | 76.96 |
| 4 | YK-319 | 75.21 |
| 5 | YK-318 | 75.56 |
| 6 | YK-316 | 70.53 |
| 7 | YK-317 | 59.18 |
| 8 | YK-320 | 71.07 |
| 9 | YK-321 | 72.34 |
| 10 | SM-102 | 69.45 |
| 11 | ALC-0313 | 51.03 |
| 12 | Compound 21 | 70.21 |
| 13 | Compound 23 | 71.50 |
| 14 | HHMA | 66.47 |
| 15 | Lipofectamine 3000 | 25.01 |

a. Difference in Cell Survival Rate

Although compared with YK-305, YK-310, YK-312, YK-319 and YK-318, other compounds only have some minor differences in the $G_1$, $G_2$, $G_3$, $R_1$ or $R_2$ groups, However, the difference in cytotoxicity is very large. For example, the cell survival rates of YK-305 and YK-310 were both increased by 20 than that of YK-317.

It can be seen from Table 15, among this series of compounds with similar structures, YK-317 had the highest cytotoxicity, with a cell survival rate of only 59.18%.

The cell survival rate of YK-305, YK-310, YK-312, YK-319 and YK-318 were 23.00%, 22.92%, 17.78%, 16.03% and 16.38% higher than that of YK-317 respectively.

Other compounds were also quite different from YK-305, YK-310, YK-312, YK-319 and YK-318.

The cell survival rate of YK-305 was 11.65% higher than YK-316, 11.110% higher than YK-320, and 9.84% higher than YK-321.

The cell survival rate of YK-310 was 11.57 higher than YK-316, 11.03% higher than YK-320, and 9.76% higher than YK-321.

The cell survival rate of YK-312 was 6.43% higher than YK-316, 5.89% higher than YK-320, and 4.62% higher than YK-321.

The cell survival rate of YK-319 was 4.68% higher than YK-316, 4.14% higher than YK-320, and 2.87% higher than YK-321.

Figure 11:
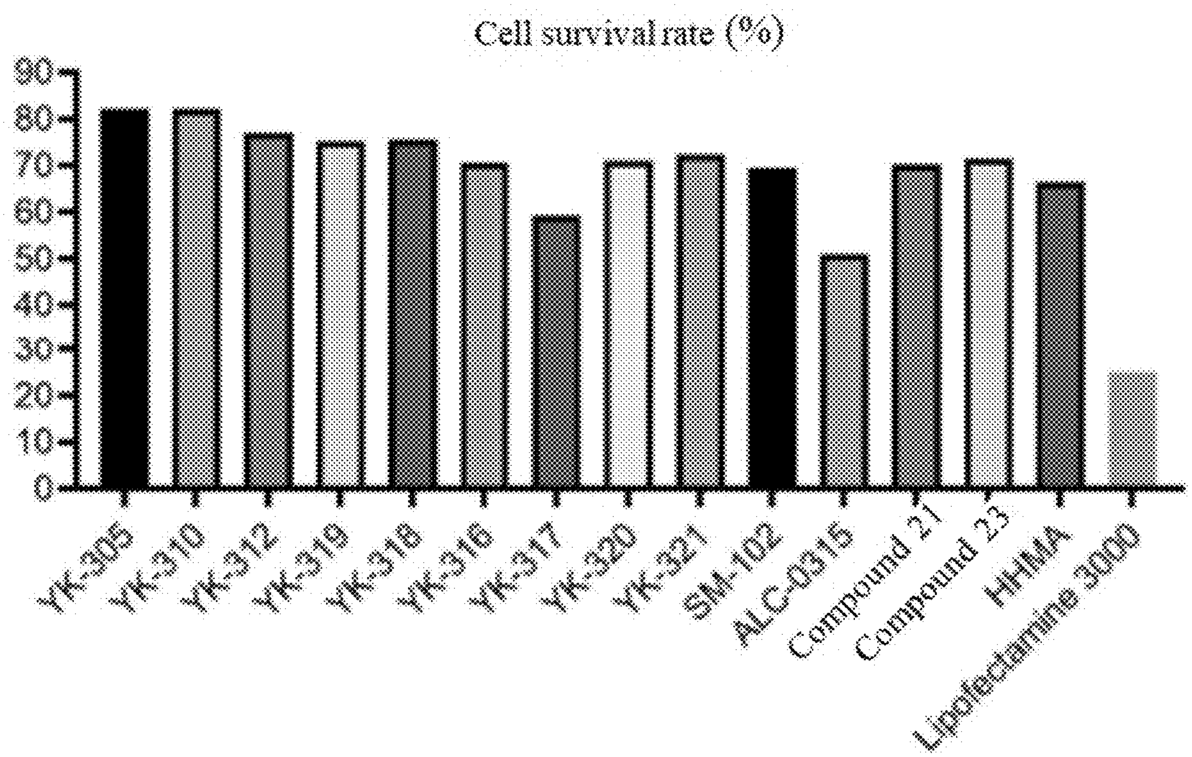
FIG. 11 shows the cell survival rate after introducing the LNP formulations of Fluc-mRNA prepared from different cationic lipids (YK-305, YK-310, YK-312, YK-319, YK-318, YK-316, YK-317, YK-320, YK-321, SM-102, ALC-0315, compound 21, compound 23 and HHMA) and a Lipofectamine 3000 formulation containing Fluc-mRNA into the cell culture medium and culturing for 24 hours.

The cell survival rate of YK-318 was 5.03% higher than YK-316, 4.49% higher than YK-320, and 3.22% higher than YK-321. (FIG. 11)

The data were analyzed using GraphPad Prism software, where any one of YK-305, YK-310, YK-312, YK-319 and YK-318 had significant differences compared with YK-316, YK-317, YK-320 and YK-321, and the cytotoxicity was significantly reduced and the cell survival rate was significantly improved.

b. Differences in Chemical Structure

The structures of this series of compounds are very similar, with only slight differences in individual groups. YK-305, YK-310, YK-312, YK-319 and YK-318 are very close in structure to other compounds; other compounds are also very similar to each other.

Brief Summary:

In a series of compounds with very similar structures designed, compared with compounds with similar structures and the $G_3$ group being $(HO(CH_2)_2)_2NCH_2CH(OH)CH_2$—, YK-305, YK-310, YK-312, YK-319 and YK-318 have the lowest cytotoxicity, and significantly improved cell survival rate. For example, YK-305 and YK-310 can be improved by 20% compared with YK-317.

At the same time, it is found that there is no correspondence between the structure of the compound and its cytotoxicity. Even if there are only some differences in the structure of the $G_3$ group, the cytotoxicity is very likely to be very different.

Therefore, screening out cationic lipid compounds with low cytotoxicity from a series of compounds with only minor differences in individual groups is very difficult and requires a lot of creative effort.

Summary:

1) The cell survival rates of LNP formulations prepared from a series of designed compounds were measured, and compounds with significantly reduced cytotoxicities compared to cationic lipid compounds in the prior art, such as YK-305, YK-310, YK-312, YK-319 and YK-318, were screened out.

The designed series of compounds are very different from the representative cationic lipids in the prior art, such as SM-102, compound 21, compound 23, HHMA and YK-009. The $G_3$ group is completely different, and other parts are also different, so there were great differences in polarity, acidity and alkalinity and hydrophilicity.

2) LNP formulations prepared from YK-305, YK-310, YK-312, YK-319 and YK-318 had the lowest cytotoxicity, and significantly improved cell survival rate compared to those prepared from the representative cationic lipid in the prior art. For example, both YK-305 and YK-310 had cell survival rates that are 30% higher than that of ALC-0315, 12% higher than that of SM-102, and 15% higher than that of HHMA.

Compared with compounds with similar structures and the $G_3$ group being $HO(CH_2)_2N(CH_3)CH_2CH(OH)CH_2$—, YK-305, YK-310, YK-312, YK-319 and YK-318 had the lowest cytotoxicity, and significantly improved cell survival rate. For example, YK-305 and YK-310 were 65% higher than YK-302.

Compared with compounds with similar structures and the $G_3$ group being $HO(CH_2)_2N(CH_2CH_3)CH_2CH(OH)CH_2$—, YK-305, YK-310, YK-312, YK-319 and YK-318 had the lowest cytotoxicity, and significantly improved cell survival rate. For example, YK-305 and YK-310 were 50% higher than YK-302.

Compared with compounds with similar structures and the $G_3$ group being $(HO(CH_2)_2)_2NCH_2CH(OH)CH_2$—, YK-305, YK-310, YK-312, YK-319 and YK-318 had the lowest cytotoxicity, and significantly improved cell survival rate. For example, YK-305 and YK-310 were improved by 20% compared with YK-317.

3) There is no correspondence between the structure of a compound and its cytotoxicity. Even compounds with small structural differences are likely to have very large differences in cytotoxicity. Therefore, its cytotoxicity cannot be predicted based on its chemical structure, and it is very difficult to screen out cationic lipid compounds with low cytotoxicity, requiring a lot of creative work.

Example 7: In Vivo Validation of the Performance of Cationic Lipid Delivery Carriers In addition, the protein expression and duration of mRNA in mice delivered by the cationic lipid delivery carriers designed were also verified. In vivo tests further prove that our LNP delivery carriers can effectively deliver mRNA into the body and make the mRNA express efficiently and sustainably.

The LNP formulation containing 10 g Fluc-mRNA was injected intramuscularly into female BALB/C mice aged 4 to 6 weeks old and weighed 17 to 19 g, and the mice were intraperitoneally injected with fluorescent imaging substrate at specific time points after administration (6 h, 24 h, 48 h and 7 d), where the mice were free to move for 5 minutes, and then the average radiation intensity (corresponding to fluorescence expression intensity) of the protein expression of the mRNA carried by the LNP in the mice was detected by the IVIS Spectrum small animal live imaging device.

Assay Results:

a. Expression of mRNA in Mice

Figure 12:
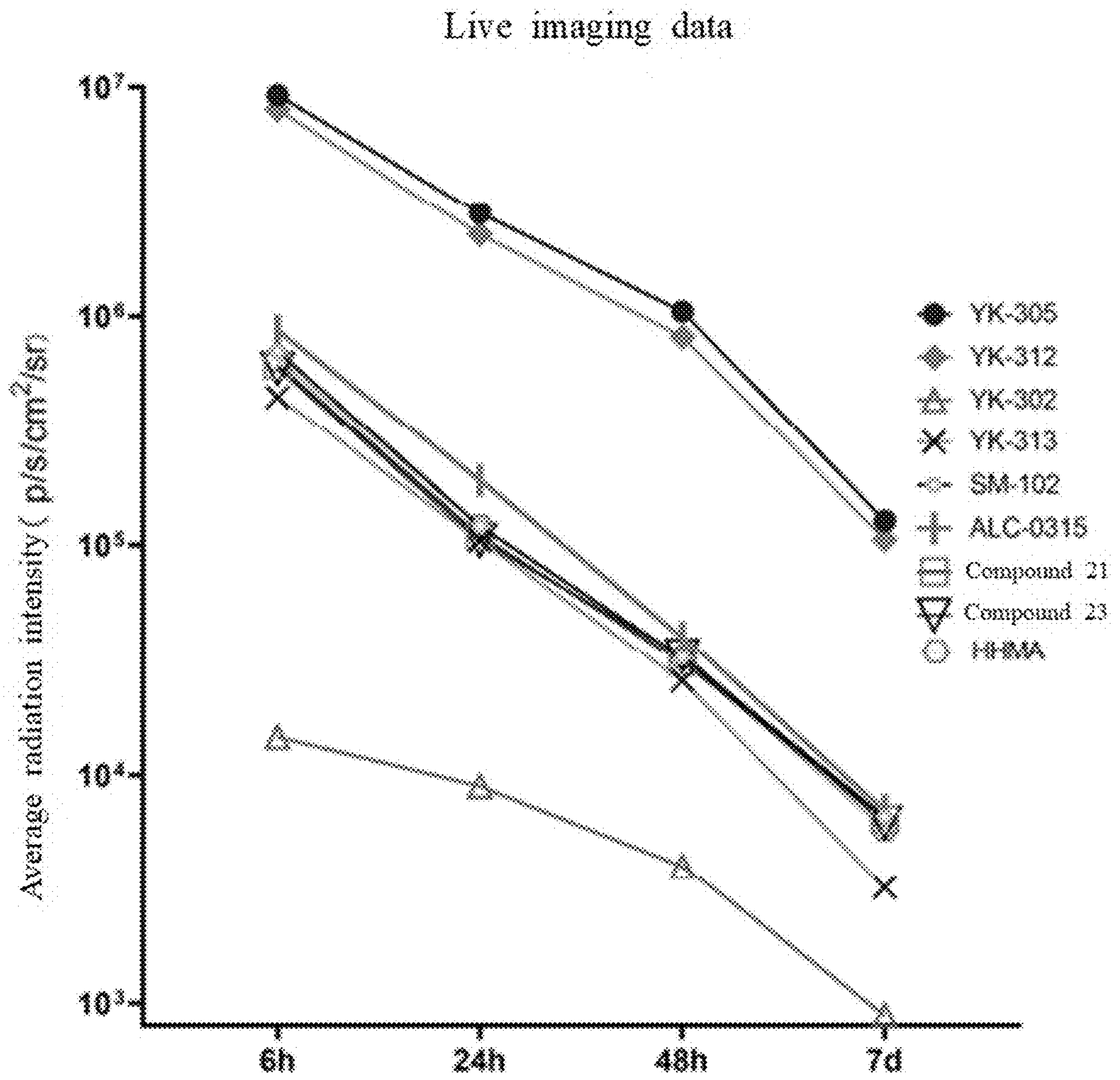
FIG. 12 shows the results of live mouse imaging tests of LNP formulations of Fluc-mRNA prepared from different cationic lipids (YK-305, YK-312, YK-302, YK-313, SM-102, ALC-0315, compound 21, compound 23 and HHMA).
Figure 13:
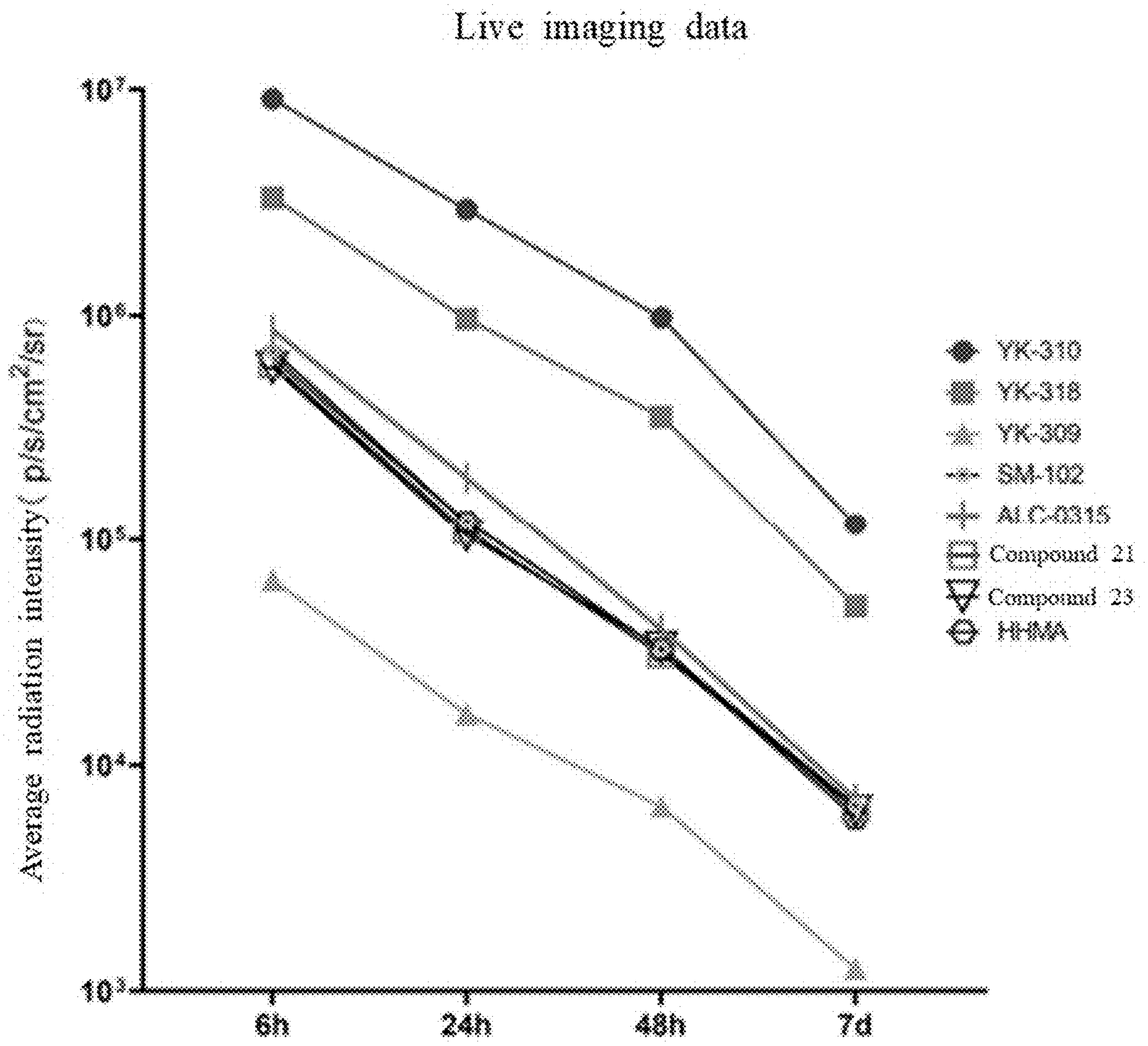
FIG. 13 shows the results of live mouse imaging tests of LNP formulations of Fluc-mRNA prepared from different cationic lipids (YK-310, YK-318, YK-309, SM-102, ALC-0315, compound 21, compound 23 and HHMA).
Figure 14:
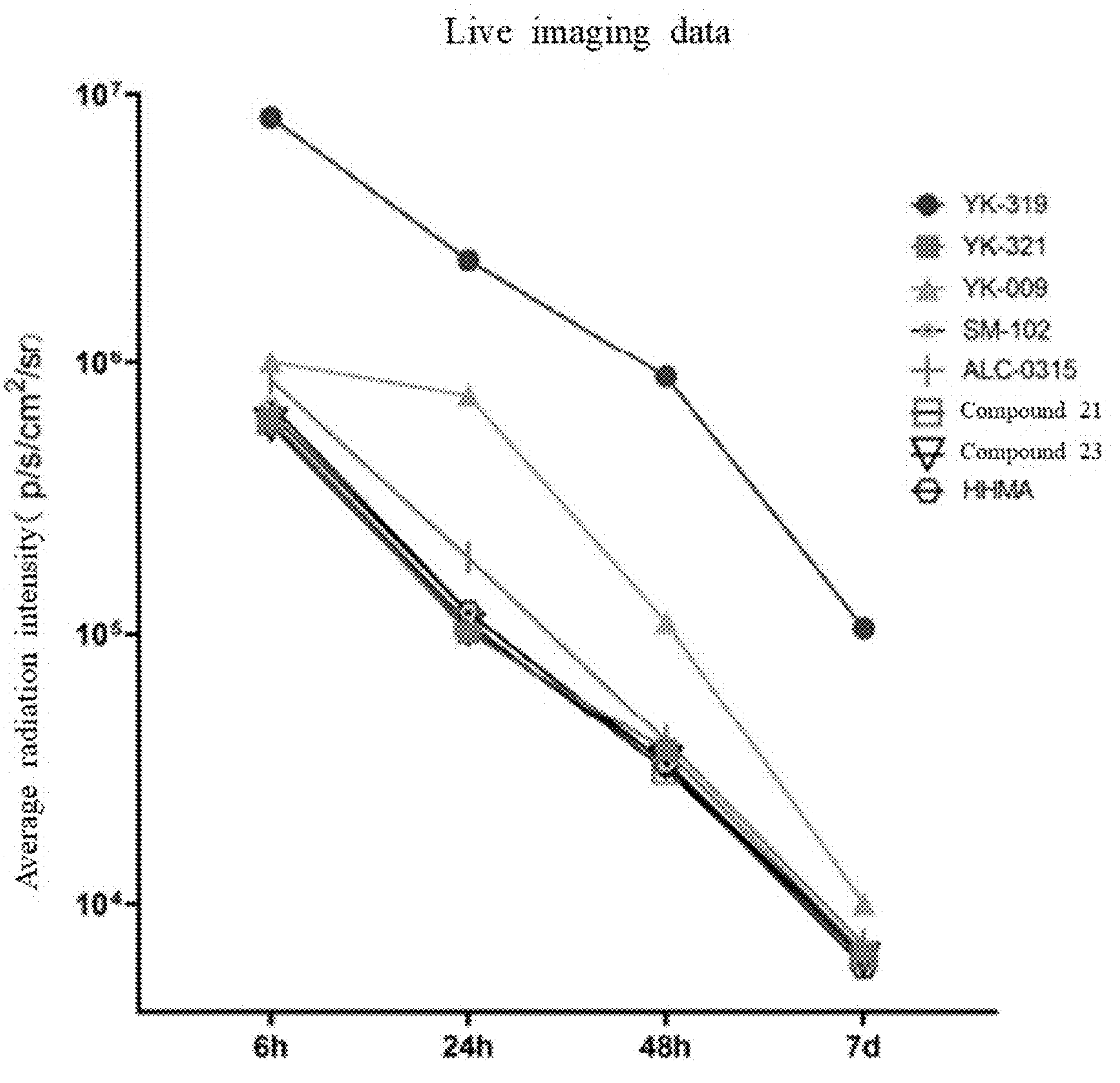
FIG. 14 shows the results of live mouse imaging tests of LNP formulations of Fluc-mRNA prepared from different cationic lipids (YK-319, YK-321, YK-009, SM-102, ALC-0315, compound 21, compound 23 and HHMA).

The average radiation intensity detection results of proteins expressed in mice by mRNA in LNP formulations are shown in Tables 16 to 19 and FIGS. 12 to 14.

(1) Among the Designed Series of Compounds, LNP Formulations Prepared from YK-305, YK-310, YK-312, YK-319 and YK-318 had Extremely High and Sustained Expression of mRNA in Mice, which were Improved Significantly Compared with the Representative Cationic Lipids in the Prior Art. For Example, Both YK-305 and YK-310 can be Up to 30 Times that of SM-102, Compound 21 and Compound 23. The Expression of mRNA in Mice was Consistent with the Cell Transfection Activity.

TABLE 16

Test data in the live imaging in mice - 1

| Serial No. | Cationic lipid | Time 6 h | 24 h | 48 h | 7 d |
|---|---|---|---|---|---|
| 1 | YK-305 | 9239340 | 2823400 | 1047720 | 127015 |
| 2 | YK-310 | 9125240 | 2952310 | 981000 | 117462 |
| 3 | YK-312 | 8009850 | 2278520 | 813200 | 105500 |

TABLE 16-continued

Test data in the live imaging in mice - 1

| Serial No. | Cationic lipid | Time 6 h | 24 h | 48 h | 7 d |
|---|---|---|---|---|---|
| 4 | YK-319 | 8230500 | 2433960 | 887680 | 104860 |
| 5 | YK-318 | 3325680 | 968540 | 356810 | 50659 |
| 6 | YK-009 | 1004580 | 754120 | 110140 | 9984 |
| 7 | SM-102 | 701230 | 120470 | 32550 | 6621 |
| 8 | ALC-0315 | 863760 | 190480 | 39810 | 7047 |
| 9 | Compound 21 | 610340 | 109840 | 30980 | 6445 |
| 10 | Compound 23 | 589400 | 104530 | 33125 | 6240 |
| 11 | HHMA | 651020 | 119940 | 32557 | 5871 |

a. Expression Differences in Mice

Table 16 lists the mRNA expression intensity of LNP formulations containing Fluc-mRNA prepared from different cationic lipids at different times in mice. Among them, YK-009 is disclosed in CN114044741B (claim 1), SM-102 is compound 25 disclosed in WO2017049245A2 (page 29 of the specification), ALC-0315 is compound 3 disclosed in CN108368028B (page 24 of the specification), compound 21 and compound 23 are disclosed in WO2021055833A1 (page 22 of the specification), and HHMA is compound 1 disclosed in CN112979483B (page 12 of the specification). These cationic lipids can be used to prepare carriers for delivering mRNA.

As can be seen from Table 12, the LNP formulations containing Fluc-mRNA prepared from YK-305, YK-310, YK-312, YK-319 and YK-318 had extremely high and sustained expression of mRNA in mice.

The average radiation intensity of YK-305 was 9239340 at 6 h, which was 13.18 times that of SM-102, 10.70 times that of ALC-0315, 15.14 times that of compound 21, 15.68 times that of compound 23, and 14.19 times that of HHMA; at 24 h the average radiation intensity was 2823400, which was 23.44 times that of SM-102, 14.82 times that of ALC-0315, 25.70 times that of compound 21, 27.01 times that of compound 23, and 23.54 times that of HHMA; at 48 h the average radiation intensity was 1047720, which was 32.19 times that of SM-102, 26.32 times that of ALC-0315, 33.82 times that of compound 21, 31.63 times that of compound 23, and 32.18 times that of HHMA; at 7 d the average radiation intensity was 127015, which was 19.18 times that of SM-102, 18.02 times that of ALC-0315, 19.71 times that of compound 21, 20.35 times that of compound 23, and 21.63 times that of HHMA.

The average radiation intensity of YK-310 was 9125240 at 6 h, which was 13.01 times that of SM-102, 10.56 times that of ALC-0315, 14.95 times that of compound 21, 15.48 times that of compound 23, and 14.02 times that of HHMA; at 24 h the average radiation intensity was 2952310, which was 24.51 times that of SM-102, 15.50 times that of ALC-0315, 26.88 times that of compound 21, 28.24 times that of compound 23, and 24.61 times that of HHMA; at 48 h the average radiation intensity was 981000, which was 30.14 times that of SM-102, 24.64 times that of ALC-0315, 31.67 times that of compound 21, 29.62 times that of compound 23, and 30.13 times that of HHMA; at 7 d the average radiation intensity was 117462, which was 17.74 times that of SM-102, 16.67 times that of ALC-0315, 18.23 times that of compound 21, 18.82 times that of compound 23, and 20.01 times that of HHMA.

The average radiation intensity of YK-312 was 8009850 at 6 h, which was 11.42 times that of SM-102, 9.27 times that of ALC-0315, 13.12 times that of compound 21, 13.59 times that of compound 23, and 12.30 times that of HHMA; at 24 h the average radiation intensity was 2278520, which was 18.91 times that of SM-102, 11.96 times that of ALC-0315, 20.74 times that of compound 21, 21.80 times that of compound 23, and 19.00 times that of HHMA; at 48 h the average radiation intensity was 813200, which was 24.98 times that of SM-102, 20.43 times that of ALC-0315, 26.25 times that of compound 21, 24.55 times that of compound 23, and 24.98 times that of HHMA; at 7 d the average radiation intensity was 105500, which was 15.93 times that of SM-102, 14.97 times that of ALC-0315, 16.37 times that of compound 21, 16.91 times that of compound 23, and 17.97 times that of HHMA.

The average radiation intensity of YK-319 was 8230500 at 6 h, which was 11.74 times that of SM-102, 9.53 times that of ALC-0315, 13.49 times that of compound 21, 13.96 times that of compound 23, and 12.64 times that of HHMA; at 24 h the average radiation intensity was 2433960, which was 20.20 times that of SM-102, 12.78 times that of ALC-0315, 22.16 times that of compound 21, 23.28 times that of compound 23, and 20.29 times that of HHMA; at 48 h the average radiation intensity was 887680, which was 27.27 times that of SM-102, 22.30 times that of ALC-0315, 28.65 times that of compound 21, 26.80 times that of compound 23, and 27.27 times that of HHMA; at 7 d the average radiation intensity was 104860, which was 15.84 times that of SM-102, 14.88 times that of ALC-0315, 16.27 times that of compound 21, 16.80 times that of compound 23, and 17.86 times that of HHMA.

The average radiation intensity of YK-318 was 3325680 at 6 h, which was 4.74 times that of SM-102, 3.85 times that of ALC-0315, 5.45 times that of compound 21, 5.64 times that of compound 23, and 5.11 times that of HHMA; at 24 h the average radiation intensity was 968540, which was 8.04 times that of SM-102, 5.08 times that of ALC-0315, 8.82 times that of compound 21, 9.27 times that of compound 23, and 8.08 times that of HHMA; at 48 h the average radiation intensity was 356810, which was 10.96 times that of SM-102, 8.96 times that of ALC-0315, 11.52 times that of compound 21, 10.77 times that of compound 23, and 10.96 times that of HHMA; at 7 d the average radiation intensity was 50659, which was 7.65 times that of SM-102, 7.19 times that of ALC-0315, 7.86 times that of compound 21, 8.12 times that of compound 23, and 8.63 times that of HHMA.

The data were analyzed using GraphPad Prism software. Any one of YK-305, YK-310, YK-312, YK-319 and YK-318 was significantly different from SM-102, ALC-0315, compound 21, compound 23, HHMA and YK-009 at each time, and the expression amount and duration were significantly improved.

b. Differences in Chemical Structure

YK-305, YK-310, YK-312, YK-319 and YK-318 are very different from cationic lipids in the prior art, such as SM-102, ALC-0315, compound 21, compound 23, HHMA and YK-009 in chemical structures. Among them, HHMA has the biggest difference in structure, in which except that one side chain connected to the central N atom is similar to one side chain of YK-305, YK-310, YK-312, YK-319 and YK-318, the other structures of HHMA are completely different. Compared with SM-102, ALC-0315, compound 21, compound 23 and YK-009, the $G_3$ group of YK-305, YK-310, YK-312, YK-319 and YK-318 is completely different, and $G_1$, $R_1$, $G_2$ and $R_2$ groups are also very different.

Brief Summary:

In a serious designed compounds, the LNP formulations prepared from YK-305, YK-310, YK-312, YK-319 and YK-318, had the highest and sustained expression of mRNA in mice, in which the expression amounts are significantly improved at 6 h, 24 h, 48 h and 7 d compared with the representative cationic lipids in the prior art. For example, YK-305 and YK-310 can be up to 30 times that of SM-102, compound 21 and compound 23. The expression of mRNA in mice is consistent with the results of the cell transfection assay in Example 6.

Moreover, YK-305, YK-310, YK-312, YK-319 and YK-318 are very different from the representative cationic lipid structures in the prior art. The $G_3$ group is completely different, and there is also a huge difference in the $G_1$, $R_1$, $G_2$ and $R_2$ groups.

The applicant unexpectedly discovered that the LNP formulation prepared from the compound designed for the first time by the applicant, which has a huge difference in structure from the cationic lipids in the prior art, had extremely high and sustained expression of mRNA in mice.

(2) YK-305, YK-310, YK-312, YK-319 and YK-318, had the Highest Amount and the Longest Duration of Expressions of mRNA in Mice Compared with a Series of Compounds with Similar Structure and $G_3$ Group being $HO(CH_2)_2N(CH_3)CH_2CH(OH)CH_2$—. For Example, the Expression Amount of YK-305 can be More than 1,000 Times that of YK-302. The Expression of mRNA in Mice was Consistent with the Cell Transfection Activity.

In order to compare the differences in the expression intensity and duration of delivered mRNA in mice using delivery carrier prepared from compounds that are very similar in structure and only have slightly different $G_1$, $G_2$, $G_3$, $R_1$ or $R_2$ groups, a series of compounds with similar structures and the $G_3$ group being $HO(CH_2)_2N(CH_3)CH_2CH(OH)CH_2$— with YK-305 were compared with YK-310, YK-312, YK-319 and YK-318.

The results show that the LNP formulations prepared from this series of compounds had very different expression amounts of mRNA in mice, among which YK-305, YK-310, YK-312, YK-319 and YK-318 had the highest expression amounts and the longest duration, for example, the expression amount of YK-305 can be up to more than 1000 times that of YK-302.

TABLE 17

Test data in the live imaging in mice - 2

| Serial No. | Cationic lipid | Time 6 h | 24 h | 48 h | 7 d |
|---|---|---|---|---|---|
| 1 | YK-305 | 9239340 | 2823400 | 1047720 | 127015 |
| 2 | YK-310 | 9125240 | 2952310 | 981000 | 117462 |
| 3 | YK-312 | 8009850 | 2278520 | 813200 | 105500 |
| 4 | YK-319 | 8230500 | 2433960 | 887680 | 104860 |
| 5 | YK-318 | 3325680 | 968540 | 356810 | 50659 |
| 6 | YK-302 | 14580 | 8956 | 4025 | 884 |
| 7 | SM-102 | 701230 | 130470 | 34550 | 6821 |
| 8 | ALC-0315 | 863760 | 190480 | 39810 | 7047 |
| 9 | Compound 21 | 610340 | 109840 | 30980 | 6445 |
| 10 | Compound 23 | 589400 | 104530 | 33125 | 6240 |
| 11 | HHMA | 651020 | 119940 | 32557 | 5871 |

a. Expression Differences in Mice

It can be seen from Table 17 that the LNP formulations prepared from YK-305, YK-310, YK-312, YK-319 and YK-318 had the highest expression amount and duration of mRNA in mice compared with a series of compounds with similar structures and the $G_3$ group being $HO(CH_2)_2N(CH_3)CH_2CH(OH)CH_2$—.

YK-305 can be up to 633.70 times that of YK-302 at 6 h, 713.70 times at 24 h, 1022.17 times at 48 h, and 330.77 times at 7 d.

YK-310 can be up to 625.87 times that of YK-302 at 6 h, 746.29 times at 24 h, 957.07 times at 48 h, and 305.89 times at 7 d.

YK-312 can be up to 549.37 times of YK-302 at 6 h, 575.97 times at 24 h, 793.37 times at 48 h, and 274.74 times at 7 d.

YK-319 can be up to 564.51 times of YK-302 at 6 h, 615.26 times at 24 h, 866.03 times at 48 h, and 273.07 times at 7 d.

YK-318 can be up to 228.10 times that of YK-302 at 6 h, 244.83 times at 24 h, 348.11 times at 48 h, and 131.92 times at 7 d.

The data were analyzed using GraphPad Prism software. Any one of YK-305, YK-310, YK-312, YK-319 and YK-318 had a significant difference from other compounds at each time, and the expression amount and duration were significantly improved.

b. Differences in Chemical Structure

This series of compounds are very similar in structure to YK-305, YK-310, YK-312, YK-319 and YK-318, except that the $G_1$, $G_2$, $G_3$, $R_1$ or $R_2$ groups are slightly different.

Brief Summary:

Compared with compounds with similar structures and the $G_3$ group being $HO(CH_2)_2N(CH_3)CH_2CH(OH)CH_2$—, the LNP formulations prepared from YK-305, YK-310, YK-312, YK-319 and YK-318 had the highest mRNA expression intensity and longest duration in mice. For example, YK-305 can be up to more than 1000 times that of YK-302 in 48 hours, and can be up to more than 300 times in 7 days. The expression of mRNA in mice was consistent with the results of the cell transfection assay in Example 6.

it is also found that there is no correspondence between the expression of mRNA in mice and the structure of cationic lipids. Even for LNP preparations prepared from a group of compounds with very similar structures and with only slight differences in the $G_1$, $G_2$, $G_3$, $R_1$ or $R_2$ groups, the degree and duration of mRNA expression in mice are very likely to be very different.

Therefore, it is very difficult and requires a lot of creative work to screen out cationic lipid compounds with high and sustained expression in animals from a series of compounds with the most similar structures.

(3) YK-305, YK-310, YK-312, YK-319 and YK-318, had the Highest Amount and the Longest Duration of Expressions of mRNA in Mice Compared with a Series of Compounds with Similar Structure and $G_3$ Group being $HO(CH_2)_2N(CH_2CH_3)CH_2CH(OH)CH_2$—. For Example, the Expression Amount of YK-305 can be Up to 160 Times that of YK-309. The Expression of mRNA in Mice was Consistent with the Cell Transfection Activity.

The expression in mice of LNP formulations containing mRNA prepared from a series of compounds with similar structures and the $G_3$ group being $HO(CH_2)_2N(CH_2CH_3)CH_2CH(OH)CH_2$— were compared with YK-305, YK-310, YK-312, YK-319 and YK-318. The results show that YK-305, YK-310, YK-312, YK-319 and YK-318 had the highest expression amounts and the longest durations, which were significantly higher than other compounds. For example, YK-305 can be up to 160 times that of YK-309.

TABLE 18

| Test data in the live imaging in mice - 3 | | | | | |
|---|---|---|---|---|---|
| Serial | | Time | | | |
| No. | Cationic lipid | 6 h | 24 h | 48 h | 7 d |
| 1 | YK-305 | 9239340 | 2823400 | 1047720 | 127015 |
| 2 | YK-310 | 9125240 | 2952310 | 981000 | 117462 |
| 3 | YK-312 | 8009850 | 2278520 | 813200 | 105500 |
| 4 | YK-319 | 8230500 | 2433960 | 887680 | 104860 |
| 5 | YK-318 | 3325680 | 968540 | 356810 | 50659 |
| 6 | YK-309 | 65680 | 16820 | 6551 | 1256 |
| 7 | YK-313 | 442180 | 104430 | 25560 | 3235 |
| 8 | SM-102 | 701230 | 130470 | 34550 | 6821 |
| 9 | ALC-0315 | 863760 | 190480 | 39810 | 7047 |
| 10 | Compound 21 | 610340 | 109840 | 30980 | 6445 |
| 11 | Compound 23 | 589400 | 104530 | 33125 | 6240 |
| 12 | HHMA | 651020 | 119940 | 32557 | 5871 |

a. Expression Differences in Mice

It can be seen from Table 18, among this series of compounds, the expression amount and duration of mRNA in mice of LNP formulations prepared from YK-305, YK-310, YK-312, YK-319 and YK-318 were the highest.

The expression amount of YK-305 was 140.67 times that of YK-309 and 20.89 times that of YK-313 at 6 h, at 24 h can be up to 167.86 times that of YK-309 and 27.04 times that of YK-313, at 48 h was 159.93 times that of YK-309 and 40.99 times that of YK-313, at 7 d was 101.13 times that of YK-309 and 39.26 times that of YK-313.

The expression amount of YK-310 was 138.93 times that of YK-309 and 20.64 times that of YK-313 at 6 h, at 24 h can be up to 175.52 times that of YK-309 and 28.27 times that of YK-313, at 48 h was 149.75 times that of YK-309 and 38.38 times that of YK-313, at 7 d was 93.52 times that of YK-309 and 36.31 times that of YK-313.

The expression amount of YK-312 was 121.95 times that of YK-309 and 18.11 times that of YK-313 at 6 h, at 24 h can be up to 135.46 times that of YK-309 and 21.82 times that of YK-313, at 48 h was 124.13 times that of YK-309 and 31.82 times that of YK-313, at 7 d was 84.00 times that of YK-309 and 32.61 times that of YK-313.

The expression amount of YK-319 was 125.31 times that of YK-309 and 18.61 times that of YK-313 at 6 h, at 24 h can be up to 144.71 times that of YK-309 and 23.31 times that of YK-313, at 48 h was 135.50 times that of YK-309 and 34.73 times that of YK-313, at 7 d was 83.49 times that of YK-309 and 32.41 times that of YK-313.

The expression amount of YK-319 was 50.63 times that of YK-309 and 7.52 times that of YK-313 at 6 h, at 24 h can be up to 57.58 times that of YK-309 and 9.27 times that of YK-313, at 48 h was 54.47 times that of YK-309 and 13.96 times that of YK-313, at 7 d was 40.33 times that of YK-309 and 15.66 times that of YK-313.

The data were analyzed using GraphPad Prism software. Any one of YK-305, YK-310, YK-312, YK-319 and YK-318 had a significant difference from other compounds at each time, and the expression amount and duration were significantly improved.

b. Differences in Chemical Structure

This series of compounds are very similar to YK-305, YK-310, YK-312, YK-319 and YK-318, except that the $G_1$, $G_2$, $G_3$, $R_1$ or $R_2$ groups are slightly different.

Brief Summary:

Compared with compounds with similar structures and the $G_3$ group being $HO(CH_2)_2N(CH_2CH_3)CH_2CH(OH)CH_2$—, the LNP formulations prepared from YK-305, YK-310, YK-312, YK-319 and YK-318 have the highest mRNA expression intensity and longest duration in mice. For example, YK-305 can be up to 160 times that of YK-309 in 48 hours, and can be up to 100 times in 7 days. The expression of mRNA in mice was consistent with the results of the cell transfection assay in Example 6.

It is found that there is no correspondence between the expression of mRNA in mice and the structure of cationic lipids. Even for LNP preparations prepared from a group of compounds with very similar structures and with only slight differences in the $G_1$, $G_2$, $G_3$, $R_1$ or $R_2$ groups, the degree and duration of mRNA expression in mice are very likely to be very different.

Therefore, it is very difficult and requires a lot of creative work to screen out cationic lipid compounds with extremely high and sustained expression in animals from a series of compounds with the most similar structures.

(4) YK-305, YK-310, YK-312, YK-319 and YK-318, had the Highest Amount and the Longest Duration of Expressions of mRNA in Mice Compared with a Series of Compounds with Similar Structure, and $G_3$ Group being $(HO(CH_2)_2)_2NCH_2CH(OH)CH_2$—. For Example, YK-310 was Increased by 29 Times than YK-321. The Expression of mRNA in Mice was Consistent with the Cell Transfection Activity.

The differences in expression in mice between the LNP formulations containing mRNA prepared from a series of compounds with similar structures and the $G_3$ group being $(HO(CH_2)_2)_2NCH_2CH(OH)CH_2$— were compared with YK-305, YK-310, YK-312, YK-319 and YK-318. The results show that YK-305, YK-310, YK-312, YK-319 and YK-318 had the highest expression amounts and the longest durations, which were significantly higher than other compounds. For example, YK-310 can be up to 29 times that of YK-321.

TABLE 19

| Test data in the live imaging in mice - 4 | | | | | |
|---|---|---|---|---|---|
| Serial | | Time | | | |
| No. | Cationic lipid | 6 h | 24 h | 48 h | 7 d |
| 1 | YK-305 | 9239340 | 2823400 | 1047720 | 127015 |
| 2 | YK-310 | 9125240 | 2952310 | 981000 | 117462 |
| 3 | YK-312 | 8009850 | 2278520 | 813200 | 105500 |
| 4 | YK-319 | 8230500 | 2433960 | 887680 | 104860 |
| 5 | YK-318 | 3325680 | 968540 | 356810 | 50659 |
| 6 | YK-321 | 615600 | 101230 | 36565 | 6586 |
| 7 | SM-102 | 701230 | 130470 | 34550 | 6821 |
| 8 | ALC-0315 | 863760 | 190480 | 39810 | 7047 |
| 9 | Compound 21 | 610340 | 109840 | 30980 | 6445 |
| 10 | Compound 23 | 589400 | 104530 | 33125 | 6240 |
| 11 | HHMA | 651020 | 119940 | 32557 | 5871 |

a. Expression Differences in Mice

It can be seen from Table 19, among this series of compounds, the expression amount and duration of mRNA in mice of LNP formulations prepared from YK-305, YK-310, YK-312, YK-319 and YK-318 are the highest.

The expression amount of YK-305 was 17.92 times that of YK-321 at 6 h, 27.89 times at 24 h, 28.65 times at 48 h, and 19.29 times at 7 d.

The expression amount of YK-310 was 17.70 times that of YK-321 at 6 h, 29.16 times at 24 h, 26.83 times at 48 h, and 17.84 times at 7 d.

The expression amount of YK-312 was 15.54 times that of YK-321 at 6 h, 22.51 times at 24 h, 22.24 times at 48 h, and 16.02 times at 7 d.

The expression amount of YK-319 was 15.96 times that of YK-321 at 6 h, 24.04 times at 24 h, 24.28 times at 48 h, and 15.92 times at 7 d.

The expression amount of YK-318 was 6.45 times that of YK-321 at 6 h, 9.57 times at 24 h, 9.76 times at 48 h, and 7.69 times at 7 d.

The data were analyzed using GraphPad Prism software. Any one of YK-305, YK-310, YK-312, YK-319 and YK-318 had a significant difference from other compounds at each time, and the expression amount and duration were significantly improved.

b. Differences in Chemical Structure

This series of compounds are very similar to YK-305, YK-310, YK-312, YK-319 and YK-318, except that the $G_1$, $G_2$, $G_3$, $R_1$ or $R_2$ groups are slightly different.

Brief Summary:

Compared with compounds with similar structures and the $G_3$ group being $(HO(CH_2)_2)_2NCH_2CH(OH)CH_2$—, the LNP formulations prepared from YK-305, YK-310, YK-312, YK-319 and YK-318 have the highest mRNA expression intensity and longest duration in mice. For example, YK-310 can be up to 29 times that of YK-321 in 24 hours, and can be up to 17 times in 7 days. The expression of mRNA in mice was consistent with the results of the cell transfection assay in Example 6.

it is found that there is no correspondence between the expression of mRNA in mice and the structure of cationic lipids. Even for LNP preparations prepared from a group of compounds with very similar structures and with only slight differences in the $G_1$, $G_2$, $G_3$, $R_1$ or $R_2$ groups, the degree and duration of mRNA expression in mice are very likely to be very different.

Therefore, it is very difficult and requires a lot of creative work to screen out cationic lipid compounds with extremely high and sustained expression in animals from a series of compounds with the most similar structures.

b. Distribution of Liposomes in Mice

The live imaging in mice results showed that the distributions of liposomes in mice prepared from different compounds were quite different. Some had protein expression in the liver, while some had no protein expression in the liver.

Figure 15:
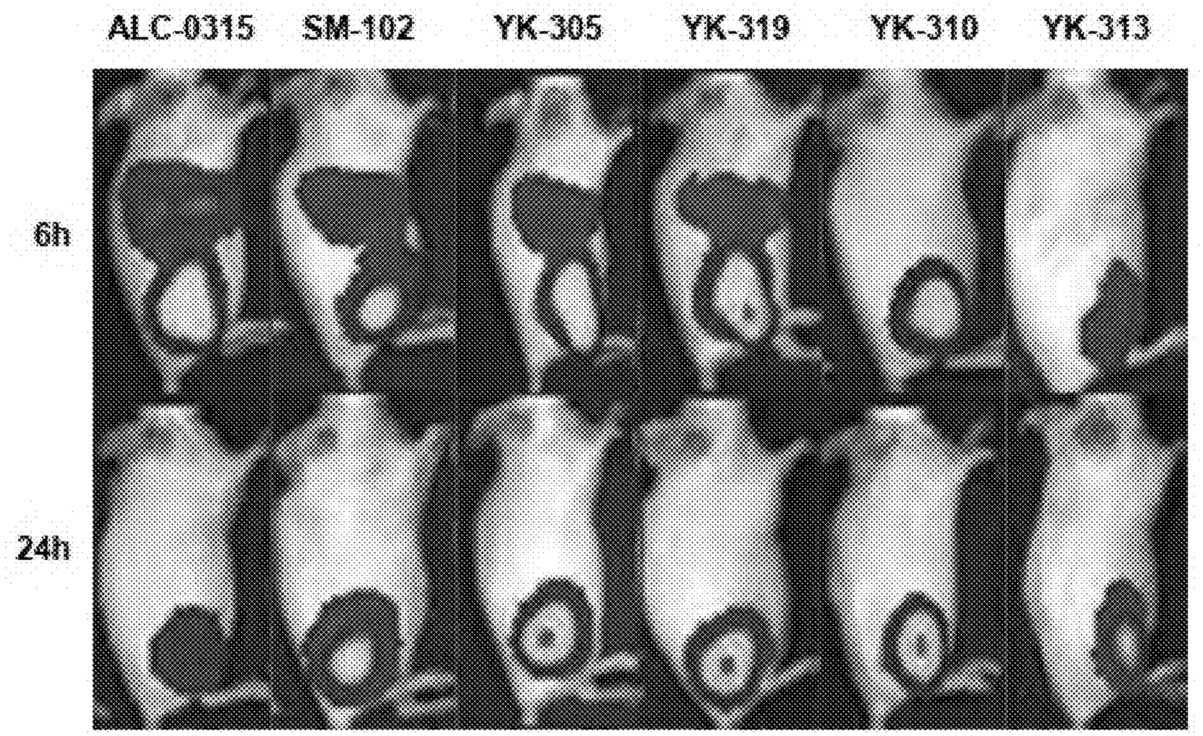
FIG. 15 shows the protein expression in mice of Fluc-mRNA LNP preparations prepared from different cationic lipids (ALC-0315, SM-102, YK-305, YK-319, YK-310 and YK-313).

Details are as follows: at 6 h, some cationic lipids, such as ALC-0315, SM-102, compound 21, compound 23, HIMA, YK-305 and YK-319, had protein expression in the liver, wherein the expression amounts for YK-305 and YK-319 were reduced compared with ALC-0315 and SM-102; while some compounds, such as YK-310 and YK-313, had no protein expression in the liver. At 24 h, the LNP formulations prepared from all compounds had been metabolized in the liver and had no protein expression. (FIG. 15) The results for compound 21, compound 23 and HHMA were similar to that of SM-102, and are not shown in the figures.

It can be seen that compared with the cationic lipids in the prior art, the liposomes prepared from the designed compounds had reduced amount of target protein expressed in the liver after intramuscular injection (YK-305 and YK-319), or will not stay in the liver and express the target protein (YK-310 and YK-313). The mRNA carried in liposomes was expressed in the liver, and the expressed proteins were metabolized by the liver, which increased the burden on the liver. Therefore, some of the designed compounds reduce toxicity of liposomes in the liver compared to representative cationic lipids in the prior art.

Brief Summary:

Compared with representative cationic lipids in the prior art, such as SM-102, ALC-0315, compound 21, Compound 23 and THA, the liposomes prepared from designed compounds have reduced target protein expression amount in the liver, or unable to stay in the liver and express the target protein. Therefore, compared with the cationic lipids in the prior art, the LNP formulations prepared from the designed compounds have reduced or no toxicity to the liver.

Summary:

1) The in vivo animal delivery tests on LNP formulations prepared from a series of designed compounds were conducted, and cationic lipid compounds with high and sustained expression of mRNA in mice, such as YK-305, YK-310, YK-312, YK-319 and YK-318 were screened out.

The designed series of compounds are very different from the representative cationic lipids in the prior art, such as SM-102, ALC-0315, compound 21, compound 23, HHMA and YK-009. The $G_3$ group is completely different, and other parts are also different, so there are great differences in terms of polarity, acidity and alkalinity, and hydrophilicity.

2) the LNP formulations prepared from YK-305, YK-310, YK-312, YK-319 and YK-318 had extremely high and sustained expression of mRNA in mice, which were improved significantly compared with the representative cationic lipids in the prior art. For example, YK-305 and YK-310 can be up to 30 times that of SM-102, compound 21 and compound 23.

Compared with compounds with similar structures and the $G_3$ group being $HO(CH_2)_2N(CH_3)CH_2CH(OH)CH_2$—, the LNP formulations prepared from YK-305, YK-310, YK-312, YK-319 and YK-318 have the highest mRNA expression intensity and longest duration in mice. For example, YK-305 can be up to more than 1000 times that of YK-302 in 48 hours, and can be up to more than 300 times in 7 days.

Compared with compounds with similar structures and the $G_3$ group being $HO(CH_2)_2N(CH_2CH_3)CH_2CH(OH)CH_2$—, the LNP formulations prepared from YK-305, YK-310, YK-312, YK-319 and YK-318 have the highest mRNA expression intensity and longest duration in mice. For example, YK-305 can be up to 160 times that of YK-309 in 48 hours, and can be up to 100 times in 7 days.

Moreover, compared with representative cationic lipids in the prior art, such as SM-102, ALC-0315, compound 21, compound 23 and HHMA, the liposomes prepared from the designed compounds have reduced target protein expression amount in the liver, or do not stay in the liver and express the target protein. Therefore, compared with the cationic lipids in the prior art, the LNP formulations prepared from the designed compounds have reduced or no toxicity to the liver.

3) There is no correspondence between the structure of cationic lipids and the high expression and sustained expression of delivered mRNA in mice. Even if the structural differences of cationic lipid compounds are very small, the expression in vivo of mRNA in animals of the LNP formulations prepared from them will be likely to be very different. It is impossible to predict whether mRNA will be highly and continuously expressed in animals based on the chemical structure of cationic lipids. Therefore, it is very difficult and requires a lot of creative work to screen out cationic lipid compounds with high and sustained expression of mRNA.

CONCLUSIONS

1. The designed series of compounds, including YK-305, YK-310, YK-312, YK-319 and YK-318 are significantly different in chemical structure from the representative cationic lipids in the prior art, such as SM-102, compound 21, compound 23, HHMA and YK-009. The $G_3$ group is completely different, and other parts are also very different. Therefore, there are also great differences in polarity, acidity and alkalinity, and hydrophilicity.

In this series of compounds designed, LNP formulations prepared from YK-305, YK-310, YK-312, YK-319 and YK-318 have significantly improved cell transfection efficiency, significantly reduced cytotoxicity, significantly increased expression amount and duration of mRNA in mice, and through which the amount of target protein expressed in the liver is reduced, or the target protein does not stay and express in the liver, resulting in reduced or no toxicity to the liver, compared with representative cationic lipids in the prior art. For example, YK-305 can be up to 17 times that of SM-102, 19 times that of compound 21, and 20 times that of compound 23; the cell survival rates of YK-305 and YK-310 can both be 30% higher than that of ALC-0315 and 12% higher than that of SM-102, 15% higher than that of HHMA; the expression amount of mRNA in mice of both YK-305 and YK-310 can be up to 30 times that of SM-102, compound 21 and compound 23.

Among the series of designed compounds with little difference in chemical structure, LNP formulations prepared from YK-305, YK-310, YK-312, YK-319 and YK-318 have significantly improved cell transfection efficiency, significantly reduced cytotoxicity, and significantly increased expression amount and duration of mRNA in mice compared with other compounds.

Compared with YK-305, YK-310, YK-312, YK-319 and YK-318, this series of compounds are only slightly different in the $G_1$, $G_2$, $R_1$, $R_2$ or $G_3$ groups, but the cell transfection efficiency of YK-305 can be up to 1,300 times that of YK-304 and 900 times that of YK-302, the cytotoxicity can be reduced by 65% compared with YK-302, and the expression amount of mRNA in mice can be up to above 1,000 times that of YK-302.

2. There is no obvious correspondence between the structure of cationic lipid compounds with intracellular transfection efficiency, toxicity to cells, and the high expression and sustained expression of mRNA in LNP formulations prepared from them in animals. Compounds with small structural differences are likely to have very large differences in transfection efficiency and/or toxicity to cells and intracellular expression.

For example, compared with YK-305, YK-302 only has 2 less C in the $G_1$ group; has a linear chain structure in the $R_1$ group, while YK-305 has a branched chain structure; has 1 more C in the single chain, and 2 less C in each single chain of the double chain in the $R_2$ group; other structures are identical, but the cell transfection efficiency of YK-305 is 900 times that of YK-302, and the toxicity to transfected cells of YK-305 is 65% lower than that of YK-302, the expression of YK-305 in mice can be up to 1,000 times that of YK-302; compared with YK-310, YK-303 only has 1 less C in the group connecting the $G_3$ group to N; other structures are identical, but the cell transfection efficiency of YK-310 is 40 times that of YK-303, and the toxicity to transfected cells of YK-310 is 18% lower than that of YK-303.

Therefore, it is very difficult and requires a lot of creative work to screen out suitable cationic lipid compounds that can simultaneously have high transfection efficiency and low toxicity to cells, as well as high and sustained expression of mRNA in mice.

3. Through unique design and extensive screening, the present disclosure has discovered some compounds, such as YK-305, YK-310, YK-312, YK-319 and YK-318, which can deliver nucleic acids with significantly improved cell transfection efficiency, significantly reduced cytotoxicity, significantly improved expression amount and duration in animals compared with other compounds in the prior art. Unexpected technical effects have been achieved.

The invention claimed is:

1. A compound of any one of the following formulas or a pharmaceutically acceptable salt thereof,

YK-305

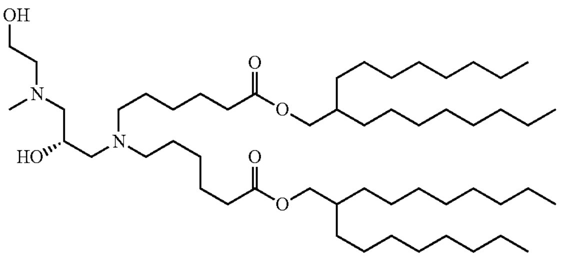

,

YK-310

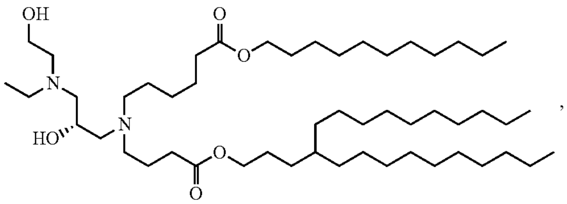

,

YK-312

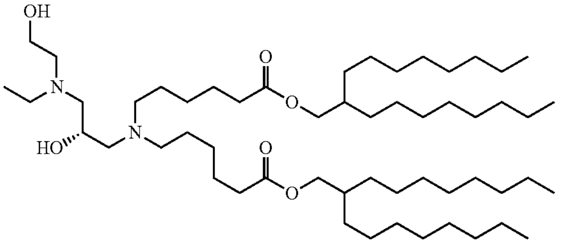

,

YK-319

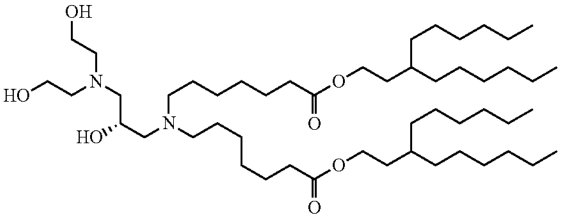

, or

YK-318

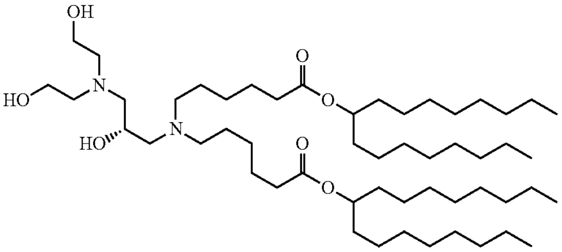

.

2. A composition comprising a carrier, wherein the carrier comprises a cationic lipid, and the cationic lipid comprises the compound according to claim 1.

3. The composition according to claim 2, wherein a molar ratio of the cationic lipid to the carrier is from 25% to 75%.

4. The composition according to claim 2, wherein the carrier further comprises a neutral lipid.

5. The composition according to claim 4, wherein a molar ratio of the cationic lipid to the neutral lipid is from 1:1 to 15:1.

6. The composition according to claim 4, wherein the neutral lipid comprises one or more of phosphatidylcholine, phosphatidylethanolamine, sphingomyelin, ceramide, sterol and a derivative thereof.

7. The composition according to claim 6, wherein the neutral lipid is selected from one or more of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and a mixture thereof.

8. The composition according claim 2, wherein the carrier further comprises a structured lipid.

9. The composition according to claim 8, wherein a molar ratio of the cationic lipid to the structured lipid is from 0.6:1 to 3:1.

10. The composition according to claim 8, wherein the structured lipid is selected from one or more of cholesterol, nonsterol, sitosterol, ergosterol, campesterol, stigmasterol, brassicasterol, tomatine, tomatine, ursolic acid, alpha-tocopherol, and corticosteroid.

11. The composition according to claim 2, wherein the carrier further comprises a polymer-conjugated lipid.

12. The composition according to claim 11, wherein a molar ratio of the polymer-conjugated lipid to the carrier is from 0.5% to 10%.

13. The composition according to claim 11, wherein the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol.

14. The composition according to claim 13, wherein the polymer-conjugated lipid is selected from one or more of distearoyl phosphatidylethanolamine polyethylene glycol 2000 (DSPE-PEG2000), dimyristoylglycero-3-methoxy polyethylene glycol 2000 (DMG-PEG2000) and methoxy-polyethylene glycol ditetradecylacetamide (ALC-0159).

15. The composition according to claim 2, wherein the carrier comprises a neutral lipid, a structured lipid and a polymer-conjugated lipid, and a molar ratio of the cationic lipid, the neutral lipid, the structured lipid and the polymer-conjugated lipid is (25 to 75): (5 to 25): (15 to 65): (0.5 to 10).

16. The composition according to claim 2, wherein the composition is a nanoparticle formulation which has an average particle size of 10 nm to 300 nm and a polydispersity coefficient less than or equal to 50%.

17. The composition according to claim 2, wherein the cationic lipid further comprises one or more other ionizable lipid compound(s).

18. The composition according to claim 2, further comprising a therapeutic or prophylactic agent.

19. The composition according to claim 18, wherein a mass ratio of the carrier to the therapeutic agent or prophylactic agent is from 10:1 to 30:1.

20. The composition according to claim 18, wherein the therapeutic or prophylactic agent comprises one or more of a nucleic acid molecule, a small molecule compound, a polypeptide or a protein.

21. The composition according to claim 18, wherein the therapeutic or prophylactic agent is a vaccine or compound capable of eliciting an immune response.

22. The composition according to claim 18, wherein the therapeutic or prophylactic agent is a nucleic acid.

23. The composition according to claim 22, wherein the therapeutic or prophylactic agent is ribonucleic acid (RNA).

24. The composition according to claim 22, wherein the therapeutic or prophylactic agent is deoxyribonucleic acid (DNA).

25. The composition according to claim 23, wherein the RNA is selected from the group consisting of small interfering RNA (siRNA), asymmetric interfering RNA (aiRNA), microRNA (miRNA), Dicer-substrate RNA (dsRNA), small hairpin RNA (shRNA), messenger RNA (mRNA), and mixtures thereof.

* * * * *